US007405287B2

(12) United States Patent
Mao et al.

(10) Patent No.: US 7,405,287 B2
(45) Date of Patent: Jul. 29, 2008

(54) METHOD OF TREATING A CANCER

(75) Inventors: Li Mao, Houston, TX (US); Jie Wang, Beijing (CN); Luo Wang, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/189,279

(22) Filed: Jul. 26, 2005

(65) Prior Publication Data

US 2006/0115829 A1 Jun. 1, 2006

Related U.S. Application Data

(60) Provisional application No. 60/598,554, filed on Aug. 3, 2004.

(51) Int. Cl.

| | |
|---|---|
| ***C07H 21/04*** | (2006.01) |
| ***C12N 15/00*** | (2006.01) |
| ***C12N 5/00*** | (2006.01) |

(52) U.S. Cl. .................... 536/23.2; 435/320.1; 435/325

(58) Field of Classification Search ................ 536/23.2; 435/320.1, 325

See application file for complete search history.

(56) References Cited

U.S. PATENT DOCUMENTS

2004/0234997 A1 * 11/2004 Li et al. ......................... 435/6

FOREIGN PATENT DOCUMENTS

| | | | |
|---|---|---|---|
| WO | WO9967397 A1 | * | 12/1999 |
| WO | WO 9967397 A1 | * | 12/1999 |
| WO | WO02009126 A1 | * | 11/2002 |
| WO | WO 2004/030615 | * | 4/2004 |

OTHER PUBLICATIONS

Xie et al., Cloning, expression and chromosome locations of the human DNMT3 gene family. Gene vol. 236, Issue 1 , Aug. 5, 1999, pp. 87-95.*

Xu et al.,Chromosome instability and immunodeficiency syndrome caused by mutations in a DNA methyltransferase gene.Nature. Nov. 11, 1999;402(6758):187-91.*

Deloukas P et al., The DNA sequence and comparative analysis of human chromosome 20.Nature. Dec. 20-27, 2001;414(6866):865-71 PMID: 11780052 [PubMed—indexed for Medline] (abstract).*

Robertson et al., The human DNA methyltransferases (DNMTs) 1, 3a and 3b: coordinate mRNA expression in normal tissues and overexpression in tumors.Nucleic Acids Res. Jun. 1, 1999;27(11):2291-8.*

Kang et al., Dnmt3b, de Novo DNA Methyltransferase, Interacts with SUMO-1 and Ubc9 through Its N-Terminal Region and Is Subject to Modification by SUMO-1 Biochemical and Biophysical Research Communications vol. 289, Issue 4 , Dec. 14, 2001, pp. 862-868.*

Okano et al., DNA Methyltransferases Dnmt3a and Dnmt3b Are Essential for De Novo Methylation and Mammalian Development. Cell. Oct. 29, 1999;99(3):247-57.*

Hansen et al., The DNMT3B DNA methyltransferase gene is mutated in the ICF immunodeficiency syndrome.Proc Natl Acad Sci U S A. Dec. 7, 1999;96(25):14412-7.*

Wijmenga et al., Genetic variation in ICF syndrome: evidence for genetic heterogeneity.Hum Mutat. Dec. 2000;16(6):509-17. Review.*

STIC search tittled "us-11-189-279-18.rup". pp. 1-3.*

SITC search tillted "us-11-189-279-18.rapbm". pp. 1-2.*

SITC search tillted "us-11-189-279-18.rag". pp. 1-5.*

Score Result 3, p. 7-11, on the attached search print out titled us-11-189-279-1.rng pp. 1-16.*

Chen et al., Physical and functional interactions between the human DNMT3L protein and members of the de novo methyltransferase family. Journal of Cellular Biochemistryvol. 95, Issue 5, pp. 902-917.*

Score. Result 1, p. 1-6, on the attached search print out titled us-11-189-279-4.rge.*

National Center for Biotechnology Information, GenBank Accession No. W76111, GenBank database; Jun. 14, 1996.

National Center for Biotechnology Information, GenBank Accession No. N88352, GenBank database; Apr. 2, 1996.

National Center for Biotechnology Information, GenBank Accession No. F12227, GenBank database; Mar. 13, 1995.

National Center for Biotechnology Information, GenBank Accession No. T66356, GenBank database; Feb. 20, 1995.

National Center for Biotechnology Information, GenBank Accession No. AA761775, GenBank database; Jan. 28, 1998.

National Center for Biotechnology Information, GenBank Accession No. G06200, GenBank database; Oct. 19, 1995.

National Center for Biotechnology Information, GenBank Accession No. G15302, GenBank database; Mar. 30, 2000.

National Center for Biotechnology Information, GenBank Accession No. AL035071, GenBank database; May 18, 2005.

National Center for Biotechnology Information, GenBank Accession No. AF135438, GenBank database; Sep. 8, 1999.

(Continued)

*Primary Examiner*—Anne Marie Wehbe
*Assistant Examiner*—Maria Leavitt
(74) *Attorney, Agent, or Firm*—Fulbright & Jaworski, LLP

(57) ABSTRACT

The present invention provides isolated nucleic acids encoding delta DNA methyltransferase 3B molecules that are involved in the treatment and prevention of cancers such as, but not limited to, lung cancer. The delta DNA methyltransferase 3B molecules of the present invention are found to play a critical role in promoter-specific methylation of tumor suppressor genes. The DNA methyltransferase 3B molecules of the present invention are provided as therapeutic targets for identifying inhibitors of DNA methyltransferase. Such inhibitors are contemplated for the treatment and/or prevention of cancers. In particular embodiments, the present invention involves the treatment and prevention of a non-small cell lung cancer.

20 Claims, 13 Drawing Sheets

OTHER PUBLICATIONS

Baylin, "Altered methylation patterns in cancer cell genomes: Cause or consequence?" *Cancer Cell*, 1: 299-305, 2002.

Belinsky et al., "Aberrant methylation of *p16*$^{INK4a}$ is an early event in lung cancer and a potential biomarker for early diagnosis," *Proc. Natl. Acad. Sci. USA*, 95: 11891-11896, 1998.

Belinsky et al., "Aberrant Promoter Methylation in Bronchial Epithelium and Spatum from Current and Former Smokers," *Cancer Res.*, 62: 2370-2377, 2002.

Brauch et al., "Molecular Analysis of the Short Arm of Chromosome 3 in Small-Cell and Non-Small-Cell Cancinoma of the Lung," *The New England Journal of Medicine*, 317(18): 1109-13, 1987.

Burbee et al., "Epigenetic Inactivation of RASSF1A in Lung and Breast Cancers and Malignant Phenotype Suppression," *J. Natl. Cancer Inst.*, 93: 691-9, 2001.

Cedar, "DNA Methylation and Gene Activity," *Cell*, 53: 3-4, 1988.

Dammann et al., "Epigenetic inactivation of a RAS association domain family protein from the lung tumour suppressor locus 3p21. 3," *Nature Genetics*, 25: 315-319, 2000.

Leu et al., "Double RNA Interference of *DNMT3b* and *DNMT1* Enhances DNA Demethylation and Gene Reactivation," *Cancer Res.*, 63: 6110-6115, 2003.

Ortiz-Vega et al., "The putative tumor suppressor RASSF1A homodimerizes and heterodimerizes with the Ras-GTP binding protein Nore1," *Oncogene*, 21: 1381-1390, 2002.

Oue et al., "DNA methylation status of *hMLH1, p16*$^{INK4a}$, and *CDH1* is not associated with mRNA expression levels of DNA methyltransferase and DNA demethylase in gastric carcinomas," *Oncology Reports*, 8: 1085-1089, 2001.

Pfeifer et al., "Methylation of the *RASSF1A* Gene in Human Cancers," *Biol. Chem.*, 383: 907-914, 2002.

Reik et al., "Epigenetic Reprogramming in Mammalian Development," *Science*, 293: 1089-1093, 2001.

Rhee et al., "CpG methylation is maintained in human cancer cells lacking *DNMT1," Nature*, 404: 1003-1007, 2000.

Rhee et al., "DNMT1 and DNMT3b cooperate to silence genes in human cancer cells," *Nature*, 416: 552-556, 2002.

Robertson et al., "The human DNA methyltransferases (DNMTs) 1, 3a and 3b: coordinate mRNA expression in normal tissues and overexpression in tumors," *Nucleic Acids Research*, 27(11): 2291-2298, 1999.

Saito et al., "Overexpression of a splice variant of DNA methyltransferase 3b, DNMT3b4, associated with DNA hypomethylation on pericentromeric satellite regions during human hepatocarcinogenesis," *PNAS*, 99(15): 10060-10065, 2002.

Shen et al., "A Novel Polymorphism in Human Cytosine DNA-Methyltransferase-3B Promoter Is Associated with an Increased Risk of Lung Cancer," *Cancer Res.*, 62: 4992-4995, 2002.

Soria et al., "Aberrant Promoter Methylation of Multiple Genes in Bronchial Brush Samples from Former Cigarette Smokers," *Cancer Res.*, 62: 351-355, 2002.

Wang et al., "A novel C/T polymorphism in the core promoter of human *de novo* cytosine DNA methyltransferase 3B6 is associated with prognosis in head and neck cancer," *International Journal of Oncology*, 25: 993-999, 2004.

Weisenberger et al., "Role of the DNA Methyltransferase Variant DNMT3b3 in DNA Methylation," *Molecular Cancer Research*, 2: 62-72, 2004.

Yakushiji et al., "Over-expression of DNA methyltransferases and CDKN2A gene methylation status in squamous cell carcinoma of the oral cavity," *International Journal of Oncology*, 22: 1201-1207, 2003.

* cited by examiner 185 should recognize all isoforms;
187 should recognize -b and -d isoform.
186 lost at the moment

SEQUENCE LISTING

```
<160> NUMBER OF SEQ ID NOS: 69

<210> SEQ ID NO 1
<211> LENGTH: 2280
<212> TYPE: DNA
<213> ORGANISM: Homo sapiens

<400> SEQUENCE: 1

gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag tacccctac gcccgcctag cccaggacag     180

ccagcagggg ggcatggagt ccccgcaggt ggaggcagac agtggagatg gagacagttc    240

agagtatcag gatgggaagg agtttggaat aggggacctc gtgtggggaa agatcaaggg    300

cttctcctgg tggcccgcca tggtggtgtc ttggaaggcc acctccaagc gacaggctat    360

gtctggcatg cggtgggtcc agtggtttgg cgatggcaag ttctccgagg tctctgcaga    420

caaactggtg gcactggggc tgttcagcca gcactttaat ttggccacct tcaataagct    480

cgtctcctat cgaaaagcca tgtaccatgc tctggagaaa gctagggtgc gagctggcaa    540

gaccttcccc agcagccctg gagactcatt ggaggaccag ctgaagccca tgttggagtg    600

ggcccacggg ggcttcaagc ccactgggat cgagggcctc aaacccaaca acacgcaacc    660

agtggttaat aagtcgaagg tgcgtcgtgc aggcagtagg aaattagaat caaggaaata    720

cgagaacaag actcgaagac gcacagctga cgactcagcc acctctgact actgccccgc    780

acccaagcgc ctcaagacaa attgctataa caacggcaaa gaccgagggg atgaagatca    840

gagccgagaa caaatggctt cagatgttgc caacaacaag agcagcctgg aagatggctg    900

tttgtcttgt ggcaggaaaa accccgtgtc cttccaccct ctctttgagg gggggctctg    960

tcagacatgc cgggatcgct tccttgagct gttttacatg tatgatgacg atggctatca   1020

gtcttactgc actgtgtgct gcgagggccg agagctgctg ctttgcagca acacgagctg   1080

ctgccggtgt ttctgtgtgg agtgcctgga ggtgctggtg ggcacaggca cagcggccga   1140

ggccaagctt caggagccct ggagctgtta catgtgtctc ccgcagcgct gtcatggcgt   1200

cctgcggcgc cggaaggact ggaacgtgcg cctgcaggcc ttcttcacca gtgacacggg   1260

gcttgaatat gaagccccca agctgtaccc tgccattccc gcagcccgaa ggcggcccat   1320

tcgagtcctg tcattgtttg atggcatcgc gacaggctac ctagtcctca aagagttggg   1380

cataaaggta ggaaagtacg tcgcttctga agtgtgtgag gagtccattg ctgttggaac   1440

cgtgaagcac gaggggaata tcaaatacgt gaacgacgtg aggaacatca caaagaaaaa   1500

tattgaagaa tggggcccat ttgacttggt gattggcgga agcccatgca acgatctctc   1560

aaatgtgaat ccagccagga aaggcctgta tgagggtaca ggccggctct tcttcgaatt   1620
```

-continued ttaccacctg ctgaattact cacgccccaa ggagggtgat gaccggccgt tcttctggat 1680
gtttgagaat gttgtagcca tgaaggttgg cgacaagagg gacatctcac ggttcctgga 1740
gtgtaatcca gtgatgattg atgccatcaa agtttctgct gctcacaggg cccgatactt 1800
ctggggcaac ctacccggga tgaacaggcc cgtgatagca tcaaagaatg ataaactcga 1860
gctgcaggac tgcttggaat acaataggat agccaagtta aagaaagtac agacaataac 1920
caccaagtcg aactcgatca aacaggggaa aaaccaactt ttccctgttg tcatgaatgg 1980
caaagaagat gttttgtggt gcactgagct cgaaaggatc tttggctttc ctgtgcacta 2040
cacagacgtg tccaacatgg gccgtggtgc ccgccagaag ctgctgggaa ggtcctggag 2100
cgtgcctgtc atccgacacc tcttcgcccc tctgaaggac tactttgcat gtgaatagtt 2160
ccagccaggc cccaagccca ctggggtgtg tggcagagcc aggacccagg aggtgtgatt 2220
cctgaaggca tccccaggcc ctgctcttcc tcagctgtgt gggtcatacc gtgtacctca 2280

<210> SEQ ID NO 2
<211> LENGTH: 2220
<212> TYPE: DNA
<213> ORGANISM: Homo sapiens

<400> SEQUENCE: 2
gtcccccgtg gagttcccgg ctaccaggtc cctgagacgg cgggcaacag catcggcagg 60
aacgccatgg ccgtcccctc ccagctctta ccttaccatc gacctcacag acgacacaga 120
ggacacacat gggacgcccc agagcagcag taccccctac gcccgcctag cccaggacag 180
ccagcagggg ggcatggagt ccccgcaggt ggaggcagac agtggagatg gagacagttc 240
agagtatcag gatgggaagg agtttggaat aggggacctc gtgtggggaa agatcaaggg 300
cttctcctgg tggcccgcca tggtggtgtc ttggaaggcc acctccaagc gacaggctat 360
gtctggcatg cggtgggtcc agtggtttgg cgatggcaag ttctccgagg tctctgcaga 420
caaactggtg gcactggggc tgttcagcca gcactttaat ttggccacct tcaataagct 480
cgtctcctat cgaaaagcca tgtaccatgc tctggagaaa gctagggtgc gagctggcaa 540
gaccttcccc agcagccctg gagactcatt ggaggaccag ctgaagccca tgttggagtg 600
ggcccacggg ggcttcaagc ccactgggat cgagggcctc aaacccaaca acacgcaacc 660
agagaacaag actcgaagac gcacagctga cgactcagcc acctctgact actgccccgc 720
acccaagcgc ctcaagacaa attgctataa caacggcaaa gaccgagggg atgaagatca 780
gagccgagaa caaatggctt cagatgttgc caacaacaag agcagcctgg aagatggctg 840
tttgtcttgt ggcaggaaaa accccgtgtc cttccaccct ctctttgagg gggggctctg 900
tcagacatgc cgggatcgct tccttgagct gttttacatg tatgatgacg atggctatca 960
gtcttactgc actgtgtgct gcgagggccg agagctgctg ctttgcagca acacgagctg 1020
ctgccggtgt ttctgtgtgg agtgcctgga ggtgctggtg ggcacaggca cagcggccga 1080
ggccaagctt caggagccct ggagctgtta catgtgtctc ccgcagcgct gtcatggcgt 1140
cctgcggcgc cggaaggact ggaacgtgcg cctgcaggcc ttcttcacca gtgacacggg 1200
gcttgaatat gaagccccca agctgtaccc tgccattccc gcagcccgaa ggcggcccat 1260
tcgagtcctg tcattgtttg atggcatcgc gacaggctac ctagtcctca aagagttggg 1320
cataaaggta ggaaagtacg tcgcttctga agtgtgtgag gagtccattg ctgttggaac 1380
cgtgaagcac gaggggaata tcaaatacgt gaacgacgtg aggaacatca caaagaaaaa 1440

-continued

```
tattgaagaa tggggcccat ttgacttggt gattggcgga agcccatgca acgatctctc   1500

aaatgtgaat ccagccagga aaggcctgta tgagggtaca ggccggctct tcttcgaatt   1560

ttaccacctg ctgaattact cacgccccaa ggagggtgat gaccggccgt tcttctggat   1620

gtttgagaat gttgtagcca tgaaggttgg cgacaagagg gacatctcac ggttcctgga   1680

gtgtaatcca gtgatgattg atgccatcaa agtttctgct gctcacaggg cccgatactt   1740

ctggggcaac ctacccggga tgaacaggcc cgtgatagca tcaaagaatg ataaactcga   1800

gctgcaggac tgcttggaat acaataggat agccaagtta aagaaagtac agacaataac   1860

caccaagtcg aactcgatca aacaggggaa aaaccaactt ttccctgttg tcatgaatgg   1920

caaagaagat gttttgtggt gcactgagct cgaaaggatc tttggctttc ctgtgcacta   1980

cacagacgtg tccaacatgg gccgtggtgc ccgccagaag ctgctgggaa ggtcctggag   2040

cgtgcctgtc atccgacacc tcttcgcccc tctgaaggac tactttgcat gtgaatagtt   2100

ccagccaggc cccaagccca ctggggtgtg tggcagagcc aggacccagg aggtgtgatt   2160

cctgaaggca tccccaggcc ctgctcttcc tcagctgtgt gggtcatacc gtgtacctca   2220
```

<210> SEQ ID NO 3
<211> LENGTH: 2121
<212> TYPE: DNA
<213> ORGANISM: Homo sapiens

<400> SEQUENCE: 3

```
gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag taccccctac gcccgcctag cccaggacag    180

ccagcagggg ggcatggagt ccccgcaggt ggaggcagac agtggagatg gagacagttc    240

agagtatcag gtctctgcag acaaactggt ggcactgggg ctgttcagcc agcactttaa    300

tttggccacc ttcaataagc tcgtctccta tcgaaaagcc atgtaccatg ctctggagaa    360

agctagggtg cgagctggca agaccttccc cagcagccct ggagactcat tggaggacca    420

gctgaagccc atgttggagt gggcccacgg gggcttcaag cccactggga tcgagggcct    480

caaacccaac aacacgcaac cagtggttaa taagtcgaag gtgcgtcgtg caggcagtag    540

gaaattagaa tcaaggaaat acgagaacaa gactcgaaga cgcacagctg acgactcagc    600

cacctctgac tactgccccg cacccaagcg cctcaagaca aattgctata acaacggcaa    660

agaccgaggg gatgaagatc agagccgaga acaaatggct tcagatgttg ccaacaacaa    720

gagcagcctg gaagatggct gtttgtcttg tggcaggaaa aaccccgtgt ccttccaccc    780

tctctttgag gggggctct gtcagacatg ccgggatcgc ttccttgagc tgttttacat    840

gtatgatgac gatggctatc agtcttactg cactgtgtgc tgcgagggcc gagagctgct    900

gctttgcagc aacacgagct gctgccggtg tttctgtgtg gagtgcctgg aggtgctggt    960

gggcacaggc acagcggccg aggccaagct tcaggagccc tggagctgtt acatgtgtct   1020

cccgcagcgc tgtcatggcg tcctgcggcg ccggaaggac tggaacgtgc gcctgcaggc   1080

cttcttcacc agtgacacgg ggcttgaata tgaagccccc aagctgtacc ctgccattcc   1140

cgcagcccga aggcggccca ttcgagtcct gtcattgttt gatggcatcg cgacaggcta   1200

cctagtcctc aaagagttgg gcataaaggt aggaaagtac gtcgcttctg aagtgtgtga   1260

ggagtccatt gctgttggaa ccgtgaagca cgaggggaat atcaaatacg tgaacgacgt   1320

gaggaacatc acaaagaaaa atattgaaga atggggccca tttgacttgg tgattggcgg   1380
```

-continued aagcccatgc aacgatctct caaatgtgaa tccagccagg aaaggcctgt atgagggtac 1440
aggccggctc ttcttcgaat tttaccacct gctgaattac tcacgcccca aggagggtga 1500
tgaccggccg ttcttctgga tgtttgagaa tgttgtagcc atgaaggttg gcgacaagag 1560
ggacatctca cggttcctgg agtgtaatcc agtgatgatt gatgccatca aagtttctgc 1620
tgctcacagg gcccgatact tctggggcaa cctacccggg atgaacaggc ccgtgatagc 1680
atcaaagaat gataaactcg agctgcagga ctgcttggaa tacaatagga tagccaagtt 1740
aaagaaagta cagacaataa ccaccaagtc gaactcgatc aaacagggga aaaaccaact 1800
tttccctgtt gtcatgaatg gcaaagaaga tgttttgtgg tgcactgagc tcgaaaggat 1860
ctttggcttt cctgtgcact acacagacgt gtccaacatg ggccgtggtg cccgccagaa 1920
gctgctggga aggtcctgga gcgtgcctgt catccgacac ctcttcgccc ctctgaagga 1980
ctactttgca tgtgaatagt tccagccagg ccccaagccc actggggtgt gtggcagagc 2040
caggacccag gaggtgtgat tcctgaaggc atccccaggc cctgctcttc ctcagctgtg 2100
tgggtcatac cgtgtacctc a 2121

<210> SEQ ID NO 4
<211> LENGTH: 2061
<212> TYPE: DNA
<213> ORGANISM: Homo sapiens

<400> SEQUENCE: 4
gtcccccgtg gagttcccgg ctaccaggtc cctgagacgg cgggcaacag catcggcagg 60
aacgccatgg ccgtcccctc ccagctctta ccttaccatc gacctcacag acgacacaga 120
ggacacacat gggacgcccc agagcagcag tacccctac gcccgcctag cccaggacag 180
ccagcagggg ggcatggagt ccccgcaggt ggaggcagac agtggagatg gagacagttc 240
agagtatcag gtctctgcag acaaactggt ggcactgggg ctgttcagcc agcactttaa 300
tttggccacc ttcaataagc tcgtctccta tcgaaaagcc atgtaccatg ctctggagaa 360
agctagggtg cgagctggca agaccttccc cagcagccct ggagactcat tggaggacca 420
gctgaagccc atgttggagt gggcccacgg gggcttcaag cccactggga tcgagggcct 480
caaacccaac aacacgcaac cagagaacaa gactcgaaga cgcacagctg acgactcagc 540
cacctctgac tactgccccg cacccaagcg cctcaagaca aattgctata acaacggcaa 600
agaccgaggg gatgaagatc agagccgaga acaaatggct tcagatgttg ccaacaacaa 660
gagcagcctg gaagatggct gtttgtcttg tggcaggaaa aaccccgtgt ccttccaccc 720
tctctttgag ggggggctct gtcagacatg ccgggatcgc ttccttgagc tgttttacat 780
gtatgatgac gatggctatc agtcttactg cactgtgtgc tgcgagggcc gagagctgct 840
gctttgcagc aacacgagct gctgccggtg tttctgtgtg gagtgcctgg aggtgctggt 900
gggcacaggc acagcggccg aggccaagct tcaggagccc tggagctgtt acatgtgtct 960
cccgcagcgc tgtcatggcg tcctgcggcg ccggaaggac tggaacgtgc gcctgcaggc 1020
cttcttcacc agtgacacgg ggcttgaata tgaagccccc aagctgtacc ctgccattcc 1080
cgcagcccga aggcggccca ttcgagtcct gtcattgttt gatggcatcg cgacaggcta 1140
cctagtcctc aaagagttgg gcataaaggt aggaaagtac gtcgcttctg aagtgtgtga 1200
ggagtccatt gctgttggaa ccgtgaagca cgaggggaat atcaaatacg tgaacgacgt 1260
gaggaacatc acaaagaaaa atattgaaga atggggccca tttgacttgg tgattggcgg 1320

-continued

```
aagcccatgc aacgatctct caaatgtgaa tccagccagg aaaggcctgt atgagggtac   1380

aggccggctc ttcttcgaat tttaccacct gctgaattac tcacgcccca aggagggtga   1440

tgaccggccg ttcttctgga tgtttgagaa tgttgtagcc atgaaggttg gcgacaagag   1500

ggacatctca cggttcctgg agtgtaatcc agtgatgatt gatgccatca aagtttctgc   1560

tgctcacagg gcccgatact tctggggcaa cctacccggg atgaacaggc ccgtgatagc   1620

atcaaagaat gataaactcg agctgcagga ctgcttggaa tacaatagga tagccaagtt   1680

aaagaaagta cagacaataa ccaccaagtc gaactcgatc aaacagggga aaaaccaact   1740

tttccctgtt gtcatgaatg gcaaagaaga tgttttgtgg tgcactgagc tcgaaaggat   1800

ctttggcttt cctgtgcact acacagacgt gtccaacatg ggccgtggtg cccgccagaa   1860

gctgctggga aggtcctgga gcgtgcctgt catccgacac ctcttcgccc ctctgaagga   1920

ctactttgca tgtgaatagt tccagccagg ccccaagccc actggggtgt gtggcagagc   1980

caggacccag gaggtgtgat tcctgaaggc atccccaggc cctgctcttc ctcagctgtg   2040

tgggtcatac cgtgtacctc a                                             2061


<210> SEQ ID NO 5
<211> LENGTH: 1808
<212> TYPE: DNA
<213> ORGANISM: Homo sapiens

<400> SEQUENCE: 5

gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag taccccctac gcccgcctag cccaggacag    180

ccagcagggg ggcatggagt ccccgcaggt ggaggcagac agtggagatg gagacagttc    240

agagtatcag agaacaagac tcgaagacgc acagctgacg actcagccac ctctgactac    300

tgccccgcac ccaagcgcct caagacaaat tgctataaca acggcaaaga ccgaggggat    360

gaagatcaga gccgagaaca aatggcttca gatgttgcca acaacaagag cagcctggaa    420

gatggctgtt tgtcttgtgg caggaaaaac cccgtgtcct tccaccctct ctttgagggg    480

gggctctgtc agacatgccg ggatcgcttc cttgagctgt tttacatgta tgatgacgat    540

ggctatcagt cttactgcac tgtgtgctgc gagggccgag agctgctgct ttgcagcaac    600

acgagctgct gccggtgttt ctgtgtggag tgcctggagg tgctggtggg cacaggcaca    660

gcggccgagg ccaagcttca ggagccctgg agctgttaca tgtgtctccc gcagcgctgt    720

catggcgtcc tgcggcgccg gaaggactgg aacgtgcgcc tgcaggcctt cttcaccagt    780

gacacggggc ttgaatatga agcccccaag ctgtaccctg ccattcccgc agcccgaagg    840

cggcccattc gagtcctgtc attgtttgat ggcatcgcga caggctacct agtcctcaaa    900

gagttgggca taaaggtagg aaagtacgtc gcttctgaag tgtgtgagga gtccattgct    960

gttggaaccg tgaagcacga ggggaatatc aaatacgtga acgacgtgag gaacatcaca   1020

aagaaaaata ttgaagaatg ggcccattt gacttggtga ttggcggaag cccatgcaac   1080

gatctctcaa atgtgaatcc agccaggaaa ggcctgtatg agggtacagg ccggctcttc   1140

ttcgaatttt accacctgct gaattactca cgccccaagg agggtgatga ccggccgttc   1200

ttctggatgt ttgagaatgt tgtagccatg aaggttggcg acaagaggga catctcacgg   1260

ttcctggagt gtaatccagt gatgattgat gccatcaaag tttctgctgc tcacagggcc   1320

cgatacttct ggggcaacct acccgggatg aacaggcccg tgatagcatc aaagaatgat   1380
```

-continued aaactcgagc tgcaggactg cttggaatac aataggatag ccaagttaaa gaaagtacag 1440
acaataacca ccaagtcgaa ctcgatcaaa caggggaaaa accaactttt ccctgttgtc 1500
atgaatggca aagaagatgt tttgtggtgc actgagctcg aaaggatctt tggctttcct 1560
gtgcactaca cagacgtgtc caacatgggc cgtggtgccc gccagaagct gctgggaagg 1620
tcctggagcg tgcctgtcat ccgacacctc ttcgcccctc tgaaggacta ctttgcatgt 1680
gaatagttcc agccaggccc caagcccact ggggtgtgtg gcagagccag gacccaggag 1740
gtgtgattcc tgaaggcatc cccaggccct gctcttcctc agctgtgtgg gtcataccgt 1800
gtacctca 1808

<210> SEQ ID NO 6
<211> LENGTH: 1967
<212> TYPE: DNA
<213> ORGANISM: Homo sapiens

<400> SEQUENCE: 6
gtcccccgtg gagttcccgg ctaccaggtc cctgagacgg cgggcaacag catcggcagg 60
aacgccatgg ccgtcccctc ccagctctta ccttaccatc gacctcacag acgacacaga 120
ggacacacat gggacgcccc agagcagcag tacccctac gcccgcctag cccaggacag 180
ccagcagggg ggcatggagt ccccgcaggt ggaggcagac agtggagatg gagacagttc 240
agagtatcag gatgggaagg agtttggaat aggggacctc gtgtggggaa agatcaaggg 300
cttctcctgg tggcccgcca tggtggtgtc ttggaaggcc acctccaagc gacaggctat 360
gtctggcatg cggtgggtcc agtggtttgg cgatggcaag ttctccgaga gaacaagact 420
cgaagacgca cagctgacga ctcagccacc tctgactact gccccgcacc caagcgcctc 480
aagacaaatt gctataacaa cggcaaagac cgaggggatg aagatcagag ccgagaacaa 540
atggcttcag atgttgccaa caacaagagc agcctggaag atggctgttt gtcttgtggc 600
aggaaaaacc ccgtgtcctt ccaccctctc tttgaggggg ggctctgtca gacatgccgg 660
gatcgcttcc ttgagctgtt ttacatgtat gatgacgatg gctatcagtc ttactgcact 720
gtgtgctgcg agggccgaga gctgctgctt tgcagcaaca cgagctgctg ccggtgtttc 780
tgtgtggagt gcctggaggt gctggtgggc acaggcacag cggccgaggc caagcttcag 840
gagccctgga gctgttacat gtgtctcccg cagcgctgtc atggcgtcct gcggcgccgg 900
aaggactgga acgtgcgcct gcaggccttc ttcaccagtg acacggggct tgaatatgaa 960
gcccccaagc tgtaccctgc cattcccgca gcccgaaggc ggcccattcg agtcctgtca 1020
ttgtttgatg gcatcgcgac aggctaccta gtcctcaaag agttgggcat aaaggtagga 1080
aagtacgtcg cttctgaagt gtgtgaggag tccattgctg ttggaaccgt gaagcacgag 1140
gggaatatca aatacgtgaa cgacgtgagg aacatcacaa agaaaaatat tgaagaatgg 1200
ggcccatttg acttggtgat tggcggaagc ccatgcaacg atctctcaaa tgtgaatcca 1260
gccaggaaag gcctgtatga gggtacaggc cggctcttct tcgaatttta ccacctgctg 1320
aattactcac gccccaagga gggtgatgac cggccgttct tctggatgtt tgagaatgtt 1380
gtagccatga aggttggcga caagagggac atctcacggt tcctggagtg taatccagtg 1440
atgattgatg ccatcaaagt ttctgctgct cacagggccc gatacttctg gggcaaccta 1500
cccgggatga acaggcccgt gatagcatca aagaatgata aactcgagct gcaggactgc 1560
ttggaataca ataggatagc caagttaaag aaagtacaga caataaccac caagtcgaac 1620

-continued tcgatcaaac aggggaaaaa ccaacttttc cctgttgtca tgaatggcaa agaagatgtt 1680
ttgtggtgca ctgagctcga aaggatcttt ggctttcctg tgcactacac agacgtgtcc 1740
aacatgggcc gtggtgcccg ccagaagctg ctgggaaggt cctggagcgt gcctgtcatc 1800
cgacacctct tcgcccctct gaaggactac tttgcatgtg aatagttcca gccaggcccc 1860
aagcccactg gggtgtgtgg cagagccagg acccaggagg tgtgattcct gaaggcatcc 1920
ccaggccctg ctcttcctca gctgtgtggg tcataccgtg tacctca 1967

<210> SEQ ID NO 7
<211> LENGTH: 2075
<212> TYPE: DNA
<213> ORGANISM: Homo sapiens

<400> SEQUENCE: 7
gtcccccgtg gagttcccgg ctaccaggtc cctgagacgg cgggcaacag catcggcagg 60
aacgccatgg ccgtcccctc ccagctctta ccttaccatc gacctcacag acgacacaga 120
ggacacacat gggacgcccc agagcagcag taccccctac gcccgcctag cccaggacag 180
ccagcagggg ggcatggagt ccccgcaggt ggaggcagac agtggagatg gagacagttc 240
agagtatcag gatgggaagg agtttggaat aggggacctc gtgtggggaa agatcaaggg 300
cttctcctgg tggcccgcca tggtggtgtc ttggaaggcc acctccaagc gacaggctat 360
gtctggcatg cggtgggtcc agtggtttgg cgatggcaag ttctccgagg tctctgcaga 420
caaactggtg gcactggggc tgttcagcca gcactttaat ttggccacct tcaataagct 480
cgtctcctat cgaaaagcca tgtaccatgc tctggagaga acaagactcg aagacgcaca 540
gctgacgact cagccacctc tgactactgc cccgcaccca agcgcctcaa gacaaattgc 600
tataacaacg gcaaagaccg aggggatgaa gatcagagcc gagaacaaat ggcttcagat 660
gttgccaaca acaagagcag cctggaagat ggctgtttgt cttgtggcag gaaaaacccc 720
gtgtccttcc accctctctt tgaggggggg ctctgtcaga catgccggga tcgcttcctt 780
gagctgtttt acatgtatga tgacgatggc tatcagtctt actgcactgt gtgctgcgag 840
ggccgagagc tgctgctttg cagcaacacg agctgctgcc ggtgtttctg tgtggagtgc 900
ctggaggtgc tggtgggcac aggcacagcg gccgaggcca agcttcagga gccctggagc 960
tgttacatgt gtctcccgca gcgctgtcat ggcgtcctgc ggcgccggaa ggactggaac 1020
gtgcgcctgc aggccttctt caccagtgac acggggcttg aatatgaagc ccccaagctg 1080
taccctgcca ttcccgcagc ccgaaggcgg cccattcgag tcctgtcatt gtttgatggc 1140
atcgcgacag gctacctagt cctcaaagag ttgggcataa aggtaggaaa gtacgtcgct 1200
tctgaagtgt gtgaggagtc cattgctgtt ggaaccgtga agcacgaggg gaatatcaaa 1260
tacgtgaacg acgtgaggaa catcacaaag aaaaatattg aagaatgggg cccatttgac 1320
ttggtgattg gcggaagccc atgcaacgat ctctcaaatg tgaatccagc caggaaaggc 1380
ctgtatgagg gtacaggccg gctcttcttc gaattttacc acctgctgaa ttactcacgc 1440
cccaaggagg gtgatgaccg gccgttcttc tggatgtttg agaatgttgt agccatgaag 1500
gttggcgaca agagggacat ctcacggttc ctggagtgta atccagtgat gattgatgcc 1560
atcaaagttt ctgctgctca cagggcccga tacttctggg gcaacctacc cgggatgaac 1620
aggcccgtga tagcatcaaa gaatgataaa ctcgagctgc aggactgctt ggaatacaat 1680
aggatagcca agttaaagaa agtacagaca ataaccacca agtcgaactc gatcaaacag 1740
gggaaaaacc aacttttccc tgttgtcatg aatggcaaag aagatgtttt gtggtgcact 1800

-continued

```
gagctcgaaa ggatctttgg ctttcctgtg cactacacag acgtgtccaa catgggccgt   1860

ggtgcccgcc agaagctgct gggaaggtcc tggagcgtgc ctgtcatccg acacctcttc   1920

gcccctctga aggactactt tgcatgtgaa tagttccagc caggccccaa gcccactggg   1980

gtgtgtggca gagccaggac ccaggaggtg tgattcctga aggcatcccc aggccctgct   2040

cttcctcagc tgtgtgggtc ataccgtgta cctca                              2075
```

<210> SEQ ID NO 8
<211> LENGTH: 2091
<212> TYPE: DNA
<213> ORGANISM: Homo sapiens

<400> SEQUENCE: 8

```
gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag taccccctac gcccgcctag cccaggacag    180

ccagcagggg ggcatggagt ccccgcaggt ggaggcagac agtggagatg gagacagttc    240

agagtatcag gatgggaagg agtttggaat aggggacctc gtgtggggaa agatcaaggg    300

cttctcctgg tggcccgcca tggtggtgtc ttggaaggcc acctccaagc gacaggctat    360

gtctggcatg cggtgggtcc agtggtttgg cgatggcaag ttctccgagg tctctgcaga    420

caaactggtg gcactggggc tgttcagcca gcactttaat ttggccacct tcaataagct    480

cgtctcctat cgaaaagcca tgtaccatgc tctggagaaa gctagggtgc gagctggcaa    540

gaccttcccc agcagccctg gagactcatt ggaggaccag ctgaagccca tgttggagtg    600

ggcccacggg ggcttcaagc ccactgggat cgagggcctc aaacccaaca acacgcaacc    660

agtggttaat aagtcgaagg tgcgtcgtgc aggcagtagg aaattagaat caaggaaata    720

cgagaacaag actcgaagac gcacagctga cgactcagcc acctctgact actgccccgc    780

acccaagcgc ctcaagacaa attgctataa caacggcaaa gaccgagggg atgaagatca    840

gagccgagaa caaatggctt cagatgttgc caacaacaag agcagcctgg aagatggctg    900

tttgtcttgt ggcaggaaaa accccgtgtc cttccaccct ctctttgagg gggggctctg    960

tcagacatgc cgggatcgct tccttgagct gttttacatg tatgatgacg atggctatca   1020

gtcttactgc actgtgtgct gcgagggccg agagctgctg ctttgcagca acacgagctg   1080

ctgccggtgt ttctgtgtgg agtgcctgga ggtgctggtg ggcacaggca cagcggccga   1140

ggccaagctt caggagccct ggagctgtta catgtgtctc ccgcagcgct gtcatggcgt   1200

cctgcggcgc cggaaggact ggaacgtgcg cctgcaggcc ttcttcacca gtgacacggg   1260

gcttgaatat gaagccccca agctgtaccc tgccattccc gcagcccgaa ggcggcccat   1320

tcgagtcctg tcattgtttg atggcatcgc gacaggctac ctagtcctca aagagttggg   1380

cataaaggta ggaaagtacg tcgcttctga agtgtgtgag gagtccattg ctgttggaac   1440

cgtgaagcac gaggggaata tcaaatacgt gaacgacgtg aggaacatca caaagaaaaa   1500

tattgaagaa tggggcccat ttgacttggt gattggcgga agcccatgca acgatctctc   1560

aaatgtgaat ccagccagga aaggcctgta tgagggtaca ggccggctct tcttcgaatt   1620

ttaccacctg ctgaattact cacgccccaa ggagggtgat gaccggccgt tcttctggat   1680

gtttgagaat gttgtagcca tgaaggttgg cgacaagagg gacatctcac ggttcctgga   1740

gtgtaatcca gtgatgattg atgccatcaa agtttctgct gctcacaggg cccgatactt   1800
```

-continued

```
ctggggcaac ctacccggga tgaacaggat ctttggcttt cctgtgcact acacagacgt   1860

gtccaacatg ggccgtggtg cccgccagaa gctgctggga aggtcctgga gcgtgcctgt   1920

catccgacac ctcttcgccc ctctgaagga ctactttgca tgtgaatagt tccagccagg   1980

ccccaagccc actggggtgt gtggcagagc caggacccag gaggtgtgat tcctgaaggc   2040

atccccaggc cctgctcttc ctcagctgtg tgggtcatac cgtgtacctc a            2091


<210> SEQ ID NO 9
<211> LENGTH: 2031
<212> TYPE: DNA
<213> ORGANISM: Homo sapiens

<400> SEQUENCE: 9

gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag tacccctac gcccgcctag cccaggacag    180

ccagcagggg ggcatggagt ccccgcaggt ggaggcagac agtggagatg gagacagttc    240

agagtatcag gatgggaagg agtttggaat aggggacctc gtgtggggaa agatcaaggg    300

cttctcctgg tggcccgcca tggtggtgtc ttggaaggcc acctccaagc gacaggctat    360

gtctggcatg cggtgggtcc agtggtttgg cgatggcaag ttctccgagg tctctgcaga    420

caaactggtg gcactggggc tgttcagcca gcactttaat ttggccacct tcaataagct    480

cgtctcctat cgaaaagcca tgtaccatgc tctggagaaa gctagggtgc gagctggcaa    540

gaccttcccc agcagccctg gagactcatt ggaggaccag ctgaagccca tgttggagtg    600

ggcccacggg ggcttcaagc ccactgggat cgagggcctc aaacccaaca acacgcaacc    660

agagaacaag actcgaagac gcacagctga cgactcagcc acctctgact actgccccgc    720

acccaagcgc ctcaagacaa attgctataa caacggcaaa gaccgagggg atgaagatca    780

gagccgagaa caaatggctt cagatgttgc caacaacaag agcagcctgg aagatggctg    840

tttgtcttgt ggcaggaaaa accccgtgtc cttccaccct ctctttgagg gggggctctg    900

tcagacatgc cgggatcgct tccttgagct gttttacatg tatgatgacg atggctatca    960

gtcttactgc actgtgtgct gcgagggccg agagctgctg ctttgcagca acacgagctg   1020

ctgccggtgt ttctgtgtgg agtgcctgga ggtgctggtg ggcacaggca cagcggccga   1080

ggccaagctt caggagccct ggagctgtta catgtgtctc ccgcagcgct gtcatggcgt   1140

cctgcggcgc cggaaggact ggaacgtgcg cctgcaggcc ttcttcacca gtgacacggg   1200

gcttgaatat gaagccccca agctgtaccc tgccattccc gcagcccgaa ggcggcccat   1260

tcgagtcctg tcattgtttg atggcatcgc gacaggctac ctagtcctca aagagttggg   1320

cataaaggta ggaaagtacg tcgcttctga agtgtgtgag gagtccattg ctgttggaac   1380

cgtgaagcac gaggggaata tcaaatacgt gaacgacgtg aggaacatca caaagaaaaa   1440

tattgaagaa tggggcccat ttgacttggt gattggcgga agcccatgca acgatctctc   1500

aaatgtgaat ccagccagga aaggcctgta tgagggtaca ggccggctct tcttcgaatt   1560

ttaccacctg ctgaattact cacgccccaa ggagggtgat gaccggccgt tcttctggat   1620

gtttgagaat gttgtagcca tgaaggttgg cgacaagagg gacatctcac ggttcctgga   1680

gtgtaatcca gtgatgattg atgccatcaa agtttctgct gctcacaggg cccgatactt   1740

ctggggcaac ctacccggga tgaacaggat ctttggcttt cctgtgcact acacagacgt   1800

gtccaacatg ggccgtggtg cccgccagaa gctgctggga aggtcctgga gcgtgcctgt   1860
```

-continued

```
catccgacac ctcttcgccc ctctgaagga ctactttgca tgtgaatagt tccagccagg   1920

ccccaagccc actggggtgt gtggcagagc caggacccag gaggtgtgat tcctgaaggc   1980

atccccaggc cctgctcttc ctcagctgtg tgggtcatac cgtgtacctc a            2031
```

<210> SEQ ID NO 10
<211> LENGTH: 1932
<212> TYPE: DNA
<213> ORGANISM: Homo sapiens

<400> SEQUENCE: 10

```
gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag taccccctac gcccgcctag cccaggacag    180

ccagcagggg ggcatggagt ccccgcaggt ggaggcagac agtggagatg gagacagttc    240

agagtatcag gtctctgcag acaaactggt ggcactgggg ctgttcagcc agcactttaa    300

tttggccacc ttcaataagc tcgtctccta tcgaaaagcc atgtaccatg ctctggagaa    360

agctagggtg cgagctggca agaccttccc cagcagccct ggagactcat tggaggacca    420

gctgaagccc atgttggagt gggcccacgg gggcttcaag cccactggga tcgagggcct    480

caaacccaac aacacgcaac cagtggttaa taagtcgaag gtgcgtcgtg caggcagtag    540

gaaattagaa tcaaggaaat acgagaacaa gactcgaaga cgcacagctg acgactcagc    600

cacctctgac tactgccccg cacccaagcg cctcaagaca aattgctata acaacggcaa    660

agaccgaggg gatgaagatc agagccgaga acaaatggct tcagatgttg ccaacaacaa    720

gagcagcctg gaagatggct gtttgtcttg tggcaggaaa aaccccgtgt ccttccaccc    780

tctctttgag gggggctct gtcagacatg ccgggatcgc ttccttgagc tgttttacat    840

gtatgatgac gatggctatc agtcttactg cactgtgtgc tgcgagggcc gagagctgct    900

gctttgcagc aacacgagct gctgccggtg tttctgtgtg gagtgcctgg aggtgctggt    960

gggcacaggc acagcggccg aggccaagct tcaggagccc tggagctgtt acatgtgtct   1020

cccgcagcgc tgtcatggcg tcctgcggcg ccggaaggac tggaacgtgc gcctgcaggc   1080

cttcttcacc agtgacacgg ggcttgaata tgaagccccc aagctgtacc ctgccattcc   1140

cgcagcccga aggcggccca ttcgagtcct gtcattgttt gatggcatcg cgacaggcta   1200

cctagtcctc aaagagttgg gcataaaggt aggaaagtac gtcgcttctg aagtgtgtga   1260

ggagtccatt gctgttggaa ccgtgaagca cgaggggaat atcaaatacg tgaacgacgt   1320

gaggaacatc acaaagaaaa atattgaaga atggggccca tttgacttgg tgattggcgg   1380

aagcccatgc aacgatctct caaatgtgaa tccagccagg aaaggcctgt atgagggtac   1440

aggccggctc ttcttcgaat tttaccacct gctgaattac tcacgcccca aggagggtga   1500

tgaccggccg ttcttctgga tgtttgagaa tgttgtagcc atgaaggttg gcgacaagag   1560

ggacatctca cggttcctgg agtgtaatcc agtgatgatt gatgccatca aagtttctgc   1620

tgctcacagg gcccgatact tctggggcaa cctacccggg atgaacagga tctttggctt   1680

tcctgtgcac tacacagacg tgtccaacat gggccgtggt gcccgccaga agctgctggg   1740

aaggtcctgg agcgtgcctg tcatccgaca cctcttcgcc cctctgaagg actactttgc   1800

atgtgaatag ttccagccag gccccaagcc cactggggtg tgtggcagag ccaggaccca   1860

ggaggtgtga ttcctgaagg catccccagg ccctgctctt cctcagctgt gtgggtcata   1920
```

-continued

```
ccgtgtacct ca                                                        1932


<210> SEQ ID NO 11
<211> LENGTH: 1872
<212> TYPE: DNA
<213> ORGANISM: Homo sapiens

<400> SEQUENCE: 11

gtcccccgtg gagttcccgg ctaccaggtc cctgagacgg cgggcaacag catcggcagg      60

aacgccatgg ccgtcccctc ccagctctta ccttaccatc gacctcacag acgacacaga     120

ggacacacat gggacgcccc agagcagcag taccccctac gcccgcctag cccaggacag     180

ccagcagggg ggcatggagt ccccgcaggt ggaggcagac agtggagatg gagacagttc     240

agagtatcag gtctctgcag acaaactggt ggcactgggg ctgttcagcc agcactttaa     300

tttggccacc ttcaataagc tcgtctccta tcgaaaagcc atgtaccatg ctctggagaa     360

agctagggtg cgagctggca agaccttccc cagcagccct ggagactcat tggaggacca     420

gctgaagccc atgttggagt gggcccacgg gggcttcaag cccactggga tcgagggcct     480

caaacccaac aacacgcaac cagagaacaa gactcgaaga cgcacagctg acgactcagc     540

cacctctgac tactgccccg cacccaagcg cctcaagaca aattgctata acaacggcaa     600

agaccgaggg gatgaagatc agagccgaga acaaatggct tcagatgttg ccaacaacaa     660

gagcagcctg gaagatggct gtttgtcttg tggcaggaaa aaccccgtgt ccttccaccc     720

tctctttgag ggggggctct gtcagacatg ccgggatcgc ttccttgagc tgttttacat     780

gtatgatgac gatggctatc agtcttactg cactgtgtgc tgcgagggcc gagagctgct     840

gctttgcagc aacacgagct gctgccggtg tttctgtgtg gagtgcctgg aggtgctggt     900

gggcacaggc acagcggccg aggccaagct tcaggagccc tggagctgtt acatgtgtct     960

cccgcagcgc tgtcatggcg tcctgcggcg ccggaaggac tggaacgtgc gcctgcaggc    1020

cttcttcacc agtgacacgg ggcttgaata tgaagccccc aagctgtacc ctgccattcc    1080

cgcagcccga aggcggccca ttcgagtcct gtcattgttt gatggcatcg cgacaggcta    1140

cctagtcctc aaagagttgg gcataaaggt aggaaagtac gtcgcttctg aagtgtgtga    1200

ggagtccatt gctgttggaa ccgtgaagca cgaggggaat atcaaatacg tgaacgacgt    1260

gaggaacatc acaaagaaaa atattgaaga atggggccca tttgacttgg tgattggcgg    1320

aagcccatgc aacgatctct caaatgtgaa tccagccagg aaaggcctgt atgagggtac    1380

aggccggctc ttcttcgaat tttaccacct gctgaattac tcacgcccca aggagggtga    1440

tgaccggccg ttcttctgga tgtttgagaa tgttgtagcc atgaaggttg gcgacaagag    1500

ggacatctca cggttcctgg agtgtaatcc agtgatgatt gatgccatca aagtttctgc    1560

tgctcacagg gcccgatact tctggggcaa cctacccggg atgaacagga tctttggctt    1620

tcctgtgcac tacacagacg tgtccaacat gggccgtggt gcccgccaga agctgctggg    1680

aaggtcctgg agcgtgcctg tcatccgaca cctcttcgcc cctctgaagg actactttgc    1740

atgtgaatag ttccagccag gccccaagcc cactggggtg tgtggcagag ccaggaccca    1800

ggaggtgtga ttcctgaagg catccccagg ccctgctctt cctcagctgt gtgggtcata    1860

ccgtgtacct ca                                                        1872


<210> SEQ ID NO 12
<211> LENGTH: 1619
<212> TYPE: DNA
<213> ORGANISM: Homo sapiens
```

-continued

<400> SEQUENCE: 12

```
gtcccccgtg gagttcccgg ctaccaggtc cctgagacgg cgggcaacag catcggcagg     60
aacgccatgg ccgtcccctc ccagctctta ccttaccatc gacctcacag acgacacaga    120
ggacacacat gggacgcccc agagcagcag taccccctac gcccgcctag cccaggacag    180
ccagcagggg ggcatggagt ccccgcaggt ggaggcagac agtggagatg gagacagttc    240
agagtatcag agaacaagac tcgaagacgc acagctgacg actcagccac ctctgactac    300
tgccccgcac ccaagcgcct caagacaaat tgctataaca acggcaaaga ccgaggggat    360
gaagatcaga gccgagaaca aatggcttca gatgttgcca acaacaagag cagcctggaa    420
gatggctgtt tgtcttgtgg caggaaaaac cccgtgtcct tccaccctct ctttgagggg    480
gggctctgtc agacatgccg ggatcgcttc cttgagctgt tttacatgta tgatgacgat    540
ggctatcagt cttactgcac tgtgtgctgc gagggccgag agctgctgct ttgcagcaac    600
acgagctgct gccggtgttt ctgtgtggag tgcctggagg tgctggtggg cacaggcaca    660
gcggccgagg ccaagcttca ggagccctgg agctgttaca tgtgtctccc gcagcgctgt    720
catggcgtcc tgcggcgccg gaaggactgg aacgtgcgcc tgcaggcctt cttcaccagt    780
gacacggggc ttgaatatga agcccccaag ctgtaccctg ccattcccgc agcccgaagg    840
cggcccattc gagtcctgtc attgtttgat ggcatcgcga caggctacct agtcctcaaa    900
gagttgggca taaaggtagg aaagtacgtc gcttctgaag tgtgtgagga gtccattgct    960
gttggaaccg tgaagcacga ggggaatatc aaatacgtga acgacgtgag gaacatcaca   1020
aagaaaaata ttgaagaatg ggcccattt gacttggtga ttggcggaag cccatgcaac   1080
gatctctcaa atgtgaatcc agccaggaaa ggcctgtatg agggtacagg ccggctcttc   1140
ttcgaatttt accacctgct gaattactca cgccccaagg agggtgatga ccggccgttc   1200
ttctggatgt ttgagaatgt tgtagccatg aaggttggcg acaagaggga catctcacgg   1260
ttcctggagt gtaatccagt gatgattgat gccatcaaag tttctgctgc tcacagggcc   1320
cgatacttct ggggcaacct acccgggatg aacaggatct ttggctttcc tgtgcactac   1380
acagacgtgt ccaacatggg ccgtggtgcc cgccagaagc tgctgggaag gtcctggagc   1440
gtgcctgtca tccgacacct cttcgcccct ctgaaggact actttgcatg tgaatagttc   1500
cagccaggcc ccaagcccac tggggtgtgt ggcagagcca ggacccagga ggtgtgattc   1560
ctgaaggcat ccccaggccc tgctcttcct cagctgtgtg ggtcataccg tgtacctca    1619
```

<210> SEQ ID NO 13
<211> LENGTH: 1778
<212> TYPE: DNA
<213> ORGANISM: Homo sapiens

<400> SEQUENCE: 13

```
gtcccccgtg gagttcccgg ctaccaggtc cctgagacgg cgggcaacag catcggcagg     60
aacgccatgg ccgtcccctc ccagctctta ccttaccatc gacctcacag acgacacaga    120
ggacacacat gggacgcccc agagcagcag taccccctac gcccgcctag cccaggacag    180
ccagcagggg ggcatggagt ccccgcaggt ggaggcagac agtggagatg gagacagttc    240
agagtatcag gatgggaagg agtttggaat aggggacctc gtgtggggaa agatcaaggg    300
cttctcctgg tggcccgcca tggtggtgtc ttggaaggcc acctccaagc gacaggctat    360
gtctggcatg cggtgggtcc agtggtttgg cgatggcaag ttctccgaga gaacaagact    420
```

-continued

```
cgaagacgca cagctgacga ctcagccacc tctgactact gccccgcacc caagcgcctc    480

aagacaaatt gctataacaa cggcaaagac cgaggggatg aagatcagag ccgagaacaa    540

atggcttcag atgttgccaa caacaagagc agcctggaag atggctgttt gtcttgtggc    600

aggaaaaacc ccgtgtcctt ccaccctctc tttgaggggg ggctctgtca gacatgccgg    660

gatcgcttcc ttgagctgtt ttacatgtat gatgacgatg gctatcagtc ttactgcact    720

gtgtgctgcg agggccgaga gctgctgctt tgcagcaaca cgagctgctg ccggtgtttc    780

tgtgtggagt gcctggaggt gctggtgggc acaggcacag cggccgaggc caagcttcag    840

gagccctgga gctgttacat gtgtctcccg cagcgctgtc atggcgtcct gcggcgccgg    900

aaggactgga acgtgcgcct gcaggccttc ttcaccagtg acacggggct tgaatatgaa    960

gcccccaagc tgtaccctgc cattcccgca gcccgaaggc ggcccattcg agtcctgtca   1020

ttgtttgatg gcatcgcgac aggctaccta gtcctcaaag agttgggcat aaaggtagga   1080

aagtacgtcg cttctgaagt gtgtgaggag tccattgctg ttggaaccgt gaagcacgag   1140

gggaatatca aatacgtgaa cgacgtgagg aacatcacaa agaaaaatat tgaagaatgg   1200

ggcccatttg acttggtgat tggcggaagc ccatgcaacg atctctcaaa tgtgaatcca   1260

gccaggaaag gcctgtatga gggtacaggc cggctcttct tcgaatttta ccacctgctg   1320

aattactcac gccccaagga gggtgatgac cggccgttct tctggatgtt tgagaatgtt   1380

gtagccatga aggttggcga caagagggac atctcacggt tcctggagtg taatccagtg   1440

atgattgatg ccatcaaagt ttctgctgct cacagggccc gatacttctg gggcaaccta   1500

cccgggatga acaggatctt tggctttcct gtgcactaca cagacgtgtc caacatgggc   1560

cgtggtgccc gccagaagct gctgggaagg tcctggagcg tgcctgtcat ccgacacctc   1620

ttcgcccctc tgaaggacta ctttgcatgt gaatagttcc agccaggccc caagcccact   1680

ggggtgtgtg gcagagccag gacccaggag gtgtgattcc tgaaggcatc cccaggccct   1740

gctcttcctc agctgtgtgg gtcataccgt gtacctca                           1778
```

<210> SEQ ID NO 14
<211> LENGTH: 1886
<212> TYPE: DNA
<213> ORGANISM: Homo sapiens

<400> SEQUENCE: 14

```
gtcccccgtg gagttcccgg ctaccaggtc cctgagacgg cgggcaacag catcggcagg     60

aacgccatgg ccgtcccctc ccagctctta ccttaccatc gacctcacag acgacacaga    120

ggacacacat gggacgcccc agagcagcag taccccctac gcccgcctag cccaggacag    180

ccagcagggg ggcatggagt ccccgcaggt ggaggcagac agtggagatg gagacagttc    240

agagtatcag gatgggaagg agtttggaat aggggacctc gtgtggggaa agatcaaggg    300

cttctcctgg tggcccgcca tggtggtgtc ttggaaggcc acctccaagc gacaggctat    360

gtctggcatg cggtgggtcc agtggtttgg cgatggcaag ttctccgagg tctctgcaga    420

caaactggtg gcactggggc tgttcagcca gcactttaat ttggccacct tcaataagct    480

cgtctcctat cgaaaagcca tgtaccatgc tctggagaga acaagactcg aagacgcaca    540

gctgacgact cagccacctc tgactactgc cccgcaccca agcgcctcaa gacaaattgc    600

tataacaacg gcaaagaccg aggggatgaa gatcagagcc gagaacaaat ggcttcagat    660

gttgccaaca acaagagcag cctggaagat ggctgtttgt cttgtggcag gaaaaacccc    720

gtgtccttcc accctctctt tgaggggggg ctctgtcaga catgccggga tcgcttcctt    780
```

-continued

```
gagctgtttt acatgtatga tgacgatggc tatcagtctt actgcactgt gtgctgcgag    840

ggccgagagc tgctgctttg cagcaacacg agctgctgcc ggtgtttctg tgtggagtgc    900

ctggaggtgc tggtgggcac aggcacagcg gccgaggcca agcttcagga gccctggagc    960

tgttacatgt gtctcccgca gcgctgtcat ggcgtcctgc ggcgccggaa ggactggaac   1020

gtgcgcctgc aggccttctt caccagtgac acggggcttg aatatgaagc ccccaagctg   1080

taccctgcca ttcccgcagc ccgaaggcgg cccattcgag tcctgtcatt gtttgatggc   1140

atcgcgacag gctacctagt cctcaaagag ttgggcataa aggtaggaaa gtacgtcgct   1200

tctgaagtgt gtgaggagtc cattgctgtt ggaaccgtga agcacgaggg gaatatcaaa   1260

tacgtgaacg acgtgaggaa catcacaaag aaaaatattg aagaatgggg cccatttgac   1320

ttggtgattg gcggaagccc atgcaacgat ctctcaaatg tgaatccagc caggaaaggc   1380

ctgtatgagg gtacaggccg gctcttcttc gaattttacc acctgctgaa ttactcacgc   1440

cccaaggagg gtgatgaccg gccgttcttc tggatgtttg agaatgttgt agccatgaag   1500

gttggcgaca agagggacat ctcacggttc ctggagtgta atccagtgat gattgatgcc   1560

atcaaagttt ctgctgctca cagggcccga tacttctggg gcaacctacc cgggatgaac   1620

aggatctttg gctttcctgt gcactacaca gacgtgtcca acatgggccg tggtgcccgc   1680

cagaagctgc tgggaaggtc ctggagcgtg cctgtcatcc gacacctctt cgcccctctg   1740

aaggactact ttgcatgtga atagttccag ccaggcccca agcccactgg ggtgtgtggc   1800

agagccagga cccaggaggt gtgattcctg aaggcatccc caggccctgc tcttcctcag   1860

ctgtgtgggt cataccgtgt acctca                                        1886
```

<210> SEQ ID NO 15
<211> LENGTH: 654
<212> TYPE: PRT
<213> ORGANISM: Homo sapiens

<400> SEQUENCE: 15

```
Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
             20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95

Val Ser Tyr Arg Lys Ala Met Tyr His Ala Leu Glu Lys Ala Arg Val
            100                 105                 110

Arg Ala Gly Lys Thr Phe Pro Ser Ser Pro Gly Asp Ser Leu Glu Asp
        115                 120                 125

Gln Leu Lys Pro Met Leu Glu Trp Ala His Gly Gly Phe Lys Pro Thr
    130                 135                 140

Gly Ile Glu Gly Leu Lys Pro Asn Asn Thr Gln Pro Val Val Asn Lys
145                 150                 155                 160

Ser Lys Val Arg Arg Ala Gly Ser Arg Lys Leu Glu Ser Arg Lys Tyr
                165                 170                 175
```

-continued

```
Glu Asn Lys Thr Arg Arg Arg Thr Ala Asp Asp Ser Ala Thr Ser Asp
            180                 185                 190

Tyr Cys Pro Ala Pro Lys Arg Leu Lys Thr Asn Cys Tyr Asn Asn Gly
        195                 200                 205

Lys Asp Arg Gly Asp Glu Asp Gln Ser Arg Glu Gln Met Ala Ser Asp
    210                 215                 220

Val Ala Asn Asn Lys Ser Ser Leu Glu Asp Gly Cys Leu Ser Cys Gly
225                 230                 235                 240

Arg Lys Asn Pro Val Ser Phe His Pro Leu Phe Glu Gly Gly Leu Cys
                245                 250                 255

Gln Thr Cys Arg Asp Arg Phe Leu Glu Leu Phe Tyr Met Tyr Asp Asp
            260                 265                 270

Asp Gly Tyr Gln Ser Tyr Cys Thr Val Cys Cys Glu Gly Arg Glu Leu
        275                 280                 285

Leu Leu Cys Ser Asn Thr Ser Cys Cys Arg Cys Phe Cys Val Glu Cys
    290                 295                 300

Leu Glu Val Leu Val Gly Thr Gly Thr Ala Ala Glu Ala Lys Leu Gln
305                 310                 315                 320

Glu Pro Trp Ser Cys Tyr Met Cys Leu Pro Gln Arg Cys His Gly Val
                325                 330                 335

Leu Arg Arg Arg Lys Asp Trp Asn Val Arg Leu Gln Ala Phe Phe Thr
            340                 345                 350

Ser Asp Thr Gly Leu Glu Tyr Glu Ala Pro Lys Leu Tyr Pro Ala Ile
        355                 360                 365

Pro Ala Ala Arg Arg Arg Pro Ile Arg Val Leu Ser Leu Phe Asp Gly
    370                 375                 380

Ile Ala Thr Gly Tyr Leu Val Leu Lys Glu Leu Gly Ile Lys Val Gly
385                 390                 395                 400

Lys Tyr Val Ala Ser Glu Val Cys Glu Glu Ser Ile Ala Val Gly Thr
                405                 410                 415

Val Lys His Glu Gly Asn Ile Lys Tyr Val Asn Asp Val Arg Asn Ile
            420                 425                 430

Thr Lys Lys Asn Ile Glu Glu Trp Gly Pro Phe Asp Leu Val Ile Gly
        435                 440                 445

Gly Ser Pro Cys Asn Asp Leu Ser Asn Val Asn Pro Ala Arg Lys Gly
    450                 455                 460

Leu Tyr Glu Gly Thr Gly Arg Leu Phe Phe Glu Phe Tyr His Leu Leu
465                 470                 475                 480

Asn Tyr Ser Arg Pro Lys Glu Gly Asp Asp Arg Pro Phe Phe Trp Met
                485                 490                 495

Phe Glu Asn Val Val Ala Met Lys Val Gly Asp Lys Arg Asp Ile Ser
            500                 505                 510

Arg Phe Leu Glu Cys Asn Pro Val Met Ile Asp Ala Ile Lys Val Ser
        515                 520                 525

Ala Ala His Arg Ala Arg Tyr Phe Trp Gly Asn Leu Pro Gly Met Asn
    530                 535                 540

Arg Pro Val Ile Ala Ser Lys Asn Asp Lys Leu Glu Leu Gln Asp Cys
545                 550                 555                 560

Leu Glu Tyr Asn Arg Ile Ala Lys Leu Lys Lys Val Gln Thr Ile Thr
                565                 570                 575

Thr Lys Ser Asn Ser Ile Lys Gln Gly Lys Asn Gln Leu Phe Pro Val
            580                 585                 590
```

-continued

```
Val Met Asn Gly Lys Glu Asp Val Leu Trp Cys Thr Glu Leu Glu Arg
        595                 600                 605

Ile Phe Gly Phe Pro Val His Tyr Thr Asp Val Ser Asn Met Gly Arg
    610                 615                 620

Gly Ala Arg Gln Lys Leu Leu Gly Arg Ser Trp Ser Val Pro Val Ile
625                 630                 635                 640

Arg His Leu Phe Ala Pro Leu Lys Asp Tyr Phe Ala Cys Glu
                645                 650


<210> SEQ ID NO 16
<211> LENGTH: 634
<212> TYPE: PRT
<213> ORGANISM: Homo sapiens

<400> SEQUENCE: 16

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
             20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95

Val Ser Tyr Arg Lys Ala Met Tyr His Ala Leu Glu Lys Ala Arg Val
            100                 105                 110

Arg Ala Gly Lys Thr Phe Pro Ser Ser Pro Gly Asp Ser Leu Glu Asp
        115                 120                 125

Gln Leu Lys Pro Met Leu Glu Trp Ala His Gly Gly Phe Lys Pro Thr
    130                 135                 140

Gly Ile Glu Gly Leu Lys Pro Asn Asn Thr Gln Pro Glu Asn Lys Thr
145                 150                 155                 160

Arg Arg Arg Thr Ala Asp Asp Ser Ala Thr Ser Asp Tyr Cys Pro Ala
                165                 170                 175

Pro Lys Arg Leu Lys Thr Asn Cys Tyr Asn Asn Gly Lys Asp Arg Gly
            180                 185                 190

Asp Glu Asp Gln Ser Arg Glu Gln Met Ala Ser Asp Val Ala Asn Asn
        195                 200                 205

Lys Ser Ser Leu Glu Asp Gly Cys Leu Ser Cys Gly Arg Lys Asn Pro
    210                 215                 220

Val Ser Phe His Pro Leu Phe Glu Gly Gly Leu Cys Gln Thr Cys Arg
225                 230                 235                 240

Asp Arg Phe Leu Glu Leu Phe Tyr Met Tyr Asp Asp Asp Gly Tyr Gln
                245                 250                 255

Ser Tyr Cys Thr Val Cys Cys Glu Gly Arg Glu Leu Leu Leu Cys Ser
            260                 265                 270

Asn Thr Ser Cys Cys Arg Cys Phe Cys Val Glu Cys Leu Glu Val Leu
        275                 280                 285

Val Gly Thr Gly Thr Ala Ala Glu Ala Lys Leu Gln Glu Pro Trp Ser
    290                 295                 300

Cys Tyr Met Cys Leu Pro Gln Arg Cys His Gly Val Leu Arg Arg Arg
305                 310                 315                 320
```

-continued

```
Lys Asp Trp Asn Val Arg Leu Gln Ala Phe Phe Thr Ser Asp Thr Gly
                325                 330                 335

Leu Glu Tyr Glu Ala Pro Lys Leu Tyr Pro Ala Ile Pro Ala Ala Arg
            340                 345                 350

Arg Arg Pro Ile Arg Val Leu Ser Leu Phe Asp Gly Ile Ala Thr Gly
        355                 360                 365

Tyr Leu Val Leu Lys Glu Leu Gly Ile Lys Val Gly Lys Tyr Val Ala
    370                 375                 380

Ser Glu Val Cys Glu Glu Ser Ile Ala Val Gly Thr Val Lys His Glu
385                 390                 395                 400

Gly Asn Ile Lys Tyr Val Asn Asp Val Arg Asn Ile Thr Lys Lys Asn
                405                 410                 415

Ile Glu Glu Trp Gly Pro Phe Asp Leu Val Ile Gly Gly Ser Pro Cys
            420                 425                 430

Asn Asp Leu Ser Asn Val Asn Pro Ala Arg Lys Gly Leu Tyr Glu Gly
        435                 440                 445

Thr Gly Arg Leu Phe Phe Glu Phe Tyr His Leu Leu Asn Tyr Ser Arg
    450                 455                 460

Pro Lys Glu Gly Asp Asp Arg Pro Phe Phe Trp Met Phe Glu Asn Val
465                 470                 475                 480

Val Ala Met Lys Val Gly Asp Lys Arg Asp Ile Ser Arg Phe Leu Glu
                485                 490                 495

Cys Asn Pro Val Met Ile Asp Ala Ile Lys Val Ser Ala Ala His Arg
            500                 505                 510

Ala Arg Tyr Phe Trp Gly Asn Leu Pro Gly Met Asn Arg Pro Val Ile
        515                 520                 525

Ala Ser Lys Asn Asp Lys Leu Glu Leu Gln Asp Cys Leu Glu Tyr Asn
    530                 535                 540

Arg Ile Ala Lys Leu Lys Lys Val Gln Thr Ile Thr Thr Lys Ser Asn
545                 550                 555                 560

Ser Ile Lys Gln Gly Lys Asn Gln Leu Phe Pro Val Val Met Asn Gly
                565                 570                 575

Lys Glu Asp Val Leu Trp Cys Thr Glu Leu Glu Arg Ile Phe Gly Phe
            580                 585                 590

Pro Val His Tyr Thr Asp Val Ser Asn Met Gly Arg Gly Ala Arg Gln
        595                 600                 605

Lys Leu Leu Gly Arg Ser Trp Ser Val Pro Val Ile Arg His Leu Phe
    610                 615                 620

Ala Pro Leu Lys Asp Tyr Phe Ala Cys Glu
625                 630


<210> SEQ ID NO 17
<211> LENGTH: 601
<212> TYPE: PRT
<213> ORGANISM: Homo sapiens

<400> SEQUENCE: 17

Met Glu Ser Pro Gln Val Glu Ala Asp Ser Gly Asp Gly Asp Ser Ser
  1               5                  10                  15

Glu Tyr Gln Val Ser Ala Asp Lys Leu Val Ala Leu Gly Leu Phe Ser
            20                  25                  30

Gln His Phe Asn Leu Ala Thr Phe Asn Lys Leu Val Ser Tyr Arg Lys
        35                  40                  45

Ala Met Tyr His Ala Leu Glu Lys Ala Arg Val Arg Ala Gly Lys Thr
```

-continued

```
        50                  55                  60

Phe Pro Ser Ser Pro Gly Asp Ser Leu Glu Asp Gln Leu Lys Pro Met
 65                  70                  75                  80

Leu Glu Trp Ala His Gly Gly Phe Lys Pro Thr Gly Ile Glu Gly Leu
                 85                  90                  95

Lys Pro Asn Asn Thr Gln Pro Val Val Asn Lys Ser Lys Val Arg Arg
            100                 105                 110

Ala Gly Ser Arg Lys Leu Glu Ser Arg Lys Tyr Glu Asn Lys Thr Arg
        115                 120                 125

Arg Arg Thr Ala Asp Asp Ser Ala Thr Ser Asp Tyr Cys Pro Ala Pro
    130                 135                 140

Lys Arg Leu Lys Thr Asn Cys Tyr Asn Asn Gly Lys Asp Arg Gly Asp
145                 150                 155                 160

Glu Asp Gln Ser Arg Glu Gln Met Ala Ser Asp Val Ala Asn Asn Lys
                165                 170                 175

Ser Ser Leu Glu Asp Gly Cys Leu Ser Cys Gly Arg Lys Asn Pro Val
            180                 185                 190

Ser Phe His Pro Leu Phe Glu Gly Gly Leu Cys Gln Thr Cys Arg Asp
        195                 200                 205

Arg Phe Leu Glu Leu Phe Tyr Met Tyr Asp Asp Asp Gly Tyr Gln Ser
    210                 215                 220

Tyr Cys Thr Val Cys Cys Glu Gly Arg Glu Leu Leu Leu Cys Ser Asn
225                 230                 235                 240

Thr Ser Cys Cys Arg Cys Phe Cys Val Glu Cys Leu Glu Val Leu Val
                245                 250                 255

Gly Thr Gly Thr Ala Ala Glu Ala Lys Leu Gln Glu Pro Trp Ser Cys
            260                 265                 270

Tyr Met Cys Leu Pro Gln Arg Cys His Gly Val Leu Arg Arg Arg Lys
        275                 280                 285

Asp Trp Asn Val Arg Leu Gln Ala Phe Phe Thr Ser Asp Thr Gly Leu
    290                 295                 300

Glu Tyr Glu Ala Pro Lys Leu Tyr Pro Ala Ile Pro Ala Ala Arg Arg
305                 310                 315                 320

Arg Pro Ile Arg Val Leu Ser Leu Phe Asp Gly Ile Ala Thr Gly Tyr
                325                 330                 335

Leu Val Leu Lys Glu Leu Gly Ile Lys Val Gly Lys Tyr Val Ala Ser
            340                 345                 350

Glu Val Cys Glu Glu Ser Ile Ala Val Gly Thr Val Lys His Glu Gly
        355                 360                 365

Asn Ile Lys Tyr Val Asn Asp Val Arg Asn Ile Thr Lys Lys Asn Ile
    370                 375                 380

Glu Glu Trp Gly Pro Phe Asp Leu Val Ile Gly Gly Ser Pro Cys Asn
385                 390                 395                 400

Asp Leu Ser Asn Val Asn Pro Ala Arg Lys Gly Leu Tyr Glu Gly Thr
                405                 410                 415

Gly Arg Leu Phe Phe Glu Phe Tyr His Leu Leu Asn Tyr Ser Arg Pro
            420                 425                 430

Lys Glu Gly Asp Asp Arg Pro Phe Phe Trp Met Phe Glu Asn Val Val
        435                 440                 445

Ala Met Lys Val Gly Asp Lys Arg Asp Ile Ser Arg Phe Leu Glu Cys
    450                 455                 460

Asn Pro Val Met Ile Asp Ala Ile Lys Val Ser Ala Ala His Arg Ala
465                 470                 475                 480
```

-continued

```
Arg Tyr Phe Trp Gly Asn Leu Pro Gly Met Asn Arg Pro Val Ile Ala
                485                 490                 495

Ser Lys Asn Asp Lys Leu Glu Leu Gln Asp Cys Leu Glu Tyr Asn Arg
            500                 505                 510

Ile Ala Lys Leu Lys Lys Val Gln Thr Ile Thr Thr Lys Ser Asn Ser
        515                 520                 525

Ile Lys Gln Gly Lys Asn Gln Leu Phe Pro Val Val Met Asn Gly Lys
    530                 535                 540

Glu Asp Val Leu Trp Cys Thr Glu Leu Glu Arg Ile Phe Gly Phe Pro
545                 550                 555                 560

Val His Tyr Thr Asp Val Ser Asn Met Gly Arg Gly Ala Arg Gln Lys
                565                 570                 575

Leu Leu Gly Arg Ser Trp Ser Val Pro Val Ile Arg His Leu Phe Ala
            580                 585                 590

Pro Leu Lys Asp Tyr Phe Ala Cys Glu
        595                 600


<210> SEQ ID NO 18
<211> LENGTH: 581
<212> TYPE: PRT
<213> ORGANISM: Homo sapiens

<400> SEQUENCE: 18

Met Glu Ser Pro Gln Val Glu Ala Asp Ser Gly Asp Gly Asp Ser Ser
  1               5                  10                  15

Glu Tyr Gln Val Ser Ala Asp Lys Leu Val Ala Leu Gly Leu Phe Ser
             20                  25                  30

Gln His Phe Asn Leu Ala Thr Phe Asn Lys Leu Val Ser Tyr Arg Lys
         35                  40                  45

Ala Met Tyr His Ala Leu Glu Lys Ala Arg Val Arg Ala Gly Lys Thr
     50                  55                  60

Phe Pro Ser Ser Pro Gly Asp Ser Leu Glu Asp Gln Leu Lys Pro Met
 65                  70                  75                  80

Leu Glu Trp Ala His Gly Gly Phe Lys Pro Thr Gly Ile Glu Gly Leu
                 85                  90                  95

Lys Pro Asn Asn Thr Gln Pro Glu Asn Lys Thr Arg Arg Arg Thr Ala
            100                 105                 110

Asp Asp Ser Ala Thr Ser Asp Tyr Cys Pro Ala Pro Lys Arg Leu Lys
        115                 120                 125

Thr Asn Cys Tyr Asn Asn Gly Lys Asp Arg Gly Asp Glu Asp Gln Ser
    130                 135                 140

Arg Glu Gln Met Ala Ser Asp Val Ala Asn Asn Lys Ser Ser Leu Glu
145                 150                 155                 160

Asp Gly Cys Leu Ser Cys Gly Arg Lys Asn Pro Val Ser Phe His Pro
                165                 170                 175

Leu Phe Glu Gly Gly Leu Cys Gln Thr Cys Arg Asp Arg Phe Leu Glu
            180                 185                 190

Leu Phe Tyr Met Tyr Asp Asp Asp Gly Tyr Gln Ser Tyr Cys Thr Val
        195                 200                 205

Cys Cys Glu Gly Arg Glu Leu Leu Leu Cys Ser Asn Thr Ser Cys Cys
    210                 215                 220

Arg Cys Phe Cys Val Glu Cys Leu Glu Val Leu Val Gly Thr Gly Thr
225                 230                 235                 240

Ala Ala Glu Ala Lys Leu Gln Glu Pro Trp Ser Cys Tyr Met Cys Leu
```

-continued

```
                245                 250                 255

Pro Gln Arg Cys His Gly Val Leu Arg Arg Arg Lys Asp Trp Asn Val
            260                 265                 270

Arg Leu Gln Ala Phe Phe Thr Ser Asp Thr Gly Leu Glu Tyr Glu Ala
        275                 280                 285

Pro Lys Leu Tyr Pro Ala Ile Pro Ala Ala Arg Arg Arg Pro Ile Arg
    290                 295                 300

Val Leu Ser Leu Phe Asp Gly Ile Ala Thr Gly Tyr Leu Val Leu Lys
305                 310                 315                 320

Glu Leu Gly Ile Lys Val Gly Lys Tyr Val Ala Ser Glu Val Cys Glu
                325                 330                 335

Glu Ser Ile Ala Val Gly Thr Val Lys His Glu Gly Asn Ile Lys Tyr
            340                 345                 350

Val Asn Asp Val Arg Asn Ile Thr Lys Lys Asn Ile Glu Glu Trp Gly
        355                 360                 365

Pro Phe Asp Leu Val Ile Gly Gly Ser Pro Cys Asn Asp Leu Ser Asn
    370                 375                 380

Val Asn Pro Ala Arg Lys Gly Leu Tyr Glu Gly Thr Gly Arg Leu Phe
385                 390                 395                 400

Phe Glu Phe Tyr His Leu Leu Asn Tyr Ser Arg Pro Lys Glu Gly Asp
                405                 410                 415

Asp Arg Pro Phe Phe Trp Met Phe Glu Asn Val Val Ala Met Lys Val
            420                 425                 430

Gly Asp Lys Arg Asp Ile Ser Arg Phe Leu Glu Cys Asn Pro Val Met
        435                 440                 445

Ile Asp Ala Ile Lys Val Ser Ala Ala His Arg Ala Arg Tyr Phe Trp
    450                 455                 460

Gly Asn Leu Pro Gly Met Asn Arg Pro Val Ile Ala Ser Lys Asn Asp
465                 470                 475                 480

Lys Leu Glu Leu Gln Asp Cys Leu Glu Tyr Asn Arg Ile Ala Lys Leu
                485                 490                 495

Lys Lys Val Gln Thr Ile Thr Thr Lys Ser Asn Ser Ile Lys Gln Gly
            500                 505                 510

Lys Asn Gln Leu Phe Pro Val Val Met Asn Gly Lys Glu Asp Val Leu
        515                 520                 525

Trp Cys Thr Glu Leu Glu Arg Ile Phe Gly Phe Pro Val His Tyr Thr
    530                 535                 540

Asp Val Ser Asn Met Gly Arg Gly Ala Arg Gln Lys Leu Leu Gly Arg
545                 550                 555                 560

Ser Trp Ser Val Pro Val Ile Arg His Leu Phe Ala Pro Leu Lys Asp
                565                 570                 575

Tyr Phe Ala Cys Glu
            580


<210> SEQ ID NO 19
<211> LENGTH: 232
<212> TYPE: PRT
<213> ORGANISM: Homo sapiens

<400> SEQUENCE: 19

Met Glu Ser Pro Gln Val Glu Ala Asp Ser Gly Asp Gly Asp Ser Ser
  1               5                  10                  15

Glu Tyr Gln Arg Thr Arg Leu Glu Asp Ala Gln Leu Thr Thr Gln Pro
             20                  25                  30
```

-continued

```
Pro Leu Thr Thr Ala Pro His Pro Ser Ala Ser Arg Gln Ile Ala Ile
        35                  40                  45

Thr Thr Ala Lys Thr Glu Gly Met Lys Ile Arg Ala Glu Asn Lys Trp
    50                  55                  60

Leu Gln Met Leu Pro Thr Thr Arg Ala Ala Trp Lys Met Ala Val Cys
 65                 70                  75                  80

Leu Val Ala Gly Lys Thr Pro Cys Pro Ser Thr Leu Ser Leu Arg Gly
                85                  90                  95

Gly Ser Val Arg His Ala Gly Ile Ala Ser Leu Ser Cys Phe Thr Cys
            100                 105                 110

Met Met Thr Met Ala Ile Ser Leu Thr Ala Leu Cys Ala Ala Arg Ala
        115                 120                 125

Glu Ser Cys Cys Phe Ala Ala Thr Arg Ala Ala Ala Gly Val Ser Val
    130                 135                 140

Trp Ser Ala Trp Arg Cys Trp Trp Ala Gln Ala Gln Arg Pro Arg Pro
145                 150                 155                 160

Ser Phe Arg Ser Pro Gly Ala Val Thr Cys Val Ser Arg Ser Ala Val
                165                 170                 175

Met Ala Ser Cys Gly Ala Gly Arg Thr Gly Thr Cys Ala Cys Arg Pro
            180                 185                 190

Ser Ser Pro Val Thr Arg Gly Leu Asn Met Lys Pro Pro Ser Cys Thr
        195                 200                 205

Leu Pro Phe Pro Gln Pro Glu Gly Gly Pro Phe Glu Ser Cys His Cys
    210                 215                 220

Leu Met Ala Ser Arg Gln Ala Thr
225                 230


<210> SEQ ID NO 20
<211> LENGTH: 285
<212> TYPE: PRT
<213> ORGANISM: Homo sapiens

<400> SEQUENCE: 20

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
            20                  25                  30

Lys Ile Lys Gly Phe Ser Trp Trp Pro Ala Met Val Val Ser Trp Lys
        35                  40                  45

Ala Thr Ser Lys Arg Gln Ala Met Ser Gly Met Arg Trp Val Gln Trp
    50                  55                  60

Phe Gly Asp Gly Lys Phe Ser Glu Arg Thr Arg Leu Glu Asp Ala Gln
 65                 70                  75                  80

Leu Thr Thr Gln Pro Pro Leu Thr Thr Ala Pro His Pro Ser Ala Ser
                85                  90                  95

Arg Gln Ile Ala Ile Thr Thr Ala Lys Thr Glu Gly Met Lys Ile Arg
            100                 105                 110

Ala Glu Asn Lys Trp Leu Gln Met Leu Pro Thr Thr Arg Ala Ala Trp
        115                 120                 125

Lys Met Ala Val Cys Leu Val Ala Gly Lys Thr Pro Cys Pro Ser Thr
    130                 135                 140

Leu Ser Leu Arg Gly Gly Ser Val Arg His Ala Gly Ile Ala Ser Leu
145                 150                 155                 160

Ser Cys Phe Thr Cys Met Met Thr Met Ala Ile Ser Leu Thr Ala Leu
                165                 170                 175
```

-continued

```
Cys Ala Ala Arg Ala Glu Ser Cys Cys Phe Ala Ala Thr Arg Ala Ala
            180                 185                 190

Ala Gly Val Ser Val Trp Ser Ala Trp Arg Cys Trp Trp Ala Gln Ala
        195                 200                 205

Gln Arg Pro Arg Pro Ser Phe Arg Ser Pro Gly Ala Val Thr Cys Val
    210                 215                 220

Ser Arg Ser Ala Val Met Ala Ser Cys Gly Ala Gly Arg Thr Gly Thr
225                 230                 235                 240

Cys Ala Cys Arg Pro Ser Ser Pro Val Thr Arg Gly Leu Asn Met Lys
                245                 250                 255

Pro Pro Ser Cys Thr Leu Pro Phe Pro Gln Pro Glu Gly Gly Pro Phe
            260                 265                 270

Glu Ser Cys His Cys Leu Met Ala Ser Arg Gln Ala Thr
        275                 280                 285


<210> SEQ ID NO 21
<211> LENGTH: 321
<212> TYPE: PRT
<213> ORGANISM: Homo sapiens

<400> SEQUENCE: 21

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
             20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95

Val Ser Tyr Arg Lys Ala Met Tyr His Ala Leu Glu Arg Thr Arg Leu
            100                 105                 110

Glu Asp Ala Gln Leu Thr Thr Gln Pro Pro Leu Thr Thr Ala Pro His
        115                 120                 125

Pro Ser Ala Ser Arg Gln Ile Ala Ile Thr Thr Ala Lys Thr Glu Gly
    130                 135                 140

Met Lys Ile Arg Ala Glu Asn Lys Trp Leu Gln Met Leu Pro Thr Thr
145                 150                 155                 160

Arg Ala Ala Trp Lys Met Ala Val Cys Leu Val Ala Gly Lys Thr Pro
                165                 170                 175

Cys Pro Ser Thr Leu Ser Leu Arg Gly Gly Ser Val Arg His Ala Gly
            180                 185                 190

Ile Ala Ser Leu Ser Cys Phe Thr Cys Met Met Thr Met Ala Ile Ser
        195                 200                 205

Leu Thr Ala Leu Cys Ala Ala Arg Ala Glu Ser Cys Cys Phe Ala Ala
    210                 215                 220

Thr Arg Ala Ala Ala Gly Val Ser Val Trp Ser Ala Trp Arg Cys Trp
225                 230                 235                 240

Trp Ala Gln Ala Gln Arg Pro Arg Pro Ser Phe Arg Ser Pro Gly Ala
                245                 250                 255

Val Thr Cys Val Ser Arg Ser Ala Val Met Ala Ser Cys Gly Ala Gly
```

-continued

```
            260                 265                 270

Arg Thr Gly Thr Cys Ala Cys Arg Pro Ser Ser Pro Val Thr Arg Gly
        275                 280                 285

Leu Asn Met Lys Pro Pro Ser Cys Thr Leu Pro Phe Pro Gln Pro Glu
    290                 295                 300

Gly Gly Pro Phe Glu Ser Cys His Cys Leu Met Ala Ser Arg Gln Ala
305                 310                 315                 320

Thr


<210> SEQ ID NO 22
<211> LENGTH: 591
<212> TYPE: PRT
<213> ORGANISM: Homo sapiens

<400> SEQUENCE: 22

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
             20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95

Val Ser Tyr Arg Lys Ala Met Tyr His Ala Leu Glu Lys Ala Arg Val
            100                 105                 110

Arg Ala Gly Lys Thr Phe Pro Ser Ser Pro Gly Asp Ser Leu Glu Asp
        115                 120                 125

Gln Leu Lys Pro Met Leu Glu Trp Ala His Gly Gly Phe Lys Pro Thr
    130                 135                 140

Gly Ile Glu Gly Leu Lys Pro Asn Asn Thr Gln Pro Val Val Asn Lys
145                 150                 155                 160

Ser Lys Val Arg Arg Ala Gly Ser Arg Lys Leu Glu Ser Arg Lys Tyr
                165                 170                 175

Glu Asn Lys Thr Arg Arg Arg Thr Ala Asp Asp Ser Ala Thr Ser Asp
            180                 185                 190

Tyr Cys Pro Ala Pro Lys Arg Leu Lys Thr Asn Cys Tyr Asn Asn Gly
        195                 200                 205

Lys Asp Arg Gly Asp Glu Asp Gln Ser Arg Glu Gln Met Ala Ser Asp
    210                 215                 220

Val Ala Asn Asn Lys Ser Ser Leu Glu Asp Gly Cys Leu Ser Cys Gly
225                 230                 235                 240

Arg Lys Asn Pro Val Ser Phe His Pro Leu Phe Glu Gly Gly Leu Cys
                245                 250                 255

Gln Thr Cys Arg Asp Arg Phe Leu Glu Leu Phe Tyr Met Tyr Asp Asp
            260                 265                 270

Asp Gly Tyr Gln Ser Tyr Cys Thr Val Cys Cys Glu Gly Arg Glu Leu
        275                 280                 285

Leu Leu Cys Ser Asn Thr Ser Cys Cys Arg Cys Phe Cys Val Glu Cys
    290                 295                 300

Leu Glu Val Leu Val Gly Thr Gly Thr Ala Ala Glu Ala Lys Leu Gln
```

-continued

```
305                 310                 315                 320

Glu Pro Trp Ser Cys Tyr Met Cys Leu Pro Gln Arg Cys His Gly Val
                325                 330                 335

Leu Arg Arg Arg Lys Asp Trp Asn Val Arg Leu Gln Ala Phe Phe Thr
            340                 345                 350

Ser Asp Thr Gly Leu Glu Tyr Glu Ala Pro Lys Leu Tyr Pro Ala Ile
        355                 360                 365

Pro Ala Ala Arg Arg Arg Pro Ile Arg Val Leu Ser Leu Phe Asp Gly
    370                 375                 380

Ile Ala Thr Gly Tyr Leu Val Leu Lys Glu Leu Gly Ile Lys Val Gly
385                 390                 395                 400

Lys Tyr Val Ala Ser Glu Val Cys Glu Glu Ser Ile Ala Val Gly Thr
                405                 410                 415

Val Lys His Glu Gly Asn Ile Lys Tyr Val Asn Asp Val Arg Asn Ile
            420                 425                 430

Thr Lys Lys Asn Ile Glu Glu Trp Gly Pro Phe Asp Leu Val Ile Gly
        435                 440                 445

Gly Ser Pro Cys Asn Asp Leu Ser Asn Val Asn Pro Ala Arg Lys Gly
    450                 455                 460

Leu Tyr Glu Gly Thr Gly Arg Leu Phe Phe Glu Phe Tyr His Leu Leu
465                 470                 475                 480

Asn Tyr Ser Arg Pro Lys Glu Gly Asp Asp Arg Pro Phe Phe Trp Met
                485                 490                 495

Phe Glu Asn Val Val Ala Met Lys Val Gly Asp Lys Arg Asp Ile Ser
            500                 505                 510

Arg Phe Leu Glu Cys Asn Pro Val Met Ile Asp Ala Ile Lys Val Ser
        515                 520                 525

Ala Ala His Arg Ala Arg Tyr Phe Trp Gly Asn Leu Pro Gly Met Asn
    530                 535                 540

Arg Ile Phe Gly Phe Pro Val His Tyr Thr Asp Val Ser Asn Met Gly
545                 550                 555                 560

Arg Gly Ala Arg Gln Lys Leu Leu Gly Arg Ser Trp Ser Val Pro Val
                565                 570                 575

Ile Arg His Leu Phe Ala Pro Leu Lys Asp Tyr Phe Ala Cys Glu
            580                 585                 590


<210> SEQ ID NO 23
<211> LENGTH: 571
<212> TYPE: PRT
<213> ORGANISM: Homo sapiens

<400> SEQUENCE: 23

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
            20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95
```

-continued

```
Val Ser Tyr Arg Lys Ala Met Tyr His Ala Leu Glu Lys Ala Arg Val
            100                 105                 110

Arg Ala Gly Lys Thr Phe Pro Ser Ser Pro Gly Asp Ser Leu Glu Asp
        115                 120                 125

Gln Leu Lys Pro Met Leu Glu Trp Ala His Gly Gly Phe Lys Pro Thr
    130                 135                 140

Gly Ile Glu Gly Leu Lys Pro Asn Asn Thr Gln Pro Glu Asn Lys Thr
145                 150                 155                 160

Arg Arg Arg Thr Ala Asp Asp Ser Ala Thr Ser Asp Tyr Cys Pro Ala
                165                 170                 175

Pro Lys Arg Leu Lys Thr Asn Cys Tyr Asn Asn Gly Lys Asp Arg Gly
            180                 185                 190

Asp Glu Asp Gln Ser Arg Glu Gln Met Ala Ser Asp Val Ala Asn Asn
        195                 200                 205

Lys Ser Ser Leu Glu Asp Gly Cys Leu Ser Cys Gly Arg Lys Asn Pro
    210                 215                 220

Val Ser Phe His Pro Leu Phe Glu Gly Gly Leu Cys Gln Thr Cys Arg
225                 230                 235                 240

Asp Arg Phe Leu Glu Leu Phe Tyr Met Tyr Asp Asp Asp Gly Tyr Gln
                245                 250                 255

Ser Tyr Cys Thr Val Cys Cys Glu Gly Arg Glu Leu Leu Leu Cys Ser
            260                 265                 270

Asn Thr Ser Cys Cys Arg Cys Phe Cys Val Glu Cys Leu Glu Val Leu
        275                 280                 285

Val Gly Thr Gly Thr Ala Ala Glu Ala Lys Leu Gln Glu Pro Trp Ser
    290                 295                 300

Cys Tyr Met Cys Leu Pro Gln Arg Cys His Gly Val Leu Arg Arg Arg
305                 310                 315                 320

Lys Asp Trp Asn Val Arg Leu Gln Ala Phe Phe Thr Ser Asp Thr Gly
                325                 330                 335

Leu Glu Tyr Glu Ala Pro Lys Leu Tyr Pro Ala Ile Pro Ala Ala Arg
            340                 345                 350

Arg Arg Pro Ile Arg Val Leu Ser Leu Phe Asp Gly Ile Ala Thr Gly
        355                 360                 365

Tyr Leu Val Leu Lys Glu Leu Gly Ile Lys Val Gly Lys Tyr Val Ala
    370                 375                 380

Ser Glu Val Cys Glu Glu Ser Ile Ala Val Gly Thr Val Lys His Glu
385                 390                 395                 400

Gly Asn Ile Lys Tyr Val Asn Asp Val Arg Asn Ile Thr Lys Lys Asn
                405                 410                 415

Ile Glu Glu Trp Gly Pro Phe Asp Leu Val Ile Gly Gly Ser Pro Cys
            420                 425                 430

Asn Asp Leu Ser Asn Val Asn Pro Ala Arg Lys Gly Leu Tyr Glu Gly
        435                 440                 445

Thr Gly Arg Leu Phe Phe Glu Phe Tyr His Leu Leu Asn Tyr Ser Arg
    450                 455                 460

Pro Lys Glu Gly Asp Asp Arg Pro Phe Phe Trp Met Phe Glu Asn Val
465                 470                 475                 480

Val Ala Met Lys Val Gly Asp Lys Arg Asp Ile Ser Arg Phe Leu Glu
                485                 490                 495

Cys Asn Pro Val Met Ile Asp Ala Ile Lys Val Ser Ala Ala His Arg
            500                 505                 510

Ala Arg Tyr Phe Trp Gly Asn Leu Pro Gly Met Asn Arg Ile Phe Gly
```

-continued

```
        515                 520                 525

Phe Pro Val His Tyr Thr Asp Val Ser Asn Met Gly Arg Gly Ala Arg
    530                 535                 540

Gln Lys Leu Leu Gly Arg Ser Trp Ser Val Pro Val Ile Arg His Leu
545                 550                 555                 560

Phe Ala Pro Leu Lys Asp Tyr Phe Ala Cys Glu
                565                 570


<210> SEQ ID NO 24
<211> LENGTH: 538
<212> TYPE: PRT
<213> ORGANISM: Homo sapiens

<400> SEQUENCE: 24

Met Glu Ser Pro Gln Val Glu Ala Asp Ser Gly Asp Gly Asp Ser Ser
  1               5                  10                  15

Glu Tyr Gln Val Ser Ala Asp Lys Leu Val Ala Leu Gly Leu Phe Ser
            20                  25                  30

Gln His Phe Asn Leu Ala Thr Phe Asn Lys Leu Val Ser Tyr Arg Lys
        35                  40                  45

Ala Met Tyr His Ala Leu Glu Lys Ala Arg Val Arg Ala Gly Lys Thr
     50                  55                  60

Phe Pro Ser Ser Pro Gly Asp Ser Leu Glu Asp Gln Leu Lys Pro Met
 65                  70                  75                  80

Leu Glu Trp Ala His Gly Gly Phe Lys Pro Thr Gly Ile Glu Gly Leu
                 85                  90                  95

Lys Pro Asn Asn Thr Gln Pro Val Val Asn Lys Ser Lys Val Arg Arg
            100                 105                 110

Ala Gly Ser Arg Lys Leu Glu Ser Arg Lys Tyr Glu Asn Lys Thr Arg
        115                 120                 125

Arg Arg Thr Ala Asp Asp Ser Ala Thr Ser Asp Tyr Cys Pro Ala Pro
    130                 135                 140

Lys Arg Leu Lys Thr Asn Cys Tyr Asn Asn Gly Lys Asp Arg Gly Asp
145                 150                 155                 160

Glu Asp Gln Ser Arg Glu Gln Met Ala Ser Asp Val Ala Asn Asn Lys
                165                 170                 175

Ser Ser Leu Glu Asp Gly Cys Leu Ser Cys Gly Arg Lys Asn Pro Val
            180                 185                 190

Ser Phe His Pro Leu Phe Glu Gly Gly Leu Cys Gln Thr Cys Arg Asp
        195                 200                 205

Arg Phe Leu Glu Leu Phe Tyr Met Tyr Asp Asp Asp Gly Tyr Gln Ser
    210                 215                 220

Tyr Cys Thr Val Cys Cys Glu Gly Arg Glu Leu Leu Leu Cys Ser Asn
225                 230                 235                 240

Thr Ser Cys Cys Arg Cys Phe Cys Val Glu Cys Leu Glu Val Leu Val
                245                 250                 255

Gly Thr Gly Thr Ala Ala Glu Ala Lys Leu Gln Glu Pro Trp Ser Cys
            260                 265                 270

Tyr Met Cys Leu Pro Gln Arg Cys His Gly Val Leu Arg Arg Arg Lys
        275                 280                 285

Asp Trp Asn Val Arg Leu Gln Ala Phe Phe Thr Ser Asp Thr Gly Leu
    290                 295                 300

Glu Tyr Glu Ala Pro Lys Leu Tyr Pro Ala Ile Pro Ala Ala Arg Arg
305                 310                 315                 320
```

-continued

```
Arg Pro Ile Arg Val Leu Ser Leu Phe Asp Gly Ile Ala Thr Gly Tyr
                325                 330                 335

Leu Val Leu Lys Glu Leu Gly Ile Lys Val Gly Lys Tyr Val Ala Ser
            340                 345                 350

Glu Val Cys Glu Glu Ser Ile Ala Val Gly Thr Val Lys His Glu Gly
        355                 360                 365

Asn Ile Lys Tyr Val Asn Asp Val Arg Asn Ile Thr Lys Lys Asn Ile
    370                 375                 380

Glu Glu Trp Gly Pro Phe Asp Leu Val Ile Gly Gly Ser Pro Cys Asn
385                 390                 395                 400

Asp Leu Ser Asn Val Asn Pro Ala Arg Lys Gly Leu Tyr Glu Gly Thr
                405                 410                 415

Gly Arg Leu Phe Phe Glu Phe Tyr His Leu Leu Asn Tyr Ser Arg Pro
            420                 425                 430

Lys Glu Gly Asp Asp Arg Pro Phe Phe Trp Met Phe Glu Asn Val Val
        435                 440                 445

Ala Met Lys Val Gly Asp Lys Arg Asp Ile Ser Arg Phe Leu Glu Cys
    450                 455                 460

Asn Pro Val Met Ile Asp Ala Ile Lys Val Ser Ala Ala His Arg Ala
465                 470                 475                 480

Arg Tyr Phe Trp Gly Asn Leu Pro Gly Met Asn Arg Ile Phe Gly Phe
                485                 490                 495

Pro Val His Tyr Thr Asp Val Ser Asn Met Gly Arg Gly Ala Arg Gln
            500                 505                 510

Lys Leu Leu Gly Arg Ser Trp Ser Val Pro Val Ile Arg His Leu Phe
        515                 520                 525

Ala Pro Leu Lys Asp Tyr Phe Ala Cys Glu
    530                 535


<210> SEQ ID NO 25
<211> LENGTH: 518
<212> TYPE: PRT
<213> ORGANISM: Homo sapiens

<400> SEQUENCE: 25

Met Glu Ser Pro Gln Val Glu Ala Asp Ser Gly Asp Gly Asp Ser Ser
  1               5                  10                  15

Glu Tyr Gln Val Ser Ala Asp Lys Leu Val Ala Leu Gly Leu Phe Ser
             20                  25                  30

Gln His Phe Asn Leu Ala Thr Phe Asn Lys Leu Val Ser Tyr Arg Lys
         35                  40                  45

Ala Met Tyr His Ala Leu Glu Lys Ala Arg Val Arg Ala Gly Lys Thr
     50                  55                  60

Phe Pro Ser Ser Pro Gly Asp Ser Leu Glu Asp Gln Leu Lys Pro Met
 65                  70                  75                  80

Leu Glu Trp Ala His Gly Gly Phe Lys Pro Thr Gly Ile Glu Gly Leu
                 85                  90                  95

Lys Pro Asn Asn Thr Gln Pro Glu Asn Lys Thr Arg Arg Arg Thr Ala
            100                 105                 110

Asp Asp Ser Ala Thr Ser Asp Tyr Cys Pro Ala Pro Lys Arg Leu Lys
        115                 120                 125

Thr Asn Cys Tyr Asn Asn Gly Lys Asp Arg Gly Asp Glu Asp Gln Ser
    130                 135                 140

Arg Glu Gln Met Ala Ser Asp Val Ala Asn Asn Lys Ser Ser Leu Glu
145                 150                 155                 160
```

-continued

```
Asp Gly Cys Leu Ser Cys Gly Arg Lys Asn Pro Val Ser Phe His Pro
                165                 170                 175

Leu Phe Glu Gly Gly Leu Cys Gln Thr Cys Arg Asp Arg Phe Leu Glu
            180                 185                 190

Leu Phe Tyr Met Tyr Asp Asp Asp Gly Tyr Gln Ser Tyr Cys Thr Val
        195                 200                 205

Cys Cys Glu Gly Arg Glu Leu Leu Leu Cys Ser Asn Thr Ser Cys Cys
    210                 215                 220

Arg Cys Phe Cys Val Glu Cys Leu Glu Val Leu Val Gly Thr Gly Thr
225                 230                 235                 240

Ala Ala Glu Ala Lys Leu Gln Glu Pro Trp Ser Cys Tyr Met Cys Leu
                245                 250                 255

Pro Gln Arg Cys His Gly Val Leu Arg Arg Arg Lys Asp Trp Asn Val
            260                 265                 270

Arg Leu Gln Ala Phe Phe Thr Ser Asp Thr Gly Leu Glu Tyr Glu Ala
        275                 280                 285

Pro Lys Leu Tyr Pro Ala Ile Pro Ala Ala Arg Arg Arg Pro Ile Arg
    290                 295                 300

Val Leu Ser Leu Phe Asp Gly Ile Ala Thr Gly Tyr Leu Val Leu Lys
305                 310                 315                 320

Glu Leu Gly Ile Lys Val Gly Lys Tyr Val Ala Ser Glu Val Cys Glu
                325                 330                 335

Glu Ser Ile Ala Val Gly Thr Val Lys His Glu Gly Asn Ile Lys Tyr
            340                 345                 350

Val Asn Asp Val Arg Asn Ile Thr Lys Lys Asn Ile Glu Glu Trp Gly
        355                 360                 365

Pro Phe Asp Leu Val Ile Gly Gly Ser Pro Cys Asn Asp Leu Ser Asn
    370                 375                 380

Val Asn Pro Ala Arg Lys Gly Leu Tyr Glu Gly Thr Gly Arg Leu Phe
385                 390                 395                 400

Phe Glu Phe Tyr His Leu Leu Asn Tyr Ser Arg Pro Lys Glu Gly Asp
                405                 410                 415

Asp Arg Pro Phe Phe Trp Met Phe Glu Asn Val Val Ala Met Lys Val
            420                 425                 430

Gly Asp Lys Arg Asp Ile Ser Arg Phe Leu Glu Cys Asn Pro Val Met
        435                 440                 445

Ile Asp Ala Ile Lys Val Ser Ala Ala His Arg Ala Arg Tyr Phe Trp
    450                 455                 460

Gly Asn Leu Pro Gly Met Asn Arg Ile Phe Gly Phe Pro Val His Tyr
465                 470                 475                 480

Thr Asp Val Ser Asn Met Gly Arg Gly Ala Arg Gln Lys Leu Leu Gly
                485                 490                 495

Arg Ser Trp Ser Val Pro Val Ile Arg His Leu Phe Ala Pro Leu Lys
            500                 505                 510

Asp Tyr Phe Ala Cys Glu
        515
```

<210> SEQ ID NO 26
<211> LENGTH: 232
<212> TYPE: PRT
<213> ORGANISM: Homo sapiens

<400> SEQUENCE: 26

```
Met Glu Ser Pro Gln Val Glu Ala Asp Ser Gly Asp Gly Asp Ser Ser
```

-continued

```
  1               5                  10                  15

Glu Tyr Gln Arg Thr Arg Leu Glu Asp Ala Gln Leu Thr Thr Gln Pro
            20                  25                  30

Pro Leu Thr Thr Ala Pro His Pro Ser Ala Ser Arg Gln Ile Ala Ile
        35                  40                  45

Thr Thr Ala Lys Thr Glu Gly Met Lys Ile Arg Ala Glu Asn Lys Trp
    50                  55                  60

Leu Gln Met Leu Pro Thr Thr Arg Ala Ala Trp Lys Met Ala Val Cys
 65                  70                  75                  80

Leu Val Ala Gly Lys Thr Pro Cys Pro Ser Thr Leu Ser Leu Arg Gly
                85                  90                  95

Gly Ser Val Arg His Ala Gly Ile Ala Ser Leu Ser Cys Phe Thr Cys
            100                 105                 110

Met Met Thr Met Ala Ile Ser Leu Thr Ala Leu Cys Ala Ala Arg Ala
        115                 120                 125

Glu Ser Cys Cys Phe Ala Ala Thr Arg Ala Ala Ala Gly Val Ser Val
    130                 135                 140

Trp Ser Ala Trp Arg Cys Trp Trp Ala Gln Ala Gln Arg Pro Arg Pro
145                 150                 155                 160

Ser Phe Arg Ser Pro Gly Ala Val Thr Cys Val Ser Arg Ser Ala Val
                165                 170                 175

Met Ala Ser Cys Gly Ala Gly Arg Thr Gly Thr Cys Ala Cys Arg Pro
            180                 185                 190

Ser Ser Pro Val Thr Arg Gly Leu Asn Met Lys Pro Pro Ser Cys Thr
        195                 200                 205

Leu Pro Phe Pro Gln Pro Glu Gly Gly Pro Phe Glu Ser Cys His Cys
    210                 215                 220

Leu Met Ala Ser Arg Gln Ala Thr
225                 230


<210> SEQ ID NO 27
<211> LENGTH: 285
<212> TYPE: PRT
<213> ORGANISM: Homo sapiens

<400> SEQUENCE: 27

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
            20                  25                  30

Lys Ile Lys Gly Phe Ser Trp Trp Pro Ala Met Val Val Ser Trp Lys
        35                  40                  45

Ala Thr Ser Lys Arg Gln Ala Met Ser Gly Met Arg Trp Val Gln Trp
    50                  55                  60

Phe Gly Asp Gly Lys Phe Ser Glu Arg Thr Arg Leu Glu Asp Ala Gln
 65                  70                  75                  80

Leu Thr Thr Gln Pro Pro Leu Thr Thr Ala Pro His Pro Ser Ala Ser
                85                  90                  95

Arg Gln Ile Ala Ile Thr Thr Ala Lys Thr Glu Gly Met Lys Ile Arg
            100                 105                 110

Ala Glu Asn Lys Trp Leu Gln Met Leu Pro Thr Thr Arg Ala Ala Trp
        115                 120                 125

Lys Met Ala Val Cys Leu Val Ala Gly Lys Thr Pro Cys Pro Ser Thr
    130                 135                 140
```

-continued

```
Leu Ser Leu Arg Gly Gly Ser Val Arg His Ala Gly Ile Ala Ser Leu
145                 150                 155                 160

Ser Cys Phe Thr Cys Met Met Thr Met Ala Ile Ser Leu Thr Ala Leu
                165                 170                 175

Cys Ala Ala Arg Ala Glu Ser Cys Cys Phe Ala Ala Thr Arg Ala Ala
            180                 185                 190

Ala Gly Val Ser Val Trp Ser Ala Trp Arg Cys Trp Trp Ala Gln Ala
        195                 200                 205

Gln Arg Pro Arg Pro Ser Phe Arg Ser Pro Gly Ala Val Thr Cys Val
    210                 215                 220

Ser Arg Ser Ala Val Met Ala Ser Cys Gly Ala Gly Arg Thr Gly Thr
225                 230                 235                 240

Cys Ala Cys Arg Pro Ser Ser Pro Val Thr Arg Gly Leu Asn Met Lys
                245                 250                 255

Pro Pro Ser Cys Thr Leu Pro Phe Pro Gln Pro Glu Gly Gly Pro Phe
            260                 265                 270

Glu Ser Cys His Cys Leu Met Ala Ser Arg Gln Ala Thr
        275                 280                 285


<210> SEQ ID NO 28
<211> LENGTH: 321
<212> TYPE: PRT
<213> ORGANISM: Homo sapiens

<400> SEQUENCE: 28

Met Glu Ser Pro Gln Val Glu Ala Asp Ser Gly Asp Gly Asp Ser Ser
  1               5                  10                  15

Glu Tyr Gln Asp Gly Lys Glu Phe Gly Ile Gly Asp Leu Val Trp Gly
             20                  25                  30

Lys Ile Lys Gly Phe Ser Trp Trp Pro Ala Met Val Val Ser Trp Lys
         35                  40                  45

Ala Thr Ser Lys Arg Gln Ala Met Ser Gly Met Arg Trp Val Gln Trp
     50                  55                  60

Phe Gly Asp Gly Lys Phe Ser Glu Val Ser Ala Asp Lys Leu Val Ala
 65                  70                  75                  80

Leu Gly Leu Phe Ser Gln His Phe Asn Leu Ala Thr Phe Asn Lys Leu
                 85                  90                  95

Val Ser Tyr Arg Lys Ala Met Tyr His Ala Leu Glu Arg Thr Arg Leu
            100                 105                 110

Glu Asp Ala Gln Leu Thr Thr Gln Pro Pro Leu Thr Thr Ala Pro His
        115                 120                 125

Pro Ser Ala Ser Arg Gln Ile Ala Ile Thr Thr Ala Lys Thr Glu Gly
    130                 135                 140

Met Lys Ile Arg Ala Glu Asn Lys Trp Leu Gln Met Leu Pro Thr Thr
145                 150                 155                 160

Arg Ala Ala Trp Lys Met Ala Val Cys Leu Val Ala Gly Lys Thr Pro
                165                 170                 175

Cys Pro Ser Thr Leu Ser Leu Arg Gly Gly Ser Val Arg His Ala Gly
            180                 185                 190

Ile Ala Ser Leu Ser Cys Phe Thr Cys Met Met Thr Met Ala Ile Ser
        195                 200                 205

Leu Thr Ala Leu Cys Ala Ala Arg Ala Glu Ser Cys Cys Phe Ala Ala
    210                 215                 220

Thr Arg Ala Ala Ala Gly Val Ser Val Trp Ser Ala Trp Arg Cys Trp
225                 230                 235                 240
```

-continued

```
Trp Ala Gln Ala Gln Arg Pro Arg Pro Ser Phe Arg Ser Pro Gly Ala
                245                 250                 255

Val Thr Cys Val Ser Arg Ser Ala Val Met Ala Ser Cys Gly Ala Gly
            260                 265                 270

Arg Thr Gly Thr Cys Ala Cys Arg Pro Ser Ser Pro Val Thr Arg Gly
        275                 280                 285

Leu Asn Met Lys Pro Pro Ser Cys Thr Leu Pro Phe Pro Gln Pro Glu
    290                 295                 300

Gly Gly Pro Phe Glu Ser Cys His Cys Leu Met Ala Ser Arg Gln Ala
305                 310                 315                 320

Thr


<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 29

tctatc                                                                  6


<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 30

acccgacccc gaaccgcgac cgtaa                                            25


<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 31

ttattagagg gtggggcgga tcgcgtgc                                         28


<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 32

caaccccaaa ccacaaccat aa                                               22


<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer
```

-continued

<400> SEQUENCE: 33
ttattagagg gtggggtgga ttgt 24

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 34
gctaacaaac gcgaaccg 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35
gggttttgcg agagcgcg 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 36
cactaacaaa cacaaacc 18

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 37
ggtttttgtg agagtgtgtt tag 23

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 38
gagttgggca taaaggtagg 20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 39

-continued

```
tgaggtacac ggtatgacc                                                19


<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 40

catgaaggga gacaccaggc                                               20


<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 41

atgccaaagc tcttccggga                                               20


<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 42

tggagatgga gacagttcag                                               20


<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 43

ggtagccggg aactccacgg                                               20


<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 44

tgctgtgaca ggcagagcag                                               20


<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 45
```

-continued tctgtgtcgt ctgtgaggtc 20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 46
tggaaggcca cctccaagc 19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 47
gcctgcacga cgcaccttcg 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 48
agatcaaggg cttctcctgg 20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 49
gagtcttgtt ctctggttgc g 21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 50
gttcagagta tcaggtctct gc 22

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic Primer

<400> SEQUENCE: 51
gttcagagta tcagagaaca agac 24

-continued

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 52
ctgccacaag acaaacagcc 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 53
gttctccgag agaacaagac 20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 54
cagtaagact gatagccatc g 21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 55
tgctctggag agaacaagac 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 56
gagacacatg taacagctcc 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 57
tgctaagcta cacacaggac 20

-continued

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 58
cgagtcttgt tctctgatac tc 22

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 59
cgagtcttgt tctctcggag 20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 60
cgagtcttgt tctctccag 19

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
Primer

<400> SEQUENCE: 61
cacgcaacca gagaacaagu u 21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
Primer

<400> SEQUENCE: 62
cuuguucucu gguugcgugu u 21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 63
aacacgcaac cagagaacaa g 21

-continued

<210> SEQ ID NO 64
<211> LENGTH: 118899
<212> TYPE: DNA
<213> ORGANISM: Homo sapiens

<400> SEQUENCE: 64
gatcatgaag tcaggagatc aagaccatcc tggctaacac ggtgaaaccc catctctatt 60
aaaaatataa aaaatcagcc gggcatggtc gcaggcacct gtagtcccag ctacttggga 120
ggctgaggca ggaaaatggc gtgaacccgg gaggcggagc ttgcagtgag ccgagatcac 180
gccactgcac tccagcctgg gcaacagggc cagacactgt ctcaaaaaaa aaagaaaagg 240
gctaaactac tttaagatgt gccgtaagta taaaacacca gatttagaaa actttgtacc 300
aaaaagtaaa atgtcattga tatttgtata tgggtaagat attgaaaaat attttgatat 360
tgtggattta agcatgcatg gcattttgat caatgatgga ccatatataa aatgatggtc 420
ccataacatt ataatggagg taaaagatcc ctgttaccta gtgattgtca cagaaatccg 480
cgcccagcca tgtttgtgtt ttaagctatg tgttactaca aaagagccaa aaagtttaac 540
aaaaccagcc tgggcaacat ggcaaaactc tgtctttaca aaaaatacaa aaattagcca 600
ggtatggtgg cgcgtgccta tagtcccagc tatttgggag gctgaggtgg aaggattgct 660
tgaacccagg agatcaaggc tacagtgagc aatgggtgac agagcgagac cctgcctcaa 720
aaaaaaaaaa aaaaaggtaa gcattcatga agtaaaaagt tacagttggc agggtgcatg 780
gcttacgcct gtaatcccag cactttggga ggttgaggca ggcagatcac ttgaggtcag 840
gagttcgtga ccagcctggc caacatggtg aaacgctgtc tctactaaaa atacaaaaat 900
tagccaggca tggtggtgca cgcctgtagt cccagctact tgggagcctg aggcaaaaga 960
atcacttgag cccaggaggt gaagtttgca gtgagccaag atcacgccac tgcactccag 1020
cctgggtgac agaggaagac tccgtctaaa acaaacaaac aaacaaaaaa aactgacagt 1080
aggctaaggt caacttatca aaaacagaaa aaaaaaaatt ttttttagg gatgggggtc 1140 tcactatgct gcccaggctg gagtgcaatg gctattcaca ggtggaatca ccatgcacta 1200
cagccttgaa atcctgggct caagtgatcc tcctgtctca gcctcccaag tagctgggac 1260
tactgtggta gctgtgccac cgtacccaac tagaaagttg tttttttttt ttttgagatg 1320
aagtctcact ctattgccca ggctggaatg cagtggtgca atcgcagctt actgcaacct 1380
ccacctctca ggttcaggcg attctcctgc cttagcctcc agagtagccg ggactacaag 1440
tgcccgccac tacacccagc taatttttgt atttttagta gagacagggt ttcatcatgt 1500
tggccaggat ggtctcgatc tcctgacctt gtgatccgcc caccttggcc tcccaaagtc 1560
ctagggtagg tgtgagccac cgtgcccggc ctatttttta tcttttatac tgtatttgta 1620
ctgtaccttt tctatttaga tttgtctaaa cacacaaata tttaccatta tagtccagtt 1680
gcctatggta ttcagtacag tcacatgctg tataggtttg tagcctagga gcaatgcgct 1740
ataccatata tcctagggtg cagtaggttt gtgtaaataa actctaggat gcttgcataa 1800
gatgaactca gggctgggca cagtggctca cgcctgtaat cccaacactc tgggaggctg 1860
aggtgggcag atcacctgag gtcaggtgtt caagaccagc ctggccaaca tggtcaaacc 1920
ccatctctac taaaaataca aaaattagct gggcatggtg gcgtgtgcct gtagtcccag 1980
ttactcggga gactgagaca gagaactggt tgaacctggg aggcggaggt tgcagtgacc 2040
cgagatcgcg ccactgcact ccagcctggg tgacagaatg agactacgtc tcaaaaaaaa 2100
aaaattaatt tccatttcta tttaattttt aaatgtggct actacaaaat gcaaagttag 2160

-continued

```
aaatgtggct tgcaaatttt tctattgcat agctcaagct tagaaccttc ctgtcgttac   2220
aagttctaag tttggttttt atctcgcaag cagcactact gtgtgggaag ttgtgggggg   2280
tatggagatg aaagaagagg ggcgctacct cctgggaagt gacaacctag cgggggaaat   2340
agatgtatct tcccagtggg ggtgagaagt gtcattctca cctatttcag cagccttggt   2400
ggtatgaaaa ggcatcccaa ccagcacaga agcaggatgc ctccaagact gccttggttg   2460
gcacctgcag cctgaagggg gagaaaaagg ctttgctagc tcccctacca tcgaggatga   2520
agacccccac tgtacacagt gtataaggtt tctttccatg tgaatcccag tgactctcct   2580
taactgggtg gaggtggaag gtgtcatcag ccttgtccca gatcgagccc ctcaggccca   2640
cagagcccca gtggggcctg gctattactg acactcatgt cacactgaga tgtaagacgg   2700
cagcccaggc caagcttccc cgggccccct cagattctcg ggccctccca ctcccctcag   2760
gcttcctcgg cctccctgcc aaacatctat ctccctttgg accccactgc tccccaaaac   2820
tccccacgcc cttagtctgt tccttcagtt ccccaaactc cttcagcctc atctagactc   2880
ccctccgtcc ctcttctagg accccaaaag ctctcctcgg ccccaggacc ccgcagaggt   2940
cccgtagtcc catctctgag accccacaaa gcctttcgga cccctcaggt ggcccttagg   3000
cctccggaga tcccttggct ccccacactc tcctcagacc ccagctcacc ttagcctcgc   3060
cccgaaccca cctcacacac cccaaacgcc cacaagacgc cgctctgtct agtctctccc   3120
aactcccgcg cacccccgga cgtccccccc accccaggcc cggatcctgg aatcacctgg   3180
gccccgcgcc ccacgccccg ccgccgggcc cacctgcgcg cccagctggt tcagctgctg   3240
catgtcgccg cccacggcct ccggcaccgg gtcctcagtg cagtgcaggc ggcccatggc   3300
gcgcgcccca gccccgcagg ttccaccgcc gccgccgccc tgctcagctt cctcctccgc   3360
tgccgctgcc accgctgccg gcctctccgc gcatccacaa ccgcactttc gccacggccg   3420
tcgcagcgca ctcctccccc ggccgccctg ggctgtccgg agccggggag ccctcgcagg   3480
gccgcggaca cgcgcggccg ccgggctccg gggaggggca ggggcggcgc cggcaccggc   3540
agacgcgagg tttcctgcca gctctcccgc tgagtgacct ttgggtacgg cgcttggcct   3600
ctctgaacct cagtttcacc atctgagaaa atgatggctg ggtagctcc ttaaatgagt    3660
taagcctcca gaaatgttta acgcagagac cggcacacaa gaggtcttca atcaatggct   3720
agctgctatt atcatcatca ctgttactat gcactccaga gatatttatg gcagcctact   3780
cgatgccaga cactggggac agggaaggga acaaagcagg ccagagtgtc tctcggagag   3840
ctgacatcag agtagagact aggtctcaac cttggaaggg catcagcatc accccagcat   3900
cacctggtat tgccgggccc cgcccccaga ggatctgatt cgaaaggcca gggtggagcc   3960
tgagaatttg catttccaat aagcacccag ggactacact ttgagacctt ctggagtgga   4020
agaaactgac ttaccaaagt ttcctcaaaa tagtgcgagg gctttgactg tgcggggcag   4080
ggagggtggt ggtgaggtgg gtgaggggag gttactgaga ccgtgatcat cactgcagcc   4140
cctcaaacac tctaaccccc atgccctctc ttcccagggg ctcctcacag ttcccaggtg   4200
aatattaccc taatccccac tggaaacatg agaaaataga gacatgctac ccagaatcta   4260
ggaactgaac gccaagccta agggcttcac ctagccccta agtccagcct tgagggtaaa   4320
gaggtaatgc cgagaaacct ggagcaggga aatgtggggg gtttggctgg ccttcctcac   4380
cagccctcct cctctcctct accctttcct gaaaatccct tctgtaaaag tataaacaaa   4440
atgtcttcta cccggcccgg cgcggtggct cactcctgta atcccagcac tttgggaggc   4500
tgaggcgggc ggatcacttg aggtcaggag tttgagacca gcctcaacat ggagaaactc   4560
```

-continued

```
cgtctctact aaaaatacaa aattagccgg gcgtagtggt gcatgtctgt aatctcagct   4620
actcgggagg ctgaggcagg agaattccct gaacccggga ggcataggtt gcggtaagcc   4680
gagatcgcgc cattgcactc cagcctgggc aacaagagcg aaactccgtc tcaaagaaaa   4740
aacaaaaaag tcttctaccc aaaggccaag cccatcccct tcagtcatta tatcattcat   4800
acattcattc aacaaatatt gagtggcaca tgcctgtggt cccagctact cggaggctga   4860
ggcaagagga tcacttgaga tcttgagatc gagactgcag tgaacccaga tggcgccact   4920
gcactccagc ctgggcgaca gagcaagacc acatctccat aaaaaaaaaa gaaggtctgc   4980
tgtgaggcag ataccatgac atgatagggg gtggggattc cacagtgaca caaccagatg   5040
aaccagatgc agtgcctggc ctctgagaag tcagaattga cccagggggc agacgcaagt   5100
gtgtgtgaaa gtattaaggg atgccaaaaa gtaggaggtg ctttgagaat gtgtacagga   5160
cacagtccga gtttggagta cctggaagag aataaacctt cgggtgacaa acagacagga   5220
actcagaggc cctactcacc gtgcaagaat tttttttttt tttttttttg agacagattc   5280
tggctctgtc acccaggctg gagtgcagtg gcacaatctc ggctcactgc aatttctgct   5340
tcccgggttc tagtgattct ccagcctcag cctcccgaat agctgggaat gcaggtggcc   5400
accaccaaac ccagctaact tttgtctttt tttttttttt ttggaaacgg agttttgctc   5460
tttttgtcca ggctggagtg caatggcgag atctcggctc actgcaacct ccgcctcccg   5520
ggttcaagtg attctcctgt ctcagcctcc caagtagctg ggattacagg catgtgccac   5580
caccccggct aattttgtac ttttagtaga gacgggtttc tccatgttgg tcaggctggt   5640
cttgaactcc ccacctcagg tgatccgcct gcctcggcct cccaaagtgc tgggtttaca   5700
ggcgcgagcc accgcacctg gcccaacttt tgtcttctta ctagagatgg gttttcaccg   5760
cattggccag gctggtctca tactcctgac ctcaagtgat ccacctgcgt cagcctccca   5820
aagtgctggc attacaggcg tgagccactg cacctggccc ggaattttta tttttaaata   5880
tttttaacct tgttaaaaaa gaagatctgg gctgggcgca gtgacgcatg cctgtaatcc   5940
tagcactctg ggaggctgag gccggtggat cacctgaggt ccggagttca agaccagcct   6000
agccaacata gtgaaaccct ggttctacta aaaatacaaa aattagccgg gcatggtggt   6060
tcatgcctgt aatcccggct actctagagg ctgaggcagg aaaatcgctt gaacccagta   6120
ggcagagatt gcagtgagcc gaaatcccac cactgcactc cagcctgagc gacagagcaa   6180
gactctgttc aaaaataaat aaataaatag ttgggggaaa aaaaaaagaa gatccccatc   6240
agggcattac atttcttcat atctttaagt gttaaatcaa ctgtttaggt ataaaaaata   6300
aaatgaacct gttttaagtt ttgttttgtt tttaacatcc tggagaaaac cactggattt   6360
cttttcattt ctgcttccac agtgactggt gctgagtcac ttgataaata ctgtatttgt   6420
ggaacggaat tagctcatgt gacagaaaat acagaaaagg aaaggaattc acttgaaact   6480
gacacccaat actataggaa tatggtgact cttcttttcc agtctttttt tttttttttg   6540
agacggagtc tctctctgtc gcccaggctg gagtgcagtg gtgctatctc ggctcactgc   6600
aagctccgcc tcccgggttc acgccattct ccggcctcag cctcccgagt agctgggact   6660
acaggtgccc gctatcacgc ttggctaatt ttttgtattt ttagtagaga cggggtttca   6720
ccgtgttagc caggatggtc tccatctcct gacctcgtga ttcacccgcc tcggcctccc   6780
aaagtgctgg gattacgggc gtgagccacc gcgcccggcc tttttccagt ctttttccac   6840
atcgcaggtc actggggttg tgtgatttgt tttcgtttta catacacagg actctcgcat   6900
```

-continued

```
ttcaccaagt tatttaataa tccctcatac tccacgtgtg gttccttgga ccagcagtgc   6960
aggcgttacc tggaagcttg ttagaaatgc tgaatctcag gctgggtgcg gtggctctcg   7020
cctgtaatcc cagcactttg ggaggctcga ggcgggcgga tcacaaggtc aagagattga   7080
gaccatcctg gccaacatgg tgaaaccccg tctctactag aaatacaaaa attggccggg   7140
cgtcatggca agcgcctgta gtcccagcta ctagggaggc tgaggtagga gaatagcttg   7200
aacccgggag gcggaagttg cagtgggccg agatcgggcc actacactct agcctgatga   7260
cagagtgaga ctatatctca caaaaaaaaa aaaaaaagaa agaaagaaag aaaaagaaat   7320
gctgaatctc attccagccc tttgggaggc cgaagcaggc agatcacctg aggtcgggag   7380
ttcgagacca gcctggccaa cgtggagaaa tcctgtctct actaaaaata caaaaattag   7440
ccaggtgtgg tggcacatgc ctgcaatccc agctattccg caggctgagg caggagaatc   7500
gcttgaattt gggaggtgga ggttgcagtg agcttagatc actccactgc acacaagctt   7560
gggtgacaga gtgagacttt gtctcaaaaa caaatgaata aataaaataa ataccgaatc   7620
tcaggtctac tagacctgct gattcaggat ctgaatttta acaagattcc caagtgattt   7680
gtgggcacat taaagtttga agtgcaaata ataacaacca ctttaagtgc tcactttgtg   7740
caggacttta ttttaagcat ttgaatacac accgtgtata atgataataa tactttgcat   7800
tgtctactga ttgtcgctca tattactttt tcttttttgt gtgtgctgaa acccaggaat   7860
gaaccattat ttctatttta atgtttacca caatgtgtta ttgctgtcgt tttatacatct  7920
gtctcctcca cttactaatt attttgtctc aggcaaatta ctaacctttc agtgcttcta   7980
tttctgtttt tatttataaa atggaaatga taatataacc ttcttggaaa gatgaaacaa   8040
gacaatgctt ataaagcatt tagcacagca actggactat ggtaagagct cagtaactgc   8100
ttggtattat tatcatttca atttttcaat cttataaaaa gaatatggca ataaacattc   8160
ctgtacacaa ttcttttcca catctgatta tttctttagg aaaaatttct aggaaggcaa   8220
ggaatattat gttcagtcct tctgggctct aaatgtcatg gggatggggt agagatgagg   8280
atgtctaatg gataccacaa aaagtagtta taaagaatga ataggctggg cgcggtggct   8340
cacacctgta atcccagcac tttgggaggc caaggcgggc agatcacctg aggtcaggag   8400
ttctagacca gcctgaccaa tatggaaaaa caccgtctct actaaaaata caaaaaatta   8460
gccgggcctg gtggtgcatg cctgtaatcc cagttactca ggaggctgag gcagaagagt   8520
tgcttgaacc caggaagcgg aggttgtggt gagctgagat cacgccattg cactccagcc   8580
ttggcaacaa gagcgaaact ccatctcaaa aaaaaaaaaa aaaaaaaaaa aacagagaga   8640
gagagagaga atgaatgaac aagggccggg ggcggtggct cacatctgta atcctagcac   8700
tttgggaggc cgaggcaagt ggatcacttg aggtcaggag ttcaagacca gcctggccaa   8760
catggtgaac ctccaactct actaaaaata caaaaattag ctgggcatgg tggcaggtgc   8820
ctgtaatccc agctacttgg gaggttgagg caagagaata gcttgaaccc aagagaagga   8880
ggttgcagtg agccaagatt gtgccattgc actccagcct gagcaataag agcaaaactc   8940
tatctcaaaa aaaaaaaaaa aaaaaaaaaa aaaaaaaaaa aaggccggcc gaggaggctc   9000
atgcctgcaa tcccagcact ttgggaggct gaggcaggca gatcacaagg tcaggagttg   9060
gagaccagcc tgatcaacat ggtgaaacac tgtccttact aaaaatacaa aaattagcca   9120
ggcttgctgg taggcacctg taatcccagc tactcaggag gctgaggcag gagaattgct   9180
tgaacccggg aggcagaggt tgcagtgagc tgagattgcg ccactgcact ccagcttggg   9240
tgacagagtg agactccatt tcaattaaaa aaaaaaaagg aagaaaagaa atgacaaata   9300
```

-continued

```
cttcaggtga aggataccct aaattccctg acttgattat tacacattct atgaaagcaa   9360
caaaatatca catataccc ataactatgt acaaatatta tgtatcaata tatttttta   9420
atatcacaag gacggatgaa ttttcaaggt aagcagaaac taaaccatta cccatgaacc   9480
atctctctga aaacacccag aaattagcat ttctgcctga acaggcacct ggtgcagttc   9540
cctgatgagg ctccgggtcc aggccctgcc cgccttccaa cccacatccc ctacatccca   9600
aagaggagac atccaagtcc tctaaattag cctccaaatc tcaaatctca tttttggctt   9660
caatgataaa atgctaccta aacatcgtcc aaaaatgctg cataatattc tatggagcaa   9720
gaattaaatg ctcataacta atccttgtgg ttgcctattt agaactctct gacttttctt   9780
tctcattaag aactttgtaa ctaacaaagg caatagataa aaaaagtctt tccaattttc   9840
tccttcacaa tccactctta gaggaaggaa ggagcagtga ttactgttaa tgtgataact   9900
ttgcagcagg aaatgcaggc cggagccagg actctcttct agagaacctc ctgcccccat   9960
ttcagcctta atgagggacc ctactccctt cattcacttt aaaatgtccc tgtggagggc  10020
aacgaaagtc ctcactccct ctcccctccc ccgcgcctgc aagtgaaagg agttcattaa  10080
gaagtagttt ctcaggcagg gaggattcct gctgggagtt tcaccaaggg gccaggtttt  10140
ccctaggaga aaggtctaac ccttcacact ctgaaatgcc aaagggcatt ttttttaaa  10200
ttaaactttt aattttgaga tcattgtaga ctcacataca gttttaagaa atgatacaga  10260
gacattcctt gtggccttta cccggtttcc ctcgatgcac agatcccaca gtgtcatcac  10320
caggatattg acattgatac agtcaagacg cagaacattt ccatggcagc aacgatctcc  10380
catgttgccc aatggcattt taacagaagg gacaagtgct agatcctcta acaaaaacta  10440
gaagaaaata ctatgaacat tttcaggtta aaaaaaaaaa actgggccgg gcatagtggc  10500
acatgcctgt aatcccagta ctttgggagg ccgaggccgg cagatcacct gaggtcagga  10560
gttcgagacc agcctagcca acatggcgaa accccgtctc tactaaaagt acaaaaatta  10620
cccagtcgtg gggcgcatg tctgtaatcc cacctactcc ggaggctgag gcaggagaat  10680
cgcttgcacc cgggaggtgg aggttgcagt gagccgagat cacaccattg cactccagcc  10740
tggacaacaa gagcgaaatt ctgtctcaaa aaaaaaagaa aaaaaaaaag cacgtaacaa  10800
aaatgtaaaa atacagttga cctagattcc tgacatctat gtcatgaaag tcattgacaa  10860
aggaaggctg gagaattgct ctagattaaa ataaataaaa aagacaagat aacaatgcaa  10920
tgtgtaattc tggatggagg taaacaattg ctataaaaga cattggcaca aaataaatgt  10980
acttaacact actgaactct gcacttagaa atagttaaga tggttgctct ttcctgtagt  11040
cccagctatc tgataggctg aagtaggagg atcccttgcg tctatgagtt ctaggcctgg  11100
gcaacatagt gagaacttgt cctcaaataa ataagaataa atagttaaaa tggtaaattt  11160
tatgtgcttt tttaaaacca caattaaaaa aatacattat tgtgacaatt gaagtctgaa  11220
cacccactgt agattagata ataatattgt atcaatgttc aatttcctga acttgataaa  11280
tgtaatttgg ttatgggaaa atgtctttgt tcttaagaaa tgcatgctca aagtactcaa  11340
ggtaaaagtg gataaaatgg ttcagggaaa aaaatgagcc aacacatgtg gtaatgtgga  11400
gatcactgat taatttctaa attggctctg agcatgctgg aagccagagg gagataagtc  11460
aatttcacct ctagtttttc atccttacac aggtaaatta atgtagataa atttctcttg  11520
ttggacttac aggagagttc caattctcca atttttatct aggacatggt gatgaatttg  11580
tttacctgtt caaaaatctt ccttcaaatg gcaggatttc tggggtaaag tttaagcctt  11640
```

-continued

```
tttaagatcc tctggcctaa gctccaatgg atgtttaagc tgtccctcta gaaatttgct  11700
ttttaaagag ccctttggca gttcctactt tgagggtgtg ggtgacaatg tctctacctt  11760
ttgggaatct cacccctcat ttcaaattca tggtaggaat cactttgcct gagaaaatga  11820
ggcctggatc tctattgtcc gctttgtttt tctctgcaga accattataa agtgaatgcc  11880
tggcctgccc tgctttaggc cagcaatgca tatcactgct gggtgctgtg aacacaatcc  11940
ggggtgtaat cttgggggac tgacctctag aactttcttt tctggactat ttttatcatc  12000
tgaaagatag aggagtcgct tcattcattc cagtagtagg tatttgttga gcacctacta  12060
tattccaggt cctgtgttgg gtgtcaggga cacagcaatg aataagatag atgactgctc  12120
tgcctctaca ctgctcaaaa tctaatgagg gaggcacacc ttatatgaag agtcacggaa  12180
agacattgca aaggagaaaa atgctaggaa ggagagtggg gggctgtcaa caggtgtaat  12240
gggggtaaac ctgtccggcg gagggaaggt aagcagatgg agcagttagc ctctgtgggg  12300
ccttaggaaa ggagcaattg agggggaagc cctggggtct tgggcatgtc acccctacct  12360
tctccctcta ctctgcaggt cagcataact tggtaatcat ttcctggcct gcagccaggg  12420
ttatcagcat gctgtgtata tggacgtcgt gaagattgga ggctgagggc cctgaccaga  12480
ggagataaga acaggtttgg acaagaagaa tccatcccct ctatgtttat ctcaaaacgg  12540
tagagcaggc tgagtctgga cccagaacaa atccaggaag tagaatccaa gaagcagaga  12600
gatgaatcaa gaatgacact aaggttttgg gcttcattcc atgctacact atctgcccca  12660
tttgacagtg aaggaagcag acgcccagag aagggaagac acctgtctga ggtcacacag  12720
tgggttaata ggagaatgag aacagaacct agaccgctga acttttcccc ttaaccatct  12780
taccctcctc agaagtcaag cctgagcttc caaaaatgaa ggaactcagg tccagggaaa  12840
ctttctgttt tgtctgaggg tgagggatga gataatgatg agtcagggct tcagggaaac  12900
gaacatttac tgattaccta atgtgggggt agatgtggtc cctgctctca gaaagctcaa  12960
agtgtgaatg aattaaagtc aatgtgacca ggcgcggtgg ctcatgccta aaatcccagc  13020
actttgggag gccgaggcag gcagatcacc tgaggtcagg agttcaagac cagcctggtg  13080
aacatggtga aaccccatct cacctaaaaa tacaaaaatt agccaggtgt ggtggtgggc  13140
gcctgtaatc ccagctactc aggaggctga ggcaggagaa tcgcttgaat ccagaaggca  13200
gaagttgcag tgagctgaga tcgcgccact gcactccagc ttgggctaca gagtgagact  13260
tcatctcaaa aaaaataaat aaataaaaca acacaaacaa caacaacaac aaaataaagt  13320
caatgttact tcatttcatg aacaacatca aatttggagg gggccatggg gtattctcca  13380
aggggcaaaa acaggtgatg tccaacagag tgaggcatgg catctctttc aagggccagg  13440
atggagaaag aaatcagtgg attcagctct ggaccccaag tcaaaagcca gaaagacaaa  13500
tcacagattt tgatttgcag ttaagccttt tctcacgagg gccactgtac ggcatccaat  13560
aataataact gctactatta tgataaataa caagcattca ttcatttgat gtcttgtctg  13620
gagaaacggg ataaaacatt atccacagac atagagactg ttgcagaatg aagggagggc  13680
tttcctgttt tcttttcttt ttttttctg atggggtctc actatgttgc tcaggctggt  13740
cttgaacccc tgggctcaaa tgatattcct gcctcggctt ccaaaagttc taggattaca  13800
ggcctgagtc accatgcctg gcatcctgtc ttctattaac taccactgtg ctaggcatgg  13860
tgcagaatat ttcactctga cctgatcacg tcactgaaaa ccctgcaaag gctccaattg  13920
ctgaaagcgt ggatgctctg attcctgtct tcttcacctg agtctgcctt cctcttcagc  13980
tgtgtgctct agccatgtgg gcctccccctc tgttccttgc ccaagccgtg ctccttgtgc  14040
```

-continued

```
ctcaggagct tagcaagtgc tgttcccaaa tcccagaaca cgtttccctc acccettagc  14100
ctgctgctta cttaaccatt gcatcccctc agatccctgc atgagcattg cttcttttct  14160
tttttctttt tttttttgag actgtctcgc tgtgtcaccc aggctggagt gcagtggcag  14220
gatcttgact cactgcaacc tctgcctccc aggttcaagt gattctcctg cttcagcctc  14280
ccgagtagct gagattagag gagcatgcca ccacgtcctg ctgatttttt ttttttttgag  14340
atggagtctc gctgtcaccc aggctggagt gcagtggcgt gatcttggct cactgcaacc  14400
tccgcttccc aagttcaagc aattctcaca cctcagcctc ccaagtagct gggattacag  14460
gcacccacca tcatgcccag ctaatttttg tatttgtgta gagatggggt ttcaccatgt  14520
tggccaggct tgtcttgaac tcctgacctc aagtgatctg ccgcctcagc ctcccaaaac  14580
gtgacttact tcttcaggaa agttttctca ggccccatga cctaattaat tttcatttta  14640
taataccctg tactcgtcat agcatttaat acaattgtag gccggccagg tgtggtggct  14700
cacacctgta atcccagcac tttgggaggc caaggcgggt ggatcacaag gtcaggagtt  14760
tgagaccagc ctgatcaaca tggagacacc ccatctctac taaaaataca agattagcca  14820
ggagtggtgg cacacgcctg taatcccagc tacttgggag gctgaggcag gagaatcact  14880
tgaacccggg aggcagaggt tgcggtgagc caagatcgag ccactgcact ccagcctagg  14940
ggatagaaca agactctgtc tccaaaaaaa aaaaaaaaaa aaaaagtaca attgtaatct  15000
tacaactatt agtgagataa atttgatgaa tgtctgtttc ctctactcag ttgtagttcc  15060
gggagggcag taaaaggact ttgcattttt cttctcagct ttattcctta ccacagtgcc  15120
tggcacagag ttcagtgaat tcaataattc aataaatatg cacaccctgg ccaggcgtgg  15180
tggctcacgc ctataatccc aacactttgg gaggcaaagg cgggtggatc acctgaggtc  15240
gggagtttga gactagcctg accaacacag agaaatgttg tctctgctaa aaatacaaag  15300
ttagccaggc ttggtggctc atgcctgtaa tcccagctac tggggaggct gaggcaggag  15360
aatcacttga atccaggagg cagaggttga ggtgagctga gatcgcgcta ttgcactcca  15420
gtctgggcaa caagagcgaa actctgtctc aaaaaaaatt aaagaaatat gcacacccct  15480
cctccaccaa tgacagaaac agggaaggaa attccgtgct ggttctgcag gggatagaga  15540
gagatggatg aactccctcc atcccaatcc cgtttgggcc ttgtttatcc cacgtgtgaa  15600
atggagatta gactccttcc tacttcacaa gggtgttgtg agagtcaaag tgtaatacac  15660
ataaaatgtt tagctcaagt gcctgagcac atggtaggct ctcagcagct attatgaaat  15720
tgcttattta ataataatta atgaatggct gggtgcggtg gctcacacct ctaatcccag  15780
cactttggga ggccgaagcg catggatcca gccgggccaa cacggtgaaa tctcgtctct  15840
actaaaaaat acaaaaatta gccaggaatg gtggcgggtg cctgtagtcc cagctacttg  15900
ggaggctgag gcaggagaat cgcttgaacc tgggaggcgg aggttgctat gagctgagat  15960
cgcaccactg cactccagcc tgggtgacag agcaagactg tctcaataat aataataata  16020
ataataataa caataataaa taatgaatat gacctggcca ggctctgtgt acttgtctag  16080
ctaggtacat ttaaggaaaa tatttcaatg acccgttttg gggttaaaaa aaggagaata  16140
ggagtctggg tgttcctgtt gaaagtgaaa ggtgaggaac ccactttgca aatgaacgtg  16200
gcctctaatg gcactaccat taggactgaa taccttacaa tggggttctt tcacatacat  16260
gggctctgcg aatccccaca gtcattctgg gaagtaggca tggctattat tattattatt  16320
actccaatta gacaagggag atgcttgagg ctcgaactcc ttagcatagc acacacagag  16380
```

-continued

```
tgggggtcac agggagatgg gggtcgagtg gaggatctag tcccagctct gccagctgta  16440
ggccccaggc aaaccacttc acttttctga acctcatttt ccttcactat aaggagaggc  16500
actagatact agatactaga ggtggactgg gcttgcctga gaggctggga gaccaaggga  16560
cagacaggac tatttggcag acactgagga tggaaggaga acatttatcc cacacctgcc  16620
aagagctgag gcagccagga aagcagtgca gcatatactc attaataata atatataggc  16680
caggcgcagt ggctcacacc tgtaatccca gcactttggg aagccgaggc gggcggatca  16740
tgaggtcagg agatcgagac tatcctggcc aacatggtga aacccccctct ctactaaagt  16800
acaaaaaaaa aattagctcg gcgtagtggc acccgcctgt aatcccagct actcgggagg  16860
ctgaggcagg ggaatctctt gaaacgggga ggcagaggtt gcagtgagcc gagatcgcac  16920
cactgcactc cagctctggt gacggagtga gaccctgtct caaaaaaaaa aatgtgtata  16980
tatatatata aaatttaaca agcattttta tggtattttc catgtggtag gcactgttca  17040
aaatgcctta catgtattaa ctcataattc tcaggaaacc cctaggaagt aggaaaaatg  17100
atctctattt taaagatgcg ctttggtagt ctgaggtggg aggatcactt agggtcagga  17160
gtttgagacc agcctggcca acatggtgaa accctgtctc cactaaaaag acgaaaatta  17220
gcccagtgtg gtggcccgcg cctgtaattc caactacgcg ggaggctgag gaaggaagaa  17280
gaatcacttg aacctgggag gcagagtttg cagtgagtca aggtcgcacc actgaactcc  17340
agcctgggca acagagtgag actctgtctc aaaaaaataa taaaataaaa taaaaataaa  17400
gatgaagaaa ttgtggcata aagaggtaat aacacatgct cacaaaaatt tctatcatac  17460
attaagtgtc tagtatgcag caggcactgt gctaagcact ttacatttgt tattaaaaac  17520
ctgtagctgc tctaagaact gaaaggtcat ggtataattt aacagaaatg taagttaact  17580
ataacatgtg tgtcagccca tcagtgtgtt gatttattag cataagagtg tctaggatct  17640
atatatgtac atgtggcttt tctttataat gttattttat tttagagatg ggggtcacac  17700
tgtgttgccc agtctggtct caaacgcttg ggctcaagcg atactcctac cttggcctct  17760
caaagtgcta ggattccaga caggagtcac cgtgcctggc ccttaatttt ctgaagaata  17820
aatttttatt taatataata tctaatttat agaagagttg taagtctagt tcaaggaact  17880
cctggatgtc ttttaaacca cattatctat ttggttcata ttttgtcctc tttgctttag  17940
caatctccct gacccataca tatgcatatt atttttctga attatttaag agtaaattgg  18000
tgatactgtg tctttttttta ttttttttct ttgagacagg gccttgctct gtcgcccagg  18060
ctggagtgca gtggcaggat catggttcac ttgtagcctc catctcccag gctcaaggga  18120
tcctcccacc ttagcctcct gagtagctgg gactacaggc acaggctacc atgcctggct  18180
aatttttttg atctttagta aagacaggca acactttgtt gcccaggctg cttctgaact  18240
taactcaaag gatcctcctg ccttggcctt tcaaagttct ggaattacag gcgtgagcca  18300
caatgcccgg ctgcctcttc taaataattt ggtgttcatc tcctaagagc aaggacactc  18360
tcttatctat gtgttgttgc tttgggtgat gaaacaaatg gtctgtaatc acagaatatg  18420
tatcccctta atgaatattc ctcaccttca tgattataat gattgtgatc tgttaaaaca  18480
caattttttt tttttgagac ggagtctcgc tctgtcgccc aggctggagt gctggagtgc  18540
agtggcacga tatcggctca ctgcaagctc cgcctcctgg gttcacgcca ttctcctgcc  18600
tcagcctcct gagtagctgg gactacaggc gcctgccact gtgcccggct aattttttgt  18660
attttttagt agagacggtg tttcacagtg ttagccagga tggtctcaat ctcctgacct  18720
cgtgatctgc ccacattggc ctcccagagt gctgggatta caggtgtgag ccaccacacc  18780
```

-continued

```
cagcctaaaa tacaatttta agtaaacatt gcaaggtgac cacacagtag gtgctcagtc  18840
aaggtttgat tacacagctg actcactctg tgtaatccct tccttctctg ggcctcagtc  18900
tcatctgaaa tggggccccc agttctcctt gcctcacatc ctcatgggtg gcagtgaggc  18960
ttaggtgaga tgatgaattt gatcaatgca cttttaaaat tgtaaagaaa ggctggacgg  19020
cagtagcctg taatcccatc actttgggag gccaaggcgg gtggatcatg aggtcaggag  19080
ttccagacca gcctggccaa tgtggtgaaa acctgtctct agtcaaaaac aaacaaacaa  19140
acaaacaaaa tttagccagg catggtggca catgcctgta atcccagcta ctcacgaggc  19200
tgaggcagga gaattgcttg aacttgggag gcggaagttg cagtgagctg agatcacacc  19260
actgcactcc agcctgggtg gcagagcaag actctgtctc aaaaaaagaa ctgtaaagaa  19320
gttctgtggg ggccgggcgt ggtggctcat gcctgtaatc ccagcacttt gggaggccga  19380
ggtgggcgga tcacgaggtc aggagatcga gaccatcctg gctaacacgg tgaaaccctg  19440
tctctactaa aaatacaaaa aaattagcca ggcgtggtgg tgggcgcctg tggtcccacc  19500
taatcgggag gctgaggcag gagaatggtg tgaacccggg aggcggagct tgcagtgagc  19560
caaaattgag ccattgcaca ccagcctggg caacagaatg agactctgtt tcaaaaaaaa  19620
aaaaagaagt tctatgccct ggggagatat caggccattt ttctacccat tctcccaaca  19680
ttcctgctcc ttcccaagtg atgggactga gacaacctgc tcacccaacc ttctgctttt  19740
tcttcctggg tttaggtggt cccagaaaat ccagcccttt ggcatctgaa ctgggcctcc  19800
ccggagttcc cactggtggc acaggcatcc tctgccacaa ttcaggacac agggtttagc  19860
tgtgggttcc tagcttaggg ttcagacaca gaggcccagg agccctcccc atagacctgt  19920
ttatttattt tatttttatt tttattttta tgagatggag tctccctctg ttgcccaggc  19980
tggagtgcag tggagtgatc tcggctcact gcaacctcca catcccaggt tcaagctatt  20040
ctcctgcctc agcctcccga gtagctgaga ttacaggcgc ccgccactac gcccggctaa  20100
tttttgtat ttttagtaga gatggggttt cgccatgttg gccaggctgg tctcgaactc  20160
ccgaccttgt gatttgcctg cctcagcctc ccaaagtgct gggattacag gcgtgggcca  20220
ccacgcccag cttcaggcct gtttatatat gctgttttct ttccaacaac aatatgcccc  20280
aggctgggca tggtggctca tgcttgtaat cccagcactt tgggaggctg aggtgggtag  20340
atcacctgag gtcaggagtt ccacaccagc ctggccaaca tggcgaaacc ccgtctctac  20400
taaaaataca aaaaattagc cggg catggt ggcaggcgct tgtaatccga gctacttggg  20460
aggctgaggc aggagactga acccaggagg cagaggttgc agtgagccga gatcgcgcca  20520
ttgcactcag cctgggtgac agattgagac tctgtctcaa aacaaaacaa aacaaaacaa  20580
aacaaaacaa aacaaaagat gtgccccaga tggtggagac aagctacagg ccctctccag  20640
agagaccccc ttcttcctgc accaatggac tggacaccaa tttgtatgtt tgtgccagaa  20700
agccaaggag tcctgctgtt cattcacaag aggccctgct gggcgccagg cagggcgctg  20760
agctgagccc atttctctct ggtatctccc tagcctctcc ccaagctctt aggtagaata  20820
agatccagta agtatagaca cttttgcggc atccaaagaa ttaacccttc actcatttac  20880
tcacctggta agagatacag ggagaaagct gtggagtaac tcagggagct ggagcccata  20940
aggcaggaaa cccatgccca ttcattcaac aaacttgtat tgagctcctt tttgatgcat  21000
cccccatcca ctataagcac ttggagaccc acacagatgt ggtttctgct cccatagtgt  21060
gtgtgtgtgt gtgtgtgtgt gtgtgtgtgt gtgtgtgtgt gtgtgtaggg gaatgtaaac  21120
```

-continued

```
aggaaaacag atatgcaaaa caatttcaga tcgcggtaag tgctaggaac agaatgaaat  21180
aggataggag tgatggacag gggagacttc aggtggagtc atcgggaaaa gcctctccat  21240
aaagtgacct tctgggagaa aaccgagggg taagaatctg gtcctgcaaa gatctgggca  21300
agaaatgtcc aggtgtaggg aacagcgagg tcaaagtcac catcacaagg aaacgcttgg  21360
tgtattgagg agcagcagag aagttggagt gaaggcagag aggggttaag gtagcatata  21420
ccttgaaagg ggaggctcct ataggggctt acaggcgata taaatcattc attcattcaa  21480
cacatattta ttgagcatct actgagatcc tgtccttagt ttactgcgtg gagacagacc  21540
acaagcaggt aaacaagcaa atatgtaagt cccaggtcag ataaatttta ggaagtgctg  21600
ttttccagtg gttcaatggt catcccaggg cagaggtggg gagacctgct gagggcggct  21660
tctccctcag tcagtccatg cctgcagggt ctggaaccca ggtagccaga gacccgctgg  21720
tcttctttcc cctcccctgc cctcccctcc cttcaagatg gctgacaaag gccgggctgg  21780
gtggaaggaa gggaggaagg gcgaggcaga gggtccaaag caggatgaca ggcaggggca  21840
ccgcggcgcc ccggtggcac tgcggctgga ggtgggggtt aaagcggaga ctctggtgct  21900
gtgtgactac agtgggggcc ctgccctctc tgagccccg cctccaggcc tgtgtgtgtg  21960
tctccgttcg ggttgaaagg agcccgggaa aaaggcccca gaaggagtct ggttttggac  22020
gtctgacccc accccctcccg cttagggctt ctgatccccc agggtgattt cactggcccg  22080
gggttgggag ggcagggggc cagggggcgg agcccgcgga gaggggcgga ggggaggctc  22140
cgagcgattt caaatttccc tcgtccccgc ccccccgttc cccccgcgcc cgggcgggga  22200
tctgagtggc tgcggcgggg gcacccccgg gcgggggcgg ggcaagagcc gggccggggc  22260
tacaagggga gtcggcaccg ccccctcccc acccactccc gctgccccgt ccggcccgcg  22320
ccgcttcctc gcagcagctg ctcccggctc cgcggccgca gcccgcgtgg acgctccgag  22380
cgccccccga cggacgggac cggctccctg gcggtcgggc gagcgggcgg caacgctgcc  22440
cggccggcag cgctggggtt aagtggccca agtaaaccta gctcggcgat cggcgccgga  22500
gattcgcgag cccagcgccc tgcacggccg ccagccggcc tcccgccagc cagccccgac  22560
ccgcggctcc gccgcccagc cgcgccccag ccagccctgc ggcaggtgag cgccccgggg  22620
ccccggggag gctcggccgc cagctgcttc gagggctgct aggggagggg acggcggggg  22680
ctcccgaagc tgccggggag agaccctctc cagggacctc ccgaggaggg gctctcgccg  22740
ggttggagac ccggctgggt ttgcggggtg aggaaacgtc cacggaccct gcttggggtg  22800
gaacggggac agcgggtggg acgcggggga catacgtctg acggggaccg gagatactag  22860
aggaagggac gcgtctgctg cctccaggag cccgaagagg agagaagctt gctcgcaggg  22920
agggggacgc gctggcttcc cggggtccag actcgaggag gaggaggtgc ccgtcgagag  22980
catgaacagg ggctttgctc atgggcaggg ggtgtaatta cctggcctct gccttgggaa  23040
aagttaaggg gcagaggagg tgaggagggg tttctgccat gcaggtgggc gtccgcccct  23100
tgcaactggg atgtggggtc ttcaggcgag gcgctgtccc ttcccccaat cccagcttta  23160
ggaaagagct cgtgagtgtg ggcttagact cgcgcgggct ggggtgtgcg ccgtggaggg  23220
cgtgaggcag agggcgacct cccggggtgc tcctgagctg agccatcaag cgcggggagc  23280
agcggggctg ccctctgcct gtgcacacct ggcccgggag gagccggccg gaggggcggc  23340
gcctccctgt cccggccacg ccgcctaccc tggggtctta ccttccattc ttagcctaac  23400
tcccgtgtgc ggctggcccc acttcccaga ctcgcacact aaggcctcaa aacctctagc  23460
accagctcct ggaagataag cttcccggct cgtggttgca tggggagggt gtattgagct  23520
```

-continued

```
ccactttatc ggggagaaag tggaagcgga gaaagaccta acaagttgta agactgcgct  23580
gcccttgggc ccaggcttcc cgctggagga tctcacctgt ggatggagtt ccgagcccag  23640
gtcttgcccg cgcctccagc tttccctgct cccttttcct cccctggtct aggagagagg  23700
ctcgctgggc ctccgtgttt ccaccctccc ccgaagctgg gaagtgtttg aattaaaggg  23760
aattaagggc agagtatgaa ctttgagttg cctcctgagt tctggatgcg gtgggttgtg  23820
gcagacgggt ggcagttttt gggaaacagc tgttatctcc tctaccaggc ctgctggggc  23880
ttcttgttca cccaccttgg aaacgccagg tgcggacttg atttttccag agttgagatg  23940
atggtactta gtttataggg ttggtataca gtaagcactc aatacatgtt tgccattgtt  24000
ggaatcacta gctagcacac gggctaagca agcttccttc cttaaggaag catagttctt  24060
agttcatcat gtgtttaaac cctgtctcgc caagttcatt gctctccgtg ccttaattat  24120
tacatctgtg aattagcaat agtcctacta atagggttgt gtaaggatga aaccagtctt  24180
atgcgtgaat taacctcttc agcccttgat cttcctcaga tgtttaggca taatagcctc  24240
taccacattg ggcctgggta aagaggcagt gggatagtgc ctgtgtaggg tcagcacatg  24300
gtgagtgttg atgtctgtac ttaataacga atagcccctc attttagggt ggccattcct  24360
gagatttggg gatggaggga ggcacccctg ccagcctctc cttttcctgc cttcatgaag  24420
gcagctctga aagcttttct caatcattgt ccacgattag ggagttggca ggaagaaccg  24480
cctttgttcc ctttcgaacg gagtcttggt tttgttttat aagggttggg gccgttttta  24540
aagccctccc ggccacgcat gggggcctac tgcaaaggtg taattgcaga actaagtgag  24600
atcctttacc ttttcccatt ggggtggaga gtgctgagac aaagggacaa ggactggggc  24660
cagtggcatc ctgctcttaa agtcatagac ataacccccca ccccttgcaa aggatggggg  24720
gaggggaaga cggtagctgg gagctgcagg ggtctaaggg aggagcaagg gaggtggggt  24780
tgagaggctg cttccttccc ttcctccagc cacgtggggc ctgtgatcca gaggcgcctg  24840
tcgcccctca ttattgcagc cccatggacc tgctgccagt gggggcttgg gcaagttctt  24900
caaggaaaac ttaccttggg attccttttc ctagaccagc tcttatgccg gctgcctcac  24960
ctccaggctc agacgccttt tccagtttca gctaaatgtg aaacttttca gaggtatgag  25020
gttgtgtgct cttcctcaca caccagtcct tagcccaggc acatactact aattgagtgg  25080
agtttttctt tttaaatcat gaattttcag gatgatttcc agtttcacgg aggaccaggg  25140
ctggtgaagt atggaattca tttcatgtgc aggccactct tgtaaaaaga gactgagcag  25200
atatgtctcc cctttgttgg ggggctcatg ttctcactgg gaccctttta caggtgatag  25260
aactgaggct ctggaagata caggtactat tacgtcttgg tggtgagcat tttctttctc  25320
ttttttttctt tctttttttt ttttttgaga cagttttgct ttgtcaccca ggctggagtg  25380
cagtggtgtg atctcagctc actgcaacct ctgcctcccg ggttcaagca attctcctgc  25440
ctcaaccttc cgagtagctg ggattacatg cgcacaccac cacgcctggc taatttttgt  25500
atttttaatt gagacggggt ttcatcatgt tggcaaggcc ggtctcaaac tcctgacctc  25560
aagtgattca cccgcctcgg cttcccaaag tgttgggatt gtaggcgtgg ctgttacacc  25620
cggctgcttt ttatttattt atttatttat tttttctttt tttctttttt tttttttttg  25680
agacggagtc tggctctgtc tcccaggctg gagtgcagtg gcgcgatctc cgctcactgc  25740
aagctccgcc cctcgggttc atgccattct cctgcctcag cctcccaagt agctgggact  25800
acaggcgccg gccaccatgc ctggctaatt ttttttgtat ttttagtaga gacggggttt  25860
```

-continued

```
caccgtgttc gccaggatgg tctcaatctc ctgacctcct gatccacccg ccttggcctc  25920
ccaaagtgct gagattacag gcgtgagcca ctgtgcctgg ctatgctttt atatgggtgc  25980
tgcctcacac ccataatccc agcacatggg agactgaggc tggaggatca cttaaggcca  26040
ggagttcaag accagcctgg ccaacgtgat aaaaccgtga ctctacaaaa aatacaaaaa  26100
gtagccaggc gtgtttgtgc atgcctgtaa tccgtgctac tgggaggctg aggcacgaga  26160
attgcttgaa cctaggaggt ggaggttgca gtgagctgag atcctgccac tgttctccag  26220
cctgggcgac agaccgagac cctgtctcta tgtgtatata tctacgtaga tatagatagc  26280
ttaagttttt tttttataa ggacaaggtc ttgctgtgtt gccaaggcta accttgaaag  26340
cctgggtcca acgatccttc tgcctcagcc ttccaaaggc ttgggattac aggtgtgagc  26400
taccacacat ggcctctagg tcacttttca ctcagatttt ttcattcatt caaacaaaat  26460
agcataggta tgacctctgc tctagtttat tttttattta cttatttatt tatattttga  26520
gacagtctcg ctctgttgcc caggttggag cgcagtggcg gttgctcact gcaacctctg  26580
cctcccaggt tcaagcaatt ctcatgcctc aacttcccga gtagctgaga ctacaggcat  26640
gcaccaccat gcctggccaa tttttgtttt gtaaagatgg ggtttcacct cattgcccaa  26700
gctagtctcc tgggctcaag caatctatcc tcctcatcct ctcaaagtgc tgggattata  26760
gacatgagcc aacacaccca aattcaattt tttttaatt attttattt tttgagatgg  26820
agtttcgctc ttgtcgccca ggttggagtg caatggcgtg gtctcggctc actgcaacct  26880
ttgcttcccg agttcaagtg attctcctgc gtcagcctcc tgagtacctg ggactacggg  26940
cgtggtggtg catgcccggc taattctgta tttttttagt agagatgggg tttctccatg  27000
ttggtcaggc tggtctcgaa ctcccaacct caggtgatct gcccacctca gcctccctcc  27060
caaagtgctg ggattatagg cgtgagccac cgtgcctggc ccaaattcaa tttttaatgg  27120
ggtccttgtc ttgttttatg ggtacaacat catttatctg cctgagaata ttgtagggtt  27180
tagtgttccc tcgtgttccc gccaatatta agggatactc aattttccag taccttgccc  27240
tgtaggtctg gctacagggc caggagactg gtgaggtctc agtctggtat ctgttcctcc  27300
acttgtccca gtctgtaagc tcttgtgtgt gttttttttt taattatttc ttttgagaca  27360
agtctcgcat tgtcacccag gctggagtgc agtggtgcga tcatagctca ctgcagcctt  27420
gaactcctgg gctcattcca gtatcctccc acttcagtct ccaaagtagc tgggacctta  27480
gtcacgtgcc accacgccca tctaattttt aaaattgttt gtagaaacat taaagtctca  27540
ctatgttgcc ccagctggtc tcaaactcct cggctcaagc aatcctgcct cagtctccga  27600
aagtgctggg actacaggtg tgagcctgtg cgcccagctg tctcatgttc ttgtccagag  27660
cctcagcctg catgtctgaa gaagagtggt tgtctccaga gcagcaggct gagggagggg  27720
acttgggagt caagggtcta actcttcctt tggaagaagg cctctctctt agtaggcttt  27780
tctggattcc agcagcattt atgtcctgtt gtatgtgtgt gttctggggc cagagctggg  27840
gctggaaccc aggctgccac tgggccccag ctcctgcaga agtgctgatg cctttgtagg  27900
gcgtttgctg cagccagaac agtgatgggc cctggcagca tggcaacatg gctcactctg  27960
ttgcttaggc tggagtgcag tggtgcgatc acagcttact gcagccttga actcctgggt  28020
caagtgatcc tctcacctca gtcacctcct gagtagctag gactacaggt gagagccacc  28080
aggcttggct aattttaatt tttttttttt ttttttgga gatggagttt cactcttgtc  28140
gcccaggctg gagtgcaatg gcgggatctc ggctcaccac aacccccgct tcccgggttc  28200
aagcaattct gactcagcct cccgagtagc tgggattaca ggcatgcacc accattcccg  28260
```

-continued

```
actaattttg tatttttagt agagatggtg tttctccatg ttggtcaggc tggtctcgaa  28320
ttccccacct caggtgatcc acccgcctcg gcctaccaaa gtgctaggat tacaggcatg  28380
agcctctgtg cctggctaat tttaaaattt tttatagaga taggctctcg gtatgttgcc  28440
caggctggtc tcaaattcct aggctcaagt gtaatcccaa agtgctggga ttacaggtgt  28500
gagccaccat gcctggtccc ttgcctgcct ttgattccta attactatca tggttcctga  28560
agcctagtag aactcatctg aatggataca ggaggctctg gagatgggaa tggggaggca  28620
ctaactaggg tcccactgag ccagctacag gcccccgctc ttttgtgaaa agatggttgt  28680
gatgaagact taagtgttca ttatattcca ggcaagccat tttctctgac tctgggagtt  28740
gtttggcacc atgggtaagg aagccctacc ccgacaatgg cactggagga agagcctcaa  28800
gcttaggcac tggctttccc aagtccttgg gtgaatttgc aaacctcacc tgtgtcctca  28860
tgttgcccta ggatgttaca tgctgagctg taagcaggat gctgaattag gggaattgct  28920
cagtactaaa tatgattgtt actacaacca caaaactagc aaggagtaga actgcattaa  28980
aacactgttg caaatttttt tattttttga gacggagtct tgctctgtcg cccaggctgg  29040
agtgcagtgg cgagatctcg gctcactgca agctctgcct tccgggttca cgccattctc  29100
ctgcctcagc ctccctagta gtagctggga ctacaggcgc ccgccacctt gcccggctaa  29160
tttttgtat ttttagtaga gacggggttt caccatgttc gccaggatgg tcttgatctc  29220
ctgacctcgt gatctgcccg cctcggcctc ccaaagtact gggattacag gcgtgagcca  29280
ccatgccggg cccactgttg caaatttctt tccaaaacct ctgccagcac atggctgaac  29340
ccacagaact ggcaggacac acaagatgcg ctgggttaag atgctttggt gctctctgtg  29400
ggttcagctg actgttttac aggcctgctt cttgaccgtt ggggtgggca gatctgagcc  29460
cccactaggt aattgtggac agtttttgaa aagtggtttt tatgtgagat catgggcttc  29520
ttttaaagcc atttgtatat atgcagttcc cttatctgca ggccttaatt ttgacatttc  29580
tgttttcctt ctcgagattt gttttctgtc cctgcagtac tgctttttcc agaatgtcat  29640
ataaatggaa tcatacatta ttattatttt tgagacagca tctcactctg ttgcccaggc  29700
tggagtgcag tggcacgatt tggcacattg caacttccgc ctcctgaatt caagcaggaa  29760
ccatacatta tatagccctt cgagtctggg ttcttttact tattgtgaga tatttgagat  29820
ttatttgtgt tatgacacgt actagcagtt atttcttact ttttaaaaaa ttttttaaga  29880
caggtctctg gagttcagta ctacaatcac agctcactgt agcctcaact ccaatgctcc  29940
agcagtcctc ccactgcagc ccccactgcc cagtagcttc gactacaggc acttgtgcac  30000
cactatgctc agttaattta aaaaaaaatt atttttgaga cagggtcttg ctctgtcact  30060
caggctagag tgcaatggca tgatctcagc tcactgcaac ctccacctcc tgggttcaaa  30120
cgattcttct gcatcagcct cctgagtagc tggaattaca ggtgcccgcc acctcatcag  30180
gctagttttt gtaatttttt tttttttctg aggcagagtt tttcactctt gttgcctagg  30240
ctggaatgca atggtgtgat ctcagctcac cgcaacctct gcctcccagg ttcaagcgat  30300
tctcctgcct cagcctccca agtagctggg attacaggca tgtgccacca ccaccagcta  30360
atttttgttg gtttgtttgt tgttgttgtt ttagtagaga tggggtttct ccatgttgat  30420
caggctggtc tcgaactccc gacctcaggt gagccgccca ccttggcctc ccaaagtgct  30480
ggaattatag gcttgagcca ccatgctccg ccttactttt tttttttttt tccttttgag  30540
acagagtttc gctctttgcc caggctggag tgcaatggca tgatcttggt tcaccacaac  30600
```

-continued

```
ctccgcctcc cgggttcaag tgattctctt gcctcagcct cctgagtagc tgggattaca  30660
ggcatgtgcc accatgcccg gctaattttg tatttttagt ggaaacgggg tttctccgtg  30720
ttggtcaggc tggtcttgaa cccctgacct cgggtgatct gcctgcctca gcctcccaaa  30780
gtgctgggat tacaggcatg agccaccatg cccggcctaa attttttttt tgtaatgttg  30840
gggtctcact ttgttgccca ggctgatctt gaactcctgg gctcaagcaa tcctcctgcc  30900
taggcctccc acattgctgg ggttacaggc atgagccact gtccctggca tctttttttt  30960
tgctgtgaat ataacatttc tagcttttct ttgtgttgtg atttttacct tttcaataca  31020
tagtgtgcaa ggacatattt tctggttacg atagaaataa tttatttgaa agtctatcca  31080
tgttgaaaca actaaaaatg ctgtgccttt atctgttggt agaagaacta agctccctta  31140
aagaaatcta gagagcagaa gagaacagga aatgagagac cacaaactaa agggagaaaa  31200
tgaacttttc aataaggctt gcaggcttgc tctagcagtt gtagtgatta aaagtagtgg  31260
caatggctgg gtgcagtggc tcacacctgt aatcccagca ctttgggagg ctgaggtggg  31320
cggatcgcct gaggtcagga gttcgagacc agcctggcca gcatactgaa accctatctc  31380
tactaaaaat acaaaaatta gccgggcgtg gtggcatgtg cctgtaatcc caaggaagct  31440
gaggcaggag aatcacttga acccaggagg tggaggggtt acagtgaccc gagatcatgc  31500
cattgcactc cagcctgggc aacagagcaa gaccgcatct caaaaaaaaa aaaaaaaaag  31560
gagtggtaaa ggataaatac caaacaaaag tgagcctcaa aacatattac atatatatgg  31620
gaagttcaaa taagagatag agttgggatg tattcatagg tgtctggctt tacttacggg  31680
gaaaaatatt aggtccctat ctcataccat atacaaataa tcaaataatt atgttgatta  31740
aacctgagtg gcctaattca aataaatgtt tctcagacag gcgagttatg ttttccgatt  31800
gtaaaagtta catgggctta aggtagttac cccccaaacc ttccttctga gtatgaattt  31860
ttatagttag agaagaaatg ctgcagagaa atggcttaaa catcaataat tgatgttgca  31920
ttatgcaggt ttcttgtttt cactttacat aactttgtct aacaataagt actgcactct  31980
ttgcccccta ttgtggaagc aggtaattta gtcaaccagt cctcttgacc gtgatttgat  32040
tgcagtgttt gctatgacaa atgggactgc agcaaccccc ttgcacagag gccttggcga  32100
gagctttgaa ctgggtggtt tctgagcagt agaatcctgt gtaacaggat atagacatta  32160
ggcattttag atgacacagt gaagattact atcccaaaga ctgaaccagt atccctgctg  32220
tgtaggtatt taggcttaag atgactaaat actgtgtaga taggtagact tgagatttaa  32280
ggcgttctta gttgaagcca caggtgcagc ctgctgtgag ggagggggca aggttgaggg  32340
ggtctctttc cagaatattg acctcctttg ccccccttggg aggggacagg gctgttggct  32400
ctgattttgc caaggggtag gtggccacag gaattgggca tagcagtgcc taggattctg  32460
ctccaatgct gcccctcatt ctctgagtta ccattgacca ctccttgggg ctgccacacc  32520
cttcaagggg ttctcaaagt ggatataggg gaaggggctg ggtgtttgtg atttctgtat  32580
aaagggcaaa aagtttagac tctaaagtta ctgtcatatc ttttcagatc tttatggtcc  32640
tagttttttt tttcctgtta cttatctaaa aggtaatgac attattttat tccagtgcgt  32700
tgacaaacat ctgagtatat tttggtgtca tgcacagtct gcagatagcc acttgtctgg  32760
tttttccctg tttggacaca tttttttttt tttttttga gatggagttt cgctcttgtt  32820
gcccaggcta gagtgcaatg gcacgatccc gagtagctgg gattacaggc atgtgccacc  32880
accccggcta attttgtatt tttagtagag agcggggttt ctccatgttg gtcaggctgg  32940
tcttgaactc ccgacctcat gtaatccgcc ctcctcggcc tcccaaagtg ctgggatcac  33000
```

-continued agacgtgagc cactgtgcct ggcttttttt tttttgaga gggagcctga gcctgtactg 33060
ttgcccaggc tggagtgcag tggctcactg cgacgtccac ctcccgggtt caagcgattc 33120
tcctgcctca gcctcctgag tagctgggac tataggtgtg tgccaccacg cctagtttat 33180
tttttgtatg gacacactct tctgataatt ctgcttacta tgccaagggc ccagcttcta 33240
ctgtaggatg acagtggtac atgtactcat gacctagagg cactgagcaa ttccccaaac 33300
gcattctgaa ttgtggaggg tgatggggtg gatacttctt gattggccct gtggtgtggt 33360
gctgtggtgg gtagccagat ggcacatgag aataagtgac ttcaggtatc atgactgtgt 33420
catctatgta ggggtccttg gtaccaactt cccagtgaat tgggtgggtt actttatttc 33480
acagattata aaactggggt ttgagagaaa tattgggctt tttttttttt tttttataac 33540
agggtcttgt gctgtcactg ggcctagagt gcagtggcat gacgatagct ttactgcagc 33600
ctcaacttcc gaggcttagg tgatcattcc ccatcagcct ccgaggaggt gggactacag 33660
gcgagtagct aggactacag gggcaggccg acacattcag ctaattttaa gaaatatttt 33720
aatagagaag aggttttgct gtgttgccca ggctggcgtt gaactcctga gcccaagctc 33780
aagccttggc ctcctaaagt ggtggtatta acaggcatga gccactgcgc ccggcagtgg 33840
tttttttttt tttttttttt ttttttacgc tttcctgtaa atctgatgtt ttctggaatt 33900
tagggtaagt tccttatcag acagagcaaa agcacagtac tgggaccttg tgttctgtca 33960
tgtgttctgc tgccgccgcc agtgtggaca gcctgagtct ggcccccttt cctttggatg 34020
tgctgtccct gctgcctgga tccttcccgc tctctacttc acctaggtgt ggtgtccctc 34080
cctgggctta cttactgcat tgttttatgg tgtctttttt ttcttttttt tttgagacgg 34140
agtctcgctc tgtcacctag gctggagtgc agtggtgcta tctccgctca ctgcaagctc 34200
tgcctcccag gttcacacca ttctcctgcc tcagcctccg gagtagctgg gactacaggt 34260
gctcaccacc atgcccggct aattttttgt gtttttagta gagacggggt ttcatcatgt 34320
tagccaggat ggtctcgagc tcctgacctc gtgatctgcc cacgtcggcc tcccaaagtg 34380
ctgggattac agacctgagc caccgcgcct ggcctttttt tttttttttt ttttttagat 34440
tcaagaagta catgtgcttg tttgttgcat gggtttatta cttactggtg gggattgggc 34500
ttctggtgta tccattaccg aaagagtgaa cgttgtacct gataggtgat ttttcaaccc 34560
ttgctccttc ccatcctccc gtctttttgg ggtctcccat gtcttgtctt gtcttgtctt 34620
gtcttttttc ttttctattt tgagatggag tctccccctt gtcgcccagg ctggagtaca 34680
gtggcacgat ctcaacctca ctgcaacccc cgcctcccgg gttcaagtga ttatcctgcc 34740
cagcctcctg agtagctggg attacatgcg cccaccacca cgaccggcta attttttttt 34800
gtatttttag tagagactgg ttacaccatg ttggtcaggc tggtctcgaa ctcctggcct 34860
caagtgatca acccgcttca gcctcccaaa gtgctgggat tacaagcgtg agccaccgcg 34920
cctggcctaa tttttttatt tttagtagag atggggtttc accatgttgg ccaggctggt 34980
cttgaactcc tgacctcggg tggtccacct gcctcagcct cccgaagtgc tgggattaca 35040
ggcttgagcc actgcacctg gccctagatt tctctaacat aggctgtgga ggtggaattt 35100
ttatttattt tttctttaaa tcaatactct ccactgaatg taggatttta gtttttaatt 35160
ttttactgca ccccaggggt tggggcagat accaaagtga cccccccttcc tgcattgtga 35220
ggtttaatta atgcaattaa catttacgaa gtgctctgaa acagctctgc tgctggtatc 35280
agcctggagg aagtgagtga catcagttct cagcattact gctgggttgg ggcgagtccc 35340

-continued

```
tgagcctcct ctgagtctaa ttgggggttg ccacctaccc ctctgtctgc cacattgcat  35400
ttgagtacat ctgacctggt tcagtcgggg cacaggcacc ctgctgcact aatgaggaag  35460
gcccctcggg gagaagcttg tgggtgggcc cacccagcac tgctgcccac tctgaatcac  35520
acgctggacc ccagcctctg ggaaagggtc agagttcacc tctcatcaca aggttaggca  35580
gccacctcct gtgaagggaa acgctcagct ggtatatcat gtcccagcca cgaagctccc  35640
ttcatccctg ggatgggtga tgcattcatt gttcataact tctgtaattc ttgtctgtct  35700
tgtctcagtt acggcaattc caggcacgtg ccctggattg cctgggcatg agatttggca  35760
ctgccacttc tctgggtgac ttaactcatc tgagtctgtt gaaggcaggg ggataataag  35820
acctgcccca ggatggggtg ggggttaaag gaggtggcag acaggctggg tgcagtggct  35880
cacgcctgta atcccaggcc aaggcgagta gatcacctga ggtcaggagt ttgagaccag  35940
cctggccaac atggtgaaac cacgtctctt ctaaaaatac aaaaattagc caggcatggt  36000
ggtgcaagtc tgtaatccca gctactcggg aggctgaggc aggagaatcg cttgaacccg  36060
ggaggtggag gttgcagtga gccgagatcg cgccactgca ctccagccca ggtgacagag  36120
acttgatctt aaaaaaagaa aaaaaaaaaa aaatccatgg tggtagacag tgttcagcct  36180
acagtaagta gggccctggg aactgttagc tacttaatgt tacagtggca gtgtgggatg  36240
atgcagttct aaatccagca tgtctgccac tctggatagg tcatattaga taaagcagtt  36300
ggcttgtgat gggggccatg ttatctggaa atgccagcct tgaatcatga agtcagtgag  36360
atacatagaa aagaggtggg ggagatttgt atccactggt acacacctga tgctaattta  36420
atttctcttg tcctgattct aagaacatgt agttaaattt gtatgttatt tactttccct  36480
atatattgat caaggaggta gtatgtcagt ctctgtcttg gtttctccat ctgcaaaaca  36540
ggaataacag tacttaccac atttaaaggt taaatgagtt aagataagta aagccaaaac  36600
agtgcctgac acatagtaac actgaaaaaa agatgacctt attgggggga tttttatata  36660
tttatatatg tgggaagaaa ggcctaggag agaagctttt attcctggat tttgagctgt  36720
gggttttgag gtctgagaaa ggaagcagga ggtgtaggga gttggggagg gcttccaggc  36780
tgagagaaca cagcagcaca tgcctcgagg ctagattgtc ttggcctgcg tgtagactga  36840
agcggggtgg gggaggaact gagctgggca tctttagtca tgggtgcagg ttctgaagtt  36900
ggtgtgcgct gtctacacag ctgtggctat aaggcaatga gggtagttaa tttcactaca  36960
aacgtagggt cgtgataaaa acagaaggaa ttttaaatga aatcacattg aattatgcaa  37020
cgagaagaaa gcatatataa gtgctcagct tgctcctggg ggacacccag gtagctagtg  37080
ccatttattg tgggtttttct tcctggactg tctctccagt acccacaggt cttgttctag  37140
gggcttgagg cttttcctga atgttgagat atgggttttg gaaggtgtgc tgcccacacg  37200
ttgggtaggc tggtggccag ttggcactgc tgaggccctg ggggaaggcc cagggtggtt  37260
aatcattgtc agcctgggtc tgtctaggag gtgagactcc tgtctggctt cttgttgacc  37320
cagttagggc ctgtctgagg aatggggttc aatgttgcct gcgaaaccca gcacacatta  37380
gaaccccagg ccctggatga aggcgaagga ggtcacatcc ttcactccag gcctctggtc  37440
tgctaccagc tcctggccac aaacaaaccc tgtgtgtcct ccccccagag cactttgggg  37500
aggtggaccc tcctggagac accaggtaca ccaggtagcc ccacctccca ctctatgcca  37560
ggcccactag gttacttagt tcactgattt ggcctgaggt gaaacgcttg aaattaatga  37620
ttattctgaa ccgacaccgc agcagctttc ctgggattct gactgctttg tctcatagga  37680
actggccata ggtcagccag cctgttcttc cgggtcaggg cttgggagaa aaagggctga  37740
```

-continued

```
gaagcagctg attggtctga ttcaggcacg tcccttgtcc ttggtagggg aaattcctta  37800
acaggtgctg atacacactc tggatcatgt gaagcacaga aagcctatgt gttatgtatc  37860
agcgcacatg tttataatct gaacaatgct gctttaacat gcatattaat cacctaggca  37920
tgacttgtgt gtgttaaaat gtcttgtgaa aatcccgctt caggccgggt gtggtggctc  37980
acgcctgtaa tcccagcact ttggtaggct gaggtgggca gatcacgagg acaagacatc  38040
gagaccatcc tggccaacat ggtgaaacct gtctctacta aaaatacaaa aatcagctgg  38100
gcgtggtggc gcatgcctgt aatcccagct actcaggagg ctgaggcagg agaatcgctt  38160
gaacctggga ggcagaggtt gcggtgagct gagatcgtgc cattgcattc cagcctggcg  38220
gaggtcgcac cactgcactg cagcctggcg acagagggag actctgtctc aaaaaaaaaa  38280
aaaatgaaaa ccctgcttca ggacatctag cttagtggtg gagatttctc cagccagctc  38340
ccacttccaa cagttcttcc aagcagctct cagttcatgg tactgtagcc tgcgtggctc  38400
ctgggccaca cagggagtag cagcagaggt ccagttgccc catgccatgg gcaggtgcag  38460
ggtctggaat tgggagctct caccacagat tgcacctctg cctgggggcg ccactgggct  38520
catcagactg agctcacggt gccccctggt gggcgatgcc agtggcgcca gtgcagcttg  38580
gagcccgcaa tacaaggtgt ggcttctaga aggtaccctg gtttgagatg ctgaggtggg  38640
aggatccctt gaggccagga gtttgaggcc agcctgggca acatagccag actctgtttc  38700
tacaaaaaat tagccacacc tggtggcaca cacctgtggg cccagctgga ggatcactga  38760
agccctggga gttgaagcct acagggagcc gtgatcacgc cactgcactc cagcctgggt  38820
gaccaagtga gaccctgtct ctaagataga tggatggatg gatggatgga tggatggatg  38880
gatggacaga tagaagataa actgcgaggc tagcacgggt tgtctggcag gggctggtat  38940
gtctccacga tggagcccga ggcagggagg cccggtgcat atggcagcag cttattgggg  39000
aagcttttcc caggcacggt tccaggacac aagggtgtgg tgtgagtgac ctggagctgt  39060
ttgtggttca gggatggggg cctggaggtc tcattatgcc taggctttta taatattttt  39120
gccaaccaaa ggtggaacaa aaagcaaagg caagtgactt ggaaaactcg gtttcagcgg  39180
ggatttatgc cctgaagttt tttactcgtt ctctatctaa tcctggccct acctcttaga  39240
tgggctatat gaccttggag aataacctag tctggatgtc agttttcttt ttctagaagg  39300
tgagctcccc agtctcccta gggggagata caggttgttg catccaacaa aatctgtgtg  39360
cccataatgt tgcaggcaat gggccagccc agaggttata gcctgccaac ccatccgtat  39420
ggccctggcc ctgtgtgtta gctgatttac ctgaccagga ggggcagcag tggggaggcc  39480
aagtcccaga ggtgagggtg aggctacaat ggatctgggg agtccccctc ctggtaactg  39540
cccccaggct ttctgcctgt gcctccatcc ttccctcctt gggaacttgg gactctgagc  39600
cccagctggt gagggaggag gggagtgagc gacaggccag cagaccaatg ggccctggag  39660
gatggggtga ggcggggctt gtgctgccat ggagaggaga gaagcggttc tgtgggggag  39720
gagggggtgg gtgggaagag gacctggaga ttgaggggaa gggagagagc aaacaaaggg  39780
gtcaggaggg aaaataatgc actggcttcc tgagcccctg cagaggctga gcagggagag  39840
ggggccaggg ccagagggga cagaggctgg cggcagacgg gccgggacag gcaggtccta  39900
aatggcattg tttgaagggg ccggctaatt gcacagagca gtctgagcct gagaccccag  39960
ccctggcctc cccactctgt cctgggtgct ggcgtctgag ccttcgggac agcctgtcca  40020
catggaacca agtcctgagc ctccaagctt ggtgaggggg aggctatggg gggcagcctg  40080
```

-continued

```
ggtggggtac ttgggcaaga gcatcaccct aagaatgcat cctggggcct tggcctgaga  40140
acacagagcc catggcgggg gaacactgtc cctctcatgt ccctgcttcc ctttcacccc  40200
acccattctg gcttctccca caggaaagca tgaagggaga caccaggcat ctcaatggag  40260
aggaggacgc cggcgggagg gaagactcga tcctcgtcaa cggggcctgc agcgaccagt  40320
cctccgactc gcccccaatc ctggaggcta tccgcacccc ggagatcaga ggtggctggg  40380
cagtggggac tggggtggtg tcaggcgctg acatagtgag cggtcactgc agacaactgg  40440
aggctttggg gagagtctct gacaacctcc accacaattc cccgggaggg aagagagctc  40500
tagcaaggag ggatgcaggg tcgagccctt cacacctgcc cgcagccctt ggcctcccct  40560
ttgggactct catctcagct gggactctga gcgtgacaca agggtgatgg ttccctgtcc  40620
tctgccagtc atgacagggg tggtctcagc atgggccctt ggagagccct tctgcagtgg  40680
gaccctctcc ccactcagag ctgggctggg gttgggaggg ggaggtctgg agtgtgcttc  40740
ctttccaccc tgccctgagc agctccagcc agctcacttg ggatcccgcc ccagctgggt  40800
tggaaagccc tgcattgtcc tctcagctgt gccatcccat ggaacttcct gcgagcgtga  40860
aagggttcta tttctgcatt gttccccaca atagccacac tctacatggg agcacttgag  40920
aagcggctga cacagcaggc agtgaattgt tcctggaaat gtagttagtg gtccctggat  40980
gggcagcacc ctgctggaag gaatcggagg gctccccttg gtaacttcag tgttggtttg  41040
ggtcctgtca cgtgcctggc ccagggctct gttgtcttag gaataaaatc agtggagaag  41100
atgaacgata ctgacggact gagagcaaat ccctgtggct gacaatagtg taggggagat  41160
cccaggccac gccacggaga aaagccccta ttagcaaggc cgttccccag actggtgcct  41220
gcccccacaa aacagactcc tggctgtttc ctctacaggc cgaagatcaa gctcgcgact  41280
ctccaagagg gaggtgtcca gtctgctaag ctacacacag gtatggtctc tgctctccct  41340
ttttcagggc tcagggactt tgtctttggc tttcatcacg tgggctgcct gaggcccata  41400
aaaactggca tctgcaaatg tatggagggt tgccgagcta gatgctttct gcatatattt  41460
ggcattattt tttcaatctg gacgatcagt tacattgcta aatctctaat atggtagtcc  41520
cctcttatct gtcattttgc tttccacgat ttcagttgct tgcagtcaac tgccgtctga  41580
aagtattaaa tggaaaatat taaatggtaa atcccagaaa taaacaattt atacatttta  41640
aattgagtgc cattctggta gcatgatgga atcttgcact gtcctgctcc gtcctgccca  41700
ggatcagtcc tgtctttgtc caacatctct atgcttaggt gctacctgcc tgttagtcac  41760
ttgtagccgt ctccgtgatc agatcagttg cagtatcaca gtggttgtgt tcaagtagtg  41820
cttgttttac ttaataacgg ctccaaagtg caggagtgat gacgctggca attcagttat  41880
gccaaagaga agccatgaag tgtttccttt aagtgaaaaa gtgaaagttc tcaaaaagga  41940
aagaagaaat catatgctga agttgttaga tctgtggtaa gaacaaatct tccagccgtg  42000
aaatcatgaa gaaggaaaaa taaatgcatg ctagttttac tgttgcacct caaactgcaa  42060
aagttatggc catgttgtgt gataagtgtg tagttaagat gggaaaggca ttaaatttgt  42120
aggtggaaga catgaacaga aatatgttct gattgacagc agtgctttgt gccagggagc  42180
attgagccta tagcaaggga tcccctgaca ccaaaccatt tacttcaagt aagggatggt  42240
tacatagatt caagaatagg tttctactga aaactataaa aatgactgga gaggctgcat  42300
ttgccaatga aaaacctgct gctacatttt cagaagagtt gaagttgatt gagaaaggaa  42360
acaatccaaa actaagactg cagtgaaacc agactcctcc agaagatgat gtctaataga  42420
acctaccttc ataaaagtgc aaaggaggaa gacactaggt cataaaccat ggaaggacag  42480
```

-continued

```
attaaccctg aatagagtac aagaagatat tttgagagag aaaccacatt catatggctt  42540
ttattaacag tatattgtaa ttgctctatt ttattattag ttgttaatct gtgcctaatt  42600
tataaattaa actttatcat aggtatgtag atatagacaa aaacagagca catatagggt  42660
tccatcttcc aaggtgtcag gcagccatgg ggggtcttgc atgtatcccc cctggataag  42720
gggagactac tgtatagcaa actgtctttt tattcctgga atgagtccaa cttggttatg  42780
gtgcattttg aagttgattt tattcatgta ttcatgaatg aaatgggtat ttttttttat  42840
tcatttattt ttgagatgaa gtctgttgcc caggctggag tgcaatggca tgatctctgc  42900
tcactgcaac ttactgcctc ccaggcccaa gcgattcccc tgcctcaggc tcccgagtag  42960
ctgggactac aggcaatgga ccaccatacc cagccaattt ttttgtattt ttagtagaga  43020
tggggtttca ccatgttggc caggctggtc tcgaactcct ggcctcaagt gagccacctg  43080
tcccggcctc ccaaagtgct gggattacaa gtgtgagcca ccatacctgg cccattttat  43140
ttctttaaat atatctatgg ttttgatgtt aggattaggt gggctcaagg aatttttttt  43200
acaagctgga agaaacttgt ctaagcttat tttaatgaat ttcaaacaat tatatcttct  43260
aagacttgct acattatcaa gctttctact tcatttactt ttccaaggtt ggatctttcc  43320
catcttgttt tgtgttcctt cctttactga caccgtctgt ttcctaatta ttcttagtag  43380
agtttgtcaa ttgggttggt tttgctcaga gccagtatca gtcataaaag tcctgggcaa  43440
tgaaaactca ccctcagctt ccattctctt ggtggtggcc aacctactta ggggactcag  43500
aaggtgggga acctaagccc tgggaggaat tagggcagct gcaggatcag aggctcagca  43560
ctgctgtttt gtttctggta gctagttacc agaaacagta atgaaatctc ttgcccacac  43620
gtttcttttt gtttgtttgt tttgttttga gacagagtct ccagtctgtc gcccaggctg  43680
gagtgcaatg gcacgatctc ggctcactgc aacctccgcc tcccaggttc aagtaatttt  43740
cctgcctcag cctcccaagt agctgggctt acaggcgtgc accaccatgc ccagctaact  43800
tttgtatttg tatttgtatt tttttttttt tttgagatgg agtcttactc ttgttcccca  43860
agctagagtg cggtggcgcg atctcggctc gctgtaacct ccacctccca ggtttaagcg  43920
gtactcctgc ctcagcctcc tgagtatgag tagctggaat tacaggcaca tgccaccatg  43980
ccctgctaat ttttgtattt ttagtagaga cagggtttcg ccatattggc caggctggtc  44040
ttgaactcct gacctcaggt gatccacccg cgtcggcctc ccaaagtgtt gggattacac  44100
gcctggccta atttttgtat tcttagtaga gatggggttt caccatcttg gccaggctgg  44160
tctggtgacc tcaggtgacc tcagtctgcc ccagactccc aaagtgttgg gattacaggt  44220
atgagccacc acaccctgca tattatttga ttcttgatgt aaccctgttg tgctatgagg  44280
gaagtactgt tattccaatt ttaaaatgag ggaaatggac tcaaagccac acagttggtg  44340
agtgaaggca agtgcttaac actccagcca gacctagctg ctcgctgctt cagcttttgt  44400
gtttggctta tgctgggttt tggtgtgagg tgtgaggcct gcacgaggaa gccctgatga  44460
catggtgcag gtttcatgcc attgcttccg gggcatctgt cgtggttggt ctgtgtctgc  44520
acccatatgc agtgtgttgt gatgagtgac ccggtctccc tgccaggcac aggcgatcag  44580
tctttcatat tgcaggtgcc ttgtttcttt gacttgctga taccctgggg tcttcatcat  44640
gttcatcatg tttccttata aaggacttga caggcgatgg cgacggggaa gatggggatg  44700
gctctgacac cccagtcatg ccaaagctct tccgggaaac caggactcgt tcagaaagcc  44760
cagctgtaag tagccacacc tcgagccaaa gcacttgtgg ccaacactct acatagcata  44820
```

-continued

```
catagcatgc tacatacata gcatagctcc ttaggggagc ttttaagaga aagtgatgaa  44880
aaaatgtttt gaaactagaa aatataagca aggctcttgg actattgttg gagggttttc  44940
tttttcttt ttttttttct gagacggagt ctcactgtgt tgcccaggct ggcgtgcaat  45000
ggcgtgatct tagctcactg caacaacctc tgcctccttg gtccaagtga ttctcctgcc  45060
acagcctccc aagtagctgg gactacacgc acctaccacc acacccggcc agtttttgta  45120
ttttcagtag agatgaagtt ttaccatgtt ggccaggctg gtctcgaact cttgacctca  45180
ggtgatccac ccaccttggc ctcctaaagt gctgggattt caggtgtgag ccactgcgcc  45240
cggctggaag gttttctcta tgtgccattt ctttcaggtg gtttttaagt tctttcttgt  45300
aacactcttg gaggtgccta ggggtgatag agtttgcagg gtggatggct cagctgctaa  45360
tgacctaggg agtccaccat ttctgtgggt ggattttgtg cctcagagtt ttgaggtatg  45420
gcaatgggaa ggcagttatt gcttatggtc acccagccct ttagagacca gactgacagt  45480
tactatccca ggtgtgggtt acagtcttcc cttcccagga tatggtctgt atcatcccct  45540
ttgtggagat gagagaagat tccagcaact taactgaggt taaacatcaa ctcttctatg  45600
cataatttgg acacaggttc tgcaacaacc aaattcatgc catttttgac aatgaacatg  45660
gagcctaagg aattctattc catcttgatg atctggtgcc ttcctgaacc cagtaattgg  45720
ccttatgctt ctttgacata aaagtttatt ttagagtgaa cacgaatttt tctttctttc  45780
tttctttctt tttttttctt ttttttgag atgcagtctc actgtgttgc ccaggctgga  45840
gtgcagtgac gtgatctcag cacactgcaa cctctgcctc cctggtccaa gtgattctcc  45900
tgcctcagcc tcctgagtag ctgtgactac aggcacccac caccatgcct ggctaatttt  45960
tgcattttta gtagagatgg ggtttcacca ttttatccag gatgatcctg aatttctgat  46020
tgcaagtgat ctgcccgcct tggcctccca aagtgctggg atcacaggca tgagcgagcc  46080
actgcgcttg gccagatttt tatttttcaa tcccaattgg caggtgccat ttcagctggc  46140
catgtctgtc tgctgtgaca ggcagagcag gacctgctgg gaattgtcgg gcatcctagc  46200
tggccacccct accacctcta ttccaagaac tggggaattc tggctggact cagtccagag  46260
tcccacctca tcacctgttc acttccagtt gtcctgaagc tggctaccag gtctccttgg  46320
ccacctgaag gcctaatcct tctggccccg ccagacccca ggcctccagt cacctaaggc  46380
ccagtgagtg tcctctcttg cttctaggtc cgaactcgaa ataacaacag tgtctccagc  46440
cgggagaggc acaggccttc cccacgttcc acccgaggcc ggcagggccg caaccatgtg  46500
gacgagtccc ccgtggagtt cccggctacc agggttggtt ccccagatgc ccagacccct  46560
gcccgcagtc tctaactggg agatatgcct cactcactgc actactggtt gtggctggta  46620
gataatctgt gtcctttttt cacactgctt ttcaggttct tgctttttct tttctctcct  46680
gggtaagctt cccgtaagcc tgttggcttc tctcctggtc tgatctcaga tgacactctg  46740
ttgggaatgg aagctttccc tgttgacttg gttcttgctc taacttggaa acaaggtaga  46800
aaacactgac atccagaact gtcttctccc tcatgtcttc ttcacctgtc ttgaggcaac  46860
cctagcgggt atggcaacat ttcactctct gagagtccct cgtcattacc catcatttgt  46920
gcctttgtca tctttctgtc tctgggacag ttacaatgac tttctccccc cttaagggat  46980
acgtgttcct ggaaaagttt cttcagcggt ctctgttctc tttaacttca gtctttcctc  47040
tttctttttg cctaggagcc atatgggggt gccgttggtc tctggtcacc gacatccttt  47100
gctctggccc aaactatgtg tccttctgtc cacagtccct gagacggcgg gcaacagcat  47160
cggcaggaac gccatggccg tcccctccca gctcttacct taccatcgac ctcacagacg  47220
```

-continued

```
acacagagga cacacatggg acgccccaga gcagcagtac cccctacgcc cgcctagccc  47280
aggacagcca gcaggggggc atggagtccc cgcaggtgga ggcagacagt ggagatggag  47340
acagttcaga gtatcaggta tggccgagag gggctcctgc ccagggtgac tgaggaccct  47400
gaacacgggg aaaaaccagt tacctgctac tgttggtaac agagcgacaa cagttgttag  47460
aagtttcgta attgtaataa ttgacatgtt tgaattctaa gtatcttcca tatgcaccac  47520
ggacctttct ttaccttaat cctctcccag acataagtca aatgccagta tttaccacgt  47580
gaatactgtg gtttttccca acatgacatt tatgtaagga ctgcaactgc gtacgttata  47640
catttcatgt acgcccgtgt gaagagacca ccaaacaggc tttgtgtgag caataaagct  47700
gtttatttca cctgagtgca ggtgggctga gtccaaaaga gagtcagcga agggagatag  47760
gggtggggcc attttctaag atttgggtag gtaaaggaaa attacagtca aagggggttt  47820
gttctctggc gggcaggagt gggggtctca aggtgctcag tgggggagtt ttttgagcca  47880
cgaggagcca ggaaaaggga tttcacaagg taatgtcatc acttaaggca aggaccggcc  47940
atttatactt cttttatggt ggaatgtcat cagttaaggt ggggcagggc atattcactt  48000
cttttgtgat tcttcagtta cttcaggcca tctgggctta aacgtgcaag tcacagggga  48060
tgcgtgcaag tcacagggga tgcgatggct tggcttgggc tcagaggcct gacaatacat  48120
attgtgattc tgttcatcag agtgcacata ctgtatatat tgtacgtatg atacctttgt  48180
agacttgctt ttttcttcta ttaagaacta gagttgcctg aggttcatgt ctggataata  48240
aatccagtgg tctgggtcat agcttaatta accgattcag gttgtttatg cttattcaag  48300
cattgctgca cgaagactcc ttacacatgt atgtatttat gtgttgttag gatccctttt  48360
ttctatgtcc attattacat tttactttgt atagaaggga tctcactatg gtgcccaggc  48420
tagtctcaaa ctcctggcct caagcgatcc tcctatctca gcctcctgag tagctaggac  48480
tacaggcgtg caccaccaag cccagctact ttataaattc ttttgtggaa atggagtctt  48540
gctgtgttgc ccgggctggt atccaactcc tggcctcaag cgatcccccct gcctcggtct  48600
cccaaagtac tgagaattac aggcatgaac cacggtgtct ggctacatct tgcattttat  48660
ggcaagcttt ttgttgccct cagggacagt ggagtggaca ggacttggcc caggatggcc  48720
tctcctcact gggatttctt catgtgggtt ttcttccagg atgggaagga gtttggaata  48780
ggggacctcg tgtggggaaa gatcaagggc ttctcctggt ggcccgccat ggtggtgtct  48840
tggaaggcca cctccaagcg acaggctatg tctggcatgc ggtgggtcca gtggtttggc  48900
gatggcaagt tctccgaggt gagtccgggg aagggcaagg ggttctgcag gcctgaggct  48960
gtgcctgcct gcctcccttt gaagacaaag gcctgggatt gtattctgca gatgtgtgag  49020
cctatgcctt cacactgtct gggaggaagg acaaaacttc ctgtgttaac cagctacagc  49080
agattccact cacacggggg acaaaagtgc tagaaagttc tggatccatg ggcagttgga  49140
ttttatgtta tttcttagat ttatcttttg ggggcagaat catcagtgtg gactctgagg  49200
ggccaggagt ggccacgtga gcaagtaccc aaaagtgttc agtggagaag cctggaagag  49260
accggaagca tggccgcggc ctcttgtcat ttagccctgg ggagagaaag gcatggagtt  49320
gggtttaggg tcacctggta tcagttgtga aaagggtttt tagtagaatt gggtatttca  49380
gagtctcttg atgattgatt ctagcctttt aaaatctttc ttggtaatga catttagctg  49440
gggaagagct gtgttgggca taactaggct gttttgattc ttacactctt tcaacaaaga  49500
ttttttttggg ggcggtgaga atggagtctc actctgttgc ccagactgga gtgcagtggt  49560
```

-continued

```
gcgatcttgg ctcactgcaa cctccgcctc ccaggttcaa acaattctcc tgcctcagcc  49620
tcctgagtgg ctggggttac aggcacctgc caccgcaccc tgctaatatt tgcattttta  49680
gtacagactg ggtttcacca tgttggccag gctggtctcc aactcctgac ctcagatgat  49740
ccacccgcct cggcctccca gtgctgggat tacaggcggg agccaccacg cctggcctca  49800
acaaagattt taatcagaca gacctatcct gtgatggtct cttagaagta aatgttagtc  49860
ctaccctcag agccctgaga gaggctaagt taggtgccta aggtcattgg gcaagttgca  49920
gcagaagcaa gccaggcagg attgaaggaa ggactgtaca ttcctgggat tcagctcaag  49980
cagagattct gtttttccca ggaattgagc taccatgggg ccatttgcca tgagctaatt  50040
gaagtttccc aagggctaca ataatatatt gggtgtggag tctcctttgt aggagagccc  50100
ctgcatgcag ttgcctgctg tgaccagcag agggaggaca agtcctgggc ccatgctggc  50160
agtgaggcag ctgcttccag ggatgggaga gcagtaactc aagtgaagga agatggattg  50220
tttgcaattg ctttgcccca tcgagacata aaatgcactt tgcaagatag agtctgaggc  50280
taatacaatg cagtgtgggg ctgtcagcat taggggatga gatgacaata tgggacctgg  50340
gtctggcctg ggcaagtgcc tgctcagcat gtgtacgctg tttgggttgt attggagcta  50400
ttgggcgctg gaaccagcac ttgtgttgga gcggtttccc cccaccagag ccacagtgtt  50460
ttctccccag tggtggtcac acccccatat aggaaatcag gcattccgtg ataaaatgga  50520
ggtttgcatg agtgtgagca ctctttacgg agactagaac attccctgtg tctttcagtt  50580
cctttttttt tttaagagat gaggtcctca ctgtcaccca ggctggagtg cagtggcact  50640
gtcttggctc actgcagcct caatcacctg ggctcaagca atccttctgc cttaacagag  50700
cagctgagac tgcaggtgca caccactgtg tttggctctt aaaagttttt gtagagatgg  50760
ggtcttgctg tgttgtccag gctagtcgaa ctcctgggct caagcgatcc tctcaactcc  50820
cactcccaaa gtgctgggaa tataggcctg agccactacg tctggccttt cagttctgat  50880
tagcatccct gaatggccat tttctctctc actggcaact cagtcagttc atgcttggtc  50940
cagggacttg gtacatcagg agacttgtgg aatatggatt aaatcacaag aactaaagtt  51000
aaataatcac aacaagtgaa aggtgctgtg tcgagcactg ttttctaaac acattcatta  51060
ggtgaactca ttttaataaa agggtaaaga gtaaacaatt atcatgctta ggaaagaagg  51120
aatatgtgca aaccctcaat gctggagcag ccacagagaa tattaggact gagcctcagg  51180
ggtccacacc agggacacct gcttggaaaa tgtatacaaa cacagggttc gcctaattgc  51240
cttcattcag agtatcctcc ttttccacag tggaagtgtc gtacctaaca aggttctgga  51300
tatctgtgtg ttgagactct gccatttcta tttttctgct tttttctttc cttcctttca  51360
aatagatgtc tgtggacttt atccccagga atggtctctt ggttaaagtg tgtgaaaatc  51420
ttctgcatct gatggacaac attgtgatag acatggcacc tgggacacac ctgtaggtgg  51480
atgttgatga tgtctttctc ttttaggtct ctgcagacaa actggtggca ctggggctgt  51540
tcagccagca ctttaatttg gccaccttca ataagctcgt ctcctatcga aaagccatgt  51600
accatgctct ggaggtaaca tgggatgagg gaatgagggc taagccctga gagcagggat  51660
gaagcaagag acccacagaa acctagctca gtgttgccaa gggtggtttg gaggggacag  51720
ggtggccagg gaggaggtaa atgacaacat aacatgatgg ccaccggatt gggcctccca  51780
acaaagggat ttgagacatc ccagctgcca cttattggga ccactaactg aatcagaagg  51840
aaagagcacg ggcagttagg ggtgcaatat tcgtatcagt gaatgtgctt ttccagagac  51900
ctcagagcct tcttatgagg gttggagttc acagcaagac agcagtggag gccagctgtc  51960
```

-continued

```
ttctatctgt gggccgtctt atcccctatg aaccattata ccctgtttct cccttcacct  52020
tgattttttc cccccacctt tgttcagcat ttaagagcca acctcttctc attgctaaag  52080
gcttcattag acactgaaat ccttggtcct tcatgtagga cacaagttaa tgtccccatc  52140
tttagggaga taaaacaaga aatctagtgc cgccttatat aagatacaga ggagatgaga  52200
tagtgctggc tggggcttct atatcttggt ggtagagtta attctgatat gtctgccttt  52260
tgagtgggag gtgaccactg acattcccta gggggaagag atcctatttg gtgcctgcat  52320
gaaaagattt aaccacaacc ccccttccga ggcctctccc tgcacaggcc cctccttcct  52380
ctgtcacata ccacagccca ggacagctgt ctggctatga aagggcccag tgtgaagggg  52440
aatgtaggcc ctggctgggg gaatccctgg gtgtggcctg gcgagcacct cctccccacc  52500
cccccattca tcacagactc tgcctttgca gaaagctagg gtgcgagctg gcaagacctt  52560
ccccagcagc cctggagact cattggagga ccagctgaag cccatgttgg agtgggccca  52620
cgggggcttc aagcccactg ggatcgaggg cctcaaaccc aacaacacgc aaccaggtgg  52680
gaatgagtcc ccatggcagc acccgctgcc tctgctggtg ggaccacttc ttgggagagt  52740
cagccacccc tgctgcccca caccccaccc agctttctag cagctggtct caactctgaa  52800
tgttggaaaa ataggagcag gcatacgaag gctgtgccag ctctatctgg cttccccggc  52860
cactttcttg ctgatggtca cgtgcatata atttgtattg aatctgacat ctgtcttgaa  52920
gtcaggatgc agtgttgact agcacctttt ttattaaagg aaaaaatagt taagctatgc  52980
tcatttgaga aaattggaaa gtgttaaaga agaatatgcc acctgctaac attttgacca  53040
gtaccatatt tctcccatta taagataact ctggtttcta gaaatccagg acttgtctta  53100
caatccatag atttaaaggc caggcctagt ggctcatgcc tgtaatcgca gcactctggg  53160
aggctgaggc gagtggatca cttgaggcga tcacctggac aacatggtga aaaatagaaa  53220
aattagcctg gtgtgcttgg catgtgcctg tggtcccagc tacccgggag gctgaggtgg  53280
gagaattggc ttgagcccag gaggcagagg ttgcagtgcg ccgagatcgc accactgcat  53340
tcaagcctgg gtgacagagc aagaccttgt ctcaaaaaag aaaacagtcc atacatttaa  53400
tgtaatgttt tttctgtttt gttttgtttt cccctcaaaa gtggttaata agtcgaaggt  53460
gcgtcgtgca ggcagtagga aattagaatc aaggaaatac ggtatttcct tcctgtcttt  53520
tgactgtgcc ctgttttcta tgcactttct tctgatttct ttgcatataa aatggtcact  53580
ggaaaagaat caaatttctt gaaaagtcaa tctgaactcc ctccccactc tcccctcaca  53640
tcccaccctc acaaataccc tccaggttaa cgttgggttg cacatccttc cagatttttc  53700
tgaacactag ttggattcct gctttcccct ttattaatat taatactgta agcactgtct  53760
gatgtcattt tgtcactaaa gggtccttaa gatttttaat ggctgtacaa ttttctttcc  53820
tagggtcaga gtcaaattta accatgtcca ttaagatttt ctgtgtagat ggaatagaaa  53880
tacaaatggg ttttacaaaa tcccatttat agaatgggag ccatattatg taaaattaaa  53940
aagtgctggg ctcagtggct cacgcttata atcccagcat tttgggatgc aaataaccat  54000
ctcttggatt tcccagcatt ttgggacgct gaggtgggca gattgcttga gctcaggagt  54060
tccaagacca gcctgggcaa caggatgtaa ccctgtttct aagagaaata caaaattagc  54120
tgggtgaggt ggtgtgtgcc tgtggaggct gaggtgggag gatcacctga gcccaggaag  54180
tcaggctgca gtttgctaag atcatgccac tgcactccag cctgggtgac acactgagaa  54240
cctgtctcaa aaaaaaaaaa aaaaaaaaaa accaaaacag aaacaaaaaa gaaagaaaaa  54300
```

-continued

```
aacgaggcca ggtgcagtgg ctcatgcctg taatcccagc actttgggag gctgaggcag  54360
gcagatccct tgtggtcggg agttcaccag cctggccagc atgatgaaac cccgtctcta  54420
ctaaaataca aaaattagcc aggtgtggtg ctgcatgcct gtaacaggct gaggcaggag  54480
aatttcttga atccaggagg cggaggttgc agtgagccaa gatccacgtc attgccctcc  54540
agcctgggca acaagaaagg aacaggtgaa attaatacaa atcatgattt ttttagcgct  54600
aaatttccaa gatgttagca ttttaatatc cagctattat aaaaactgag atagtctaca  54660
tttatagtgc tggtttcaaa atttcactta ttttatatat tttacatatt acatatttta  54720
cagatctcaa ttttgatgct aaatttgcaa tgaaaatact tgatctgtat taactatata  54780
cagattcttg actaaataca gatgtagatg gttaaacaca aattaactaa attcataaaa  54840
cgtgcatttg agaaagcaga ctcatatgtc taggctagtc ttaatgagcc agttagttga  54900
cttacttgtc agtgttttaa ttaaccttaa atgcagaatt catttcctca acagtttcaa  54960
gttctcagta gccacccccct atgcctactg cccagcatgt cagatatcac agacatgggt  55020
atgccaggct tttagctttg aatcgagctt tgctctctga gctgagtcat ttttacatcc  55080
tagttgtagc catttaaaac cttgtaaaca tgtgttaagg atcctgggtg caaggggttt  55140
tgaatgagct cctgttgtga gttgcccatc aaggggccat atacattcag tgtggacccc  55200
ctgtcatgcc ccaattgcag ctggtaccca ggcatagcat ggtcttgtcc tgggcccgca  55260
ttctctctgg accctcctac caagccacgg ctgcagtcta attacctttc acagagaaca  55320
agactcgaag acgcacagct gacgactcag ccacctctga ctactgcccc gcacccaagc  55380
gcctcaagac aaattgctat aacaacggca aagaccgagg ggatgaagat cagagccgag  55440
gtgattgttg ggtacctggg atcatgggac agatgggagg aggacgctgc agatcaggaa  55500
ttgatctgta cccggctccc tgacctcatc tcatgccttc ttcttttctc aatagaacaa  55560
atggcttcag atgttgccaa caacaagagc agcctggaag gtaacgttct ctccctccca  55620
gtcatccccc tcacaccctg gctagggctc taggcctgcc ttgtcctggc tcatccaccc  55680
tgtcagggtt taacccagag ctctgttcct taacctcagg ccaaggccta tttctggacc  55740
ctgcatctta gttgctagtt tatggaatga gttgccaatt gtgcccctta agagaaaggt  55800
acaggaaggg tatggtgagg aacaagggaa gctgggccat tttggccggg agagccataa  55860
cctaaaacca agattactgg tatcatgaac cttcccaaag aagaactgca actaacaagc  55920
ttttagtcac ttgcctactg tcaggctaaa tactctgctt gccctggctg ggattgccca  55980
ctggattgga tactctgatc agaatatacc tcatggaata cagaatgtgt gaggatgaag  56040
tctcccttgc ttccttaacc cctagttact caatgttgaa taggaaaaca ccacatccct  56100
gacccagaga acccggggaa gagcttcggt ttagaaatcc tattccccaa gactcactcc  56160
cccatctggc taggtaggga tgcttgtttg tgggttttat aaaggtccta tctacccagc  56220
cagggatgca actccatgct gacctggtga tatgaaggga aggcagggtt gcctactggt  56280
taaaggacct ggattctgaa attacagcca tttgctgttt acagggtgtg ggcatgggca  56340
agtcctatca tgagacaaca agccaattgg agtcaccaca aaatccttag tgtcccagta  56400
tttaaagctt ctcaaggatt gtcacaccag ggaggtcccc ctgctcagcg ttctgcctga  56460
catcatccta ctggggcagc cccttgccca tcttgatgtt ccccatctgt gaagtaggga  56520
tgccacctgg aagcattgtt gagtggtaga agctgtgagg catggcctga ggtgcaaaga  56580
gtccttggca agctgctggc ctggagggaa atcttaggaa ctgagagacc ccaggcttta  56640
gcagctggtg tcagggcctc aactgccaaa agccacaacc ctgtttttct tacagatggc  56700
```

-continued

```
tgtttgtctt gtggcaggaa aaaccccgtg tccttccacc ctctctttga ggggggctc  56760
tgtcagacat gccgggtaag tcctcctact actgccctgg accttcctcc ccttgcctcc  56820
tctaactccc ctctccttcc caacagcacc tgtgtggaga ctcagtgaag cccactcatc  56880
ccagctgcct tgcactctgc ctctggggca ggatggggga cagctgtcac agaggccaat  56940
ggcacgcagg tcacagccag ttgtcctttt aaaggacacc aagccaccag cagtgtgttc  57000
tgcagctgta tcctagggcc tccaccagca agccggcagg gcctgccctt ctctggtctc  57060
cgatttcact ggtgtttctc tctggctgcc aggatcgctt ccttgagctg ttttacatgt  57120
atgatgacga tggctatcag tcttactgca ctgtgtgctg cgagggccga gagctgctgc  57180
tttgcagcaa cacgagctgc tgccggtgag cactgggccc tgtggggtgg atgtgggtgg  57240
gcccccaagg ctcctacgtt cctgcagtct gcagacagct gtctgttgaa tggaatccta  57300
ggcatgggaa tagggagcta atttgccctg gaagcagcac acagggttta tattttgtgg  57360
tggctgtggt tgtagcataa ttggagtaga actcatgtat agggaacggc tcttttttt  57420
gagacagggt ctccctgtgt tgcccagggt gtacagtgac atgatcatag gtcactgcag  57480
cctccaattc ctgtgctcaa gcaatcctcc cacctcagcc tcctgaacag cttgattata  57540
ggcacatgcc atcacaccca gctagttatt cttttttttt tttgaggtgg agtcttgctc  57600
tgtcacccag gctggaatgc agtggcacaa tcttggctca ctgcaacctc tgcctccagg  57660
gtacaagcaa ttctcgtgcc tcagcctccc aagtagctgg aattataagt gcggagcacc  57720
acgcccagat aatttttgtg tttttagtac agacagggtt tcaccatgtt gaccaggctt  57780
gtctcgaact cctgacctca ggtgatccac ctgccccagc ctctcaaatc ccagcactcc  57840
caaagttctg ggattacagt catgatccac cgtgcctggc ctattttttg taataaataa  57900
aaagtgtaat aaacgctgcc tcggctggtc tcaaatccct ggggtcaagc cattctccta  57960
cctcagcctc ccaaagcccc agagttgtag gtgtgagcca ccacacccag ctagaagtgc  58020
tcttaatagg ccaagagcat gagggaaggg gatgagtagg gtgtcaggga aggctaattc  58080
cctggtttgc cagttggcct gtaatccaaa gtgtccatgg aatgaagtag gttgtcggga  58140
gagcatttct gatcagagag cctgtgggat taagggggtt ggggcatcca aggaagacgt  58200
cagggaagcc cgtactgcac agggccccgc aggctatgct gttaagcagc cgatcctagg  58260
taagctttca ggagggggtt ggcatttccc tgtggaagtg gtaagggggt ggcacaggag  58320
accagctctg acaaaggcat cccttctccc tgccactggg tccaggtgtt tctgtgtgga  58380
gtgcctggag gtgctggtgg gcacaggcac agcggccgag gccaagcttc aggagccctg  58440
gagctgttac atgtgtctcc cgcagcgctg tcatggcgtc ctgcggcgcc ggaaggactg  58500
gaacgtgcgc ctgcaggcct tcttcaccag tgacacgggg cttgaatatg taagccacag  58560
gctcccgcct ctaccaccac agatcccagg ggcacagggt gttggaaagc tctggaattc  58620
tcagaaagag taatagaagt aaagacacgt tgtacctctt ggagcctcaa tggctgagag  58680
acctggcgaa ttgccagctc ctctgcacgg ttttcagccg tgccagggtt cattcactcc  58740
ctccttgccg gcttctcagc gtatggattt tcaggggcct gatgaagaaa tggttgtatg  58800
tagccttctg agttagcaga gctgagaggg aaggaaacag tagaaatgaa ttttctagtt  58860
cttagaggga agccctaggt cattcctgtc tggggtgata ccttttcatg tgtgcctctg  58920
tgcatacata tctggctcat gtccaaggat aaattgacca ttccttgcca aatgcaggct  58980
cgtgtggtac acacttgtct ccccaatccc catcaagcct tcagtgggct ttttgcagtg  59040
```

-continued

```
gctacggcaa ggtttgaagc cctctgagca gggtcagcct gcccctccct cagagcttga  59100
gtctttgccc tgtgccttca ccaccatgac ctccttcctt acctggcagg aagcccccaa  59160
gctgtaccct gccattcccg cagcccgaag gcggcccatt cgagtcctgt cattgtttga  59220
tggcatcgcg acaggtgagt tcggggaaca cctggagaca ctgctatcgt gtcacaacag  59280
ggtagccagg gagtcagaag gcatggttaa ggtgtctgac atcagtggca agaaaggtcc  59340
ctggggatta ccagccctga aaaaaaccct gtctccttgt ttctctccac cttctcaacc  59400
accttgcagt cttggtcatt gagttttatt tatttatttt ttcgagatgg agtctccctt  59460
tgtcacccag gttagagtgc aatggcgtga tctgtgctca ctgcagcccc catctccgag  59520
gttcaagtga ttctctcctc agcctcccaa gtagctggga ttacaggtgc tcaccaccac  59580
gcccagctaa tttttatatt tttcgtagag acggggtttc tccacgttgg tcaggttggt  59640
ctcgaattcc tgacctcaag tgatctgccc accttggcat cccaaaccgc tgggattaga  59700
gacatgaacc accgtgcctg ggcagtcttg gtcattttaa aaggacatac atcttagctg  59760
ttacacttta ttttttatgt gcagttatct tgaacttgat tttcattcca catgcataag  59820
tataattgga gataaactag ttaacaacta ctgctacctc tggttttggt tcccttcttt  59880
tcctcctata tggagtttac acagccaata tgtgtggtgc gtgtacagcc tttgctggat  59940
tgaacgcatg tgatacagtc atgaggaact gttcatttta ccatagcagg gagtggagga  60000
aatgagctgc tgtgtgctca gcatcattta tgcttctgtg tctctctggc ccccacaggc  60060
tacctagtcc tcaaagagtt gggcataaag gtaggaaagt acgtcgcttc tgaagtgtgt  60120
gaggagtcca ttgctgttgg aaccgtgaag cacgagggga atatcaaata cgtgaacgac  60180
gtgaggaaca tcacaaagaa aaatgtgagg gcagtctgta ccttgcgggc ctcatctctt  60240
cctgtctttt tccccagtcc tccacaccct gaaacccaca tgtaggcccc atccctgaga  60300
ccccagaaaa aaggattgaa atcctgtggg aatcttaagc attaggttag ggtcagaagt  60360
ggagttggtg accaagcaag attctatttt tttctggaga cagtctccct ctggagtgca  60420
gtggcatgat ctcagctcac tgtaacctct gcctcccggg tttaagcgat tctcttgcct  60480
cagcctccca aagtgctggg attacaggca cctgccacca tgctgggcta atttttatat  60540
ttctagtaga gttggggttt ctccatgttg gccaagctgg tctcgaactc ctgacctcag  60600
gtaatccacc cccgccgtca gccttcctgg gattacaggt gtgagccacc tcgtccagcc  60660
ccacgcaaga ttctagaagt gggtccagct ctctttccct ctgtccacac cctcatcctg  60720
actctgtctc tctctttcag attgaagaat ggggcccatt tgacttggtg attggcggaa  60780
gcccatgcaa cgatctctca aatgtgaatc cagccaggaa aggcctgtat ggtgagcatc  60840
cttctctctg gcagtccctg gagagcctat gtcacctgac cactggccca ggtgcagcag  60900
cctgagaagg agccacttgc ttctggccaa gttactggca gcatcagggg cctgttggtg  60960
ctgcctacgc tccatagtaa atcctcagcc cacaagggaa ataccctagt aaatagtgcc  61020
ctgctgctgc ctgtgtccct gctgtcattc aggtggacat agactggtag gcatcaccct  61080
gaactgtcag gaggccattg ggaacctgct ggtctcaggg aataaggtgg gttgggctgg  61140
aggtttcaaa tgaaccctgc gctgtcatct tttctgagca cagagggtac aggccggctc  61200
ttcttcgaat tttaccacct gctgaattac tcacgcccca aggagggtga tgaccggccg  61260
ttcttctgga tgtttgagaa tgttgtagcc atgaaggttg gcgacaagag ggacatctca  61320
cggttcctgg aggtgaggga atctggggac ctgattgtca cagacagcca gggcagggaa  61380
agcgctgctg gcagtgatga ttggtgggtg ttgccaacat tgggaatgac tttcccgttc  61440
```

-continued

```
ttggtctggc tagatccaat agtgagggat tcagtgggtt ctcttagtac atggaaaata  61500
tttttttga gacagggtct tgctctgtca cccaggctga agtacagtgg cattattaca  61560
gctcactgga gcctcaaaca gctgggctca ggcaatcctc ctacctcagc ctcccaaatg  61620
gctgggacta caggggcaca ccaccgtgcc cagccaattt ttgtattttt ggtagagaca  61680
gggtcttggt atgttgcaca ccctagtctt gaactcctgg gctcaagcaa tccgcccacc  61740
tcccaacgtg ttgggattgg agatagagat gtgagccacc atcccctgcc agtacaagga  61800
aaataattga tctctaatct cagcccaact ctttgaagtc agaaatgatg aaacaaacca  61860
tcatctgctg ttaaggactc atgagatttg actcaatttt ttactctaga gagttttctc  61920
atttttgata tgaaaactgc tttagaccag gcacagtggc tcatgtctgc agtcctagca  61980
ttttgggagg ctgaggttgg aggatcactt gagcccacgg tgtatcatat tttgtaataa  62040
tctggcgtat cccaggggat accgtctcag aatctgcagg tttgacctta tctctttagc  62100
taccattagc atagtatgag ggcatttacc atgtcctcta gccagcctcc tgatggcagt  62160
aggtctttcc tgttttggag gatccgtgcc tcatccatag tcagggaata gccctgtcac  62220
ctgcaaaggt ctggttgaca ctgaaactct aataataggc tcctaacagt aaccttcttt  62280
ctccccacag tgtaatccag tgatgattga tgccatcaaa gtttctgctg ctcacagggc  62340
ccgatacttc tggggcaacc tacccgggat gaacaggtaa caaagggctc ttagtgggtc  62400
aggtaacagc caagttaaat atgtgataac aagctctgac attcaagcct tcctagaaag  62460
acctggctct gctgagaaat agttatactt ggatttcaga ccacctgtgg tcgtgcgggt  62520
tgatctctgt taagatgttc agcaagtacc tgggaatctc tgtaggagtc ccactcttac  62580
ctgttgtaag ctgctgatgg acctgatcct aaaagtccca cgtggctggg tgtggtggct  62640
cacgcctgta atcccagcac tttgggaggc cgaggctgga ggatcgcttg agcccaggag  62700
ttctagacta gcctgggcaa caaagtgaga ccccgtctct acaaaaaaat aaagaaaaat  62760
acaagtctca tgagctgtgg ccagactgtg tacctccttc ctgccaggga tctctcaaga  62820
cttgagcttg ttgatgctcc tgcccttcac ctctcctccc cgttgatgta gtgacagccg  62880
tctggaaatg gaagtagatt gttgttaccg gtgcctttcc tcctgccctg gagatgaagc  62940
gatcttggcc aggctcatgg tgaccaacca ggtggcagag ctgctatgac aaacaatagc  63000
ccaaagacta tgtccctcag attctcatca ccaggagcat ttcatatttt gttatcgtat  63060
actaaaaaca gtcttcttca gacactctga aagccacaaa gcagctttgc tgaggattaa  63120
ttatttcttc tatatgtggt ttcaaggaga agaacttgct aattaagatg taaaatgtta  63180
tggtaatgtg acatcccaga cttgcaaatg agttgagctt aaaacattct cctgtagaag  63240
gaggcatgga aacataataa ccttctgcca cttagtgaag tgtggacaga ggtgagggtc  63300
ctggggtagc ttggaggatt tttgttggtc accttgcccg tgtacttggc taagcagcca  63360
gtcttagggt gccatgtctg tgtctggaat taaatgggtt aatgctttca acatttgaac  63420
tcccagtagg ccaggcactg ttacgctgtt gccattttca tggttaaaca catcatgtcg  63480
atagtgacat gccgaagggg gagggagaga agacaatgat ttggggttta ttgctggcgg  63540
atggacattg gaagggttga tggggaaggc ttctcattct agcgaaggtc ctaagtgaag  63600
ggatggaccc atgcagttat tagagtactc caggtgggaa gagggtctgg gatgatggga  63660
aacatcccca gaccagctca gagcacccta ggtggggtgg ctgggagaga aggaccaagt  63720
aacttgggcc ttaatgtggt accgctgaaa tcactttggc atgggaagtt acagatgaga  63780
```

-continued tgaattgtgc tttggttcat ggtagtttct gggtggatta tagacaataa caggatggag 63840
gcgggaatgg ggagacaagt gaagggacta gactgctcaa agaaggagag atgactgatt 63900
atgatgttat gccccaggag gtgccatcca tagagaacac agtgtgagtg gtggcccctg 63960
gggtttgcag cacagcaatc ctgtgactta gcaaggacgg atcagattca acatatgtgg 64020
agggtaggac atttgctgat gcattggatg tgtaggctat gaggtggaaa gagcagtgag 64080
acctgatgca gatctgatgc tgtgactaag ctctgcaggc ttataggatg ggtgtgtcag 64140
gcatcattta ggggacagac ccaagtcatc tggcttgttt agagcttaat cttatagtca 64200
gcacaaggcg gggctgtgca gtgtcctttt cttctgggcc ctcagctccc ctgggtccat 64260
gtcggaggta ggaatgggga tagaggtagc atttgaagcc tggcaggtga ggtcaaggaa 64320
atctatcagt ctaggggaaa tatgtgttgt gatttcctca gcccctcttg taggcacggt 64380
tcccgttctc atgtctgagt tgtttggcct tgacgttcct aacacaggtt actatggccg 64440
tccctgcgtc cagtcctctt gcaccagttt ctgttctgga gctgctcaac tactttcagt 64500
tctagccctt gcccttctta gtcatctgtt tgcctctctc tgcatttgca aaataatttt 64560
caagggtgaa agttaaaagg gtgcttagtc tttttttttt tttttttttt tggaacctta 64620
agagacaggg tctgtctccc aggctggagt gcagtgttgt aatcataact cactgtagcc 64680
tccaactcct aggcttaagc gatcctcctg ctttgaactc ccaaattgct gggattaagg 64740
gtaggaacca ctgcaggcgg ttgccattca cttttaaagc ctcctgaggc tgtatcccca 64800
gcagtgagcc accaaaccgt gggtgtgata tgataattgt atcaggtaga cccacaaaaa 64860
tctattccaa gctcctcact ttaaaataga caggaagccc aaaggggtag tgtgactcgc 64920
tcaagctcag tcagtgagca gtgtggagct gggacctgag gtttctcctg ccctacccca 64980
tgcagtgttc ctgctcaatg ggaacctgac tttgaagtcc aggcagggga gcattacctc 65040
ctggatgctg ggctgtcccc tctagcccat ccttggcttt ggcacacagg cttgtgctca 65100
tgccaggatc attttcatca tttatttgta gccaagttca ctgccagggc acatctctgc 65160
aacatagacc ctcactccca ccttgtgcct agcagaggac cctctatagc tagtaagaag 65220
taatgggttt tggctgttcc caggcccgtg atagcatcaa agaatgataa actcgagctg 65280
caggactgct tggaatacaa taggatagcc aaggtaagac gagctgtggc cctctggaaa 65340
aatgcacttg gtgacctcca agtggggact tgggagatga ccttggtgtt tgattggttc 65400
ctactcctcc ccccacgtga cttcctggtg ttgggcttcc ctctcccaca tgattgttct 65460
gtcccatcct caaatacaga gactaggaga cattcgtgat aagtaatcac gacgagaaaa 65520
ggcaactagt ctttttaatt ttagtactgg atacataaag acaaagagtt tcagctggcc 65580
ctctcaggga gaaaggaatc attaatcctt ttgccaaaaa attaatttgc tgtcaagtca 65640
tagaatatga agacctccat aaacctaaat ctcaatgttt gcatcaagct aagatccatt 65700
ttctaaactc caattgagca ttctctgtat ctgggtggtt tttacttttt tacttaatct 65760
tgcttgatca ggaactctgg tgtcttcttg gccccccacg tgatctcgtt catggtcact 65820
tttttgttta tctcattttc tctgaggctg gtccttcctg ttaacgtctt ggcatttgtg 65880
ggaagcacaa aatgttcttg tctctccaac tctgcttttc gctccctgcc ctgccattcc 65940
tctcccgcgc ctgccctctc ccttccatct ttcccaggta cttttctctc ccagccctgc 66000
cactcttctg ccgcacctgc gctctcccct ccatctttcc caggtacttt tgagccttga 66060
ctccccaggt cccttcattc tgtgctcact ccatgatgtc attttgttct ccagttaaag 66120
aaagtacaga caataaccac caagtcgaac tcgatcaaac aggggaaaaa ccaacttttc 66180

-continued

```
cctgttgtca tgaatggcaa agaagatgtt ttgtggtgca ctgagctcga aaggtgagca  66240
aggctgcact tggagaggga aactgtgtag atcaaaacac aaatgggcag acatgggcag  66300
gtgcttacct tcattcttga tggcctcact gccctttggt gttactgggg cgaggagtaa  66360
taatacccttt tcatagttcg cccttatttc ctgacaaaaa tggcggaggg ggtgtggtgg  66420
tggtgaggaa tctgagacat gaggtcatta ggccacacca tctgtctgtt ggctgcactg  66480
ccgtgacatc tgcctgtccc aacatgctgg gacactacga tgtgtgagaa gccagtgaaa  66540
gaaaacccca cagacatgcc attcttgaag acttcagttt gctcattcta taaatgattc  66600
cttcttagcc acagtttatc ctctccttcc ctttctttgg gctaagtttg tctgttttga  66660
tgcaaataac catctcttgg atttcagttc tgttctgttc tgttttcttt cactcctcta  66720
ttgtttgttc attttgctta tactattttt taaaaatcat tatttgctat agtgattatg  66780
gctttgaaca ttcctcttta catgtattct gtattctgaa ggctttgata tagagtattt  66840
tcattccaga tatttcactt ctataactca tttaatttct tctttgactt accaacagtt  66900
ttctgagtat aaaagtaact tctgattagt atttatgctg tagattattc tgtatggacc  66960
taaacctaaa atggttggtg cagatggctg acattgtgta gacgctaaga ccaagcaaga  67020
cacaggcctg aggtatcaca tctttggcat gtttctgaat aacccacgca gccattggcc  67080
tgttgggatg acttttagta ttggattgta tacctgagta acactgaggc tcagcctctg  67140
tagcctcttt ccaggcctgg tagaatccta tagaggaagc ttttggtata tttgatgcca  67200
tctgcctgga gtcatctagc atggtccttc atccggcagc tgggtttgaa gagggaagga  67260
aaactctggt tgcctgagcc tgtgatgact gaaaatctag gctgtttttg agtgaccttg  67320
ttccttatta aggaaattgc ttaacttctc ccatcatagt gttttgaaaa tggatacatt  67380
gctggctggc tgatttagta tgcatgcatt tattctagga aggtcctctg agcaccaact  67440
ctatgccaag agtatggtgc taggcctgca caaaacgggg gactttcatt tgtgagcaat  67500
ttgtaagcaa gtgttctgaa ttaagggctc tgaatttagg tccttgggga ccttactgat  67560
gggactgagg gatggcgagg gcagaaagag tgggacctgg ctggttgagg ctgtcaacat  67620
cctggaggca cttctgactt gctgtctttt cactccggta cccccaggat ctttggcttt  67680
cctgtgcact acacagacgt gtccaacatg ggccgtggtg cccgccagaa gctgctggga  67740
aggtcctgga gcgtgcctgt catccgacac ctcttcgccc ctctgaagga ctactttgca  67800
tgtgaatagt tccagccagg ccccaagccc actggggtgt gtggcagagc caggacccag  67860
gaggtgtgat tcctgaaggc atccccaggc cctgctcttc ctcagctgtg tgggtcatac  67920
cgtgtacctc agttccctct tgctcagtgg gggcagagcc acctgactct tgcaggggta  67980
gcctgaggtg ccgcctcctt gtgcacaaat cagacctggc tgcttggagc agcctaacac  68040
ggtgctcatt ttttcttctc ctaaaacttt aaaacttgaa gtaggtagca acgtggcttt  68100
tttttttcc cttcctgggt ctaccactca gagaaacaat ggctaagata ccaaaaccac  68160
agtgccgaca gctctccaat actcaggtta atgctgaaaa atcatccaag acagttattg  68220
caagagttta atttttgaaa actggctact gctctgtgtt tacagacgtg tgcagttgta  68280
ggcatgtagc tacaggacat ttttaagggc ccaggatcgt tttttcccag ggcaagcaga  68340
agagaaaatg ttgtatatgt cttttacccg gcacattccc cttgcctaaa tacaagggct  68400
ggagtctgca cgggacctat tagagtattt tccacaatga tgatgatttc agcagggatg  68460
acgtcatcat cacattcagg gctatttttt cccccacaaa cccaagggca ggggccactc  68520
```

-continued

```
ttagctaaat ccctccccgt gactgcaata gaaccctctg gggagctcag gaaggggtgt  68580
gctgagttct ataatataag ctgccatata ttttgtagac aagtatggct cctccatatc  68640
tccctcttcc ctaggagagg agtgtgaagc aaggagctta gataagacac cccctcaaac  68700
ccattccctc tccaggagac ctaccctcca caggcacagg tccccagatg agaagtctgc  68760
taccctcatt tctcatcttt ttactaaact cagaggcagt gacagcagtc agggacagac  68820
atacatttct cataccttcc ccacatctga gagatgacag ggaaaactgc aaagctcggt  68880
gctccctttg gagatttttt aatccttttt tattccataa gaagtcgttt ttagggagaa  68940
cgggaattca gacaagctgc atttcagaaa tgctgtcata atggttttta acacctttta  69000
ctcttcttac tggtgctatt ttgtagaata aggaacaacg ttgacaagtt ttgtggggct  69060
ttttatacac tttttaaaat ctcaaacttc tatttttatg tttaacgttt tcattaaaat  69120
tttttttgta actggagcca cgacgtaaca aatatgggga aaaaactgtg ccttgtttca  69180
acagtttttg ctaattttta ggctgaaaga tgacggatgc ctagagttta ccttatgttt  69240
aattaaaatc agtatttgtc tataactgtc tgatgtccct tttcttctgc aggtcagatg  69300
gatgggacat gggggagggc ctggctaaca tgtcagggtg ggagtttgga agtaggtgat  69360
tcattcattc atgtattcaa acgcaatgtg accccaagct gactggagct tacttacagt  69420
gtaatacact ggttctgcac cattggctca cgcctgtaat cctagccagg gtgggcggat  69480
cttttcagtc caggagttcg aaaccagcct tgccaacatg gcaaaacccc gtccgtacaa  69540
aaaaaaaacc aataatccag gctgggcacg gtggctcatg cctgtaatct aagcactttg  69600
ggaggccaag gcgggcagat cacaaggtca ggagatcgag accattctgg ctaaccctgg  69660
aaaccctgtc tctactaaaa atacaaatta gccaggtgtg gtagtcccag ctactctcag  69720
gaggctgagg cagaagaatg tcgtgaaccc aggaggcgga gcttgcagtg aacctagacc  69780
gtgccactgc actccagcct gggcaacaga gcaagactcc gtctccagaa aaaaaaaaaa  69840
aaagaatcca gcacatctgc ttcccttgga gggcttgtca gggctgtggt tgctggccca  69900
acctccagag tttctgactc caagtggacc ctaggaattt tcagtcacac ggtggcacaa  69960
ttactgctca ttgcagcctg gacttcccgg actcaagtga tcctcctctg tcagcctcca  70020
agtagctggt accacaggca tgcaccacca cacccagcct gaccctagga atttgatgcc  70080
actatccagg gaacacaccg gactagtgaa tgggtatcta actcatggtt cccaaatatg  70140
gcttgagtgt ctgaattcat ttaaaagctc catgtgtggg acacctgttt ccagacatac  70200
agatattggg gaactgatca aggtgataat cacctctagc aaaagatcct aatgatgatt  70260
ctcacagttt gtcgcgcttc ggtgggattc tataccttat tccacagctc ccaagttgat  70320
gtgttgcagg tcaaccacct tccgtgaggg ggctaattgg gagtggccct gtggtcccag  70380
cctagcccgt gtcctctacc ctttggagtg tgattctcag catgccccca actaaaatcc  70440
tggccttcaa tgagcactca cgatgtcggt tgcccttcta agcctaatat tgcaacacca  70500
gtaatcccat tttactttac atggggttcc ccaggcagaa gtcccaaggc cagagcccat  70560
cgggccacac tcatctccag cctttggtca gggaaaaagg ttaatgctgg ttagctagcg  70620
catttagaga gggaataggg tggtgcactt ggggttcacc cactgaacac cagtcagacc  70680
gagcacctct gagcctccca ggccatgtgt gagttgggct ataatcatgg ccatctctta  70740
aataaggtca ggtttctaaa gggcctggcc cagggtttgg ggagggaaga agcttccaga  70800
gtggaaggat gaacatgtta ttagaaaggt gcttcaggac tagaacagcc cacgtgcagg  70860
ttgccatggt gagataactg gcaattagca agctagcccc acacaacctc ccctgcctcc  70920
```

-continued

```
ccgggtattg agaccccagg gacctgggcc acccaattaa gccatcttgt gtacaatgct  70980
gcaccaaata ccaggacagg atgaagccag ctaaacagcc ctggcctcga aaccctaaga  71040
cagacgggca agccctccag atgaggggtc cttggcgtcc tggcctgctt gttggagttg  71100
ggggactcag agggagtatg ggggtaattc ttgtgttttc tcaagatgag gttaggctgg  71160
tatctgagtg atcccaggtg ttgaggcagg gggagaatgc agtgagtgtt ctgatctggg  71220
gaaagaggtt ggagtttgaa tcctatgtgg gcctttgctg aagcagtctt tgggtttgct  71280
tggatttgtg tctggggtct ggcatgtttc tgtgtcactt ggagcaagca gatgacttaa  71340
cctcttgggg tttttcatct ctcacctaaa aggtggagat accagcccgg tcaacatggt  71400
gaaaccccat ctcgaccaaa aaagacaaaa attagctggg cgtggtggca tgcacctgtc  71460
atcccagcta ctgggtgtgg ctgaggtggg agaatggctt gaacccggga aatggaggtt  71520
gtcgctgtga gctgagatcg caccactgca ctccagcttg ggcgacagag tgagactctg  71580
tctcaacaac aaaaaaaagt gataaaatgg aaataataaa tcctacctac ttcatagggt  71640
tactgaagtt caaaggccag atctaggtaa agtgctttgc ctgacacctg gcaggcaata  71700
aacttcacat atatgagatg gcattattgt aaaaatgaga cctattaatc aatgcagtgc  71760
taatgacaat gaagactgga tgcacgtagt gatagtaaca cacaatgttt atcaataata  71820
atagccatag gccaggcacg ctggcacaca ccttgcaatc ccagcacttt gggaggctga  71880
agtaggcaga tcacttgagt tcaggatttg agaccagcct gggcagcacg gagagggttt  71940
cacacccccc tctacaaaaa aattttaaaa ttagccaggt atggtggcac gcccctgtag  72000
tccagctact cgggaggctg aagtgagagg accacttgac ctcaggaggt ggaggttgca  72060
gtgagccgag attgcgccac tgcattccag cctgggcaac agtgagaccc tgcctcatac  72120
aataatagta atacttttta aaaggcaggg taatatttcc ccagatgttg tcagcagcta  72180
ggctgactgg tgtcaactgt agcaacagtg gcatcgggtg tggaacttgt gcccctcacc  72240
acccccacca tcctgtagag atcccaatgc tccttgcgag ggttcccatc ctgtctccac  72300
ttccctgcta atttgtgacc ttgggcgtgc ttgggccttg tttacccaac tataaaatag  72360
ggataaatatc aacatcacag agctgatgcg cggatcaaac aattcagtat atgtgaggca  72420
catgggatgg ggactgaatg ctgagtaaat gacagtgaca aatgacccaa aaatgctttt  72480
ttattactgt tagagaattc tggcaaccct gtgaggcctg attaccatga ttataagtaa  72540
gagaactgac tccaaggagg tctcatcaca tacccaaggt cacccagcta gcagcaaaag  72600
gagttgtgca ttggaatctg ctctgggaag ccagtctact ttttctcctt ggtctcacct  72660
gcatctttgt tcttgtttgt tgttttgctg gagcttgaaa ttacctgctg ccctttgtag  72720
cattttgccc tccttcctag cttccttccc ttccttttat cctgcctact tctccccttt  72780
ctttctttcc tttttgtgta actttattgg tttttttttt gagacggagt atcgcttgtc  72840
gcccaggctg gagtgcagtg acgtgatgtc ggctcactgc aagctctgcc tcctgggttc  72900
atgccattct cctgcctcag cctcctgagt agctggaact ataggcgccc gccaccacgc  72960
ccggctaatt tttttttatt ttttagtgga gacggagttt caccgtgtta gccaggatgg  73020
tctcgatctc ctgacctcgt gatctgcccg ccttggcctc ccaaagtgct gggattacag  73080
gcgtgagcca ccgtgcctgg ccactgatcc accgcgcccg gccacgtaac tttattgatt  73140
tttaaaaact ttaaattatg ccaggcacgg tggctcacac ctgtaatccc agcactttgg  73200
gaggcaaggc gggcggatca cgaggtcagg agatcgagac catcctggct aacacggtga  73260
```

-continued aaccccgtct ctactaaaaa tacaaaaaat tagctgggtg tggtggcggg cgcctgtagt 73320
cccagctact ggggaggccg aggcaggaga atggcatgaa cctgggaggc ggagcttgca 73380
gtgagccgag atcatgccac tgcactccag cctgggtgac agagcgagac tccatctcaa 73440
aaaaaaaaaa acaaaaaccc cacaactttt aactaaaaaa tacgcaggcc aagtgtggtg 73500
gcacacgcct gtagtcctgg ctacttggga ggctgaggtg ggaggattac ttgagcttat 73560
gagtttgagg ctgcagtgag ctgtgttcct gccattgact ccagcctggg tgacagagca 73620
agactctgtc tctaaaaaaa ttactaaaaa ttggtaattt tggacttaca gaaaacttgc 73680
aagaatagta gaaagaattc ctaaatactc ataacccaaa ttccccagat attaacatat 73740
tgtcacattt cctttgtcat cttctctata tattaataac atttttctga tctcggctca 73800
ctgcaacctc tgcctcctgg gttcaagcga ttctcttgcc gcagcctccc aattagctgg 73860
gattacaggt gactgccacc gtgcctgact aatttttcta tttttattag agacggagtt 73920
tctccatgtt agccaggctg gtctggaact cctgacctca ggtgatttgc ccgcctcagc 73980
ctcccaaagt gctgggatta caggcgtgag ccaccatgcc cggctaattt ttttgtattt 74040
tttagtagaa acggggtgtc tccatgttgg tcaggctggt ctcgaactcc cgacctcagg 74100
tgatccgccc acctcagcct cccaaagtgc taggattaca ggcgtgagcc atcatgtccg 74160
gcctgttttt atttttaagg ctcccaatta attgtgaaat atgcaaacag aacagtgcat 74220
aaagcctggt gctttaggct ttgtaaccta tctttgttct ctaagctttg gttcatccca 74280
aggtctgagc attgctgaaa gaaaacagag gttggcgtta ctggagttgg taactgctca 74340
ttctgagtct ttgcacatgc tgttctccac ctgtaacagc cttctcccct ttccaggctg 74400
gtcctccagt tcttgcctct tccaggaaaa tttctttgca cctattctga gcagaattag 74460
gagcccttct ccaatctgaa tcctccttcc ctatgtatag atagaagaat cgggctgggt 74520
gcaatggctt atgtctgtaa tcccagcact ttgggaggct gaggtgggca gatcacctga 74580
ggtcaggagt acaagaccag cctggccaac atgatgaaaa cttgtctcta ctaaaaatac 74640
aaaattagcc gggtgtggtg gcacatgcct gtgatcccag ctacttggga ggctgaggca 74700
agagaatcgc ttgaacctgg aaggcagagg ttgcagtgag cctggatggc gccattgcac 74760
tccagcctgg gcaacaggag tgatactcca tctcaaaaaa aaaaaaagaa gaagaattgg 74820
ctgggcgctg tggctcacac ctgtaatccc agcactttgg gacgctgagg tgggcagatc 74880
atttgaagtc aggagtttga gactagccta gccaacaggc tactacctgt ctctactgaa 74940
aatacaaaaa ttagccgggt gtggtggtgc aggcctgtaa tcccagctac ttgggaggct 75000
gaagcgggag aattgcttga actcaggaag cggaggttgc agtgagcaga gatcacacca 75060
ctgcactcca gcctggttga cagagcgaaa caccgtctca aaaacaaaac aaaacacaag 75120
aagaatctat ctcaccacaa agcactatgt attataattt ctgatttttt tttttttttt 75180
ttttttttag gcagcgtctt gctctgttgc ctaggcttga atgcagtgtg gtgatcacag 75240
gctcactgca gcctcgacct cccaggatcc attgatcctc ccacctgagc ctccagagta 75300
gctgggactt caggtgcatg ccaccacgct tggctgattt taaaattttt ttgtggagtt 75360
tgaatcttgc catgctgtct ctccttggcc tcccaaagtg ctgggattac aggcatgagc 75420
caccacatct ggcctataac ttcttatttt tgtagtcttc tcctccatga gtttgtgaga 75480
ttctcaaagc agcttgatct cccaacatca ttatttagtt caataaagtt gtcatacatt 75540
tgtaaaactc aggccttgaa gtacaattat tttgtttgtt ttgtttttgg acaggagagt 75600
cataatttct atctgtgata atgagattgc ttcacatatt aaaacagttg ctttaagata 75660

-continued catattacat ctccggagcc atttctctta caggatggag attctttttt ctttttaccc 75720
tctggccttt tgctgtcaag gcttaatctg acccagataa ccttggccag ctttttcctc 75780
agtgagaaga gtggatgcta gcaggttacc tggcccaatg tcagtttttt gggagctgtc 75840
ttgggagggt agatgagttg tactttagag ggccttgctc ctctaaaata gagttatctc 75900
ctgtaacttc ctgtgtctcc agaattaggt ccaaactttc taggctggct tttttttttt 75960
ccccacctgg agacagaatc tcactctgtc gcccaggctg gagtgccgtg gtgtgatctc 76020
agctcactgc aacctctgcc tccctggttc aagcgattct cctgccttag cctcctgagt 76080
agctgggatt acagacgcat gccaccatgc cctgctaatt tttgtatttt tagtagagat 76140
ggggtttcac catattggcc aggctggtct cgaactcctg acctcaagtg atccgcccac 76200
cttggcctcc caaagtgctg ggattacaga gccatcatgc cactgcaccc ggcctagagg 76260
cttttcctga tttggttttc tacactgatc tcatccccca tactaatgtc ctcactccag 76320
accaaaatgg cctgcaggta atgctgatac caattaattg acataattta ataactgact 76380
ttagacgaaa ggactcagaa atcacattta ttgagcacat actatgtgct aggcgcagtc 76440
tgataacttt atacacttcc catttaattc taacagaatt tgaacccaga catactggct 76500
tcgccgttta ttatttagcc taatgaaaag ttaatgtctt tgtggataaa acagaggtgg 76560
ctgggtgtgg tggctcacgc ttgtaatccc agcactttag gaggccaagg tgggcggatc 76620
acgaggtcag gagtttgaga ccagcctggc caatatggtg aaaccctgtc tctactaaaa 76680
atacaaaaat tagccgggca tggtggtgtg tgcctggaat cccatctact caggaggctg 76740
aggcaggaga atggcttgaa cccaggaggc ggaggttgca gtgagccgag atcacacaat 76800
tccactccag cctgggcgac agagtgtctc tgtttcttcg tttttttaaaa agaatataaa 76860
taaataaaat acaggtaaca gatgttgcat caaagcactt ataaatatct ttagttgatt 76920
atctatgctt gacatcagct caccataatg ttcatattac tgctgtcgct ataatcattt 76980
gttacatggt tttttattct ttattgttgc ctcttttttt ttctttttct tttcttttttt 77040
tttttttttt gagttggagt cttgctcttt tgcccaggct ggagtgcaat ggtgccatct 77100
cggctcattg caacgtccac ctcctgggtt caagcaattc tcctgcctga gcctctcgag 77160
tagttgggat tataggtgtc cgccaccatg cccagctaat ttttgtattt ttagtagaga 77220
cggggtttca ccatgttggc caggctgttc tccaactcct gacctcgtga tttgccgacc 77280
tcagccttcc gaagtgctgg aattacaggc acgagccacc gcgcctggct tttcttgcct 77340
tttttttgctc aaactctgtt tttttttttt ctttgagaca gagtcttgct ctatcaccca 77400
ggcgggagtg cagtggcacg atctcagctc actgcaacct ccacctcctg ggttcaacca 77460
attctcctgc tccatcctcc caagtagctg ggattacagg cgcgcgccac cacgcccaac 77520
taatttttgc atttttagta gagacggggt ttcaccacgt tggtcaggct agtctcagac 77580
tcttgacctc gtgatccgcc cacctcggcc tcccaaagtg ctgggattac aggcatgagc 77640
caccacaact ggccttgctc aaactctttt gccaaggtaa ctcctcatct ttcatggtaa 77700
gtgtcatttc tgggaagctt ttccacacta cctaggagag gtcatgtctc ttgtggtgtg 77760
ctcttggagc agtactcgag accgaagtat tgaaatgcct ctagacctgc tgataaacag 77820
ctcctgcccc agcttcccca cccattcttc cctgaacgtc ttactgggtt tcagcaacta 77880
actgggtgag atttggccta gagggacctc taggcccctg ctccacacag tggaagtacc 77940
atcagcccac cacataatgt ccctgcctag cattgagcct gatttgtaat ttaacaagga 78000

-continued

```
tttgtgtcat tagttgtgtc ccctttgcct cccctgccag tctggaaact ttaagaggtc  78060
agaagctgtg tctagttttc gtttttatct cttagagatg gagtttcact ctgtttccca  78120
ggcctggagt gcagtggcgt gatctttgct cactgcagcc tcgaactcct gggctcaagc  78180
gatcctcctg ccccagcctt cccagtagct ggaactaaag gcacgtacca ccatgatcag  78240
attgtgtctt tttttcacca gggcctgatt ggtcagggaa aatatttgtt gaatacttga  78300
ataaatgata cccagacaaa aaaagtcagc ttgaaatctg gatctacctc tgacactgag  78360
tgagtcaatt ggcctctttg tccctcagtt tctttctgct gtaaagtggt gcagttcctc  78420
tttttttctt ttttagacga agtctgactg caacctctgc ctcccaggtt caagtgattc  78480
tcctgcctca gcctcccaag tagctgggat tacaggcgcc caccaccatg cccggctaag  78540
ttttgcattt ttagtagaga tggggtttcg ccatgttgga caggctggtt tccaactcct  78600
gacctcaggt aattcatccg ccttggcctc ccaaagtgtt gggattacag gtgtgagcca  78660
ccacgcccag cccagttcct ccttcagcca aggctctctt gagaatgtaa gggccaggtg  78720
tggtggctca cgcctgtaat cccagcactt tgggaggccg atgcgggtgg atctctcgag  78780
cccaggagac cagcccagcc tgggcaacat ggcaagaccc catctcttaa aaaaaaaaaa  78840
aaaaaaaaga gggagtgggc aagagagaat gtatgtacag ccattgggaa acaacccgga  78900
acaggactca ggaggtcctt gctcctgtgg actttacagg agacagacag taaaggcaca  78960
agatgccttc ttatggtact aagaagaaaa tatgccgcat gatattgcag atgggggggc  79020
gggggcgtca cagaacgtga cttttttttt tttttttga gacagagtct tgctctgtcg  79080
cccagactgg agtgcagtgg tgcagtctcg cctcactgcc acctccgtct cctgggttca  79140
agtgattctc ctgcctcagc ttcccaagta gctggaatta caggcgccca ccaccacgcc  79200
aggctaattt ttgtattttt agtagagatg gggtttcact atgttggcca ggctggtctc  79260
aaactcctga cctcaggtga tcctcccacc tgggcctccc aaagtgctgg gattaaaggc  79320
gtgagccact gcacccggcc cagaaagttg acttctaagc gtttccccaa agtgtctatt  79380
aggtatcttt atgattcaat aacccattct tacagaaatt aattgtaagc ctgggagcgg  79440
tggctcacgc ctgttatccc agcgctttgg gaggctaagg cgggaggatc gcttgaggcc  79500
aagagttcga gaccaccctg ggcaacacag cgagacctcc atacatctct aagcaaaaaa  79560
aaaaaaaaat tcattgtaaa agcaattttc tttttggtta ctgccatagg gattttgtaa  79620
ctgagtcaca ccgggccgag gcgggacctc attggctgcg accgaccacg tgccgcagtc  79680
gccccggcgg tcggggcccc gcccctcggc taccgttctg tggatcaggg gccgagctcc  79740
gcccccggcg cgcggctgag accctctcta taaaaggagc cggcggagga tggcgagcct  79800
ttacgtcggc gcgtaacgag ggggtgcgtg tgaggtcatc gcgcgggcgg gcgggcgggg  79860
tctggcggtt tgaacgagac gaagacggaa ccggagccgg ttgcgggcag tggacgcggt  79920
tctgccgaga gccggtgagc cggctagcgg gcccgggggg tgcggctggg ggggcggccg  79980
cgtgggccaa ggccgggcgt gcgcgggcag gccctacggg cagcgccagg gccgttccac  80040
acggcggtgc tgttcgagcc gggtggggga agggcggggc cgtcacccgg cgcgcgcggg  80100
ctgggcctgg gggcgcgcgc tgcgctctgc tcagggggcg gggtctcggg ccggaagtgg  80160
gctgctgcta cgcggggtgg gggtttctgg gccgccgctg aggtgtggtc cctgcgctgc  80220
agcgactgga ggtcccaggg tggttgggcc ctgggagggt gtgggcgagg tgggccgtcc  80280
tgggagctct ggggacgcac attgtgggag gccgtgttgc ctgagggccg agagatcggg  80340
tggtggagtc agacctgggt tgggttccgt gcggtgtgac cttggacagg tgctttaacc  80400
```

-continued

```
gctgtggatc tcagcttcct catctgtaaa acggggacag taatactacc cacattaaac  80460
tcttagcgcg atgtatggca gaaagtaagc cagctcttgg actccctcct ttcttcagtg  80520
tgtgtttatt gaatgcccac taggtgttgg gcaccgtgct aaaccctggc tgttttcccg  80580
ggaacaaaga tttgctctcc aggaatccac attatgatga gcaggaggac agtataacgg  80640
gatggtatca acagtgctag ttcagtccct acttcacagt tgccctcgga tgctgcaggg  80700
cagagcttga cctctgcccc attttgggga tgaggatcct ggggcccatt gagggaggtt  80760
atgctaggcc gggcatccgc ttctccgatg gcatgtctct aacagtagta atgataatag  80820
cagctctttg ttagttgggc acttgttttg tgtcaagcac tgttaagtgc tccatgtggc  80880
tttgtgtctt ttaatactaa cactgtcttt aagagagatt ctcttcttcc tttttttttt  80940
tttttgaga cagagtttta ttctgttgcc caggcgtgca gtggcaccat cgctcactgc  81000
aacctccgcc tcccgggttc aagcgattct cgtgcctcag cctcccgagt agtcgggatt  81060
acaggcgcgc gccaccaagc ccggctaatt gttgtatttt ttagtagaga cgaggtttcg  81120
ccatgttggc caggctgttg tcgaactcct gacctcaagt gatctgtccg cctcggcctc  81180
caaagtgttg ggattacagg tgtgagccac cgcgcctggc aagagagatt actttcattt  81240
tacaaataag gggtctgaga ctctgagagg cggagtgtct tatgcagccc agcaagtggc  81300
tgaaccccca cctgggactt cagtgtctag gctcttaacc tctttattac actttctccc  81360
tgaggtccag agctacacat ccagatgtgc cctttgtggt ggtgcgtcaa agtgcctagc  81420
acagtttttg gcacagaggg aagcttagga cgtgatgtgc cttttgctta agtgttttca  81480
tgtagatttt tgtttaatcc ttaccaccac tttgtgcaga gatactgttt tacccatttt  81540
acaggatgag ccatttgtga tgcaggaaga ttaagtgact tgcccacggt cacataggtc  81600
ctttctggtg gcacctcctt cccccacttt acatagggct tattgtggtg ccttgaaagt  81660
aatagagtgc tttagagcca gcgttgaatt tgtataggtt tgggatcttg ctaggagagc  81720
tgctgaagga agagagattc ctgggtaggt ttgagggagc tttttcatgg tggtggtgga  81780
aacctggatc aggaagcctt gtaagggtga gatttgtgtg gtagtcatgg gtcttccatg  81840
gctgccaatg atggaattgt gaaggaaggg tgagctggag ctctgttttg attgtcagga  81900
ggagccaatt aattgattga gtcggtggat gttcattgta catccacagg gtgcctaatc  81960
catgtattta gtggctgcag cgtttgtgga gcacgtggga ccaggtatta atgtactgct  82020
aatgaaagtt ttaaattata tgatgatgaa aggccattaa tgtttttgga gctggggtgt  82080
ggtcaggaga cacacatggc tttaccagct gcttagattt tatagcagca tgatgcacac  82140
gatacagtat atataggaat gtcgccataa tagattacaa ttgctcagct gggaccatgt  82200
ctttttgtt tgaatgtctc tggtacctga ttttgcgcac agtattttgt tcattcaagg  82260
attttaaaca agggaggcac ttgctgtgat ttgtgattca ggaaattctc tctggtttgc  82320
tgtgtaagaa cagattgaca cagacaaatt tgaagactgt tgcagtgcat ctccgtgcaa  82380
gatggtgctg gcaggtctca ggcgcactgt ttttggcatt ggagatagga ggatgagtga  82440
gacaaggtcc ctaccctaca tcttgtttgt taaatacctc ttaaatttga tgccatgcca  82500
aatattttat gtaccttatc taatttaaac ccttctatga cccttttcag ataggtggct  82560
ttaacttgta agggaactga ggtacattga gtttaagtaa cttgcctaag atcacacaac  82620
taatgagtga ctgcctcaca ttcaaaccca tgtcctcctg gcttgaaatc ctcagctgtt  82680
tgcatcgagt ggattgcttc ctggcccaaa tctggctcga gaatggttca gaaataacga  82740
```

-continued gataatgaca attcattgtg ggacttccta tcataaaggt ttgaatgaat tgctctggaa 82800
acatagggat taatttccca gtggagtcag taactaaatt gtgttggtgt cttgcataac 82860
atggttttat cagctgattt ggggagtgta acagtgttga tgatttgctt tctgacaagt 82920
ttatatagac acatttttct ctctttgacg ctgttctgcc aacctgaaaa taagtagtga 82980
gtgcttgcta tgtgcaagat actatgaggt gcctgggaga tgtgagggca cgcagacctg 83040
gcaagttatt gacctctaca gacctcagtc accccataaa aaggggactg gatgggtgga 83100
tttgcctctt ctggctgtca cattctgtgg cttggtgagt caggaggctt gcagcagctt 83160
agtgcaggag actgatgtgg aaagaccaac tctagtcact aggtggaggg aacgaagtac 83220
cgtaagagag caaggggctg ggatctcagg attgttccag attgctctgc atctttcccc 83280
tgcccctccc cactggtaat gttgctgtct tatgaaatga agaaaattgt taagtgtcta 83340
ggtcactatg aagtctctgg tatttcatag tgtgtcctca tggtgactgc tcagggattt 83400
gatttagatc tggattagcc tgcctttatc ttgagtcttc cctccctact gtctgttctc 83460
tactagtagt caatgtgatc tttttcaaac tgtaatgaga gcaagattct accgcactta 83520
aaacctgaaa gtgcctgggt gtggtggctc atgcctgtaa tcccagcacc ttgggaggct 83580
gaggcggagg attgtttgag gctgggccgc aaaatgagac ctggtctcta caaaaaatta 83640
aaaaattagc tgggcttggt ggtgaccatc tgtagtccca gctacttggg aagatgagtc 83700
aagaggatgg cttgagcctg ggaagtcagg gctgcagtga gccgtgattg tggcattgca 83760
ctccagcctg ggtgacagag tgacaccctg cctcaaaaaa caaacccaac agtggatttc 83820
ttaatagaat aaaatcctaa ctccttctgt tcccacctca ggctctgctc tccttgctca 83880
ctgggctgga gagccctatc tctagagctt catgtggttg cttctttctc tgatccttaa 83940
gctcaactgt tcatctcaga gaggcttcct ctgaccacat tccgtaaacc ccgttgcata 84000
agtggttggt atgaaatgat gtttgttggt gtatttggtc agtgtcagac tttgcaccac 84060
tagaatgtga actccctgtg gacaggcacc ttgtctcttg cttttctgta tcctggtccc 84120
tagaacagtg cctagcacgc ggtagagcta gtaaacattt gtagaatgag tgacggttga 84180
ctacactggt gctcatagac aataacgccc acatttacta gcatttgaaa attagactca 84240
ttgctgtgtg tttattgttt tgaatttgaa agcctagcag aaaagggagg gaagagaatg 84300
tggaggctgg ggctgggcag gcttgcctgc caaccccagg gcctctcttg tcctcacctg 84360
taaaatgagg gacatgaagt gaaccttgca gagggctgtc agggttaaac aacaagtgtc 84420
tgtgaagtat ctggcactta ggcccacaga tgccctacca ttgccaggta gctctgcaga 84480
gaattaacta caaggattct tcacctgtaa ggtcatttga tactgccttt ttaatatcta 84540
ggtattgaaa agctgattta ctttttcaat tatgaaagaa tttatagttt tttttttttt 84600
tttggaaata ggatctcact gcctcaacct cttggactca ggcgctcctc ccacgtcagc 84660
ctcccaaagt gctggtatta caggcatgtg ccagtgtgcc tggcctaggt atagtcttta 84720
aggaaaattt gggaagtagt gaaaactata aataggaatt aataaaaacc catcgggcca 84780
ggcgtggtgg ctcacgcctg taatcccagc actttgggag gcctaggtgg gtggatcacc 84840
tgaggtcagg agttctagac cagcctggct aacatgctga aatcctgtct ctactaaaaa 84900
tacaaaaatt agccaggcat ggtggcatgc gcctgtaatc ccaggtactt gagaagctga 84960
ggcaggaaaa tcacttgaac ctgggaggcg gaggttgcag tgagttgaga tcgtgccatt 85020
gcactccagt ctgggcacca gagcaagact gtctcaaaaa aaaaaaaaaa agaaagaaac 85080
aaacaaacaa aaaaccatta tctgaagaaa attgtaacat tttgatatct ttatgggtaa 85140

-continued

```
ctttgggctg atgttttcta aacagaaagc attctcgttt atgcatctgc ctcccatcat  85200
aaaagcactt actcatccct ttatttagtg cctcttatag tttagaattg tatattaatc  85260
acattaaaat ggggcctcaa ttttagtctg gctggtgttg ggcagttcat ttcaggtcat  85320
gtttgtatgt ggaaatccag attctgtggc tggaatctta gtgtctctcg tttggcctca  85380
tggggaagaa ggtgaggctt aaaaagtcaa tgtacctagg ctgggcgcag tggctcacac  85440
ctgtaatccc agaactttgg gaggccaagg tgagtggatc acctgaggcc agtagttcaa  85500
gaccagcctg gccaacatgg tgaaacccca tctctactaa aaatacaaaa attagctggg  85560
tgtggtggta cacgcctgta atcccagcta ctcgggaggc tgaggcagga gaattacttg  85620
aacttgggag gttgcagttg agtcgaggtc gtgccactgc actccagcct gggcgacaga  85680
gtgagactct gtctcaaaat aaaataaaat aaaataaaat aaaattgagt gttcctacag  85740
gtttgctttt ggtgactctc taggaaacac ttgaccttac ttgcatgcct aatgtaacac  85800
aggcccttct cttttcttcc catgctttag aagatggcag tgaacgtata ctcaacgtca  85860
gtgaccagtg ataacctaag tcgacatgac atgctggcct ggatcaatga gtctctgcag  85920
ttgaatctga caaagatcga acagttgtgc tcaggtaaga gaaatctgct ggatcatttt  85980
tctaggaaag cctgtaggtt tttcaggaat gtgaaggcct gtatctgact gcaaagccac  86040
acacagaggt tcagggtctt tgttagggcc accctgtttc ttcctctcag ccctgccttt  86100
gcttctgctt ccaaaggaac tttttttttt tttttttttt ttgacagagt ctcgctctgt  86160
tgcccaggct ggagtgcagt ggcgcgatct cggctcactt caagctccgc ttcccgggtt  86220
cacaccattc tcctgcctca gtctcctgag tagctgggac tacaggcgcc tgccaccacg  86280
cctggctaat ttttttgtat ttttttagt ggagatgggg tttcaccgtg ttagccagga  86340
tggtcttgat ctcctgacct catgatctgc ctgcctcggt ctcccaacgt gctgagatta  86400
caggtgtgag ccaccacgcc cggccttttt tttttttttt tttttttttt gagatggggt  86460
ctggcgctat tgcccaggct ggagtgcagt ggtgcagtct tggctcactg caaccttcgc  86520
ctcccgggtt caagcgattc tcctacttta gcctccaaag tacctgggac tacaggcgtg  86580
catcaccaca cctggctaat ttttttgtat ttttagtgga gacggggttt caccatgagg  86640
tcgaactcgt gacctcaaat gatctgcctg cctcagcctc ccaaagtgct gggattacag  86700
gcatgagcca ccatgcctgg ttggaactat acttaaataa agagtgtgct ctggcctgca  86760
ggtccaccat cttctgctct agagactgca ttctgaggcc tgaagctcag ccccgacttc  86820
ttggtgtcta ttattgtgca tccagattgc atgttttatt tgaggacagt aattgtatta  86880
actactgtct gctgttctag ttttatgttc atcagtggca tttcttattc ccaagaagta  86940
caagatcaaa gtctagcaaa tatcatttca gccacaattt tatggaacta ctgtttaaca  87000
ataatttggc aaagatgtaa tgatttaaag tctcggtgtg gtggctcacg cctataatcc  87060
cagcactttg ggaggctgag gcaggcagat cacctgaggt caggagttca agaccagctt  87120
ggccgacatg gtgaaacccc gtctctacta aaagtacaaa aaaattagcc gggggtggtg  87180
gcaggcgcct gtaatcccag ctgctctgga ggctgaggca ggagaaacgc ttgagcccgg  87240
gaggtggagg ttacagtgag ccaagatcgc accactgcac tccagcctgg gtgataagag  87300
cgagactccg tctcaaaaaa atgaaaaata agtagtgatt taaaagaaga acaaaaacat  87360
ggtctctttc tatgtatgct aatcgtatga cgtgggaaac tagaaagaag aaaacaaaaa  87420
aatgccttat aattccacta ttcaagccgg ctactgttca ctcactaatc atgagccact  87480
```

-continued

```
gtgcctgccc tggatcgatc ttaaattact gccattgctt ggccgggtgt ggtggctcgt  87540
gcctgtaatc tcagcacttt gggaggccga ggcgggtgga tcatgaggtc aggagtttga  87600
gaccagcctg gccaacatag tgaagccccg tctctgctaa aaatacaaaa aattagccag  87660
gcttggtggc acgcacctgt agtccagcta cccgggaggc tgaggcagga gaatcgcttg  87720
aacctgggag gtggaggttg cagtgagccg agatcatgcc actgcactcc agcctgggtg  87780
acagagcgag gctctgtctc aaaaaaaaaa aaaatttatt gccgttgctt ataggatttt  87840
ttcttttttt tttttgagtt cagcttctgc ccttccttat tttatagctg ggtcctagtc  87900
tcggtcttag tttcattgac ttgtcttgtt atttccttgg tgaggtgtat ttaatcttgg  87960
ttttacggat ggtcagatgg aggctacgtg tgaagctgta cagtaacaca gtggtgccca  88020
agagttgtgt ttattcagca ttaattactt tgctgatcat agacaacagg ctgttagcct  88080
tagatctgtg ctgtgtcccc cccaccattt tctattagtt tcctcattat tcatttccct  88140
atccccattt gtgtgaggct tttaaagcac ttgtttgacc tgtgttctgt gactaatgtg  88200
aggatgaggt catcctagtt ttcactggag ccagcttttt accagcaatt ccctctaaaa  88260
tttacctttt tctgtaaata tattccaaag tctatttcac ttagttaatt ggaaaatgtg  88320
atctttaatg tttagataag ttgtatatgt gctgatcggg ctctaggttt atctcattca  88380
ggcagagagc tgttgtagac aggactgggc ataaagaggc ttcagtctgc tctgagccat  88440
gtgacttttg acaagaccct taatgtctta gttcttcatc tgtgaactgg ggcagcgata  88500
cctggcccac ttgttggcca gtgtgagaat cacctataat aacagctttc agataactga  88560
ctgtgtgcca gaccctggaa atgagtgcag gtcatttgat gggggcacat cctcctttta  88620
cagatgagga gactaaccct ggggcacagc ttatgtatta cagaacctgg ttttgaacca  88680
gatctttctg agcacacagc ccacatgcat cctgctgcat acttgttata tcttttatag  88740
aaacatttgg aggggattaa acaaatgtaa attacaaatg taaattacat atagttaatt  88800
atagtgatac tgtttcacta taaagtctgt gaggtttgtc agttgttttt tttttctttt  88860
tgagactgga ggctggagtg cagtggcgtg atctcggctc actgcaacct ccgcctccca  88920
ggttcaagcg attctcctgc ctcagactcc tgaggagctg ggattacagg tgcgtgccac  88980
ctgtaatttt tgtattttta ctagagacgg ggtttcaccg tggtggtcag gctggtcttg  89040
aactcctgac cttgtgatcc gcccacctcg gcctcccaaa gtgctaggat tacaggtgtg  89100
agccaccgcg cctgggtggt atgtcagttt tgtctcatgt ctgctacttt tcccaaataa  89160
agtgcttttt ctccctagaa aagggtaagt gcaggacact taactgtgat ttgtaaacaa  89220
acttgttcat tcataactag tcttcttgaa agccgtataa gatgtctctt ggagtatgta  89280
gatggttgca ttgtgtttca cattggtgtt tagaaaatga ggtcttgctt ccagtatgag  89340
agcagacagg atgagacaca gacattgtct ctctgaagaa ggcccgctgc caggggtttg  89400
gagtcagaga aagtgaggct cctcaactcc ttgtgcttac tgaggcccaa ggagaattcc  89460
aggagctttt gatgctggtg ccagatcctt cctaacctca tctctgatga gcagaggatc  89520
tagcagacca gagttctcca ctaaacacag ctttacaaag taggaataca tttcttcctt  89580
gagagggcaa agtgctgagg tcctttgtta atctgcctgc tgcctgtgaa gtggccaaat  89640
tttgtcagca gtgggctctc ctacccccaa cagtgagctg agcctttgct tggctctggt  89700
agagggagat taggcaagga taactttcag tgaaagattt ggcaggttgt ttcaagattc  89760
attaatacat tctgtagtct ccgtagtttg gagagctagt catcaagtat tttggaaaga  89820
tagtcatcat gaggaaaaac ctggtcaaag agaatgattt ttatgagagc tttttttttgt  89880
```

-continued

```
cagaaaggga gtactggttg cttttgtgaa ttgttcctgt gttgcattcc atattcaggc  89940
ccctctgcat tttctcaaga gcacagcttg gtcctctgca catgtagagg ggtctcactg  90000
aatgtattcg gctctcccct tctcctcctt gtcttctccc tccagcctgg cttcctttat  90060
gggttccttc gcagcaaagg tgttgatgtt cccaggcaaa tggtagattc ctttctcctc  90120
agcttaatgt ggggccccga cagcccttga gttcatgtaa gacagcttgg cgatcttgct  90180
tctgctgcac tgctaatgac atggtcctcc tgctctggga gtgtgttatc acacctgtaa  90240
ccaggcctct cccagctcag atctggtctg atatttctgt ttatgggata cttttgccct  90300
acctgtcatt acttaaaatc tcagctttgt tttctcctca ggctagctcc cttttccagg  90360
tactccattt ggggccatga ttccatcttt cttccagtgt cccaggcctg agaagcatct  90420
tttgaggcta attcacagtt ttatttgtct tctgaaagag cttctagatc cagccccttc  90480
tcagattgct cactgctgct gcagtggcct cctgactgaa cactaagttc cctctaagtt  90540
cccagccccc accttccctt ttgttatatt gcataagtct gcagcctttc tgagggactg  90600
gttttatcaa gtcacatttc tgatcaagga agtatctctt caaacttttt tttttttttt  90660
gaggcggagt ctcgctctgt tgcccaggct ggagatctcc gctcactgca agctccacct  90720
cccaggttct caccattctc tgcctcagcc tcccaagtag ctgggactac aggcgcccgc  90780
caccacaccc ggctaatttt tttgtatttt tagtagagac ggggtttcac cgtgtttgcc  90840
aggatggtct cgatctcctg acctcgtgat ccgcctgcgt cggcctccca aagtgctggg  90900
attacaggtg tgagccaccg cgcccagcct cttcaaacat ttttgcctaa gtcttcaagc  90960
acctccttga tttttccctt gctttacata aagcaaacca aaacagaaga taggaagctc  91020
atttcttctt gattatgaat agttaggtct tcattaaaaa aaattaaagg ccaggtgtgg  91080
tagttcatgc ctgtaatcca gcactttggg aggccgaagt gagaggatca cctgagccca  91140
ggaatttgag atcagcctgg gcaacatgac aaaaccttgt ctctaaaaaa gaaaaagaaa  91200
catgaagaga atcatactcg cataaaagtc tatcaggagg actggatgcc aatatttatg  91260
taattgattc tttctctttt tagaaatagg gaaataaata agaatgtttc tttctttttt  91320
ttttattcct gtacaatttt ggtaaccagt ttcatgcata agttgttgac tttttttttt  91380
tttaactcct gtgcaatttt ggtaaccagt ttcattcata agtcattgtc tctttttttgt  91440
tgtttttttt ttgagacgga gtcttgctct gtctcccagg ctggagtgca atgaatggtg  91500
cgatctcagc tcactgcaac catcgcctct cgggttaaag cgattctcct gcctcgggtt  91560
cccaagcagc tgggactaca ggcatacgcc accacgcctg gccaattttt ttgtattttt  91620
aatagagacg ggatttcatc atgttggtca ggctggtctc gatctcctga cttcaggtga  91680
tctgcccgcc ttggccttcc aaagtgttgg gattacaggt gtgagccacc gcgcttggcc  91740
aatttttctt ttttttaatt gtgtaaaata gtactgggta aaataccact gtggatatag  91800
ttgctgaata gattgtcttc tatttgggtt tttaaaaaaa gttcgtccgt ttcaaaaaaa  91860
aaaaaaaaaa caaaagaatg ccctcagtgt acttttgttg gatgagtaaa taaatcagtc  91920
acctcagaaa tcaaggcctt aaccttctga agatcctttc ttaattaaga atgtcaccct  91980
ggtcactgaa gtgcccctgc tctcgtttat gttgactttc caaaaataac ggtaaccgaa  92040
catgctggaa ccagcagaga actggttcgg cctgacctca agtaagttga atatgcattt  92100
tatggcagtc ttgaattctg cagattactt attacttaac cactggttta gcttcccaag  92160
cttgttcctt tggcaaatta gccctggaag ggcagtaaag tacacagtga agcctgctgt  92220
```

-continued gaattaggag agttcagttt gtcggcatta gagaaataat cttcctggaa agtttaagca 92280
gtaataaaac actttttgga aaaaaaaaat gggcaagtgg gggaaggaat gaaatgggat 92340
gaaatattgc aataatttat tacagtagtc tctttttttt tttttttttt gagacgaggt 92400
ctctctctgt cccccaggct ggagtgcagt gatgtgatca tggctcactg cagtccttga 92460
cctcttgggc tcaagtgatc ctccttcttc agcctcctga gtaactggaa ccacaagggc 92520
atgccaacac gccaagctaa ttttggtatt ttttgtagag acagggtttc accatgttgc 92580
ccaggctgtt ctcgaactgc tggactcaag tgatccacct gcttccctaa gtgttgagat 92640
tacaggcgtg agctacggtg cctggcctta tcatagtagt ctttatttat ttatttttga 92700
gccagagttt cgcttttttt tttttttttt tttttttgag acagtgcagt ggcctgagag 92760
aatcgcttga actcaggaag tagaggttgc ggtgagccga gatcacgcca ctgcactcca 92820
gcttggcaac agagcgagac tctgtctcaa aaaaaataaa taaataaaaa attaatagag 92880
gaacacaaaa atgtcttcta ttcaactttg ttaattaaat gacgggttgg ctgggtgctc 92940
tacaaaaaga ataaaaaact agttgggcgt tggtggcacg tgcctatagt cccgctactc 93000
cagaggctga ggtgggagga tcacttgagc ctgggaggca gaagttgcag tgagctgaga 93060
ttgtgccact gcactccagc ctgggcgaca gtgagaccct gtttcgaaaa gaaaagaaaa 93120
gaaatgatag gttaaatgta tttagagatg taaaaagccc agggagacag acgtcttagg 93180
gaaaaaaatg ttttttaatc tagatcaagg atggatcttg gaaattgcct cctgaagagg 93240
agggtatatc tttgtgaaaa atcagaaaat gtcacttttg ttattttctt ttctgtattt 93300
taggcattca tttttgtttc tagtggtcat tttattgtca tgatgattac caataaagaa 93360
caggagtttt aaaattttgt agaaacactc cttttctcct tgttataggc ttctgggttg 93420
caagtatgtt gtagaatata tggggtgaaa accacagtct tgttacaggt tttagaaatt 93480
gacttcacat gaagttagtg aagcttttgg tttttgtagg tctacttcac aattttaaaa 93540
attgtatttg gtttaagtgg gtctgggaag aagttcaccc tgcttcttta attgtatttt 93600
tctgttgccg ttgttctttc aggggctgcg tattgtcagt ttatggacat gctgttccct 93660
ggctccattg ccttgaagaa agtgaaattc caagctaagc tagaacacga gtacatccag 93720
aacttcaaaa tactacaagc aggttttaag agaatgggtg ttgacaaagt aagtaaacgt 93780
tatcttttat tgtggttaat gttccttaat gatcgttact aaggaggtag atgctagctt 93840
atgactttgg acattttctt ttttttctta atttatctag ttaacttttc tcagttaaca 93900
cagaatttac tgggagcagt ttgcccctac cttcttgccc ctattcccct tgcttgtttc 93960
tttcttcatc gtctgtgaag ttagtaactg tttagaggag tcagcctgta aatttgtaca 94020
gtgattttta tttttaaaaa attcctgtgt aatctctagt agtctggaat ctaactctct 94080
taatctggat ttacttctgt aaaagcatac tgtatgtaga atagttccag tagagaagat 94140
tctaggccag gcgtggtggc tcacacccgt aatcccagca ctttggaggc tgaggtggag 94200
aagattctag aaatacttgc tttttataga aggttacaag gaggctccgt ggtgggtgct 94260
ggaaaactcc tttctgcccc caaaggtttt tgaaggtaac agaaacatgg tccaccaggc 94320
atggtttagc acaaacattt aatgtttagc acaaatatta cctctgtttt agtagataat 94380
agattaagta gtttatccct tcccccaccc ttgtgaaggg tttatccttt taagccattt 94440
ttggggggat aacttttttt ttttatggca aaggtagtaa cacccccaat tatcttgctg 94500
gtgtctggtt tttatttatt ttgaaatcag ggtttttttt taattttagt tttgtctcta 94560
caatatataa aataggcatt tatagtataa gaatatcact taactttcca ggcatagttt 94620

-continued

```
aaatagagtt catatacagt aattttgcat tcattattat ggaattttat tttttgaata  94680
tggaaaatgt ctaaagtata taaaagtaat aatagtgtat aaacaataaa tagtaaatag  94740
tgtaatgatc cctcatgtaa ctcaatggtt agcatggcca attttgtttt atatctaatt  94800
ctatcctatc ctatgtattc tgggttattg aagtgagtac agaggtaata tttgtgaatg  94860
tttcagtatc aagcaaagta acttttaaaa attatatttg tcagaggggt ggatatatta  94920
ttggatatat tctttttata atacattgca actggaatct ttggagatta aaagatagtt  94980
aaaagccagg catggtggct catgcctgta gtcctagcta ctctggaggt tgaggcagga  95040
gcatcatttg aactcaggag tttgaggcag cagtgagcta tgattgcagc ataagactcc  95100
agcctgggca acagagcaag accccatctc taaaaaagat taaaaagtta agttgtggcc  95160
aacacttcag tgatttgaat acttgaaaac acagtattct tgtataatag aaatacttac  95220
agggtcctta tgtatatttg ttattttttg tgtgtgtgtt tttattggtg ttttttttt  95280
ttttttgaga tgaggtcttg ctgtgttgcc agtgctggtc taaattcctg gactcaagca  95340
gtcctcaaga tagctaggat tgcaggtggg cagccctgcc cccagcaagc atgttttaat  95400
aggatttgga attacttgga aaacatgtca ttttgtaaaa atttatcctg agactgattc  95460
tgcatcttga tctattttca ggttagaatt attctttttt cttttctttt cttttctttc  95520
tttttttttg agacagagtc tcactctgtt gcccaggctg gagtgcagtg gtgcaatctc  95580
agctcactgc aacctccacc tcccgggttc aagtgattct cgtgcctcag cctcctgagt  95640
agctgggatt acagacgccc gccaccacac ccggctaatt tttgtatttt tagtagagac  95700
agggtttcac catattggcc aggctggtct cgaactcctg acctcaagtg atctacctgc  95760
cttgacctcc caaagtgttg ggattacagg tgtgagccac cacgcccggc ccagaatttt  95820
cttgaacaca gttcattgta gatgcctttg gttggtttgt gcaatggatt tttcttccct  95880
tttcttaaat ggggtctctc tctgtcaccc aggctggagt gcagtggcac agtctcgact  95940
cactgcaacc tctgtctcct gggctcaagc agtccaatct cagcctccca aggagctggg  96000
accataggcg catgccacca cacctgccta atttttttgt atttttggta gagcctaggt  96060
gtcaccatgt tgcccaggct ggtctcaaac tcttgcccgc cttggcctcc caaagtgctg  96120
ggtttacagg catgagccac tgtgcctggc ctgtgcagtg gatttcatgc tttgtgatag  96180
gcattgtggc catgcaagtt atatagcgga cctactcttt atagcataat gcacttttgt  96240
atcacgtctt acgatgtgct tggatggatg tgtgtatgtg acttatatgg tacttgttcc  96300
tttttgtttt ctgattcctt ttcatacatt tgagagagtg gggaggggtt gggaagtgta  96360
ggtactcttg aaggcaaact gcatgaaact tgctttataa atttaggggc ttagccctaa  96420
ggtctctaaa atattttttt ctccttttgg cagagcttta taatgaattg atgcatggac  96480
tagtttgatg cttgccaaaa gcctcttttt tggggctaaa cagttgtttt tctctgcaga  96540
taattcctgt ggacaaatta gtaaaaggaa agtttcagga caattttgaa ttcgttcagt  96600
ggttcaagaa gtttttcgat gcaaactatg atggaaaaga ctatgaccct gtggctgcca  96660
gacaaggtca agaaactgca gtggctcctt cccttgttgc tccagctctg aataaaccga  96720
agaaacctct cacttctagc agtgcaggta aaaaaacaac cccaaaacgt ttccaaaaaa  96780
tagcgttcca gatattcatt cagcgttcaa ctagaatttt tttcagtagc cataggctta  96840
gggatcttaa gaaatataat cccaggcatg tggccagagt atggattttg gcatcaggca  96900
gataacggtg tgtgtcctta ggtgtctgta gccctgtgta agcaacttca actctgcccc  96960
```

-continued

```
acagtttcct cctctataaa atgggaattt taatacttgc cccagagggt ttttgaaact  97020
tgaacaagtt actgtatgca gttttgccaa agctctagaa atccatcagg ctagctcatg  97080
taagagagca ttagtttgtt ccaaaacaag ggcattttta cagagcccta ggatgggaag  97140
ttataccaga gctgaactcc ttgaaggaag tgtgtaggtc tctcagggac tgctcttggc  97200
tgtctgtgtt attctctctg tagaccagct tcctgtgtat actcacagct tccctacctg  97260
ccctagaact ttagctgcta ggtgactttg gcttgccatg gtgctagcag agtcaggggc  97320
gggggtaggg gagaggctga ttttacatac cttctcaaaa gggtatgggc ttggtagctt  97380
tcccaagatg tgtttacatt agtatagaat gtgtatattt tggggcaggg tagatactct  97440
acagatgcta atttcttctt ttccagagga tggcaagaat attagttaag gtttcataat  97500
acctagagag aggcttgttc atctgataga gagggtaggt tgagtgcttt ctaaatagct  97560
taatggagag acaattcgca tgccatataa ttatattttt atatttaaag tataaagtta  97620
aacggttttt aatatatcca aagaattgtg taactatcac cacaatcaat tttagaacat  97680
tttcatcact ctgaaaagaa accctgtgct gggcgcagtg gctcatgcct gtaaatccca  97740
gcgctttggg aggctgaggc aggcagatca cttgaggtca ggagtttgag accagtctgg  97800
ccaacatggt gaaaacccat ctctactgaa atacaaaaat tatctgggca tggtggtgca  97860
tgcctgtaat cccagctact caggaggctg aggcaggaga atcgcttgaa cccaggaggt  97920
ggaggttgca gtgagccaag atcgcaccac tacactgcag cctgggtgag agagacagac  97980
gctgtctcaa gaaaaaaaat agaaagaaac cttgtacata gttaatagtt gtcacttccc  98040
actttcccca gctttacccc ctccctccag ccctaagcaa ccacttatct gctttctgtc  98100
tctggatttg ccagttctaa acttttccta tacatggagt catagagtat gtgatctttt  98160
gtgtctggct tcttttgctc agcctgctgt tttcaaggtt catccatgcc ctagcatgta  98220
tcagtccttc attctttttt attgtggaat aatattccat tgcatgccta tacctcattt  98280
gattcagcag ttcatggtct tttgcgttgt ttcccacttt atggcagata ggaataatgc  98340
tgctgtgaac gttcatatac ggcttctgtg tggacctaca agttttgatt tctctcagtt  98400
acagacccaa gagtatatac tctgggagca gaattgctaa ttgctgtgcc atgtgttaac  98460
tctgtattta accttttgca gaactacctg ttttccaaag tgcctcagct ctttacattc  98520
ccatcagcag ggttcccgtt tctctagata ttgagtactt tttattcttt acctgtttag  98580
aatgggaaac tacatagata accccgtgca tttcatattt cagatgctgc taccagttga  98640
gtggagacgt gcattaagca tttagtcttt gggataaacg tgctagagag agtcatccag  98700
aggaaatgcc tattactgtg ggtgacaggc cttgtgatta tagtttgggg tgttaggaag  98760
atgagatatt ttcaaacctg gcatgtaata tgcaaacttt acaaaataat tgctaagtag  98820
gtgaatcatc agtgatatat ataccttgag gtttagccca ttcttgatta attttacttg  98880
tagataggtt ggctccttta ctcctttttt cttgtctttg tctgcttttg gctgtaaata  98940
ctgagagacg tctataaata ctagtcagtg tgatgctttt ctctcctcac tcttctaaac  99000
tccttctaaa aggtaagcag agatgaagat tttaaagcaa ttcatgggaa gagcaggctc  99060
tcctgctctt atggattccc tccctcttcc actccaagga gtctgaggtg aggagttagg  99120
agggacctaa ctttccagat ggggagcagt gggcacctgg caacagccga gactgtgtgc  99180
tcatgtctag cgtgaagttt gcctttgctc tacgaagctg gatttggttt gtagatgtgt  99240
taactaaatc ttagctgttg taaccaacat gaaacaacct gtttgtggat ttggtcagag  99300
ctgggttaag gtggatcatc tctgtgcacc agaatgactg taccccttc agatggtagt  99360
```

-continued

```
cctgttcacc gcagtggaga aaagacctca ctgaaggact tattcccagc atgaaacatc  99420
atgacagaaa ttggtactta actctgctgc caggatagaa accactcagt aggcaaatgt  99480
gggagcgttg tcttgcatgc gggggctctc tagcattggt tcccttcact gaacacctgt  99540
gcaaggcaga tggtcacagc ttctccatgt tgtcttgtgg attttttgtt tgtttgggct  99600
ggaattactc cttttcaaaa acctgtgctc tctttttcag ctccccagag gcccatctca  99660
acacagagaa ccgctgcggc tcctaaggct ggccctggtg tggtgcgaaa gaaccctggt  99720
gtgggcaacg gagacgacga ggcagctgag ttgatgcagc aggtgggcac ccctgtgttt  99780
agcacgtgag tcacctcggg ggataggatc cttgcggtgg ccagggtgcc ttatccgtgt  99840
tcttaaatga acacctgcct tgtttgcttg ccagagcatg tgacacgtgt gagcctcagg  99900
tgctgtgcgg ggagcatgaa cgtggagatg taagagagag atcaggtgtg cctgggctct  99960
cttagtgtgg cagaagcctg tgctcggaag ccagtgctta gactagaatc ctgttgaatg 100020
tttctggaat gctgccaggg acctgggatt tggagaatga aagataaagg aggtctcctt 100080
tttgaataat ttaataaaaa ggattccgca gtctctctgc tgagtcctag actggggtca 100140
ctggagattg gaattcagag tggaactggt atgaaaagcc tgtggctctt ctagttctgt 100200
tcttagtaat tgggtgattc gaaatgtctt cttcaggagt aaatgtcctt aaggcacctg 100260
tcagaggtct ctgtggatca aaacaagttt tagactttta gacattttcc cactaatcct 100320
tgtaattggt tggtttgctt gctttcagat gattcttttt gttaattcta tttttaaat 100380
tttgttttat taaaaaagtt tttttaataa aatagagata gggtctcact atggtgccaa 100440
ggctggtctc taactcctga gctcaagtga tccccctgcc tgagcctccc aaagtgctgg 100500
agttacaggt gtgagtcacc acgcctggct ccattgaaaa aatctgggat gctctgtgat 100560
tccagtgagt ttgggattgc atccttttac ttttctaaaa gccaagtcct gaaacttgag 100620
ggaattgatt tctaatgcag aacctctcat gacccacact cagacttcta agagatcagg 100680
acagtgagaa cctgcccaaa aatcacattt cactttttta ttttttattt tcttttttg 100740
agacggagtc ttgctgtgtc gcccaggctg gagtgcagtg gcgtgatctc agctcactgc 100800
aacctccgcc tcccaggttc aagggattct tccgcctcag cctcccgagt agctgggact 100860
acagtcgtgc gccaccacgc ctggctgatt tttgtatttt tagtagagac agggtttcac 100920
catattggcc aggctggtct ccaactcctg acctcagatg atccacctgc cttggcctcc 100980
cagtgctggg attacaggca tgaaccactg cgcctggccc acatttcact tttcgttct 101040
ttcatttgtg tgtgccccgt ggtcttaggt gccttgggag tgtccaggtg actgggtcac 101100
cgtcctcatc cttggagtgg gtgtggctga cttgagcacc cgctggggct gttactttga 101160
agtacagaag cctcggagaa caaggagaga cttcctgtaa ctatttcaag acatggattt 101220
caaacacagg aagcagtttc agaaagaaat acgagagagt aaagagtggt taatgttgag 101280
gctgggtagc agcgacttga tctgtgctct ccgagagagc gtgccaggtt ctgcagtgtg 101340
gctgctctct gctcagctct tttttttttt taattattat tattattata ctttaagttt 101400
tagggtacat gtgtacaacg tgcaggttag ttacatatgt atacatgtgc catgctggtg 101460
cactgcaccc actaactcgt catctagcat taggtatatc tcccaatgct atccctcccc 101520
cctcccccca ccgcacaaca gtccccagag tgtgatgttc cccttcctgt gtccatgtgt 101580
tctcatccgc tcagctctta tcctgggtga tggagcccag gcttggggtt ccatagattg 101640
agggagaagt aggagtgtct ctgtcagtta acttctatct ggacaagtca gcctctctga 101700
```

-continued acttactgcc tcacgtgtga agtggggctg acacttgctc acagcagttg agcagattat 101760
atgagctgaa tgttaagtgc ctggaatggt gtttgttgcc aataccactg ggataaatgt 101820
cagtggataa aagactgtga tgattatggt tcttgttcat ggtcttgata gagtagaata 101880
atgttcttta aaagttcaca ggaaccagtt tttttttttg gcttgtgtga aataatatgc 101940
gtaaatggtc ataacaaaag tagccaacat tttatttatt tatttattta tttttatttt 102000
tatttttttg acacggaatc tcactctgtc gcccaggctg gagtgcagtg gcgcgatctt 102060
tgctcactgc aagctccgcc tcctgggttc acgccattct cctgcttcgg cctccccagt 102120
agctgggact acaggcaccc gccaccacgc ctggctaagt ttttgtattt ttagtagaga 102180
cgaggtttca ccgtgttagc caggatggtc tcgatcttct ggccttgtga tccatctgcc 102240
tcagcctcct aaagtgctag cattacaggc gtgagccaca gtgcccagcc atagctaaca 102300
ttttaaaagt gcttatgtca tgcacagtgt aagcacttaa tttcactttc gcagcaaccc 102360
tgtgaggttt tacacataag gataataagg cttggagagg ttaaataact tgagctagga 102420
tttgaaccca ggtatacctg tctccagaac ctagatcagt cagtccctgc tgaatgggga 102480
attgaggaag aggttatttg atttatctaa ggtatacaga tgtttctttt ccttgcaccc 102540
acctttggaa actgtaagta ctcaccagat aatgactctg ggcaaattgc tgctaagcgt 102600
tgatgagagt accaaggcat gggagatctg tcctagacct agacaggttt gatacacttg 102660
gagaagatgg acttggtgcc tgcctgtgtt caagtcccag atgagggtta cggaaggcaa 102720
gaaccacaac tcttatgggg gagagtgtga ttggggtctg aggaggcttc cttccctgag 102780
agggtgacca gaattagctg ctttggatgg tcggtgttgt agaacttcaa cagtcgaggt 102840
tgggagggat tgtggtcttg aagaggctta taactctgtt gcatgtccat cggtgctggg 102900
gaacattgag aggctaagtt tgcagaggct gaaggtcact aaccaggtgc tttgttgatc 102960
ctggaaggct gggatcaaat gctcataccc agctggttca accctgacat agaagtactg 103020
tgtttggcct gcacagagtt ttatttattt atttatttat ttattaaata taaaggattt 103080
gtctccaggt tgtcaaagtc cttcccttac ctgttaccac ctctcttggc tcatttacat 103140
tatctggccc ctcctgaaag tttttgcatt tgcagccctt tgtaaatatg gaaaatggag 103200
ccacgtgggc ttgtcaggct gtgggaaaaa cagtgtatct gcacacacta ccttgtggta 103260
ttcgtatcct tgggagatct gcaaagattc tacattccta agtcgtcctg gagaaattta 103320
cttttagttg attttagtcc aaagcagtgc tgtccaatga aggtagaagg tgagtcagaa 103380
gtgtgagcta cctgatttac atggtctagt agctacatta aaaagaataa aaagaaatag 103440
gtaaaattaa ttttagcaac acatcatcta atatgtaaaa aataatactc cagcatataa 103500
tcaaatataa ataatgatca atgagctgtt ttacatttga agactctgct aggtctttga 103560
aatcaggtgt gtatgtgata cttgtagctc atctcagtgg cactggccac gtttaagtgt 103620
ttatatagac acatgtggtt gatggctact gtggccagtg caggcctgaa acactgactt 103680
ggggcttctt aggttataac tattgcttta cctcaagata aggttctaag agtgacctta 103740
attactagct acaggttttt tttttttttt tcttttggag atggagtttt gctctgtcac 103800
acaggctgga gtgcagtggc gtgagctcag ctcactgcaa cctctgtctc tcaggttcaa 103860
atgatactcc tgccccagcc tcccaagtag ctaggattat aggtgcctgc ctccacgccc 103920
agctaattct tgtattttta gtagagacag ggtttcacca tgttggccag gccggtctcg 103980
aactcctgac ctcaggtgat ctggccgtct tggcctccca aggtgctggg attacagatg 104040
tgagccactg cacctggcca agccacagat ttttaataac ctcatgaata cagacttgaa 104100

-continued

```
aggagtgcca cgtgaaagcc agtgtcttag tatatatttt tttagtgatt tagtgtttgt 104160
tatgtgtgta tagttatgag caatatcatg gacagatgca acttttggcc tttataggtg 104220
ggacccagaa ggctgggtat ctggtttggc cttgataatt tgttggacag agaaggtttt 104280
aaagggtttg agagggtagc attagtgaaa ctagtgaaac taggtggata ccaagctagc 104340
attccttttt tttttttttt tttttttttt ttttttgtgg cgtgatctca gctcactgca 104400
acttccgcct cccgggttca agtgattccc ctgcctcaac ctcctgagta ggtgggacta 104460
caggtgcaca ccaccatgcc cagctaattt ttatattttt atagagacgg ggattcacca 104520
tgttggccag gatggtcttg atctcttgac ctcgtgatcc gcctgccttg gcctcccaaa 104580
gtgctgggat tacaggcgtg agccactgcg cctggccagc attccttttc ataagctctt 104640
tcgacttcct ttcttccttg gtcattaatg ccaccaggca tgtgattaga aggccccttc 104700
cctgcctttt ggattgtgga gctgtagctc tgagtctgct tcccgctggg gctggtcggc 104760
tcttggcctg tgtatcccct gctctttggg gctgttggtt tcaggaaagg cagcaaactg 104820
cagcaaaagc agaggtgggg acagtgaggg aaaatggatg atttagcttt gccggccacc 104880
aggcagtagc tgtactgtat gtatgtatgt atgtatgtat gtatgtatgt atgtatgtat 104940
gaatgaatga atgaatgatt gaatgagaca gggtcttgct gtgtctccca gactagagtg 105000
taatggtcca ttgatagctt actgcagcct tgaactcctg ggctcagaca atgttcctgc 105060
ttcagcctct taagtatctg gtactatagg catacaccac cctacctggc taatttttag 105120
atttttttgt agagacaggt tttgccatgt tgcccaggct ggtctcaagt tcctggcctc 105180
aagcgatcct ctcaccttga cctcccaaag ctttgggatt gcagatgtga gccacggcag 105240
ctggcccctc tagtacttta ttgaaacttt caattatttt ttatttctgc ggctggtaaa 105300
ggaatagtga aaggctgtct agaactgtga ttctggtttg gtctaacaag actttgatga 105360
tgaactttga aattcgtttt gataaaattg tcctggtggt gtcacctgat cctcatctct 105420
ggatgctttt tgactgcagg ttataaagag ggtcctttct cctgggatga gacttgatct 105480
cctctgttgt gtttggtgtc ttcatcaggc tgtggggaag ctagataagc tgtttatttc 105540
tgtttttaaa tttttattat ttattttttta aaaagatgga gccttgctat gttgtcacaa 105600
ctggctttta actcttgggc tcaagcaatt ctcccgactc agcctctaga gtagctgaga 105660
cgcgtgcgcc actccacctg acatgcttca gtttttgtgg ctgtgagttc agaaggctgg 105720
actagatgat ttctctggtc ccttctggct tgtagaattc ccttctgccg aggtcgttct 105780
cagtggctgt acctttgatt ttgttgcttt actttccatg ctgctctgtg gccctgacct 105840
gtaaatacag gtttttgcaa cttgcattca ttgacagtta aatggaattc acttgtcata 105900
gatgtgaata cagtacactg gaatgaagat gccccatggt taaagtacac acaggactat 105960
gagtgttata acttttattg gtcttggcta gatagagtcc tggcctaagg actgagacag 106020
atttcttcat agcctcttaa tgggaatcag agaccctcag tggggctcat ggagggtcag 106080
agcactttcc attgggcttc caaagagttc cattgagccc tttccagggt cctttctatt 106140
gacccccctca tgcaatcaga cctggacttg attgtccagt cccttggtaa ggactcagtt 106200
tatgattgtc agctaccttg ctaggctgta attgtctcag gcttccctag tttttctcc 106260
ttaatccttt ttcagtccct gagaagcttc tacatgtttc aaggggtagt ctgctctttc 106320
tgggagctgt taccgtcaag gttgctataa acaaatccat gttgtttatc tgaggctgaa 106380
gaaaattgac attaaactga tgtggttttt gtctgtgttg ggtttgatc aaagaccaca 106440
```

-continued tctcctttg ggttagaagt ctgcctgata ttttattgcc atactaatgc caagcatctc 106500
accctttta atgtcttgtg caggtcaacg tattgaaact tactgttgaa gacttggaga 106560
aagagaggga tttctacttc ggaaagctac ggaacattga attgatttgc caggagaacg 106620
agggggaaaa cgaccctgta ttgcagagga ttgtagacat tctgtatgcc acagatgtat 106680
gtgtttgaca tgaggatatt ttctttccat tttacataga agggttggtg aactctgtgc 106740
tgatgcttgt tgtattccag tgttgcattc atcaaaagac ttcatcttta acccctcaaa 106800
gtcagccaga gggcatctct gcccagcttt agcttctgcc tgaggtctgt gagcttttga 106860
agaaggaata ggacaaggag gtggctggct tgcccagcat ctgtagtatg tggccactga 106920
taggtgatga gtgccacaaa ctgctcttag ccagaagcaa cccatgtcct cactccaccc 106980
cacctcctat tgcttggatc cctcagcttc agttgctgcc tccattttat cagggcccgg 107040
ggcatgcccg gaaaagcagg cacatgctcc ctttttcacg gcgtgcccac atatcacgtc 107100
atgtctgggt atgcctttct cctccctcct aggagtttgc ctggttctca ctccctcaaa 107160
gtactctatg atcaagtttc tttggatcca tgtttattgc acagtcaaat ctgttgatat 107220
taatcacgac atgttagttg atcagggaag actcattttt ttctagattt aggattgtta 107280
tccggctgtg tccactgttt aatggtgatg tttgtaattc tgtgtgccta gcaaggtctg 107340
taggatcaaa ctacaaactt ctggtagtat gtgtagcact atgcaaatac aaggtagtaa 107400
taatgctgtt actgtcactg tccttgagac atatcttgtg aatttcaggg gattaagaca 107460
gatgactgaa aagttgataa tctgttgaat aaatctttaa tttagagctt gctctgtgct 107520
atgtaatgaa aaaaagacaa cgaagatata gggggtcctt ggtttagtct gagtattatt 107580
ttagtggagc cacatcttaa gtaagttcag ctatagagat ttagttaata gaaataagat 107640
ggtggttgaa agagaagtct gattttacag cagaatagta tagtaatttc ctgctctgag 107700
tccatgccag aatgccctgt agtgagaatg aggtgtgtgg gagtcatgaa tctgcttttt 107760
ccttgtgcac tcaatttttc tgccactgat gttgggtcag tcttgctgtt gtgaatattt 107820
tgggtaaagc atggctccta agtataacaa aaggaaggca taaaaggaaa gctggctgca 107880
tagacagttt attgagagaa gatgttagag tactgaactt tacaggggac ttcaggaatt 107940
tttgagggaa attttttttt ttttttagtg acggggatct cactttattg cccaggctgg 108000
agtgcctggt ggtgcgatca tggctcactg cagctttgac ctcctgggtc aagcagtcct 108060
gcctcgaccc cgctggggag tagctgggac tacaggcatg tcccaccagg cttggctagt 108120
tttttttttt ttcgagacat tgtctcactg tgttacccag gctggtcttg aacttctggg 108180
ctcaagcctt ggccttccaa agtgctagga ttacaggcat gagccatcac acctggcctt 108240
ctttcttctt taaaaaacag ttttattgaa gtataactga cataataaac tgcacatatt 108300
taaaatgtac ctttgatgac atgggtgaaa ttaccaccat aatgaagaca atgtaaatat 108360
gcatcacttt caaaagtttg agggtaaatt tgactgtgct cagtttttgt ctttggtgag 108420
atgcaattct actacccaag aaataaaata gcagtcacct ggcctgtata gagccaggaa 108480
gaaccattgt ttttaagagg ctgtaagtat gaggaaagtg aactcacagt agaaatggat 108540
ctttcagtgg ctttcccctc tcattttcct atttcaggaa ggctttgtga tacctgatga 108600
agggggccca caggaggagc aagaagagta ttaacagcct ggaccagcag agcaacatcg 108660
gaattcttca ctccaaatca tgtgcttaac tgtaaaatac tccctttttgt tatccttaga 108720
ggactcactg gtttcttttc ataagcaaaa agtacctctt cttaaagtgc actttgcaga 108780
cgtttcactc cttttccaat aagtttgagt taggagcttt taccttgtag cagagcagta 108840

-continued ttaacaccta gttggttcac ctggaaaaca gagaggctga ccgtggggct caccatgcgg 108900
atgcgggtca cactgaatgc tggagagatg ttatgtaata tgctgaggtg gcgacctcag 108960
tggagaaatg taaagactga attgaatttt aagctaatgt gaaatcagag aatgttgtaa 109020
taagtaaatg ccttaagagt atttaaaata tgcttccaca tttcaaaata taaaatgtaa 109080
catgacaaga gattttgcgt ttgacattgt gtctgggaag gaagggccag accttggaac 109140
ctttggaacc tgctgtcaac aggtcttaca gggctgcttg aaccctcata ggcctaggct 109200
ttggtctaaa aggaacattt aaaaagttgc cctgtaaagt tatttggtgt cattgaccaa 109260
ttgcatccca gctaaaaagc aagaggcatc gttgcctgga taatagagga tgtgtttcag 109320
ccctgagatg ttacagttga agagcttggt tttcattgag catttctcta tttttccagt 109380
tatccccgaa atttctatgt attatatttt ttggggaagt gaggtgtgcc cagtttttta 109440
atctaacaac tacttttggg gacttgccca catctctggg atttgaatgg ggattgtatc 109500
ccattttact gtcttttagg tttacattta ccacgtttct cttctctgct ccccttgccc 109560
actggggact cctctttggc tccttgaagt ttgctgctta gagttggaag tgcagcaggc 109620
aggtgatcat gctgcaagtt ctttctggac ctctggcaaa gggagtggtc agtgaaggcc 109680
atcgttacct tgggatctgc caggctgggg tgttttcggt atctgctgtt cacagctctc 109740
cactgtaatc cgaatacttt gccagtgcac taatctcttt ggagataaaa ttcattagtg 109800
tgttactaaa tgttaatttt cttttgcgga aaatacagta ccgtgtctga attaattatt 109860
aatatttaaa atacttcatt ccttaactct ccctcatttg ctttgcccac agcctattca 109920
gttcctttgt ttggcaggat tctgcaaaat gtgtctcacc cactactgag attgttcagc 109980
ccctgatgta tttgtattga tttgtttctg gtggtagctt gtcctgaaat gtgtgtagaa 110040
agcaagtatt ttatgataaa aatgttgtgt agtgcatgct ctgtgtggaa ttcagaggaa 110100
aacccagatt cagtgattaa caatgccaaa aaatgcaagt aactagccat tgttcaaatg 110160
acagtggtgc tatttctctt ttgtggcctt ttagactttt gttgccctaa aattccattt 110220
tattgggaac ccattttcca cctggtcttt cttgacaggg ttttttttcta ctttaaacag 110280 tttctaaata aaattctgta tttcaagagt atcatgtctt ctgaaatttg tcttgccctg 110340
ggtatatgct gttaggttca agtgatggga aaccagtgct tctttcttca gtgaggactg 110400
atcttttcac atcctttact gatttttcag atgtgcttat ttcttcttct tcttcttttt 110460 ttttttttt tttttgagat ggagtcttgg tctgtcgccc aggctggagt gcagtggcat 110520
gatctcggct cactgcaacc tctgcctccc aggttcaaac agttctctgc ctcagcctcc 110580
caagtagctg ggattatagg cacccaccac cacgcccggc taatttttgt gtatttttag 110640
tagagatggg gtttcaccat cttggccagg ctgatcttga actcctgacc tcgtggtcca 110700
cccacctcag cctcccaaag tgctgggatt acaggcgtaa gccaccgtgc tcggtcagat 110760
gtgcttattt ctaagctgac ttcttttttc ttcattcaca ttatattgta cagcctcctg 110820
ctttttaaaa ttctcgttgc tgtaagaggt ttttcctctc ggaagtccaa ggcctggcct 110880
atctgctgtg aagccttttc agggcatttc cttctgagaa atatagcagg acagtgcttg 110940
gcagatgact gtggggagat tttttttttt ttttttctg aaggtgtgat tctttcttcc 111000
tttctttttt gagacagggt ctccctctgt tgcccagtct ggagtgcagt ggcatgatct 111060
tggctcactg cagccttgcc ctcttgggtt caagcgatcc tcccacctca gcctcgtgag 111120
tagtggggac tacaggcatg caccaccatg cccagctaaa ctttgtattt tttgtagaga 111180

-continued

```
tggggtcccc ttatgttgcc caggcttgtc ttgaactcct gggctcaagt gatcctccca 111240
ccttgacctc ctaaagtgct gggattacag gtgtgagcca ctgcacccag ccctgaaagt 111300
atgtttcaaa gtcagttaac atgatcttaa tctataaaat aatctaaaat tgtcaccatt 111360
tttttctccc ttataaaatt atatgctatt agaaatgagt tcaaaaggag acttgctgcc 111420
atttctgtc agaaataaag ttaaatgggc agagatagtg tgttgtagga tatgtagagt 111480
catggttatg gatgctctat aaacccaacc tgatgatctt gacaagggtt gcacccatag 111540
ttaatggtat gatacctccc ttaaagtgtt aaataccttc agaaggaatt tgacaccata 111600
tgtattggtc atctacaaga agataccttc caggagtgca aggagtttgt gaagatactg 111660
ttggctactg tcaattgaga agttaccttg gtaaagagag aagccaaaac tgtgggtatc 111720
tgaccaagtg cattgacctg gctcttgaat ttgaagcaca tacagtcttt gctgcttggt 111780
ttgcttggca ggttctgtgt ttcatgaagg ataggtaaac aaatgggttc tctggctcaa 111840
tttggatcat tgttcatgct gatgattctc aaactgatgg gcttcagaat cacatgggga 111900
acttgtttga cataatgtat ttataaaaat tcatcaccag agattctgag tttggaggtt 111960
gaaaacctgc attttaattt gggccttatc tacatgtctg caattttaaa taataattct 112020
ggcaagggga acatcagact tgagtcctct tgcaggtctc tcctgctttg tgagttttga 112080
gctatttgac ctctcttgtt cttacatgca agacagagat gatgattttg gctgacgtgc 112140
ctccctcact gggtacttgt tgggattaga aggagctgat ggaccaaaaa aaaacagcac 112200
cacaaagcta aaaagctctg tacagacaag aggcattatt tatggcacaa gttcttcaga 112260
tctggtctga aattctgttt atagattaga aaaagcttag gacagggctt ttgtatcctc 112320
agaattcgga agggcattcc ttcagacagg ctttgggtgt tttgtaaaat acacccaaag 112380
tatttccttt tcagcatggt atatggacaa gtagaactcc cttatgtctt caggctctta 112440
tgtttatcct gtttttgttt tcttttaaat gaagattcaa tgtctcagat tcattgatta 112500
aaaacccata ttttcttcaa gatttactct ctagaatgtg aagggttttg aaaaggaagc 112560
atttttcttt tgccctagcc aaggtgatcc tctgtagttt ttcttttaag gattgtttta 112620
gaagattgag tataaaggac tccttttgtg atgttgacca tagttcattg caaagtccac 112680
aaataaaaat ccaagcttta ggcctgatca gcctagtcag attagcttgc tagcatgtgg 112740
gtgacccaaa tctgattgtt gacaacagag aacattgctt tgaaacaagc tgaacctcag 112800
tctgtgatca gtgttgtgaa ccacccgtca tttttctggt ctggcactgt tgtaatatgt 112860
cttttttttt ttttttttt tttccccaga cagtcttgct ctgtcaccca ggctggagtg 112920
cagtggcacg atcttggctc actgcaacct ccacctccca ggctgaagca gttcccgtac 112980
ctcagcctcc tgagtagctg ggattacagg cctgtgccac tatgcctggc taatttttgt 113040
attttcagta gagatggagt tttgccatgt tgcccaaggt agtctcgaac tcctggcctc 113100
aagtgatcca cctgtcttgg cctcccaaag tgctgggatt acaggtgtga gccaccactc 113160
cctgcttgat atcatacttt tggattcaca catttagttt gtaaaatgtc aaaaccagat 113220
gagttcatat ttatttctgt atcttcatga cgcttgctgc ttttttctc ttcattttca 113280
catgcgaggg tataactgag tgttcagggt tttctctgaa agcctgaagg gattgtgtac 113340
ttttacattg aacttgactg cagttagaac cattaaccta gatgacttca gccaaattat 113400
gtattgtttt tgtttttgtt tttttgagac agggtctcct gtcacccagg ctggagtgca 113460
gtggcacagt catggctcat gacagcctca acttcctggg cttcagctgt cctcccacct 113520
caacctccat agtagctggg actgtagtgc acaccaccat gcctggctgg ctaatttttt 113580
```

-continued tttttttttt ttttttgaga cagagtttca ttcttgttgc ccaggttgga gtacagtggt 113640
gccatcttgg ctcactgcaa cctccgcctc ctgggttcaa gcgagtctcc tgcctcaacc 113700
tcgagagtag ctgggattac aggcgcccac caccacaccc agctaatttt tgtgttttta 113760
gtagagacgg ggttttgcca tgttagccag gctggtctgg aactcctgac ctcaggtgat 113820
ccacctgcct cggcctccca aagtgctggg attacaggcg tgagccacca tgcccggcca 113880
atttttggt atttttgta gagacggggt ttgctatatt gcaggctggt cttgaacccc 113940
tgggctcaaa caatttaccc atctcttcct ccccaaatgc tgggaggtgt gagtcactgt 114000
gcctggccca aattgctata tagccgtgac ttgtgaaggt ctgttccccc tttggtttaa 114060
tctgatttgg gaagtaatgt taccttagtc cttggagtgc agaagctttc tctgtactct 114120
attgaggttg tatccagtag cttcattaat ttggttatct aggtgagcag gtcaagcctt 114180
agagtcaaat ttctaggctc ctcaatctag aaccttaaat cttgaggtgc gtgtgtgtat 114240
caaaattgta aataactctc gtttccttgt attggaggct ctcaggttct gaaatgtgaa 114300
atggaaatag ccttcataga cacgtttctg agtgtgagga ggcagttctt tgtcctgtga 114360
ccatttgaaa gcaaaccagg ttacccacca atgcctagaa ctttgtaagt ggcatcaaga 114420
tataaattta taattgtaaa ataacctatc agcagtttgg ggctgggtgt catggctcat 114480
gcctgtaatc ccagcacttt gggaggccag tgcagaagga ttgcttgagc ccaggagttt 114540
gaaactagcc tgggcaacat agcaagagac cctgtctcta tttaaaagat tttatatata 114600
tatatgatca tatataatat atataagata tatatgatca tatatataat atatatatat 114660
atgatcatat atatcttata tatatatatg cagtttggaa ttctatttgt cttgccttat 114720
ttgcttttta aaaatttcta ccttagtttt ttcctggttt actttgagtg ttttttttgta 114780
gtcggaggag attgttggtg cggctgggtg taggtatgag gcagaggagg aagagtaatt 114840
tattccatct actgagcctt tcatttactt tctgttttag cagtagagtg ggatgtcgga 114900
agcttttgtt gggtgagagt caatctgtca gggtaaatct taaaaagctg gatttgtggt 114960
ttagttacta gttactgtgt ctccagtgga gacaaagatt agtttttaag atttagcctt 115020
aatggatgat tcacaaattg caatgcagag tattgaagtt aagtccaagg tcaagcacac 115080
aagtgggtaa aactgaacat atgaaatggg tgtgtggctg gcacccacct ctgaccttta 115140
ctgaaataaa tgaggaagac ggtgctgtaa gtggaatgcc acggaccagg agttaagacc 115200
agagtcctct gctaggccct gcatctgaag tctgcagagc atggcttttc attggctcag 115260
tgaggagttg agtcctggtt cagaaaaagt taccgaggtc tgtaaaagtc agtaggatac 115320
cggaacaaga aagagtggga gagtgtacag ttcccagcga acattgccag tggaggctaa 115380
ttttcaccag tgaagggcga ttttgataga aaagcacagt gtctcaacta cttgtggttt 115440
ttgattctga aagaggaggc tttggcagga gcaataatac acgtggccta ccacctgttt 115500
ggctttttcc ccacaggttg caagctgcag ggagggcctt gctaattcta gtacctccat 115560
ccccgaatcg tctaaatgta ttttacccag gacctgtcat ggtttatctg agtgaccagt 115620
ttcctttcct ctcttgctta tttatcatgt tcatatttat atttttcata atggggccta 115680
tttatatatt ttgaagtagt tctagtgatt ttaagatcca gcaaaacttc aaggtcatct 115740
ggattttggt gttctattta agttttctaa cttgatacag tcttttttttt tttttttgta 115800
ttttgtatgt ttttctacaa aatgtgagag agttaagcat gtataattac atatgactgc 115860
tgttttcact ttgaaatttt aaatcctgct tgggagaatg gaataagcta ttgtgttttt 115920

-continued

```
tgcaggcagc tatgggatat cccaatttgt ccctccctcc tccttaattt tgaagcctga 115980
gagaggaagt aataatttc tttttttttt ttttttttgg tagggatggg gtttgactat 116040
gctgtgcagg ttggtctgca actcctaagc tcaagtgatc cgccctcctc cgcctcccaa 116100
agtgctggga ttacaggcct gagccaccgt gcctggtctg aagaagtaat aattttaaga 116160
ttcagtgttg agtgaaataa atgtattctt aaaaatttct aagagtgttt aactctctga 116220
cctaatattt aatattttcc ccaatcatta ggaagtgctt ttttgttgtt gttgttgttt 116280
tttttccagg cagggtctcg ctctgtcacc caggctggag tgcagtggca tggtcacggc 116340
tcactgcagc cttgacttcc cgggctcaag tgattctccc acctcagcct cccaaggagc 116400
tggaactgct cagctaattt tatttttgta gagacagggt ctggctatgt tccccaggct 116460
ggtctcaaac tcctgggctc aagcagtcct ccaccactcc tggccaagaa gtgccttttt 116520
tttttttttt tttttaaag tagctgctga acacaggaga atctgccttt ttcttgaatc 116580
gtggtttttt tgtttttttt tttttcaaga cggagtgttg ctgttgtcgc ccgggctgga 116640
gtgctgtggt gcgatcttgg ctaattgcaa cctccgcctc ccagattcaa gcgattgtcc 116700
tgcctcagcc tcccgagtag ctgagattac aggcacgcac caccgtgcct ggctaatttt 116760
tgtgttttta gtagaaacag gatttcacca tgttggccag gctggtctca aactcctgac 116820
cttgtgatcc acctgcctcg gcctcccaaa gtgctgggtt tacaggcgtg aaccactgca 116880
cccggcctga atcatggttt tttgaaacca ttggcatctg aacctgtagc tctctctggt 116940
agtgttgtgt ggttttaaat gtcatgtgag ctgagttact gacctcaacc tactgccaga 117000
tgaaggtgtg atcctgtgat accaatcttg agggtccctt ctagttttag cagtcagtga 117060
cttctcttgt ttatttttgt ttgaaaaagt aaaaggctct ctttttggct atagagttgc 117120
atcttgaaat ttttgacaaa ttacatagag ctgaagaagg atacaagttt tgatatctta 117180
aaatcacagg gttgaagctt gaaaggacag tattggcatt gcagctaagt gggagtgtga 117240
ggaagcgcct tctctagggc aggtaattgc atctgttaat gtggtccttg ggcccctgag 117300
ttgctgcctt ccaatcagaa ttcccttagc attagccagt gacgcctgaa ttaatctcag 117360
gtaggacttc taactttttt ccaaaattat ttttgtgcag aggtttatct agatttttct 117420
tctaaatgtc ctcctcccca cttgttttat tattactgtt tttttctctc tttaattttt 117480
tttttttttt aatagagaca tggtctcact atgttgcctg ggctgatctc agactcctgg 117540
gctcaagtga tcctcctgcc tcagcttccc aaagtgctgg gattataggc gtgagccatt 117600
gcgcctggct ctgttactgt ttttctaacc tgagttactt aggatcatat tttcattctt 117660
ttttaaaaag atgggagttt tctgaacttt tccttaacta aaaagtggaa tgcatcttaa 117720
tattttcctt tttttacttg tgtttctccc cagggaggga aaaacatatt tattgtgaca 117780
gaatttagca tattttaggc cacattaaaa tactgataaa tgtattaatc agtgaaaata 117840
ggttatagtg aaaaatatat accatttgat taataaaaat gttattggaa aaatgcaaga 117900
actgctgtaa gaattgctaa cattgtgttg gaaaataaat atactaagct aagaaacaat 117960
gggaaactgt catatgtagg gccaacagcc tttttttttt taaacccttc caatttatta 118020
atatctagtc taataaaccc tgatttatag gacctctgca cctttttttga ctttttattc 118080
atccattctt aatattctac actatgacaa aatccttaaa actccattat tgatgaaatg 118140
ggaacagact tttgtttttg tatgttggtg ttctctgagt ggtgaaggcc cagggagaat 118200
gttttgtttg gtggtcactt agcatttgaa aacatccact tccttgtgac ttagctgggt 118260
atcttttaac atctggaagc cacgtccctg attgaaatct ctggagacaa cttacctttc 118320
```

-continued

```
accaacttgt ctgccaaatt gcaccatgga ccaagattgc agtggctgca tcaagtctag 118380

gcctgccctg aagtctggat ttgtaagtcc cccatttcaa atggggcaga aggcagagga 118440

gcagaggagc cactgtgcct ttcgctgtcc tggagccagt tggccttctg gttttggtga 118500

accctgcttt tataagagga ctccctggca tcttccagtt tcccgctact tgttttatgt 118560

attattttat gtctgtgttt gtcctggagt gctgtaactc ctttcactgt ctgctgtaag 118620

ttcaacttct tcaataaaag aaatgtttca aattggatga aaaatggttc tgtgattatg 118680

gtttgtggga cgggttctga tgcttcattt atgttcttca tacggaattc tgtctcattt 118740

ccctagttct aaatatgacc agcagaccca gagttccatc tcgacttcat aaaggagctg 118800

tcttggactg ggaacagctg ccaatgtctt tgttgagatg ggagttggaa agtgttagca 118860

ctttgccaga ctttgccagc aagattaact gaggagatc                        118899
```

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic Primer

<400> SEQUENCE: 65

```
ctctattcca                                                        10
```

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 66

```
Glu Ser Pro Gln Val Glu Ala Asp Ser Gly Asp
  1               5                  10
```

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 67

```
Gly Leu Lys Pro Asn Asn Thr Gln Pro Glu Asn Lys Thr Arg Cys
  1               5                  10                  15
```

<210> SEQ ID NO 68
<211> LENGTH: 1077
<212> TYPE: DNA
<213> ORGANISM: Homo sapiens

<400> SEQUENCE: 68

```
tgctgtgaca ggcagagcag gacctgctgg gaattgtcgg gcatcctagc tggccaccct     60

accacctcta tcccaagaac tggggaattc tggctggact cagtccagag tcccacctca    120

tcacctgttc acttccagtt gtcctgaagc tggctaccag gtctccttgg ccacctgaag    180

gcctaatcct tctggccccg ccagacccta ggcctccagt cacctaaggc ccagtgagtg    240

tcctctcttg cttctaggtc cgaactcgaa ataacaacag tgtctccagc cgggagaggc    300
```

-continued

```
acaggccttc cccacgttcc acccgaggcc ggcagggccg caaccatgtg gacgagtccc    360

ccgtggagtt cccggctacc agggttggtt ccccagatgc ccagacccct gcccgcagtc    420

tctaactggg agatatgcct cactcactgc actactggtt gtggctggta gataatctgt    480

gtcctttttt cacactgctt ttcaggttct tgctttttct tttctctcct gggtaagctt    540

cccgtaagcc tgttggcttc tctcctggtc tgatctcaga tgacactctg ttgggaatgg    600

aagctttccc tgttgacttg gttcttgctc taacttggaa acaaggtaga aaacactgac    660

atccagaact gtcttctccc tcatgtcttc ttcacctgtc ttgaggcaac cctagcgggt    720

atggcaacat ttcactctct gagagtccct cgtcattacc catcatttgt gcctttgtca    780

tctttctgtc tctgggacag ttacaatgac tttctccccc cttaagggat acgtgttcct    840

ggaaaagttt cttcagcggt ctctgttctc tttaacttca gtctttcctc tttctttttg    900

cctaggagcc atatgggggt gccgttggtc tctggtcacc gacatccttt gctctggccc    960

aaactatgtg tccttctgtc cacagtccct gagacggcgg gcaacagcat cggcaggaac   1020

gccatggccg tcccctccca gctcttacct taccatcgac ctcacagacg acacaga      1077
```

```
<210> SEQ ID NO 69
<211> LENGTH: 1077
<212> TYPE: DNA
<213> ORGANISM: Homo sapiens

<400> SEQUENCE: 69

tgctgtgaca ggcagagcag gacctgctgg gaattgtcgg gcatcctagc tggccaccct     60

accacctcta ttccaagaac tggggaattc tggctggact cagtccagag tcccacctca    120

tcacctgttc acttccagtt gtcctgaagc tggctaccag gtctccttgg ccacctgaag    180

gcctaatcct tctggccccg ccagacccca ggcctccagt cacctaaggc ccagtgagtg    240

tcctctcttg cttctaggtc cgaactcgaa ataacaacag tgtctccagc cgggagaggc    300

acaggccttc cccacgttcc acccgaggcc ggcagggccg caaccatgtg gacgagtccc    360

ccgtggagtt cccggctacc agggttggtt ccccagatgc ccagacccct gcccgcagtc    420

tctaactggg agatatgcct cactcactgc actactggtt gtggctggta gataatctgt    480

gtcctttttt cacactgctt ttcaggttct tgctttttct tttctctcct gggtaagctt    540

cccgtaagcc tgttggcttc tctcctggtc tgatctcaga tgacactctg ttgggaatgg    600

aagctttccc tgttgacttg gttcttgctc taacttggaa acaaggtaga aaacactgac    660

atccagaact gtcttctccc tcatgtcttc ttcacctgtc ttgaggcaac cctagcgggt    720

atggcaacat ttcactctct gagagtccct cgtcattacc catcatttgt gcctttgtca    780

tctttctgtc tctgggacag ttacaatgac tttctccccc cttaagggat acgtgttcct    840

ggaaaagttt cttcagcggt ctctgttctc tttaacttca gtctttcctc tttctttttg    900

cctaggagcc atatgggggt gccgttggtc tctggtcacc gacatccttt gctctggccc    960

aaactatgtg tccttctgtc cacagtccct gagacggcgg gcaacagcat cggcaggaac   1020

gccatggccg tcccctccca gctcttacct taccatcgac ctcacagacg acacaga      1077
```

METHOD OF TREATING A CANCER

The present invention claims priority to U.S. Provisional Patent Application Ser. No. 60/598,554, filed Aug. 3, 2004, which is incorporated by reference herein in its entirety.

BACKGROUND OF THE INVENTION

The government owns rights in the present invention pursuant to grant number DAMD17-01-1-01689-1 from the Department of Defense and grant numbers CA 68437 and CA 91844 from the National Cancer Institute.

FIELD OF THE INVENTION

The present invention relates generally to the fields of molecular biology, cancer biology and cancer therapy. More particularly, it concerns identification of therapeutic targets of DNA methyltransferase 3B molecules, such as, for example, delta DNA methyltransferase 3B variants, for treating a cancer including, but not limited to, lung cancer, and/or selecting a patient for treatment based on expression of the molecules.

DESCRIPTION OF RELATED ART

In the United States, lung cancer leads all other cancers in both incidence and mortality rate (Khuri et al., 2001). Lung cancer is the primary cause of cancer death among both men and women in the United States and worldwide.

Non-small cell lung cancer (NSCLC) constitutes 80% of all primary lung cancers, which are the leading cause of cancer-related death in both men and women in the United States (Greenlee et al., 2001). Despite advances in the treatment of the disease over the past two decades, the prognosis of patients with NSCLC has improved only modestly, with the 5-year overall survival rate increasing from 11% in the 1970s to 15% in the late 1990s (Greenlee et al., 2000). Patients with early-stage NSCLC generally have a better survival than those with advanced-stage tumors. For example, patients with stage I NSCLC are expected to have an approximate 60% 5-year overall survival rate after surgical resection of their primary tumors, while those with stage IIIA disease have an estimated 25% 5-year overall survival rate after surgery followed by radiation with or without chemotherapy.

Biological features of NSCLC are determined by underlying molecular alterations of the tumors, including inactivation of tumor suppressor genes (Niklinksi et al., 2001; Fong et al., 2003; Hirsch et al., 2001). Besides mutations and deletions of genes, it is now clear that de novo promoter hypermethylation is a common mechanism to inactivate tumor suppressor genes (Zochbauer-Muller et al., 2002; Foracs et al., 2001; Merlo et al., 1995). The $p16^{INK4a}$ tumor suppressor gene located on 9p21 encodes a cyclin-dependent kinase inhibitor important for G1 cell cycle arrest (Zhang et al., 1999; Koh et al., 1995). Promoter hypermethylation of this gene has been frequently observed early in lung carcinogenesis, including in individuals exposed to tobacco carcinogens who do not exhibit evidence of cancer (Kim et al., 2001; Toyooka et al., 2001; Soria et al., 2002).

In contrast to $p16^{INK4a}$, which is inactivated early in lung carcinogenesis (Soria et al., 2002; Belinsky et al., 1998), hypermethylation of another tumor suppressor gene, RASSF1A, occurs relatively late (Belinsky et al., 2002; Dammann et al., 2000; Pfeifer et al., 2002; Burbee et al., 2001), suggesting RASSF1A might be important in NSCLC progression. The RASSF1A tumor suppressor gene is located at 3p21, a region frequently deleted in NSCLC (Brauch et al. 1987). RASSF1A has been shown to bind to the Ras-GTP binding protein Norel, consistent with its role as a negative effector of Ras oncoprotein (Ortiz-Vegas et al., 2002).

It is that believed that DNA methytransferases play a critical role in the hypermethylation status of these tumor suppressor genes. Thus, DNA methyltransferases provide novel therapeutic targets in the treatment of cancers.

SUMMARY OF THE INVENTION

The present invention regards a new class of DNMT3B isoforms, referred to herein as deltaDNMT3Bs, ΔDNMT3Bs or DDNMT3Bs, that play an important role in tumorigenesis. The expression of these isoforms is initiated through a novel promoter, in specific embodiments. In particular aspects of the invention, the abnormal expression of the isoforms correlates with promoter methylation of tumor suppressor genes, thereby leading to at least partial inhibition of their expression. In other aspects, inactivation of the isoforms restores expression of a tumor suppressor gene, such as the exemplary RASSF1A gene, through demethylation of relevant hypermethylated promoters. In specific embodiments of the invention, the isoforms provide therapeutic targets of cancer that comprise inactivation of tumor suppressor genes, such as RASSF1A, through inactivation of promoter hypermethylation. Thus, the present invention provides a novel mechanism for providing cancer therapy separate from other methylation preventing agents by utilizing deltaDNMT3B in a novel promoter-specific demethylation.

In one aspect of the invention, deltaDNMT3B2/4 participates in regulation of RASSF1A promoter-specific methylation. The rapid demethylation of the promoter, activation of the gene expression, and prolonged inheritable effect of a single siRNA or antisense treatment, for example, provide significant implications in cancer therapy.

As described herein, at least seven transcription variants of DDNMT3B were identified as the result of alternative pre-mRNA processing. DDNMT3B variants but not DNMT3Bs were the predominant transcripts in both non-small cell lung cancer (NSCLC) cell lines and primary tumors. A striking association was observed between expression of DDNMT3B4, for example, and promoter methylation of RASSF1A, but a weaker association was observed with p16INK4A promoter methylation. A specific knockout of DDNMT3B4/2 by RNA interference or antisense approach results in a rapid and prolonged demethylation of RASSF1A promoter and reactivation of RASSF1A gene expression but not p16INK4A in NSCLC cell lines. Therefore, in specific aspects of the invention, DDNMT3Bs, such as DDNMT3B4/2, play an important role in maintenance of promoter-specific methylation of RASSF1A and shed light in understanding mechanisms of tissue-specific methylation. In specific embodiments, the isoform may bind directly to a promoter with specific DNA structure to prevent methylated cytosine from being demethylated or alternatively to prevent the structure from being repaired by DNA repair mechanisms. In further specific embodiments, the isoform interacts with specific chromotin structures of the promoters and forms complexes to protect the modified DNA structure.

Although in particular aspects the present invention provides methods and compositions of cancer therapy for cancers involving inactivation of tumor suppressor promoters through hypermethylation, such as the exemplary RASSF1A, the invention may be useful for any cancer, including lung cancer, brain cancer, prostate cancer, colon cancer, breast cancer, ovarian cancer, pancreatic cancer, liver cancer, spleen cancer, cervical cancer, melanoma, leukemia, head and neck cancer, esophageal cancer, thyroid cancer, testicular cancer, and so on. In a specific embodiment of the invention, the present invention is particularly useful for non-small cell lung cancer.

In an embodiment of the present invention, there is an isolated DNA methyltransferase-3B variant nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. In a specific embodiment, the nucleic acid sequence is comprised in an expression vector, for example, a viral or plasmid vector. The viral vector may be an adenoviral vector, an adeno-associated viral vector, a retroviral vector, a lentiviral vector, a herpes viral vector, polyoma viral vector or hepatitis B viral vector. The expression vector may be comprised in a non-viral delivery system. The non-viral delivery system may comprise one or more lipids. In a specific embodiment, the nucleic acid sequence is operatively linked to a promoter.

In an additional embodiment of the present invention, there is an isolated nucleic acid sequence encoding a DNA methyltransferase-3B variant having the amino acid sequence of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28.

In a further embodiment, there is a host cell comprising a nucleic acid sequence encoding a DNA methyltransferase-3B variant according to the present invention, wherein the nucleic acid sequence may be comprised in a vector.

In an additional embodiment of the present invention, there is an isolated DNA methyltransferase-3B variant having the amino acid sequence of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28.

In another embodiment of the present invention, there is a method of identifying an inhibitor of delta DNA methyltransferase 3B (dDNMT3B) activity, comprising: (a) providing in a cell or cell-free system a DNA methyltransferase 3B polypeptide corresponding to the sequence of SEQ. ID. NO:15, SEQ. ID. NO:16, SEQ. ID. NO:17, SEQ. ID. NO:18, SEQ. ID. NO:19, SEQ. ID. NO:20, SEQ ID NO:21, SEQ ID NO:22, SEQ. ID. NO:23, SEQ. ID. NO:24, SEQ. ID. NO:25, SEQ. ID. NO:26, SEQ. ID. NO:27, or SEQ ID NO:28; (b) contacting the DNA methyltransferase with a candidate substance (c) selecting an inhibitor of the DNA methyltransferase by assessing the effect of said candidate substance on DNA methyltransferase activity and (d) manufacturing the inhibitor.

In particular aspects of the invention, the candidate substance is a protein, a nucleic acid, a small molecule, an organo-pharmaceutical, or a combination thereof. The protein may be an antibody that binds immunologically to a dDNMT3B variant. The providing step may be further defined as providing a nucleic acid that encodes the DNA methyltransferase 3B polypeptide. In specific embodiments, the candidate substance is a nucleic acid, such as, for example, an antisense molecule or an siRNA molecule. In a particular embodiment, assessing comprises assaying for dDNMT3B activity, such as, for example, assessing the effect of the candidate substance on dDNMT3B activity comprises assaying for DNA methylation, which may be further defined as assaying for DNA methylation of a promoter. In a specific embodiment, the assessing step comprises polymerase chain reaction, a restriction endonuclease-based assay, or both.

In another embodiment of the present invention, there is a method of inhibiting the growth of a cancer cell comprising administering to the cell an effective amount of an inhibitor manufactured according to the present invention. In a specific embodiment, the administering of the inhibitor is further defined as inhibiting the enzymatic activity of DNA methyltransferase. The cell may be of any kind, but in specific embodiments the cancer cell is in a human. The cancer cell may be a cancer cell of the bladder, blood, bone, bone marrow, brain, breast, colon, esophagus, gastrointestine, gums, head, kidney, liver, lung, nasopharynx, neck, ovary, prostate, skin, stomach, testis, tongue, or uterus.

In particular embodiments, the cancer cell is a lung cancer cell, such as a malignant cancer cell or a metastatic lung cancer cell. In another specific embodiment, the lung cancer is a non-small cell lung cancer, a small cell lung cancer or a rare lung cancer cell. In another specific embodiment, the non-small cell lung cancer is a squamous cell carcinoma, an adenocarcinoma or a large cell carcinoma. The rare lung cancer cell may be an adenoid cystic carcinoma, a mesothelioma, a hamartoma, a lymphoma or a sarcoma. The lung cancer may be a carcinoid tumor. In a specific embodiment, the method further comprises inducing apoptosis in a cancer cell.

In another embodiment of the present invention, there is a nucleic acid sequence that is antisense to at least a portion of a DNA methyltransferase 3B nucleic acid of SEQ. ID. NO:1, SEQ. ID. NO:2, SEQ. ID. NO:3, SEQ. ID. NO:4, SEQ. ID. NO:5, SEQ. ID. NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. The nucleic acid sequence may be further defined as an siRNA sequence. The nucleic acid sequence may be further defined as being antisense to an exon/intron junction of a DNA methyltransferase 3B nucleic acid. In a specific embodiment, there is a DNA sequence encoding the antisense nucleic acid sequence.

In a specific embodiment, there is a pharmaceutical composition comprising a nucleic acid sequence of the present invention, in a pharmaceutically acceptable vehicle.

In an additional embodiment of the present invention, there is a method of inhibiting the growth of a cancer cell comprising providing to the cell an effective amount of a pharmaceutical composition in accordance with the present invention. In specific embodiments, the cancer cell is in a human cancer patient.

In specific aspects of the invention, there is selecting of a patient for treatment based on the expression of molecules of the invention. This is because in certain embodiments only tumors with abnormal expression of these molecules will respond to a therapy, such as an inhibitor, and therefore selection of patients based on the expression of the molecule is needed and may be considered part of treatment.

In certain aspects of the invention, small molecules are developed to target, for example exon-exon junctions and/or structures formed by these junctions to inhibitor the molecules.

Embodiments discussed with respect to one embodiment or example of the invention may be employed or implemented with respect to any other embodiment of the invention.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—PCR products of methylated or unmethylated p16INK4a promoter from primary NSCLC and corresponding normal lung tissues. FIG. 1B—PCR products of methylated or unmethylated RASSF1A promoter from primary NSCLC and corresponding normal lung tissues. Molecular weight markers are listed on left side Neg indicates negative controls using unmethylated DNA Pos indicates positive controls using methylated DNA and methylation-specific primer sets Ts indicate primary tumors Ns indicate corresponding normal lung tissues; U indicates unmethylated promoter and M indicates methylated promoter.

FIG. 5A—Expression of DNMT3B by RT-PCR using different 5' primers located at exon 2 (E1), exon 4 (E3), and exon 6 (E5) of DNMT3B. FIG. 5B—Primer extension assay showing expression initiation sites of DNMT3B6.

FIG. 6A—Schematic representation of reagents utilized in the assay. FIG. 6B—Effect of C/T transition polymorphism (C46359T) on the DNMT3B6 promoter activity. FIG. 6B—Effect of T-C transition polymorphism on promoter activity of DNMT3B6.

FIG. 7A—Relative expression levels and pattern in NSCLC cell lines and paired primary lung cancers. FIG. 7B—Structural scheme of novel ΔDNMT3B isoforms.

FIG. 8A—Location of the primers used to amplify individual ΔDNMT3B variants in this study. FIG. 8B—Expression patterns of ΔDNMT3B variants in NSCLC cell lines 1-7 represent ΔDNMT3B1-7, respectively. FIG. 8C—Expression patterns of DNMT3Bs, with more proximal exons corresponding to ΔDNMT3B1-4 and ΔDNMT3B6. FIG. 8D—Multiplex PCR using primer sets for DNMT3B1 and ΔDNMT3B1 with different ratios in concentration (concentration of DNMT3B1 primer set was serially diluted from 1-9 and serially increased from 1-9 1, DNMT3B1 primer set alone 9, ΔDNMT3B1 primer set alone 5, equal concentrations for both primer sets). The upper band represents the DNMT3B1 product and the lower band represents the ΔDNMT3B1 product. The lower panel shows relative intensity of the product bands.

FIG. 9A—Expression of ΔDNMT3B1, ΔDNMT3B2, and ΔDNMT3B4 at different time points after treatment measured by RT-PCR. FIG. 9B—Promoter methylation status of p16INK4a and RASSF1A at different time points after treatment measured by MSP. FIG. 9C—RASSF1A gene expression status at different time points after treatment measured by RT-PCR. For A, B, and C, M indicates size marker 1, treated with medium alone 2, treated with lipofectamine alone 3, treated with lipofectamine plus 40 nM GAPDH-specific siRNA 4, treated with lipofectamine plus 40 nM scramble siRNA 5, treated with lipofectamine plus 10 nM ΔDNMT3B4/2-specific siRNA 6, treated with 20 nM ΔDNMT3B4/2-specific siRNA 7, treated with 40 nM ΔDNMT3B4/2-specific siRNA 8, treated with 40 nM ΔDNMT3B4/2 antisense RNA –, negative control +, positive control. FIG. 9D—DNMT1 protein level in cells treated with or without ΔDNMT3B4/2-specific siRNA at the 48-h time point measured by Western blot analysis. The open circles indicate unmethylated cytosine residuals, and the solid circles indicate methylated cytosine residuals in the CpG sites. Each line represents DNA from a single clone. FIG. 9E—Methylation status of individual CpG sites in a RASSF1A promoter region from cells treated with or without ΔDNMT3B4/2-specific siRNA.

FIG. 10A—Cell indexes (measured every 30 min) reflecting the cell number and the area of cell attachment to the plastic surface using ACEA RT-CES System. FIG. 10B—Cell cycle distribution measured by flow cytometry. (A) treated with medium (B) treated with lipofectamine alone (C) treated with lipofectamine plus 40 nM GAPDH-specific siRNA (D) Treated with lipofectamine plus 40 nM scramble siRNA (E) treated with lipofectamine plus 10 nM ΔDNMT3B4/2-specific siRNA; (F) treated with 20 nM ΔDNMT3B4/2-specific siRNA (G) treated with 40 nM ΔDNMT3B4/2-specific siRNA (H), treated with 40 nM ΔDNMT3B4/2 antisense RNA.

DESCRIPTION OF ILLUSTRATIVE EMBODIMENTS

I. The Present Invention

Figure 1:
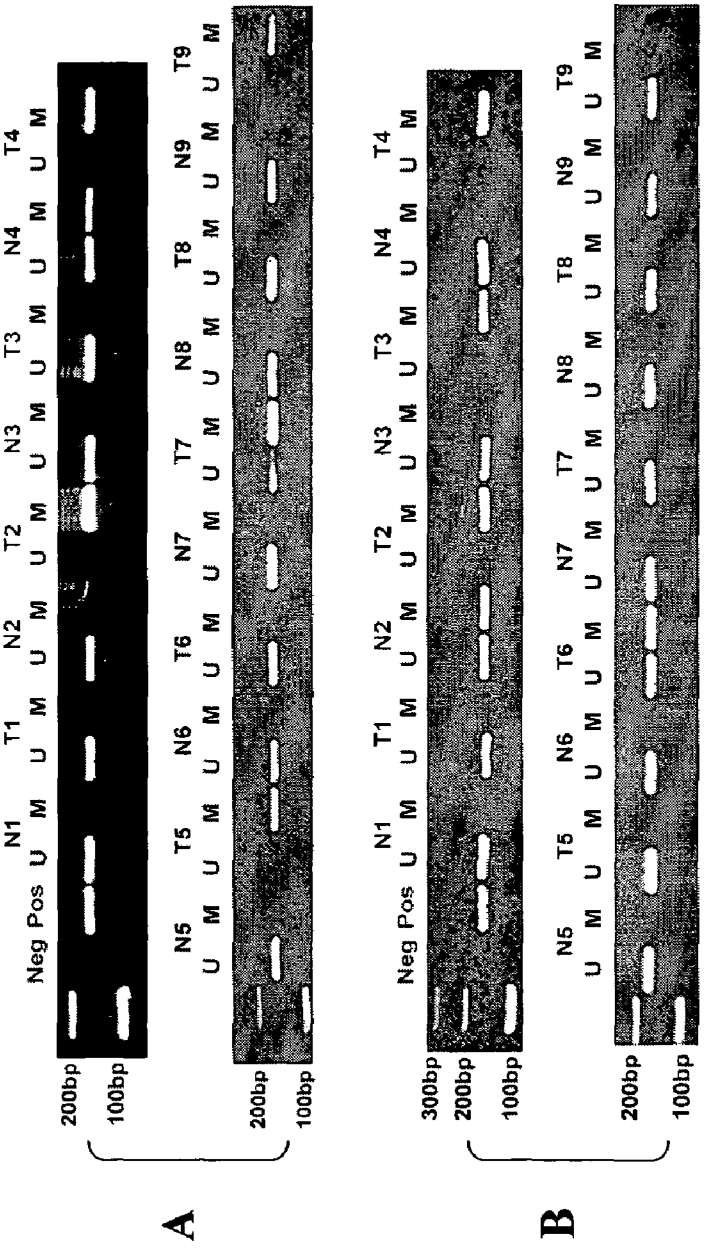
FIGS. 1A-1B. Examples of promoter methylation status measured using MSP.

The present invention overcomes the deficiencies of the current cancer therapies involving demethylating agents. Currently tested demethylating agents in cancer therapy are non-specific (therefore toxic), have low efficiency (only partial demethylation can be achieved), and are transient (DNA is methylated quickly after drug withdrawal), for example. Thus, studies to understand functions of individual DNA methyltransferases and variants thereof in the control of promoter specific methylation may lead to development of novel strategies for cancer therapy.

In specific aspects, the present invention relates to the identification of a novel DNA methyltransferase 3B (DNMT3B) subfamily, delta DNA methyltransferase 3B (ΔDNMT3B, DDNMT3B, or dDNMT3B), whose expression is initiated through a novel promoter. The present invention provides seven transcription variants of ΔDNMT3B that were identified as the result of alternative pre-mRNA processing.

The association between the promoter methylation status and tumorigenesis was examined, and it was determined that expression of ΔDNMT3B is a critical factor in promoter methylation of tumor suppressor genes, such as RASSF1A, in primary tumors. This indicates that inhibitors targeting delta DNA methyltransferase variants of the present invention may be useful to remove promoter demethylation, subsequently allowing expression of tumor suppressors.

The strong correlation between expression of a particular DNA methyltransferase variant and methylation of a specific gene promoter in primary tumors has never been reported previously. Knockout of an exemplary DDNMT3B variant resulted in demethylation of a specific promoter and activation of its gene expression, and this supports the critical role of the variant in control of the gene-specific promoter methylation. The complete demethylation of the promoter, such as in a 12 hour period, for example, indicates a novel, replication-independent mechanism regulating methylation in CpG sites, which provides information concerning gene-specific promoter methylation and replication-independent DNA demethylation.

The present invention provides at least nucleic acid and polypeptide or peptide compositions of the dDNMT3B subfamily and novel DNA methyltransferase 3B inhibitors, specifically delta DNA methyltransferase 3B (dDNMT3B) inhibitors, as therapeutic agents for treating or preventing cancers. Inhibition of DNMT3B may be of any suitable kind, including agents that inhibit at least partially one or more of the following: transcription, post-transcriptional process, translation, post-translational process, and/or protein activity and/or half-life, for example.

II. DNA Methyltransferase 3B (DNMT3B)

DNA methylation plays an essential role in normal development of a mammalian embryo by regulating gene transcription through genomic imprinting, X chromosome inactivation, and genomic stability (Jaenisch, 1997; Jones and Gonzalgo, 1997; Robertson and Wolfee, 2000, Surani, 1998). It is believed that DNA methylation patterns in somatic cells are established during gametogenesis and early embryonic development via consecutive waves of demethylation and de novo methylation (Monk et al., 1987).

DNMT3 consists of DNMT3A and DNMT3B and has been shown to be the major de novo DNA methyltransferases that preferentially methylate the cytosine in CpG sites (Okano et al., 1998; Li and Jaenisch, 2000). Human DNMT3B is highly homologous to the mouse gene and comprises 24 exons spanning about 47-kb of genomic DNA (GeneID: 1789 and 13436; GenBank Accession No. AL035071 (SEQ ID NO:64)). Two alternative 5' exons of DNMT3B have been reported. However, both of these are believed to result in the same full-length DNMT3B protein (DNMT3B1 and DNMT3B2) (Robertson et al., 1999). Three additional transcriptional variants (DNMT3B3-6) resulting from alternative splicing have also been reported (Robertson et al., 1999). Some of the variants lacking the DNA methyltransferase activity compete with variants with the enzyme activity resulting in DNA hypomethylation (Saito et al., 2002), suggesting a complex role of the DNMT3B variants.

Increased expression of DNMT3B has been frequently observed in human cancer cell lines and primary tumors compared to most of the normal tissues except testis, pancreas, thyroid, and bone marrow (Robertson et al., 1999; Saito et al., 2002; Oue et al., 2001). Although the expression level of DNMT3B was found to be higher in cancer cell lines and primary tumor tissues, most of the studies did not find a strong association between the expression level of DNMT3B and promoter methylation status of tumor suppressor genes (Oue et al., 2001; Yakushiji et al., 2003; Sato et al., 2002), suggesting the presence of a more complex mechanism in regulating methylation of these promoters. In fact, only a small number of CpG-rich promoters are methylated in normal adult tissues or tumor tissues and these methylated promoters are different in different tissues, a phenomenon termed as "tissue-specific methylation" (Reik et al., 2001; Cedar, 1988). The methylation in CpG-rich promoter regions results in transcriptional silencing of corresponding genes, a major mechanism to inactivate tumor suppressor genes in tumorigenesis (Baylin et al., 2002).

Because the expression of DNMT3B might be highly regulated in the cell cycle, it was believed that the increased expression observed in tumors might be merely a reflection of an increased proliferation status (Robertson et al., 2000). Several recent studies further underscore this notion by demonstrating that the maintenance of methylated promoters of tumor suppressor genes could only be effectively disrupted when both DNMT3B and DNMT1 genes were knocked out while a single knockout of either DNMT3B or DNMT1 had minimal effects (Rhee et al., 2002; Rhee et al., 2000; Leu et al., 2003). However, these studies did not address potential effects of individual variants of DNMT3B. A dominant-negative effect of DNMT3b4, which lacks methyltransferase enzymatic motifs, in competing with DNMT3b3 has been suggested and resulted in DNA hypomethylation on pericentromeric satellite regions (Saito et al., 2002).

During tumorigenesis, de novo DNA methylation occurs in certain promoters, particularly tumor suppressor genes (Jones and Gonzalgo, 1997; Robertson and Wolffe, 2000). Global analysis of promoter methylation in different tumors indicates a number of promoters, including genes unlikely critical in tumorigenesis, are methylated. However, the patterns in terms of which genes and the total number of genes vary depending on the tumors (Esteller et al., 2003), suggesting that de novo promoter methylation occurring in tumorigenesis is a complex biologic operation. Weisenberger et al. (2004) recently studied several DNMT3B variants for their role in methylation of selected sequences and found that certain DNMT3B variants, despite the lack of a catalytically active domain, may still be biologically important in controlling methylation of certain sequence structures, although such variants alone may be not sufficient for the control.

The nucleic acid sequence of the seven exemplary ΔDNMT3B variants of the invention is provided respectively in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. The corresponding encoded amino acid sequences for SEQ ID NOS: 1-7 are provided respectively in SEQ ID NO:15, SEQ ID NO:16, SEQ ID NO:17, SEQ ID NO:18, SEQ ID NO:19, SEQ ID NO:20, and SEQ ID NO:21. In specific embodiments, exemplary ΔDNMT3B variants lacking the C-terminal enzymatic domains are provided respectively in SEQ ID NO:8, SEQ ID NO:9, SEQ ID NO:10, SEQ ID NO:11, SEQ ID NO:12, SEQ ID NO:13, and SEQ ID NO:14. The corresponding encoded amino acid sequences for SEQ ID NOS: 8-14 are provided respectively in SEQ ID NO:22, SEQ ID NO:23, SEQ ID NO:24, SEQ ID NO:25, SEQ ID NO:26, SEQ ID NO:27, and SEQ ID NO:28.

III. Nucleic Acids Encoding DNA Methyltransferase 3B Molecules

In particular embodiments, the present invention provides isolated nucleic acid sequences encoding DNA methyltransferase 3B variants, and more particularly, delta DNA methyltransferase 3B (dDNMT3B) inhibitors such as antisense or siRNA molecules, for treating or preventing a cancer. In further particular embodiments, the present invention provides isolated nucleic acid sequences of DNA methyltransferase-3B variants comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, for example. The term "comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14" means that the nucleic acid sequence substantially corresponds to a portion of SEQ ID NO:1 to SEQ ID NO:7. In some embodiments, the present invention employs a nucleic acid sequence that is antisense to at least a portion of the coding sequence of a DNA methyltransferase 3B polypeptide, and these nucleic acids correspond to the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

The term "nucleic acid" generally refers to at least one molecule or strand of DNA, RNA or a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. An "isolated nucleic acid" as contemplated in the present invention may comprise transcribed nucleic acid(s), regulatory sequences, coding sequences, or the like, isolated substantially away from other such sequences, such as other naturally occurring nucleic acid molecules, regulatory sequences, polypeptide or peptide encoding sequences, etc.

Nucleic acids according to the present invention may comprise an entire DNA methyltransferase 3B polynucleotide, or any fragment or variant of DNA methyltransferase 3B as set forth herein. A nucleic acid of the present invention may be derived from genomic DNA, i.e., cloned directly from the genome of a particular organism. It is contemplated that the nucleic acids of the present invention may comprise complementary DNA (cDNA). The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a polynucleotide of a given DNA methyltransferase 3B variant may be represented by natural or synthetic variants that have slightly different nucleic acid sequences but, nonetheless, encode the same or homologous protein (Table 1). As used in this application, the term "polynucleotide" refers to a nucleic acid molecule that has been isolated free of total cellular nucleic acid. In exemplary embodiments, the invention concerns a nucleic acid sequence essentially as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, and SEQ ID NO:14.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 80%, preferably at least about 90% and most preferably about 95% of nucleotides that are identical to the nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14 are contemplated. Sequences that are essentially the same as those set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14 may also be functionally defined as sequences that are capable of hybridizing to a nucleic acid sequence containing the complement of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14 under standard conditions. The term "functionally equivalent codon" is used herein to refer to codons that encode the same amino acid, such as the six codons for arginine or serine (Table 1), and also refers to codons that encode biologically equivalent amino acids, as discussed herein.

Naturally, the present invention also encompasses nucleic acid sequences that are complementary, or essentially complementary, to the sequences set forth herein, for example, in SEQ ID NO:1. Nucleic acid sequences that are "complementary" are those that are capable of base-pairing according to the standard Watson-Crick complementarity rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein, for example SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, and SEQ ID NO:14 under relatively stringent conditions such as those described herein. Such sequences may encode an entire DNA methyltransferase 3B molecule or functional or non-functional fragments thereof.

The hybridizing sequences may be short oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of about 15, 16, 17, 18, 19, 20, 21, 22, 23, 24, 25, 30, 35, 40, 45, 50, 55, 60, 70, 80 or more base pairs will be used, although longer polynucleotides are contemplated. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of the probe and the target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other instances, hybridization may be achieved under conditions of, for example, 50 mM Tris-HCl (pH 8.3), 75 mm KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 μM $MgCl_2$, at temperatures ranging from approximately 40° C. to about 72° C. Formamide and SDS also may be used to alter the hybridization conditions.

IV. Vectors Comprising Nucleic Acid Encoding DDNMT3B Molecules

Within certain embodiments of the present invention, an isolated nucleic acid sequence comprising a delta DNA methyltansferase 3B variant may be comprised in an expression vector. Expression requires that appropriate signals be provided in the vectors, which include various regulatory elements, such as enhancers/promoters from both viral and mammalian sources that drive expression of the genes of interest in host cells. Expression vectors utilized in the present invention may be a viral or plasmid vector.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, etc.), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a DNA methyltransferase molecule. In some cases, DNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. It is contemplated in the present invention, that virtually any type of vector may be employed in any known or later discovered method to deliver nucleic acids encoding a DNA methyltransferase molecule. Where incorporation into an expression vector is desired, the nucleic acid encoding a DNA methyltransferase molecule may also comprise a natural intron or an intron derived from another gene. Such vectors may be viral or non-viral vectors as described herein, and as known to those skilled in the art. An expression vector comprising a nucleic acid encoding a DNA methyltransferase molecule may comprise a virus or engineered construct derived from a viral genome.

The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing the DNA methyltransferase molecules or inhibitors thereof, such as antisense or siRNA molecules of the present invention or (ii) to transform cells in vitro or in vivo to provide therapeutic molecules for gene therapy. Thus, the present invention contemplates viral vectors such as, but not limited to, an adenoviral vector, an adeno-associated viral vector, a retroviral vector, a lentiviral vector, a herpes viral vector, polyoma viral vector or hepatitis B viral vector.

In particular embodiments of the invention, a plasmid vector is contemplated for use to transform a host cell. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, the commercially available pSupervector (OligoEngine, Seattle, Wash.) and pSilencer™ siRNA expression vectors (Ambion, Austin Tex.). Other vectors that may be employed in the present invention include, but are not limited to, the following eukaryotic vectors: pWLNEO, pSV2CAT, pOG44, PXT1, pSG (Stratagene) pSVK3, pBSK, pBR322, pUC vectors, vectors that contain markers that can be selected in mammalian cells, such as pcDNA3.1, episomally replicating vectors, such as the pREP series of vectors, pBPV, pMSG, pSVL (Pharmacia), adenovirus vector (AAV pCWRSV, Chatterjee et al. (1992)) retroviral vectors, such as the pBABE vector series, a retroviral vector derived from MoMuLV (pG1Na, Zhou et al., (1994)); and pTZ18U (BioRad, Hercules, Calif.).

Regulatory Elements. Throughout this application, the term "expression construct" is meant to include any type of genetic construct containing a nucleic acid coding for a DNA methyltransferase 3B molecule of the present invention in which part or all of the nucleic acid encoding sequence is capable of being transcribed. The transcript may be translated into a protein, but it need not be. Expression includes both transcription of a gene and translation of mRNA into a gene product. In other instances, expression only includes transcription of the nucleic acid encoding a gene of interest.

In preferred embodiments, the nucleic acid encoding a delta DNA methyltansferase is under transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," and "under transcriptional control" means that the promoter is in the correct location and orientation in relation to the nucleic acid to control transcriptional initiation and/or expression of that sequence.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

Promoters such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Selectable Markers. In certain embodiments of the invention, cells containing a nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Multigene Constructs and IRES. In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Host Cells. As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a DNA methyltransferase 3B molecule or antisense or siRNA or a construct thereof. Therefore, recombinant cells are distinguishable from naturally occurring cells that do not contain a recombinantly introduced nucleic acid.

In certain embodiments, it is contemplated that nucleic acid or proteinaceous sequences may be co-expressed with other selected nucleic acid or proteinaceous sequences in the same host cell. Co-expression may be achieved by co-transfecting the host cell with two or more distinct recombinant vectors. Alternatively, a single recombinant vector may be constructed to include multiple distinct coding regions for nucleic acids, which could then be expressed in host cells transfected with the single vector.

V. Methods for Identifying Inhibitors DNA Methyltransferase 3B Activity

A. Inhibitors of Delta DNA Methyltransferase 3B

The present invention further comprises methods for identifying, making, generating, providing, manufacturing or obtaining inhibitors of delta DNA methyltransferase 3B activity. Delta DNA methyltransferase 3B nucleic acid or polypeptide may be used as a target in identifying compounds that inhibit, decrease or down-regulate its expression or activity in cancer cells, such as lung cancer cells. In other embodiments, compounds screened for would demethylate a hypermethylated promoter, such as a tumor suppressor gene promoter in a cancer cell. These assays may comprise random screening of large libraries of candidate substances; alternatively, the assays may be used to focus on particular classes of compounds selected with an eye towards structural attributes that are believed to make them more likely to inhibit the function of delta DNA methyltransferase 3B molecules. By function, it is meant that one may assay for inhibition of activity of delta DNA methyltransferase 3B in cancer cells, for demethylation of a methylated promoter or inhibition of the ability of the delta DNA methyltransferase 3B to methylate a promoter, and/or for the ability to increase apoptosism, for example.

To identify, make, generate, provide, manufacture or obtain a delta DNA methyltransferase 3B inhibitor, one generally will determine the activity of the delta DNA methyltransferase 3B molecule in the presence, absence, or both of the candidate substance, wherein an inhibitor is defined as any substance that down-regulates, reduces, inhibits or decreases delta DNA methyltransferase 3B expression or activity. For example, a method may generally comprise:

a) providing in a cell or cell free-system a DNA methyltransferase 3B polypeptide corresponding to the sequence of SEQ ID NO:15, SEQ ID NO:16, SEQ ID NO:17, SEQ ID NO:18, SEQ ID NO:19, SEQ ID NO:20 or SEQ ID NO:21;

b) contacting the DNA methyltransferase with a candidate substance; and c) selecting an inhibitor of the DNA methyltransferase by assessing the effect of the candidate substance on DNA methyltransferase 3B activity. Upon identification of the inhibitor, the method may further provide manufacturing of the inhibitor.

Assays may be employed to assess the effect of the candidate substance on DNA methyltransferase activity, such as the following exemplary assays: (1) methylation specific PCR (MSP) or bisulfide sequencing analysis may be used to determine methylation status of specific promoters (2) RT-PCR may be used to determine reactivation of gene expression as a result of promoter demethylation of specific genes (3) global gene expression status measured by using DNA microarrays can be used to determine promoter methylation/demethylation status following manipulation of individual DNA methyltransferases; and/or (4) vectors containing specific promoter sequences with or without methylation may be co-transfected with vectors carrying individual DNA methyltransferase sequence into cells to determine at least one in vivo role of each isoform in controlling promoter methylation.

DNA methylation is a major determinant in the epigenetic silencing of genes. It is a complex process wherein three DNA methyltransferases catalyze the addition of a methyl group from S-adenosyl-L-methionine to the 5-carbon position of cytosine. A number of methods known to one of ordinary skill in the art may be used to detect DNA methylation. For example, such methods may include an enzyme based methodology or by chemical modificaton. In particular, such assays may include restriction endonuclease-based assays, restriction-enzyme based techniques, or developing methods based on polymerase chain reaction of sodium bisulfite-modified DNA, but is not limited to such. DNA array based techniques such as a differential methylation hybridization (Huang et al., 1999) assay may also be employed to perform a screen for hypermethylated promoter in a variety of cancer cell samples. PCR based methodologies may include methylation-sensitive restriction fingerprinting (Huang et al., 1997) to screen for changes in DNA methylation in tumors.

1. Inhibitors

As used herein the term "candidate substance" or "candidate compound" refers to any molecule that may potentially inhibit the activity of a delta DNA methyltransferase 3B molecule, that negatively affects its expression, or both. A delta DNA methyltransferase 3B inhibitor may be a compound that overall affects delta DNA methyltransferase 3B activity, which may be accomplished by inhibiting delta DNA methyltransferase 3B expression, function, or more directly by preventing its activity. Any compound or molecule described in the methods and compositions herein may be an inhibitor of delta DNA methyltransferase 3B activity.

The candidate substance may be a protein or fragment thereof, a small molecule, or even a nucleic acid molecule. It may prove to be the case that the most useful pharmacological compounds will be compounds that are structurally related to delta DNA methyltransferase 3B or other DNA methyltransferases, or that binds delta DNA methyltransferase 3B. In specific embodiments, the inhibitors may be dominant negative forms of the known DNMT3B forms or of the inventive DDNMT3B variants. Using lead compounds to help develop improved compounds is known as "rational drug design" and includes not only comparisons with known inhibitors, but predictions relating to the structure of target molecules.

Candidate compounds or inhibitors of the present invention will likely function to inhibit, decrease or down-regulate the expression or activity of delta DNA methyltransferase 3B in a cancer cell such as a lung cancer cell. Such candidate compounds may be inhibitors or regulators of DNA methyltransferases may have the ability to demethylate a methylated promoter or may likely be involved in controlling cellular proliferation in a cancer or tumor cell, such as lung cancer cells. These candidate compounds may be antisense molecules, ribozymes, interfering RNAs or siRNAs, antibodies (including single chain antibodies), small molecules, and/or organopharmaceuticals, but are not limited to such.

2. Rational Drug Design

The present invention also provides methods for developing drugs that inhibit delta DNA methyltransferase 3B activity that may be used to treat a cancer, such as lung cancer. One such method involves the prediction of the three dimensional structure of a validated DNA methyltransferase target using molecular modeling and computer stimulations. The resulting structure may then be used in docking studies to identify potential small molecule inhibitors. Inhibitors identified may then be tested in biochemical assays to further identify delta DNA methyltransferase 3B drug targets for cancer treatment, e.g., lung cancer treatment.

Rational drug design is therefore used to produce structural analogs of substrates for delta DNA methyltransferase 3B. By creating such analogs, it is possible to fashion drugs which are more active or stable than the natural molecules, which have different susceptibility to alteration or which may affect the function of various other molecules. In one approach, one would generate a three-dimensional structure for the delta DNA methyltransferase 3B targets of the invention or a fragment thereof. This could be accomplished by X-ray crystallography, computer modeling or by a combination of both approaches.

It is also possible to use antibodies to ascertain the structure of a target compound inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Such libraries, including combinatorially generated libraries (e.g., peptide libraries), provide a rapid and efficient way to screen a large number of related (and unrelated) compounds for activity. Combinatorial approaches also lend themselves to rapid evolution of potential drugs by the creation of second, third and fourth generation compounds model of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be a peptide, polypeptide, polynucleotide, small molecule inhibitors or any other compounds that may be designed through rational drug design starting from known inhibitors or stimulators.

Other suitable compounds include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition, it is also contemplate that sterically similar compounds may be formulated to mimic the key portions of the structure of the inhibitors. Such compounds, may include peptidomimetics of peptide inhibitors. Regardless of the type of inhibitor identified by the present screening methods, the effect of the inhibition by such a compound results in the regulation of delta DNA methyltransferase 3B activity as compared to that observed in the absence of the added candidate substance.

The term "drug" as contemplated herein is intended to refer to a chemical entity, whether in the solid, liquid, or gaseous phase which is capable of providing a desired therapeutic effect when administered to a subject. The term "drug" should be read to include synthetic compounds, natural products and macromolecular entities such as polypeptides, polynucleotides, or lipids and also small entities such as neurotransmitters, ligands, hormones or elemental compounds. The term "drug" is meant to refer to that compound whether it is in a crude mixture or purified and isolated.

3. In Vitro Assays

A quick, inexpensive and easy assay to run is an in vitro assay. Such assays generally use isolated molecules, and can be run quickly and in large numbers, thereby increasing the amount of information obtainable in a short period of time. A variety of vessels may be used to run the assays, including test tubes, plates, dishes and other surfaces such as dipsticks or beads.

One example of a cell-free assay is a binding assay. While not directly addressing function, the ability of a compound to bind or contact to a target molecule, such as DNA methyltransferase of the present invention, in a specific fashion is strong evidence of a related biological effect, which can be assessed in a screening assay. For example, binding of a molecule to a delta DNA methyltransferase 3B molecule of the present invention may, in and of itself, be inhibitory, due to steric, allosteric or charge-charge interactions. The delta DNA methyltransferase 3B molecule may be either free in solution, fixed to a support, and/or expressed in or on the surface of a cell. Either the delta DNA methyltransferase 3B molecule or the compound may be labeled, thereby permitting measuring of the binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

4. In Cyto Assays

The present invention also contemplates identifying compounds for their ability to inhibit a delta DNA methyltransferase 3B variant disclosed herein, in cells. Various cell lines can be utilized for such screening assays, including cells specifically engineered for this purpose. The present invention particularly contemplates the use of cancer cells, such as lung cancer cells. Depending on the assay, culture may be required. The cell is examined using any of a number of different physiologic assays. Alternatively, molecular analysis may be performed, for example, looking at protein expression, mRNA expression (including differential display of whole cell or polyA RNA) by methods as described herein and that are well known to those of skill in the art.

5. In Vivo Assays

In vivo assays involve the use of various animal models, including transgenic animals that have been engineered to have specific defects such as overexpression of a delta DNA methyltransferase 3B molecule, or that carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

In such assays, one or more candidate substances are administered to an animal, and the ability of the candidate substance(s) to alter one or more characteristics, as compared to a similar animal not treated with the candidate substance (s), identifies an inhibitor. The characteristics may be any of those discussed above with regard to delta DNA methyltransferase 3B activity, or it may be broader in the sense of "treating" the condition present in the animal.

Treatment of these animals with test compounds will involve the administration of the compound, in an appropriate form, to the animal. Administration will be by any route that could be utilized for clinical or non-clinical purposes, including but not limited to oral, nasal, buccal, topical or by a nebulizer or atomizer. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve measuring toxicity and dose response which can be performed in animals in a more meaningful fashion than in in vitro or in cyto assays.

VI. DNA Methyltransferase Inhibitors for Cancer Therapy

The present invention embodies a method of treating cancer such as lung cancer, by the delivery of a delta DNA methyltransferase 3B inhibitor to a cancer cell. Such a cell may be located in a patient having a cancer. Examples of cancers contemplated for treatment include leukemia, ovarian cancer, breast cancer, lung cancer, colon cancer, liver cancer, prostate cancer, testicular cancer, stomach cancer, brain cancer, bladder cancer, head and neck cancer, melanoma, and any other cancer that may be treated by inhibiting or decreasing the enzymatic activity of delta DNA methyltransferase 3B. Such inhibitors may include antisense molecules, RNA interference or siRNA methodology, or ribozymes.

A. Antisense Methodology

As discussed above, the present invention may also employ an antisense molecule in inhibiting the activity of a DNA methyltransferase, such as delta DNA methyltransferase. Antisense methodology takes advantage of the fact that nucleic acids tend to pair with "complementary" sequences. By complementary, it is meant that the polynucleotides are those capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation targeting RNA leads to double-helix formation. Antisense polynucleotides, when introduced into a target cell, specifically bind to their target polynucleotide and interfere with transcription, RNA processing, transport, translation and/or stability. Antisense molecules, or DNA encoding such antisense molecules, may be employed to inhibit gene transcription or translation or both within a host cell, either in vitro or in vivo, such as within a host animal, including a human subject.

Antisense molecules may be designed to bind to the promoter and/or other control regions, exons, introns or even exon-intron boundaries of a gene. It is contemplated that the most effective antisense constructs will include regions complementary to intron/exon splice junctions. Thus, it is proposed that a preferred embodiment includes one or more antisense molecules with complementarity to regions within about 50 of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme see below) could be designed. These molecules, though having less than 50% homology, would bind to target sequences under appropriate conditions. It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

In particular aspects of the invention, siRNA compositions may target an exon-exon junctions, such as of particular variants, including the exemplary one comprising sense strand provided in SEQ ID NO:61 and the antisense strand provided in SEQ ID NO:62, which targets the exemplary sequence of SEQ ID NO:63.

B. RNA Interference (RNAi)

The present invention also contemplates the use of RNA interference in inhibiting, reducing or downregulating the activity of delta DNA methyltransferase 3B molecules of the present invention. RNA interference (also referred to as "RNA-mediated interference" or RNAi) is a mechanism by which gene expression can be reduced or eliminated. Double stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp, 1999; Sharp and Zamore, 2000; Tabara et al., 1999; Hutvagner et al., 2001; Tuschl, 2001; Waterhouse et al., 2001; Zamore, 2001). Activation of these mechanisms target mature, dsRNA-complementary mRNA for destruction. Moreover, dsRNA has been shown to silence genes in a wide range of systems, including plants, protozoans, fungi, *C. elegans, Trypanasoma* and *Drosophila* (Grishok et al., 2000; Sharp, 1999; Sharp and Zamore 2000).

RNAi offers major experimental advantages for the study of gene function. These advantages include a very high specificity, ease of movement across cell membranes, and prolonged down-regulation of the targeted gene. RNAi may be used to identify genes that are essential for a particular biological pathway, identify disease-causing genes, study structure function relationships, and implement therapeutics and diagnostics. As with other types of gene inhibitory compounds, such as antisense and triplex forming oligonucleotides, tracking these potential drugs in vivo and in vitro is important for drug development, pharmacokinetics, biodistribution, macro and microimaging metabolism and for gaining a basic understanding of how these compounds behave and function.

In RNAi the dsRNA is typically directed to an exon, although some exceptions to this have been shown (see Plasterk and Ketting, 2000). Also, a homology threshold (probably about 80-85% over 200 bases) is required. Most tested sequences are 500 base pairs or greater, though sequences of 30 nucleotides or fewer evade the antiviral response in mammalian cells (Baglioni et al., 1983; Williams, 1997). The targeted mRNA is lost after RNAi. The effect of RNAi is non-stoichiometric, and thus incredibly potent. In fact, it has been estimated that only a few copies of dsRNA are required to knock down >95% of targeted gene expression in a cell (Fire et al., 1998).

Due to a potent antiviral response pathway in mammalian cells that induces global changes in gene expression when the cells are challenged with long (>30 nucleotides) dsRNA molecules, RNAi was used in non-mammalian cells. This limitation in the art was overcome by the discovery of a method to bypass the antiviral response and induce gene specific silencing in mammalian cells (Elbashir et al., 2001). Several nucleotide (nt) dsRNAs with 2 nt 3' overhangs were transfected into mammalian cells without inducing the antiviral response. These small dsRNAs, referred to as small interfering RNAs (siRNAs) proved capable of inducing the specific suppression of target genes. In addition, it was demonstrated that siRNAs could reduce the expression of several endogenous genes in human cells. The use of siRNAs to modulate gene expression in mammalian cells has since been demonstrated (Caplen et al., 2001; Hutvagner et al., 2001).

Thus, small interfering RNA (siRNA), which are generally 12-15 or 21-23 nucleotides in length and which possess the ability to mediate RNA interference are also contemplated in the present invention. For example, such siRNA may be of at least 21 nucleotides. siRNAs of the present invention may be synthesized chemically or may be produced recombinantly. They may be subsequently isolated and/or purified.

When made in vitro, siRNA is formed from one or more strands of polymerized ribonucleotide. When formed of only one strand, it takes the form of a self-complementary hairpin-type or stem and loop structure that doubles back on itself to form a partial duplex. The self-duplexed portion of the RNA molecule may be referred to as the "stem" and the remaining, connecting single stranded portion referred to as the "loop" of the stem and loop structure. When made of two strands, they are substantially complementary. siRNAs of the present invention may be synthesized chemically or may be produced recombinantly. They may be subsequently isolated and/or purified. dsRNA for use as siRNA may also be enzymatically synthesized through the use of RNA dependent RNA polymerases such as Q beta replicase, Tobacco mosaic virus replicase, brome mosaic virus replicase, potato virus replicase, etc. Methods for synthesizing dsRNA are well-described (Fire et al., 1998). Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, a procedure may be employed to aid this time intensive procedure. The sum of the individual dsRNA species is designated as a "dsRNA library."

Reaction conditions for use of these RNA polymerases are well known in the art (U.S. Pat. RE 35,443, and U.S. Pat. No. 4,786,600, each incorporated herein by reference). The result of contacting the appropriate template with an appropriate polymerase is the synthesis of an RNA product, which is typically double-stranded. In some instances a single stranded RNA or single stranded DNA template may be utilized. If utilizing a single stranded DNA template, the enzymatic synthesis results in a hybrid RNA/DNA duplex that is also contemplated as useful as siRNA.

The templates for enzymatic synthesis of siRNA are nucleic acids, typically, though not exclusively DNA. A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al. (1986), and U.S. Pat. No. 5,705,629, each incorporated herein by reference. A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells (see for example, Sambrook, 2001; incorporated herein by reference). Methods for the production of siRNA to induce gene silencing can be found in United States Patent Application 20030166282, incorporated herein by reference.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended protocol.

C. Ribozymes

The present invention also contemplates the use of DNA methyltransferase 3B specific ribozymes to down-regulate or inhibit delta DNA methyltransferase 3B enzymatic activity. Ribozymes are RNA-protein complexes that cleave nucleic acids in a site-specific fashion. Ribozymes comprise of eight classes including seven that modify the nucleic acid backbone which include hammerhead, hairpin, HDV (hepatitis delta virus), ribonuclease P, group I intron, group II intron, and VS ribozyme. The eighth type, the ribosome's peptidyl transferase center, builds peptide bonds.

Ribozymes have specific catalytic domains that possess endonuclease activity (Kim and Cook, 1987;; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Michel and Westhof, 1990; Reinhold-Hurek and Shub, 1992). This specificity has been attributed to the requirement that the substrate binds via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990).

VII. Generating Antibodies Reactive with DNA Methyltransferase 3B Molecules

In a particular embodiment, the present invention contemplates antibodies that are immunoreactive with a DNA methyltransferase 3B or variants thereof. Such an antibody can be a polyclonal or a monoclonal antibody, although in a preferred embodiment the antibody is a monoclonal antibody. Means for preparing and characterizing antibodies are well known in the art (see, e.g., Harlow and Lane, 1988). Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for an antigen may be prepared using conventional immunization techniques, as are generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the antibodies of the present invention will find useful application in standard immunochemical procedures, such as ELISA and Western blot methods and in immunohistochemical procedures such as tissue staining, as well as in other procedures which may utilize antibodies specific to DNA methyltransferase 3B variants.

In general, both polyclonal and monoclonal antibodies against delta DNA methyltransferase 3B variants of the present invention may be used in a variety of embodiments. For example, they may be employed in antibody cloning protocols to obtain cDNAs or genes encoding other DNA methyltransferase 3B molecules. They may also be used in inhibition studies to analyze the effects of delta DNA methyltransferase 3B in cells or animals. Antibodies comprising DNA methyltransferase 3B variants will also be useful in immunolocalization studies to analyze the distribution of these molecules during various cellular events, for example, to determine the cellular or tissue-specific distribution of DNA methyltransferase 3B polypeptides at different points in the cell cycle. A particularly useful application of such antibodies is in purifying native or recombinant DNA methyltransferase 3B molecules, for example, using an antibody affinity column. The operation of such immunological techniques are well known to those of skill in the art.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

It is also well known in the art, that the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide or cell expressing high levels. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

VIII. Delivery of a DNMT3B Inhibitor to a Cell

In some embodiments of the present invention delivery of a nucleic acid encoding a DNA methyltransferase inhibitor such as an antisense or siRNA or an expression construct thereof to a cell is contemplated. Virtually any method by which nucleic acids can be introduced into a cell, or an organism may be employed with the current invention, as described herein or as would be known to one of ordinary skill in the art.

Such methods include, but are not limited to direct delivery of a nucleic acid by: injection (U.S. Pat. Nos. 5,994,624, 5,981,274, 5,945,100, 5,780,448, 5,736,524, 5,702,932, 5,656,610, 5,589,466 and 5,580,859, each incorporated herein by reference) microinjection (Harland and Weintraub, 1985; U.S. Pat. No. 5,789,215, incorporated herein by reference); electroporation (U.S. Pat. No. 5,384,253, incorporated herein by reference Tur-Kaspa et al., 1986; Potter et al., 1984) calcium phosphate precipitation (Graham and Van Der Eb, 1973; Chen and Okayama, 1987; Rippe et al., 1990) using DEAE-dextran followed by polyethylene glycol (Gopal, 1985) direct sonic loading (Fechheimer et al., 1987) liposome mediated transfection (Nicolau and Sene, 1982; Fraley et al., 1979; Nicolau et al., 1987; Wong et al., 1980; Kaneda et al., 1989; Kato et al., 1991) receptor-mediated transfection (Wu and Wu, 1987; Wu and Wu, 1988) microprojectile bombardment (PCT Application Nos. WO 94/09699 and 95/06128; U.S. Pat. Nos. 5,610,042 5,322,783 5,563,055, 5,550,318, 5,538,877 and 5,538,880, and each incorporated herein by reference) agitation with silicon carbide fibers (Kaeppler et al., 1990; U.S. Pat. Nos. 5,302,523 and 5,464,765, each incorporated herein by reference) PEG-mediated transformation of protoplasts (Omirulleh et al., 1993; U.S. Pat. Nos. 4,684,611 and 4,952,500, each incorporated herein by reference) desiccation/inhibition-mediated DNA uptake (Potrykus et al., 1985) or any combination of such methods.

In other embodiments, it is contemplated that a nucleic acid encoding an siRNA or an expression construct thereof may be delivered to a cell by hydrodynamic transfection/injection, or by liposomes.

It is also contemplated in the present invention that a siRNA may be delivered directly to a cell. In other embodiments, the siRNA may be delivered to a cell indirectly by introducing one or more vectors that encode both single strands of a siRNA (or, in the case of a self-complementary RNA, the single self-complementary strand) into the cell. The vectors of these embodiments contain elements of the templates described above such that the RNA is transcribed inside the cell, annealed to form siRNA and effects attenuation of the target gene expression. See WO 99/32619, WO 00/44914, WO 01/68836 (each of which is expressly incorporated herein by reference) and references therein for further examples of methods known in the art for introducing siRNA into cells. In some embodiments, an siRNA of the present invention may be delivered along with components that enhance RNA uptake by the cell, stabilize the annealed strands, or otherwise increase inhibition of DNA methyltransferase 3B activity.

Wherein the inhibitor is not a nucleic acid, such as an antibody, for example, standard means in the art may be utilized to deliver the inhibitor, such as by liposomes.

IX. Therapeutic/Pharmaceutical Compositions

In some embodiments, the present invention provides a method of treating or preventing a cancer by providing or administering to a patient a therapeutically effective amount of DNA methyltransferase 3B inhibitor, such as a delta DNA methytransferase 3B inhibitor which includes but is not limited to an antisense or siRNA molecule.

"Therapeutically effective amounts" are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

Diseases contemplated for treatment with the DNA methyltransferase 3B inhibitors of the present invention include, but are not limited to, cancers. Examples of cancers contemplated for treatment with a delta DNA methyltransferase 3B inhibitor may include breast cancer, lung cancer, head and neck cancer, bladder cancer, bone cancer, bone marrow cancer, brain cancer, colon cancer, esophageal cancer, gastrointestinal cancer, gum cancer, kidney cancer, liver cancer, nasopharynx cancer, ovarian cancer, prostate cancer, skin cancer, stomach cancer, testis cancer, tongue cancer, or uterine cancer. In some instances the cancer to be treated using a delta DNA methyltransferase 3B inhibitor as disclosed herein, may be a malignant or metastatic cancer but not limited to such.

To inhibit DNA methylation, kill cells, induce cell cycle arrest, inhibit cell growth, inhibit metastasis, inhibit angiogenesis or otherwise reverse or reduce the malignant phenotype of cancer cells, using the methods and compositions of the present invention, one would generally contact a cell with the DNA methyltransferase 3B inhibitor, in particular a delta DNA methyltransferase inhibitor. The terms "contacted" and "exposed," when applied to a cell, tissue or organism, are used herein to describe the process by which the therapeutic compositions of the invention is delivered to a target cell, tissue or organism or are placed in direct juxtaposition with the target cell, tissue or organism. To achieve cell killing or stasis, an amount effective of the therapeutic composition is delivered to one or more cells to kill the cell(s) or prevent them from dividing.

Pharmaceutical aqueous compositions of the present invention comprise the delta DNA methyltransferase 3B inhibitor and/or an additional agent(s) dissolved or dispersed in a pharmaceutically acceptable carrier or aqueous medium. The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The actual dosage amount of a delta DNA methyltransferase 3B inhibitory composition of the present invention (and/or an additional agent) for administration to a patient can be determined by physical and physiological factors such as body weight, severity of condition, idiopathy of the patient and on the route of administration. With these considerations in mind, the dosage of a lipid composition for a particular subject and/or course of treatment can readily be determined.

Treatment may vary depending upon the host treated and the particular mode of administration. For example, in the invention the dose range of a DNA methyltransferase 3B inhibitor may be about 0.5 mg/kg body weight to about 500 mg/kg body weight. The term "body weight" is applicable when an animal is being treated. When isolated cells are being treated, "body weight" as used herein should read to mean "total cell weight". The term "total weight may be used to apply to both isolated cell and animal treatment. All concentrations and treatment levels are expressed as "body weight" or simply "kg" in this application are also considered to cover the analogous "total cell weight" and "total weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for a DNA methyltransferase 3B inhibitor of the present invention.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. As is well known in the art, a specific dose level of active compounds such as a delta DNA methyltransferase inhibitor, for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, and general safety and purity standards as required by FDA Office of Biologics standards.

A delta DNA methyltransferase 3B inhibitor as a therapeutic agent may be administered to a subject more that once and at intervals ranging from minutes to weeks. One would generally ensure that a significant period of time did not expire between the time of each delivery, such that the agent would still be able to exert an advantageous effect on the cell. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of delta DNA methyltransferase 3B inhibitor to a patient may be by any method know in the art for delivery of a therapeutic agent to a patient. The inhibitors of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage. For example, a delta DNA methyltransferase 3B inhibitory composition of the present invention may be formulated for parenteral administration, e.g., formulated for injection via the intravenous, intramuscular or sub-cutaneous routes, though other routes such aerosol administration may be used. The delta DNA methyltransferase 3B inhibitory compositions of the present invention may be formulated for non-pressures preparations, such as in a nebulizer or an atomizer. The preparation of an aqueous composition that contains the a delta DNA methyltransferase 3B inhibitory composition of the present invention and/or and additional agent as an active ingredient will be known to those of skill in the art in light of the present disclosure, as exemplified by Remington's Pharmaceutical Sciences, 16th Ed. Mack Publishing Company, 1980, incorporated herein by reference. Moreover, for human administration, it will be understood that preparations should meet sterility, pyrogenicity, general safety and purity standards as required by FDA Office of Biological Standards.

Typically, such compositions can be prepared as injectables, either as liquid solutions or suspensions solid forms suitable for preparing solutions or suspensions upon the addition of a liquid prior to injection can also be prepared and the preparations can also be emulsified. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area. The compositions will be sterile, be fluid to the extent that easy syringability exists, stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain aspects of the invention, the DNA methyltransferase inhibitor (e.g., siRNA molecule) may be prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In some aspects of the invention an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate a sweetening agent, such as, for example, sucrose, lactose, saccharin or combinations thereof a flavoring agent, such as, for example peppermint, oil of wintergreen, cherry flavoring, orange flavoring, etc. or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations suitable for administration may include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Although it is most preferred that solutions of a delta DNA methyltransferase 3B inhibitory composition of the present invention (and/or a additional agent) be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), lipids (e.g., triglycerides, vegetable oils, liposomes) and combinations thereof. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

It is particularly contemplated that suitable pharmaceutical compositions will generally comprise, but are not limited to, from about 10 to about 100 mg of the desired molecule or agent admixed with an acceptable pharmaceutical diluent or excipient, such as a sterile aqueous solution, to give a final concentration of about 0.25 mg/ml to about 2.5 mg/ml with respect to the conjugate, in, for example, 0.15M NaCl aqueous solution at pH 7.5 to 9.0. The preparations may be stored frozen at −10° C. to −70° C. for at least 1 year.

X. Combination Therapy

In order to increase the effectiveness of the compositions described herein, such as inhibitors of the ΔDNMT3B variants, including siRNA, antisense RNA, antibodies, small molecules, and so forth, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations at the same time, wherein one composition includes the expression construct and the other includes the second agent(s) or in succession of one another Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that inhibitors of ΔDNMT3B variants could be used similarly in conjunction with chemotherapeutic, radiotherapeutic, or immunotherapeutic intervention, for example, in addition to other pro-apoptotic or cell cycle regulating agents.

Alternatively, the inventive therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various exemplary combinations may be employed, wherein the therapy of the present invention is "A" and the secondary agent, such as radio- or chemotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | | B/B/A/B | A/A/B/B | A/B/A/B | A/B/B/A | B/B/A/A | |
| B/A/B/A | | B/A/A/B | A/A/A/B | B/A/A/A | A/B/A/A | A/A/B/A | |

Administration of the therapeutic compositions of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

In particular, the present invention may relate to providing additional therapy for treatment of NSCLC. In these instances, compositions of the present invention may be useful for combination therapy with the exemplary NSCLC chemotherapeutic agents, for example, Camptosar (irinotecan CPT-11) Camptothecin Carboplatin (Paraplatin) Cisplatin (Platinol) Epirubicin Gemzar (gemcitabine) Navelbine (vinorelbine) Oxaliplatin Taxol (paclitaxel) or Taxotere (docetaxel).

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent, for example, are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with therapy of the present invention. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the therapy provided by the present invention. Delivery of a composition of the present invention in conjuction with a vector encoding a therpeutic gene product will have a combined anti-hyperproliferative effect on target tissues. Alternatively, a single vector encoding both genes may be used. A variety of proteins are encompassed within the invention, including inhibitors of cellular proliferation, such as p53, p16, C-CAM, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC, for example and regulators of programmed cell death, such as a Bcl 2 family member (e.g., BclXL, BclW, BclS, Mcl-1, A1, Bfl-1) or counteract Bcl 2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor interferon alpha, beta, and gamma IL-2 and other cytokines F42K and other cytokine analogs or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Study population. One hundred nineteen patients who were diagnosed with pathologic stage I-IIIA NSCLC and had undergone lobectomy or pneumonectomy for complete resection of their primary tumors at The University of Texas M. D. Anderson Cancer Center between 1994 and 2001 were included in the study. The selection of these patients was based on available fresh tumor tissues and corresponding normal lung tissues. The clinical information and follow-up data were based on chart review and on reports from the tumor registry service. Informed consent for the use of residual resected tissues for research was obtained from all the patients in the study. The study was reviewed and approved by the institution's Surveillance Committee. None of the patients with stages I or II disease received adjuvant chemotherapy or radiotherapy before or after surgery. Among 49 patients with stage IIIA disease, 5 received preoperative chemotherapy or chemo-radiotherapy, 20 received postoperative concurrent chemo-radiotherapy, 17 received postoperative radiotherapy alone, and 2 received postoperative chemotherapy alone, and 5 received no additional treatment.

DNA extraction and methylation-specific polymerase chain reaction. Frozen tumor tissues and corresponding distant normal lung tissues were homogenized, and genomic DNA was extracted by digestion of the homogenized tissues in a buffer containing 50 mM Tris-HCl (pH 8.0), 1% sodium dodecyl sulfate, and 0.5 mg/ml proteinase K at 42° C. for 36 h. The digested products were purified with phenyl-chloroform twice. DNA was then precipitated using the ethanol precipitation method and recovered in distilled DNase-free water.

For the methylation-specific polymerase chain reaction (MSP), 1 μg of genomic DNA from each tissue sample was used in the initial step of chemical modification. Briefly, DNA was denatured by NaOH and treated with sodium bisulfite (Sigma Chemical Co., St. Louis, Mo.). After purification with Wizard DNA purification resin (Promega Corp., Madison, Wis.), the DNA was treated again with NaOH. After precipitation, DNA was recovered in water and was prepared for polymerase chain reaction (PCR™) using specific primers for either the methylated or the unmethylated p16$^{INK4a}$ or RASSF1A promoter: p16-MAS (5'-ACCCGAC-CCCGAACCGCGACCGTAA-3'SEQ ID NO:30) and p16-MS (5'-TTATTAGAGGGTGGGGCGGATCG-CGTGC-3'SEQ ID NO:31) for the methylated p16$^{INK4a}$ promoter p16-

UAS (5'-CAACCCCAAACCACAA-CCATAA-3'SEQ ID NO:32) and p16-US (5'-TTATTAGAGGGTGGGGTGGAT-TGT-3'SEQ ID NO:33) for the unmethylated p16$^{INK4a}$ promoter RASSF1A-MAS (5'-GCTAACAAACGCGAACCG-3'SEQ ID NO:34) and RASSF1A-MS (5'-GGGTTTTGCGAGAGCGCG-3'SEQ ID NO:35) for the methylated RASSF1A promoter and RASSF1A-UAS (5'-CACTAACAAACACAAACC-3'SEQ ID NO:36) and RASSF1A-US (5'-GGTTTTTGTGAGAGTGTGTT-TAG-3'SEQ ID NO:37) for the unmethylated RASSF1A promoter. PCR™ was carried out in 25 μl containing about 100 ng of modified DNA, 3% dimethyl sulfoxide, all four deoxynucleoside triphosphates (each at 200 μM), 1.5 mM $MgCl_2$, 0.4 μM PCR™ primers, and 1.25 U of HotStarTaq DNA polymerase (Qiagen, Inc., Valencia Calif.). DNA was amplified in 500-μl plastic tubes for 35 cycles at 95° C. for 30 seconds, 56-64° C. for 60 seconds, and 70° C. for 60 seconds followed by a 5-minute extension at 70° C. in a temperature cycler (Hybaid Omnigene, Woodbridge, N.J.). PCR™ products were separated on 2.5% agarose gels and visualized after staining with ethidium bromide. For each DNA sample, primer sets for methylated DNA and unmethylated DNA were used for analysis. CpGenome™ universal methylated DNA (Chemicon International, Temecula, Calif.) was used as a positive control, and water replacing for DNA was used as blank controls. The hypermethylation status was determined by visualizing a 150-bp PCR™ product for the p16$^{INK4a}$ promoter and a 169-bp PCR™ product for the RASSF1A promoter with the respective methylation-specific primer sets. All PCRs were repeated twice, and the results were reproducible.

Statistical analysis. The $\chi^2$ test or Fisher's exact test were used to test the association between categorical variables. The Cochran-Armitage trend test was used to test the trend of methylation among differentiation levels. Overall survival, disease-specific survival (i.e., survival rates among people who died of lung cancer-related causes specifically), and disease-free survival (i.e., recurrence, metastasis, or cancer death was considered an event) were analyzed. Survival probability was estimated using the Kaplan-Meier method. The log-rank test was used to compare survival times among groups. Cox regression was used to model the risks of p16$^{INK4a}$ and/or RASSF1A promoter hypermethylation on survival time, with adjustment for clinical and histopathologic parameters (age, sex, tumor histology, tumor size, smoking status, and adjuvant treatment). All statistical tests were two-sided, and $P<0.05$ was considered statistically significant.

Cell Lines and Primary Tissues. Human NSCLC lines H157, H226, H292, H358, H460, H522, H596, H1299, H1792, H1944, Calu-6, SK-MES, and A549 were purchased from the American Type Cell Culture (Rockville, Md.). Cells were cultured in DMEM supplemented with 10% heat-inactivated fetal calf serum (FCS), 2 mM L-glutamine, 100 IU/ml penicillin, and 100 mg/ml streptomycin at 37° C. in the presence of 5% $CO_2$.

One hundred and nine paired primary tumor tissues and corresponding normal lung tissues from patients with primary NSCLC were obtained from surgically resected specimens collected in the Department of Pathology at The University of Texas M. D. Anderson Cancer Center and stored at −80° C. until the experiment. The study was approved by the Institutional Review Boards in The University of Texas M. D. Anderson Cancer Center.

RNA Extraction and RT-PCR. Total RNA for each cell line and clinic sample was isolated using Tri-Reagent (Molecular Research Center, Inc., Cincinnati, Ohio) according to manufacturer's instruction. Approximately 1 μg of total RNA from each sample was used to conduct reverse transcription reaction in a 20 μl volume using Superscript II RNase H-reverse transcriptase (GibcoBRL Life Technologies Inc., Grand Island, N.Y.). The synthesized cDNA was either used immediately for PCR™ amplification or stored at −20° C. for further analysis.

Figure 9:
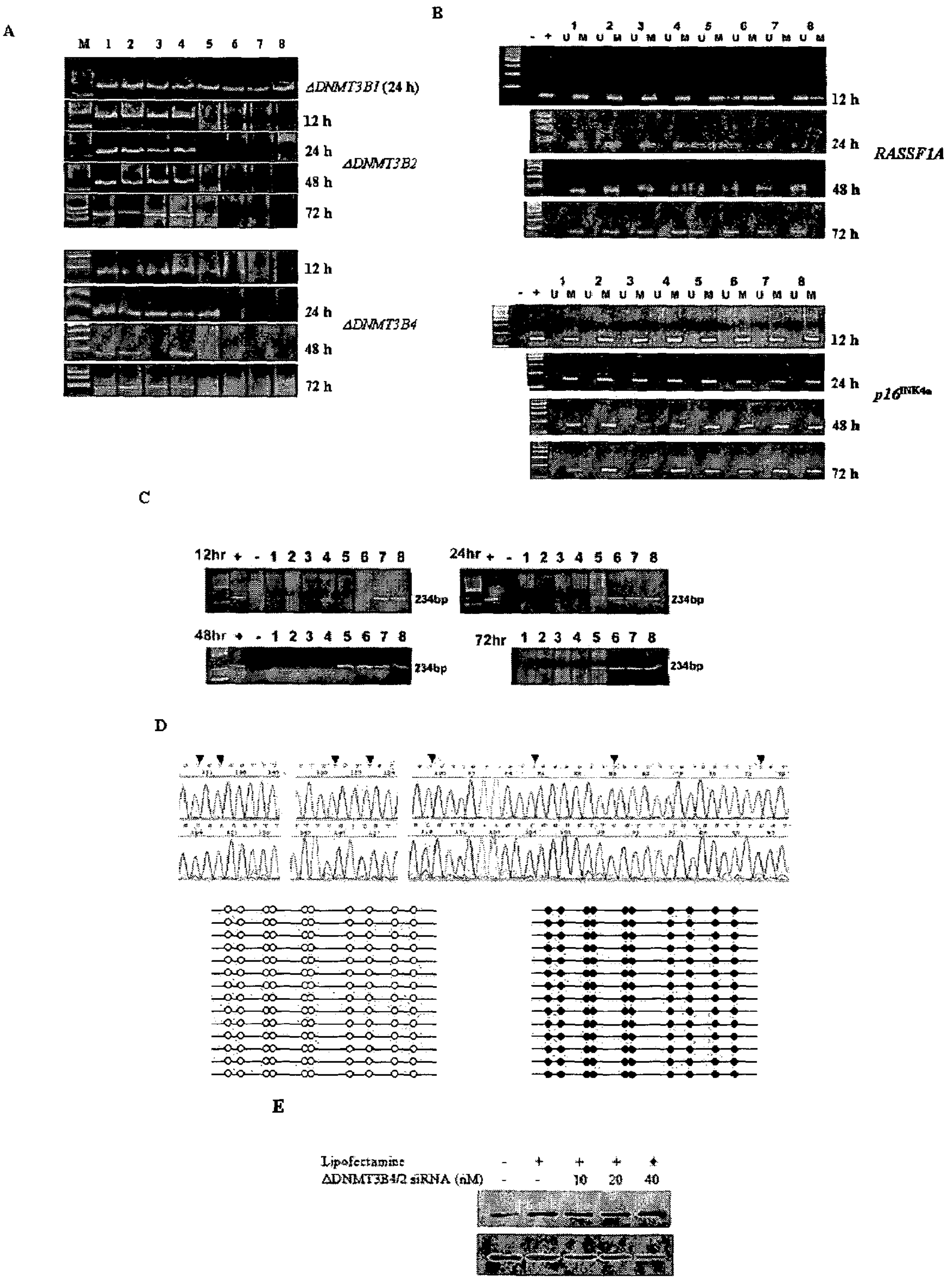
FIGS. 9A-9E. Effects of ΔDNMT3B4/2 knockout on H1299 cells.

The mRNA expression level of total DNMT3Bs was detected by using primer set of the forward primer S1 (5'-GAGTTGGGCATAAAGGTAGG-3'SEQ ID NO:38) and the reverse primer 1AS1 (5'-TGAGGTACACGGTATGACC-3'SEQ ID NO:39) located at exon 17 and 3'-untranslation region of DNMT3B1, respectively. The 5'-end forward primers E1 (5'-CATGAAGGGAGACACCAGGC-3'SEQ ID NO:40), E3 (5'-ATGCCAAAGCTCTTCCGGGA-3'SEQ ID NO:41), E5 (5'-TGGAGATGGAGACAGTTCAG-3'SEQ ID NO:42), and the reverse primer 1AS1 were further used to detect DNMT3Bs (FIG. 9A).

PCR™ reaction was performed in a 12.5 μl volume containing 0.5 μl RT products, 7% DMSO, 1.5 mM dNTPs, 6.7 mM $MgCl_2$, 16.6 mM $(NH_4)_2SO_4$, 67 mM Tris, 10 mM β-mercaptoethanol, 6.7 μM EDTA, 0.5 μM of both the forward and the reverse primer, and 0.625 unit of HotStar Taq DNA polymerase (Qiagen, Inc., Chatsworth, Calif.). Amplification was carried out with an initial denaturing step at 95° C. for 15 min, followed by 35 cycles of 95° C. for 30 s, 58-62° C. for 1 min, and 72° C. for 1 min in a thermal cycler (Hybaid PCR™ Express, Middlesex, UK) with a last extension step of 72° C. for 10 min. The PCR™ products were mixed with 6× loading buffer containing 0.5 mg/ml of ethidium bromide and separated by electrophoresis on a 2% agarose gel.

Primer Extension and Nuclease S1 Mapping. To determine the exact starting site of ΔDNMT3B transcript, the standard primer extension and S1 mapping methods were used with the γ-$^{32}$P-ATP end-labeled antisense primer 3B6AS (5'-GG-TAGCCGGGAACTCCACGG-3'SEQ ID NO:43). For primer extension, briefly, 1 μg of total RNA was mixed with $^{32}$P-labelled primer. The mixture was incubated at 70° C. for 15 minutes and following at room temperature for 10 min, respectively. Extension reactions (20 μl) consisted of 50 mM Tris (pH 8.3), 75 mM KCl, 3 mM $MgCl_2$, 10 mM dithiothreitol, 1 mM each dNTP, and 200 U SuperScript™II reverse transcriptase (GibcoBRL Life Technologies Inc., Grand Island, N.Y.). Reactions were incubated at 37° C. for 15 min. The products were mixed with loading buffer (95% formamide, 20 mM EDTA, 0.05% bromophenol blue and 0.02% xylene cyanole FF), denatured at 98° C. for 5 minutes, and then separated on a 12% acrylamide-7 M urea denatured gel. Radioactive signals were detected by autoradiography.

Nuclease S1 mapping was performed with a 1080 bp DNA fragment which was amplified using the forward primer E4INT-1 (5'-TGCTGTGACAGGCAG AGCAG-3'; SEQ ID NO:44) and the reverse primer ESAS (5'-TCTGTGTCGTCT-GTGAGGTC-3'SEQ ID NO:45). After cloned this fragment into PCR®2.1-TOPO® vector (Invitrogen Corp., Carlsbad, Calif.), a 320 bp fragment of single strand DNA probe used for S1 nuclease mapping was generated by single-primer PCR™ using $^{33}$P-labelled internal primer 3B6AS. The PCR™ condition was same as above. This single-strand 320 bp PCR™ product was separated in a 2% agarose gel and purified using QIAquick gel extraction kit (QIAGEN Inc., Chatsworth, Calif.) followed by recovering in 50 μl Tris buffer (10 mM Tris.Cl, pH8.5).

Total RNA from different samples was co-precipitated with 50 ng of recovered 320 bp $^{33}$P-labelled probe. Samples were dissolved in 30 μl of hybridization buffer (40 mM MOPS, pH 6.4, 1 mM EDTA, 0.4 M NaCl and 80% formamide) and incubated at 85° C. for 15 min. After hybridization for overnight at 54° C. based on the GC content of the projected fragment, the samples were digested for 1 h at 37° C. with S1 nuclease (GibcoBRL Life Technologies Inc., Grand Island, N.Y.) in the buffer containing 30 mM sodium acetate, pH 4.6, 1 mM zinc acetate, 5% glycerol, and 0.28 M NaCl. The resulting products were detected as described in primer extension section.

Construction of ΔDNMT3B Promoter and Luciferase Assay. The putative 1080 bp ΔDNMT3B promoter was amplified with primer set of E4INT-1 and E5AS. This fragment contains upstream 355-bp from ΔDNMT3B transcription starting site, first exon and first intron of ΔDNMT3B. After inserting the fragment into pGL3-basic vector (Promega Corp., Madison, Wis.), plasmids containing both forward (F) and reverse (R) directions of the insert were used for transient transfection.

A549 and H157 were used for transient transfection using FuGENE 6 Transfection Reagent (Roche Diagnostics Corp., Indianapolis, Ind.) according to protocol of the manufacturer. The plasmid pCH110 (Amersham Pharmacia Biotech, Inc., Piscataway, N.J.) was used as an internal control to monitor transfection efficiency. The signal was detected using a Luciferase Assay System (Promega Corp., Madison, Wis.) in a luminometer (Lumat LB 9507) (Berthold, Oak Ridge, Tenn.). The values of luciferase activity were normalized against those of β-galactosidase expressed by plasmid pCH110.

Detection of individual ΔDNMT3B Splicing Variants. The expression levels of specific DNMT3B and ΔDNMT3B variants in NSCLC cell lines and primary tissues were determined by using specific primer sets corresponding to individual DNMT3B or ΔDNMT3B variants. For ΔDNMT3B1, the inventors used 1S, 5'-TGGAAGGCCACCTCCAAGC-3' (SEQ ID NO:46), as the forward primer and 1AS, 5'-GCCTGCACGACGCACCTTCG-3' (SEQ ID NO:47), as the reverse primer for ΔDNMT3B2, 2S, 5'-AGATCAAGGGCTTCTCCTGG-3' (SEQ ID NO:48), as the forward primer and 2AS, 5'-GAGTCTTGTTCTCTGGTTGCG-3' (SEQ ID NO:49), as the reserves primer for ΔDNMT3B3, 3S, 5'-GTTCAGAGTATCAGGTCTCTGC-3' (SEQ ID NO:50), as the forward primer and 1AS as the reverse primer for ΔDNMT3B4, 3S as the forward primer and 2AS as the reverse primer; for ΔDNMT3B5, 4S, 5'-GTTCAGAGTATCAGAGAACAAGAC-3' (SEQ ID NO:51), as the forward primer and 3AS, 5'-CTGCCACAAGACAAACAGCC-3' (SEQ ID NO:52), as the reverse primer for ΔDNMT3B6, 5S, 5'-GTTCTCCGAGAGAACAAGAC-3' (SEQ ID NO:53), as the forward primer and 4AS, 5'-CAGTAAGACTGATAGCCATCG-3' (SEQ ID NO:54), as the reverse primer for ΔDNMT3B7, 6S, 5'-TGCTCTGGAGAGAACAAGAC-3' (SEQ ID NO:55), as the forward primer and 5AS, 5'-GAGACACATGTAACAGCTCC-3' (SEQ ID NO:56), as the reverse primer. A common forward primer E1, 5'-TGCTAAGCTACACACAGGAC-3' (SEQ ID NO:57), was used for DNMT3B variants and specific reverse primers were used to distinguish individual variants as following: 1AS for DNMT3Bs corresponding to ΔDNMT3B1 and ΔDNMT3B3 2AS for DNMT3Bs corresponding to ΔDNMT3B2 and ΔDNMT3B4 6AS, 5'-CGAGTCTTGTTCTCTGATACTC-3' (SEQ ID NO:58), for DNMT3B corresponding to ΔDNMT3B5 7AS, 5'-CGAGTCTTGTTCTCTCGGAG-3' (SEQ ID NO:59), for DNMT3B corresponding to ΔDNMT3B6; and 8AS, 5'-CGAGTCTTGTTCTCTCCA G-3' (SEQ ID NO:60), for DNMT3B corresponding to ΔDNMT3B7.

DNA extraction and MSP. Frozen tumor tissues and corresponding distant normal lung tissues were homogenized and genomic DNA was extracted by digestion of homogenized tissues in buffer containing 50 mM Tris-HCl (pH 8.0), 1% sodium dodecyl sulfate, and 0.5 mg/ml proteinase K at 42° C. for 36 h. The digested products were purified with phenyl-chloroform twice. DNA was then precipitated using the ethanol precipitation method and recovered in distilled DNase-free water. For MSP, 1 μg of genomic DNA from each tissue sample was used in the initial step of chemical modification. Briefly, DNA was denatured by NaOH and treated with sodium bisulfite (Gigma Chemical Co., St. Louis, Mo.). After purification with the use of Wizard DNA purification resin (Promega Corp., Madison, Wis.), the DNA was treated again with NaOH. After precipitation, DNA was recovered in water and was ready to add to a polymerase chain reaction (PCR™) with the use of specific primers for either the methylated or the unmethylated p16$^{INK4a}$ or RASSF1A promoter, as described previously (Soria et al., 2002). PCRs were carried out in 25 μL containing about 100 ng of modified DNA, 3% dimethyl sulfoxide, all four deoxynucleoside triphosphates (each at 200 μM), 1.5 mM $MgCl_2$, 0.4 μM PCR™ primers, and 1.25 U of Taq DNA polymerase (Life Technologies, Inc., Gaithersburg, Md.). DNA was amplified for 35 cycles at 95° C. for 30 seconds, 60° C. for 60 seconds, and 70° C. for 60 seconds, followed by a 5-minute extension at 70° C. in a temperature cycler (Hybaid Omnigene, Woodbridge, N.J.) in 500 μL plastic tubes. PCR™ products were separated on 2.5% agarose gels and visualized after staining with ethidium bromide. For each DNA sample, primer sets for methylated DNA and unmethylated DNA were used for analysis. CpGenome™ universal methylated DNA (Chemicon International, Temecula, Calif.) was used as positive controls, and water replacing for DNA was used as blank controls. CpGenome™ universal methylated DNA (Chemicon International, Temecula, Calif.) was used as positive controls, and water replacing for DNA was used as blank controls. The hypermethylation status was determined by visualizing a 150-base-pair PCR™ product for p16$^{INK4a}$ and a 167-base-pair PCR™ product for RASSF1A with the respective methylation-specific primer sets. All PCRs were repeated twice, and the results were reproducible.

siRNA and antisense RNA transfection. siRNA specifically targeting to the junction of exon 5 and 7 of ΔDNMT3B were designed based on principles published previously (Elbashir et al., 2001) and synthesized chemically (Ambion). Both annealed siRNA and corresponding oligonucleotides of single strands were ordered and exemplary sequences were as follows: sense strand: 5'-CACGCAACCAGAGAACAAGUU-3' (SEQ ID NO:61); antisense strand: 5'-CUUGUUCUCUGGUUGCGUGUU-3' (SEQ ID NO:62). An exemplary target sequence for annealed siRNA is as follows: 5'-AACACGCAACCAGAGAACAAG (SEQ ID NO:63). siRNA specifically targeting GAPDH and siRNA negative (scramble) control were also purchased from Ambion. Briefly, a defined number of cells ($5\times10^5$) were incubated in 6 well plastic plates for 12-24 h in DMEM with 10% FCS to achieve 60-70% cell confluence before transfection. Different concentrations of ΔDNMT3B-specific siRNA (10 nM to 80 nM), antisense oligo-dioxynucleotide (40 nM), 40 nM GAPDH-positive or negative siRNA, or medium alone were mixed with Lipofectamine 2000 (Invitrogen) according to the manufacturer's instructions and added into each well in serum-free condition. After transfection for 4 h at 37° C., cells were washed with phosphate-buffered saline (PBS) and cultivated in DMEM medium that contained 10% FCS. At 12, 24, 48, and 72 h after transfection, cells were harvested and stored at −80° C. until the time of RNA, DNA and protein extraction.

Bisulfite sequencing of RASSF1A promoter. MSP products from isolated genomic DNAs treated with either 40 nM siRNA-GAPDH or 40 nM siRNA-ΔDNMT3B4/2 were gel-purified using QIAquick gel extraction kit (QIAGEN Inc., Chatsworth, Calif.) followed by recovering in 50 μl Tris buffer (10 mM Tris Cl, pH 8.5) and then cloned into a TA cloning vector (Invitrogen). Inserts in individual plasmid molecules were then sequenced using the ABI PRISM 377 DNA Sequencer (Perkin-Elmer, Foster City, Calif.).

Western blotting. Cells treated by siRNA were washed once with PBS and collected by scraping in 200 μl of lysis buffer [50 mM HEPES, 0.5 M sodium chloride, 1.5 mM magnesium chloride, 1 mM EGTA, 10% (v/v) glycerol, 1% Triton X-100, and 5 μl/ml of Protease Inhibitor Cocktail (Sigma)]. The lysates were incubated on ice for 1 h with intermittent vortexing followed by centrifugation at 40,000 g for 10 min at 4° C. Equal amounts of protein from each treatment group were diluted with loading buffer, boiled, and loaded onto 7.5% SDS-polyacrylamide gel. Samples were electrophoresed at 150 to 180 V for 3 to 4 h, and separated proteins were transferred to polyvinylidene fluoride membrane. Proteins were detected by incubation with antibodies against DNMT1 (BD Biosciences) followed by blotting with horseradish peroxidase-conjugated anti-mouse secondary antibody (Sigma). Signals were then detected using a ECL Western blotting detection kit (Amersham, Piscataway, N.J.).

Statistical analysis of DNMT3B data. Summary statistics, including frequency tabulation, means, standard deviations, median, and range, were given to characterize subject characteristics and the expression of ΔDNMT3B variants. The chi-square ($\chi^2$) test or Fisher's exact test was used to test the association between two categorical variables. The McNemar's test was used to test changes in any ΔDNMT3B variants between tumor tissue and adjacent normal tissue. The logistic model was applied to model the association between ΔDNMT3B variants and p16$^{INK}$4a and RASSF1A promoter methylation. All statistical tests were two-sided, with a 5% type I error rate. Statistical analysis was performed with standard statistical software, including SAS Release 8.1 (SAS User Guide, Cary, N.C.) and S-Plus 2000 (S-plus 2000 Guide to Statistics, Mathsoft, Inc., Seattle, Wash.).

Example 2

Clinical Characterization of Patients

Clinical characteristics of all patients enrolled in the study are summarized in Table 2. Among the 119 patients, 47 (39%) were female and 72 (61%) were male. The mean age (±standard deviation) of the population was 64.3±10.1 years (range, 39-84 years). At the censor date of Nov. 14, 2003, the median follow-up period was 51 months (range, 16-130 months). Of the 70 patients with stage I or II disease, 29 (41%) were still alive, 35 (50%) died of lung cancer, and 6 (9%) died of unrelated causes. No significant difference in 5-year overall, disease-specific, and disease-free survival rates were observed by tumor stage, gender, smoking status, differentiation status, and histologic subtype in this patient group. Among the 49 patients with stage IIIA disease, 18 (37%) were still alive, 29 (59%) died of lung cancer, and 2 (4%) died of unrelated causes. In this group of patients, smokers had significantly poorer 5-year survival rates than the non-smokers did (P=0.047, P=0.03, and P=0.03 for 5-year overall, disease-specific, and disease-free survival rates, respectively). Thirty-five (71%) of the 49 patients received postoperative radiotherapy with (26 patients, including 5 with preoperative chemotherapy) or without (9 patients) concomitant chemotherapy, while 14 patients received no adjuvant therapy after surgery.

TABLE 2

Characteristics of Patents and Tumors

| | P16$^{INK4a}$ Promoter Methylation | | RASSF1A Promoter Methylation | | |
|---|---|---|---|---|---|
| | Absent | Present | Absent | Present | Total |
| Patients | 58 (49%) | 61 (51%) | 73 (61%) | 46 (39%) | 119 (100%) |
| Gender* | | | | | |
| Female | 23 (49%) | 24 (51%) | 33 (70%) | 14 (30%) | 47 (39%) |
| Male | 38 (53%) | 34 (47%) | 40 (56%) | 32 (44%) | 72 (61%) |
| Mean age (± standard deviation) | 65.0 ± 10.9 yr | 63.5 ± 9.1 yr | 65.1 ± 10.2 yr | 63.0 ± 9.9 yr | 64.3 ± 10.1 yr |
| Smoking status | | | | | |
| Non-smoker | 22 (58%) | 16 (42%) | 25 (66%) | 13 (34%) | 38 (32%) |
| Smoker | 39 (48%) | 42 (52%) | 48 (59%) | 33 (41%) | 81 (68%) |
| Histologic type | | | | | |
| Adenocarcinoma | 34 (57%) | 26 (43%) | 40 (67%) | 20 (33%) | 60 (50%) |
| Squamous cell carcinoma | 23 (47%) | 26 (53%) | 27 (55%) | 22 (45%) | 49 (41%) |
| Large cell carcinoma | 2 (29%) | 5 (71%) | 6 (86%) | 1 (14%) | 7 (6%) |
| Other | 2 (67%) | 1 (33%) | 0 (0%) | 3 (100%) | 3 (3%) |
| Differentiation** | | | | | |
| Well | 5 (45%) | 6 (55%) | 9 (82%) | 2 (18%) | 11 (9%) |
| Moderate | 25 (50%) | 25 (50%) | 32 (64%) | 18 (36%) | 50 (42%) |
| Poor | 31 (53%) | 27 (47%) | 32 (55%) | 26 (45%) | 58 (49%) |

TABLE 2-continued

| Characteristics of Patents and Tumors | | | | | |
|---|---|---|---|---|---|
| | P16$^{INK4a}$ Promoter Methylation | | RASSF1A Promoter Methylation | | |
| | Absent | Present | Absent | Present | Total |
| Stage | | | | | |
| I & II | 37 (53%) | 33 (47%) | 42 (60%) | 28 (40%) | 70 (59%) |
| IIIA | 24 (94%) | 25 (51%) | 31 (63%) | 18 (37%) | 49 (41%) |
| Stage I & II, 5-year overall survival | 61.7% | 28.3% | 50.6% | 41.1% | 46.5% |
| Stage III, 5-year overall survival | 53.5% | 10.8% | 45.6% | 0% | 30.8% |

*Subset analysis indicated that male patients had a higher rate of RASSF1A promoter methylation than females in stage IIIA group (P-0.03).
**Subset analysis indicated that poorly differentiated tumors had a higher rate of RASSF1A promoter methylation than well or moderately differentiated tumors in stage IIIA group (P = 0.04).

Example 3

Determining Methylation Status of Promoters

Using MSP, the methylation status of the p16$^{INK4a}$ and RASSF1A promoters in 119 primary tumors and the corresponding normal-appearing lungs was determined (FIG. 1). Promoter methylation was detected in 58 (49%) and 46 (39%) of the tumor tissue for the p16$^{INK4a}$ and RASSF1A promoters, respectively, compared with 13 (11%, including 4 samples whose corresponding tumors lacked methylation of the p16$^{INK}$4a promoter), and 4 (3%) in the corresponding normal-appearing lung tissues (P<0.0001). Unmethylated promoters of p16$^{INK4a}$ and RASSF1A were detected in all the normal-appearing lung tissues, and in 60% of tumor tissues, most likely because of the presence of normal cells in the tumor samples. In patients with stage I or II NSCLC, tumors with methylation of the p16$^{INK4a}$ promoter had a higher frequency of RASSF1A promoter methylation than those without p16$^{INK4a}$ promoter methylation, 58% versus 24% (P=0.005), suggesting that RASSF1A promoter methylation tends to occur in tumors with p16$^{INK4a}$ promoter methylation since RASSF1A promoter methylation occurs late in lung carcinogenesis (Belinsky et al., 2002) and Mao et al. unpublished data). However, this association was not significant in tumors from patients with stage IIIA disease (44% versus 29%; P=0.28). Altogether, 30 tumors (25% 19 stage I/II stage IIIA) showed concomitant methylation of both p16$^{INK4a}$ and RASSF1A promoters.

Example 4

Association Between Methylation Status and Other Patient Characteristics

The potential association between the methylation status of p16$^{INK4a}$ and RASSF1A promoters and sex, age, smoking history, histology, differentiation, and tumor stage was analyzed. RASSF1A promoter methylation was more frequently observed in poorly differentiated tumors (50%) than in moderately differentiated (26%) or in well-differentiated tumors (0% P=0.04) from patients with stage IIIA NSCLC, but there was no such association in tumors from patients with stage I/II disease (P=0.48). Additionally, tumors from male patients with stage IIIA NSCLC exhibited a significantly higher frequency of RASSF1A promoter methylation (47%) than did those from female patients (13% P=0.03). No significant association was observed between the methylation status and the other parameters analyzed.

Example 5

Effect of Promoter Methylation on Patient Survival

Figure 2:
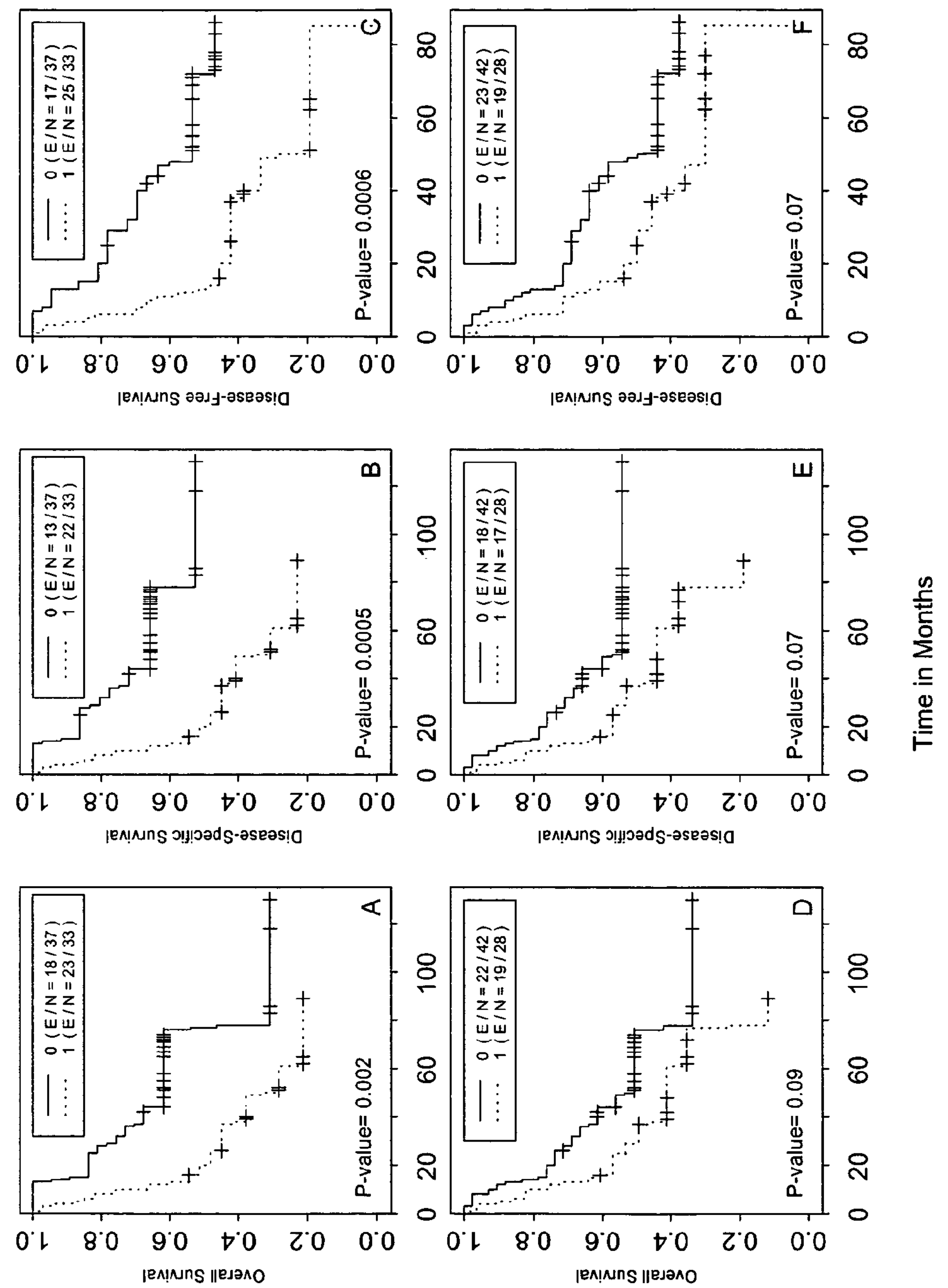
FIGS. 2A-2F. Association between the p16INK4a promoter methylation status (FIGS. 2A, 2B, and 2C) or RASSF1A promoter methylation status (FIGS. 2D, 2E, and 2F) and overall, disease-specific, and disease-free survival. 0 indicates groups without methylation of promoter 1 indicates groups with methylation of promoter. E/N indicates number of events/total number in each group.
Figure 3:
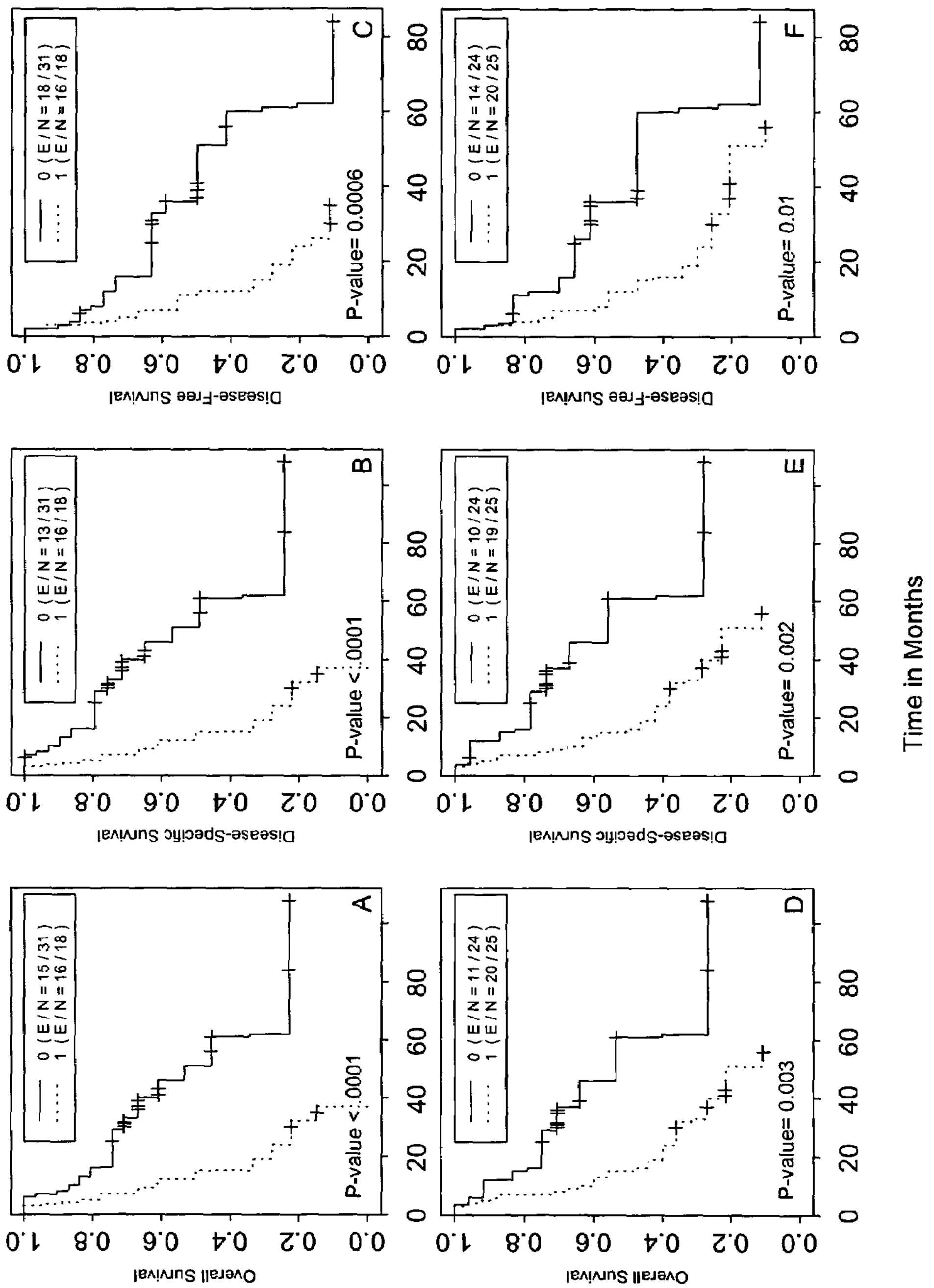
FIG. 3. Analysis of the effect of $p16^{INK4a}$ and RASSF1A promoter methylation on patients' survival in patients with stage IIIA tumors.

The effect of p16$^{INK4a}$ and RASSF1A promoter methylation on patients' survival was also analyzed. Because stage IIIA patients often received adjuvant treatment after surgery while stage I/II patients received only surgery, the two groups separately were analyzed. In the stage I/II group, patients whose tumors contained p16$^{INK4a}$ promoter methylation had significantly poorer 5-year overall, disease-specific, and disease-free survival rates (P=0.002, P=0.0005, and P=0.0066, respectively) than did patients whose tumors had no p16$^{INK4a}$ promoter methylation (FIG. 2A-2C). However, the association between the RASSF1A promoter methylation status and 5-year survival rates was not significant (P=0.09, P=0.07, and P=0.07, respectively) (FIG. 2D-2F), although patients whose tumors carried RASSF1A promoter methylation performed poorer. Multivariate analysis, included clinical parameters and promoter methylation status, indicated that p16$^{INK4a}$ promoter methylation was the only independent predictor of 5-year overall, disease-specific, and disease-free survivals. In patients with stage IIIA disease, in contrast to those with stage I/II tumors, the RASSF1A promoter methylation status was strongly associated with 5-year overall, disease-free, and disease-specific survivals (P<0.0001, P<0.0001, and P=0.0006, respectively FIG. 3A-3C), as was the p16INK4a promoter methylation status (P=0.003, P=0.002, and P=0.01, respectively, for 5-year overall, disease-specific, and disease-free survival rates FIG. 3D-3F). Although both RASSF1A and p16$^{INK4a}$ promoter methylation status were independent predictors of survival, RASSF1A was a stronger predictor for 5-year overall, disease-specific, and disease-free survival (hazard ratio=4.76, P<0.0001; hazard ratio=6.29, P<0.0001; and hazard ratio=3.41, P=0.0007 versus hazard ratio=2.89, P=0.007; hazard ratio=3.16, P=0.005, and hazard ratio=2.36, P=0.02, respectively).

Example 6

Effect of RASSF1A Inactivation on Tumors

Figure 4:
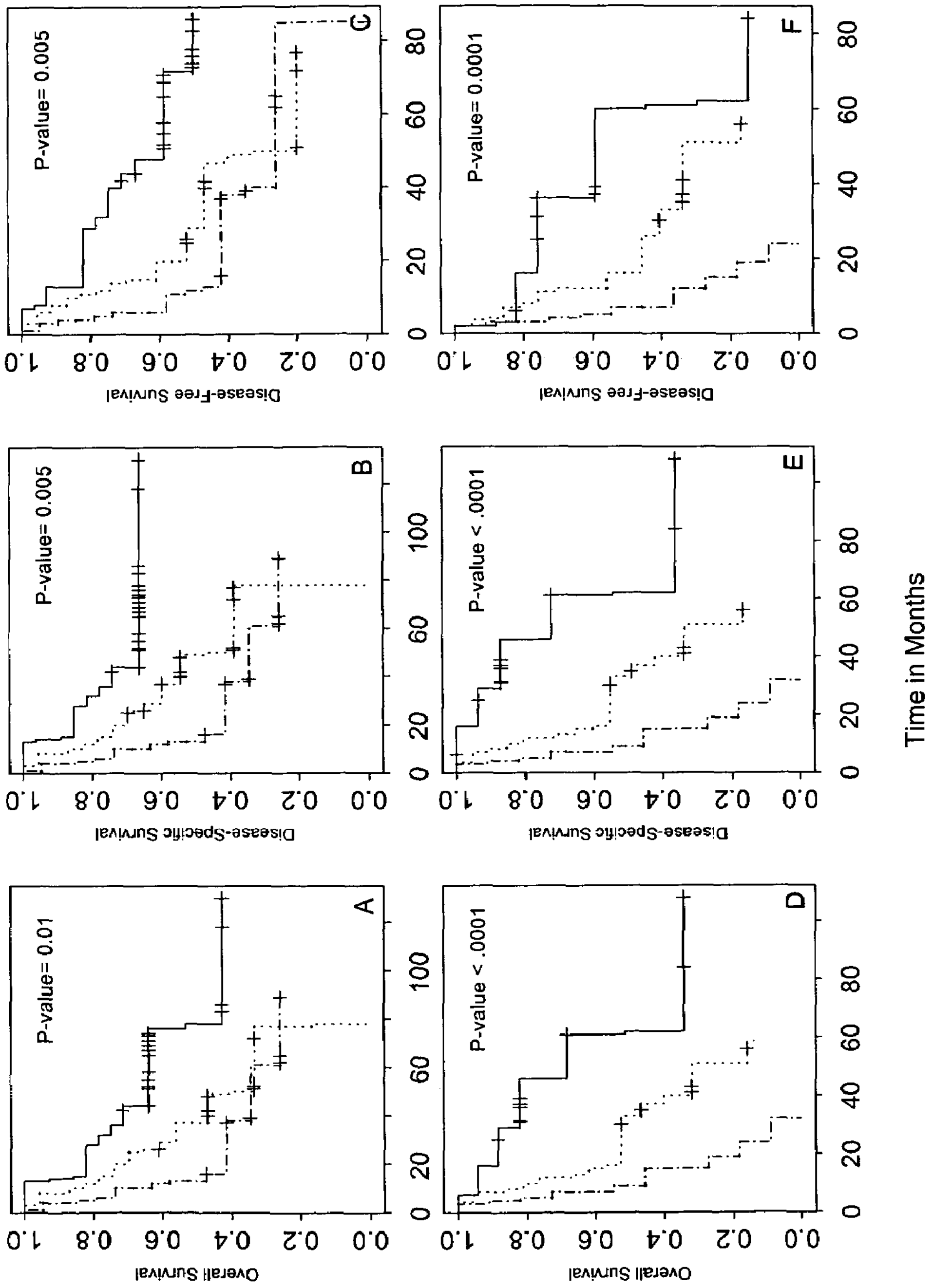
FIG. 4. Association between the p16INK4a promoter methylation status (A, B, and C) or RASSF1A promoter methylation status (D, E, and F) and overall, disease-specific, and disease-free survival. - indicates groups without promoter methylation (number of events/total in group [E/N]: 12/28 for A 9/28 for B, 12/28 for C 6/17 for D 5/17 for E and 9/17 for F) ••• indicates groups with methylation of the p16INK4a or the RASSF1A promoter (E/N: 16/23 for A 13/23 for B 16/23 for C 14/21 for D 13/21 for E 14/21 for F) - - - indicates groups with methylation of both promoters (E/N: 13/19 for A 13/19 for B 14/19 for C 11/11 for D-F).

To determine whether RASSF1A inactivation might have an added biologic value in patients whose tumors also carried p16$^{INK4a}$ promoter methylation, the 5-year survival rates of the group whose tumors had methylation of both genes' promoters were analyzed. In patients with stage I/II disease, the 5-year survival rates of patients whose tumors had methylation of both genes' promoters were significantly worse than in patients whose tumors had no promoter methylation or methylation of only one gene's promoter (P=0.01, P=0.005, and P=0.005, respectively, for 5-year overall, disease-specific, and disease-free survival rates; FIG. 4A-4C). Although the number of patients was small in the stage IIIA group, the association between patients whose tumors had methylation of both genes' promoters and poor survivals was striking (FIG. 4D-4F). All 11 patients (100%) in this category died of lung cancer within 3 years after surgery, while 13 (62%) of the 21 stage IIIA patients whose tumors had methylation of only one gene's promoters died of lung cancer in 5 years, and only 5 (29%) of the 17 patients whose tumors had no promoter methylation died of lung cancer in 6.5 years (P<0.0001 by log-rank test FIG. 4F).

Because 35 (71%) of the 49 patients with stage IIIA tumors received postoperative radiotherapy and 26 (53%) of the patients received adjuvant chemotherapy, it was determined whether these treatments had affected the predictive value of the methylation markers. Despite the small sample size, RASSF1A promoter methylation status remained a predictor of overall survival in radiotherapy and non-radiotherapy groups (P=0.0004 and P=0.008, respectively, for overall survival) as well as in chemotherapy and non-chemotherapy groups (P=0.001 and P=0.01, respectively, for overall survival).

Example 7

Identification of ΔDNMT3B

To determine expression levels of DNMT3B1 in normal lung tissues and lung cancer tissues, 12 pairs of primary NSCLC tissues were analyzed and matched to adjacent normal lung tissues using RT-PCR with a set of primers located at exon 17 and exon 23 of DNMT3B1 respectively. Expression of DNMT3B1 was found to be either undetectable or at trace level in the vast majority of the normal lung tissues analyzed while high expression was detected in 6 (50%) of the 12 tumors. To validate the finding, several additional sets of primers were designed that allow for the amplification of DNMT3B1 mRNA at different exon locations closer to the transcriptional initiation site of the gene.

It became evident that the expression level of the gene was much lower when a primer located at exon 2 (E1) or a primer located exon 4 (E4) was used compared to the expression level when a primer located at exon 6 (E5) of DNMT3B1 was used as a sense primer (FIG. 5A), suggesting the presence of additional transcripts which exclude exons 2 to 4. To confirm this observation, other primer sets at these regions were tested and the results were found to be consistent with the previous observation (data not shown). To exclude the possibility of contamination with homologue molecules in the RT-PCR products, each of the RT-PCR products were sequenced. The sequences matched perfectly to the originally reported DNMT3B1 sequence (GenBank accession number (AN): AL035071; SEQ ID NO:64).

Figure 5:
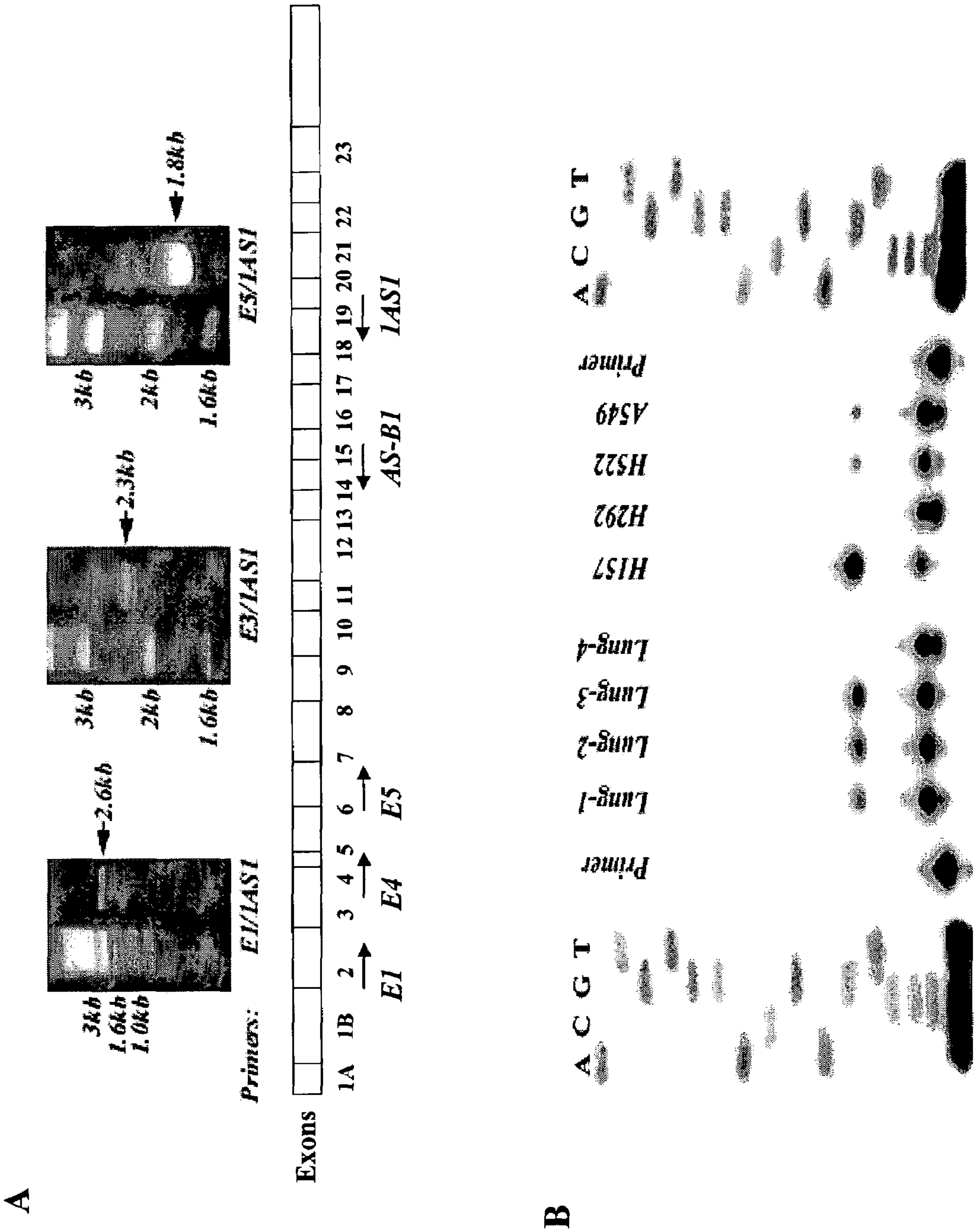
FIGS. 5A-5B. Expression of DNMT3B6.

To determine the exact start point(s) of the novel transcriptions, a primer extension assay was performed with RNA templates from lung cancer tissues and NSCLC cell lines using a primer (3B6AS) located at exon 5 of DNMT3B1. Two major transcriptional initiation sites located at nt 46502 and nt 46506 within exon 5 of DNMT3B1 (GenBank AN: AL035071; SEQ ID NO:64) were detected, respectively (FIG. 5B). This partial exon 5 was then named as the first exon of the novel transcript containing either 28-bp or 24-bp depending on which transcriptional initiation site it derives from. The initiation sites were validated using nuclease S1 RNA mapping analysis (data not shown). The new transcript from these starting sites was designated as ΔDNMT3B because it lacked 5 prime exons of DNMT3B.

Example 8

Characterization of ΔDNMT3B Promoter

Figure 6:
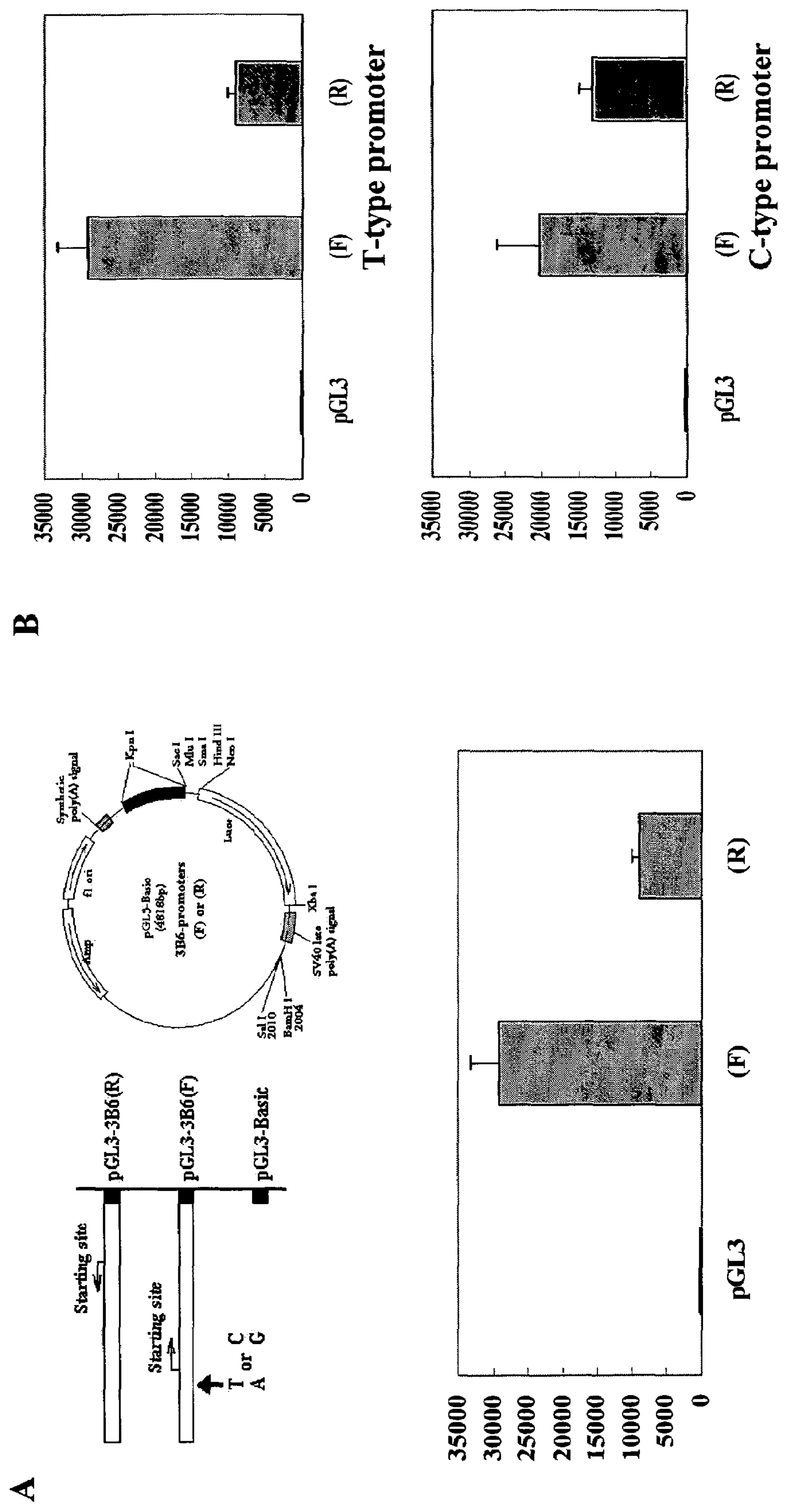
FIGS. 6A-6B. Promoter activity of DNMT3B6 detected by luciferase assay.

To determine the existence of a potential promoter upstream of the newly identified transcript, a 1080 bp-DNA fragment containing the upstream 355-bp from a ΔDNMT3B transcriptional initiation site, exon 1, intron 1, and partial exon 2 of ΔDNMT3B was constructed into a vector containing a reporter gene. The forward DNA fragment demonstrated a stronger promoter activity than the reverse DNA fragment. Serial plasmids with both forward and reverse sequences of the DNA fragment with various deletions were constructed. Using these constructs, it was shown that a core 477-bp sequence (SEQ ID NO:68 and SEQ ID NO:69) between 502-bp and 26-bp upstream of the ΔDNMT3B transcription initiation site is the critical region maintaining the promoter activity (FIG. 6A). Interestingly, a common thymidine (T)/cytosine (C) polymorphism was found in the promoter region of ΔDNMT3B located at 286-bp upstream from the ΔDNMT3B transcriptional initiation site, which changes a consensus TFIID (CTCTATTCCA SEQ ID NO:65) binding site to a GATA-1 (TCTATC SEQ ID NO:29) binding site. The promoter comprising the T nucleotide is provided in SEQ ID NO:68, and the promoter comprising the C nucleotide is provided in SEQ ID NO:69. A stronger promoter activity was detected with the T allele than the C allele (18-fold vs. 12-fold compared to the control, respectively) (FIG. 6B), suggesting the genome carries T allele may be subject to higher expression of ΔDNMT3B.

Example 9

Expression of ΔDNMT3B Variants in NSCLC Cell Lines and in Primary NSCLC

Figure 7:
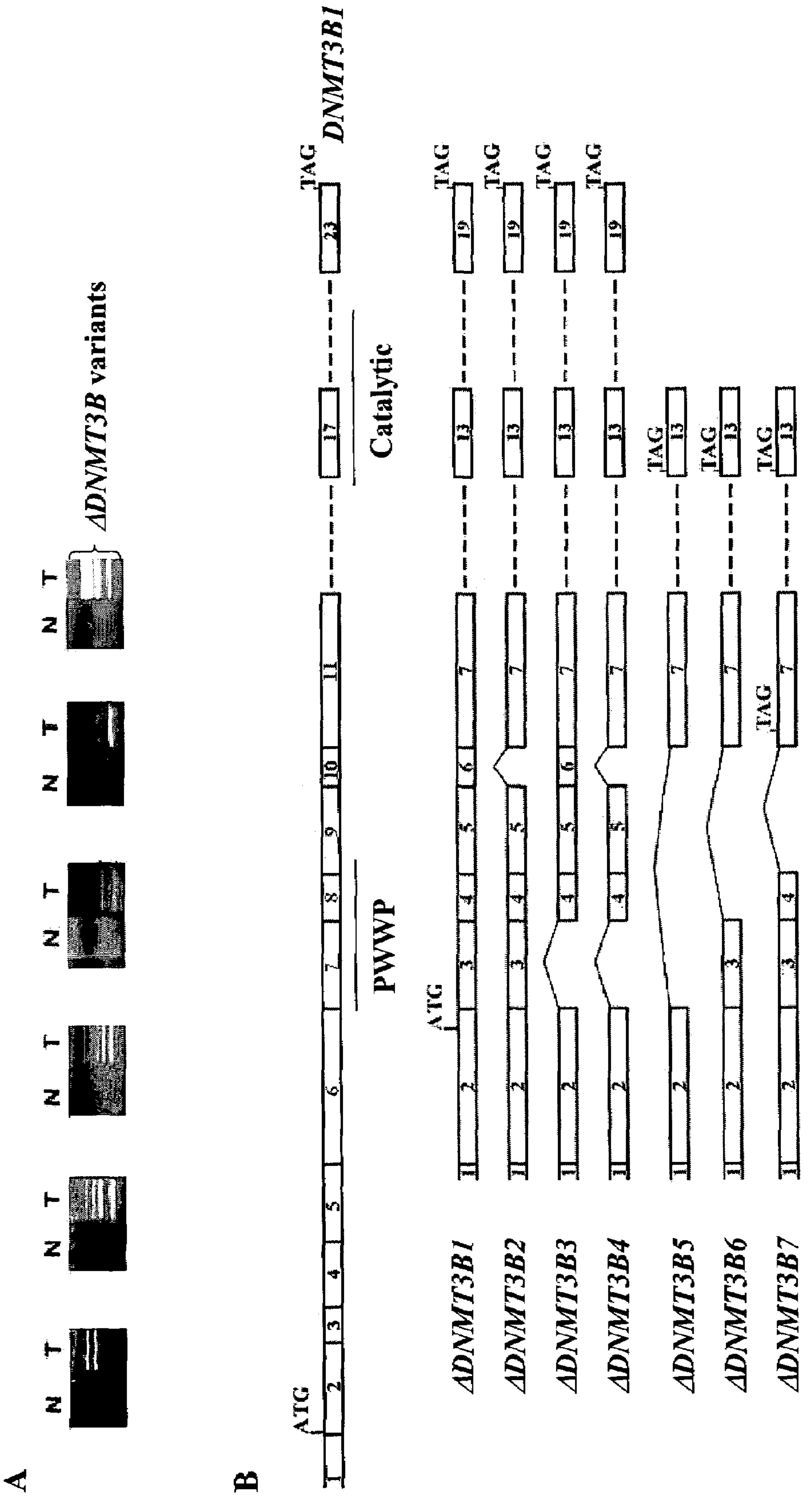
FIGS. 7A-7B. Identification of ΔDNMT3B variants highly expressed in lung cancer.

During the studies, it was noted that the presence of various sizes of RT-PCR products using a single pair of primers (E5 and AS-B1, FIG. 5A) for proximal exons, suggesting the presence of splicing variants (FIG. 7A). By sequencing analysis, it was found that the transcripts initiated from this novel promoter may generate at least 7 transcriptional variants through inclusion or exclusion of different combinations of exons 3, 4, 5, and 6 of ΔDNMT3B, designated as ΔDNMT3B1-7 (FIG. 7B, SEQ ID NOS:1-7). The predicted translation of ΔDNMT3B is at position 194, where a good kozak consensus sequence presents (Kozak, 1987a; Kozak, 1987b Kozak, 1989), from the transcription initiation site. A comparative analysis of the putative amino acid sequences derived from the variants show that ΔDNMT3B lacks 200 amino acids at the N-terminal compared to DNMT3B1; ΔDNMT3B1 and ΔDNMT3B2 contain a complete PWWP (proline-tryptophan-tryptophan-proline) motif while other variants either contained partial of the PWWP motif or completely lacked of the structure (FIG. 7B); ΔDNMT3B5-7 lack the enzymatic domains due to the alternative reading frames as a result of the alternative splicing (FIG. 7B).

Figure 8:
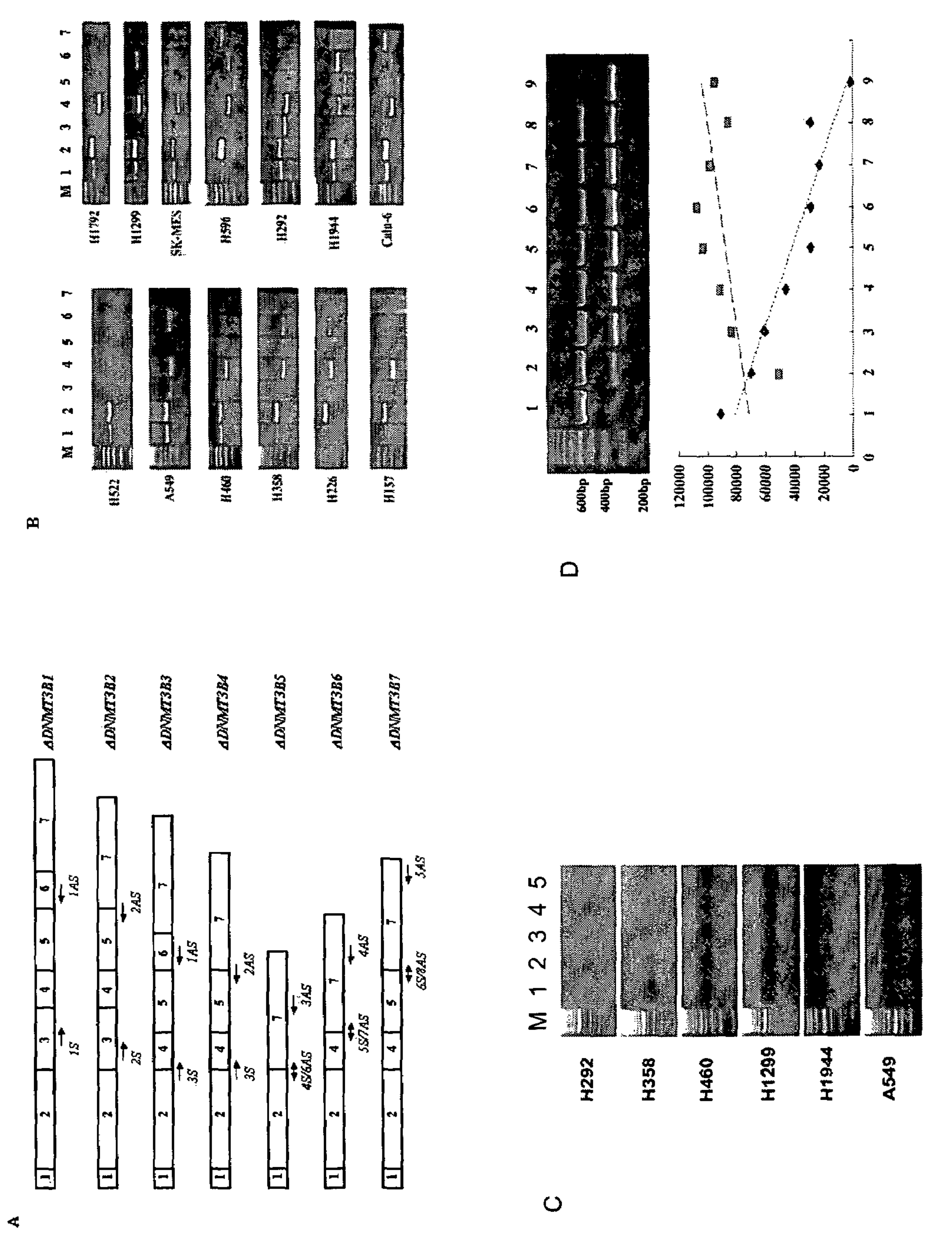
FIGS. 8A-8D. Alternative or aberrant splicing variants of ΔDNMT3B subfamily.

To identify the individual ΔDNMT3B variants, specific PCR primer sets were designed on the basis of their splicing patterns (FIG. 8A). The ΔDNMT3B1 and ΔDNMT3B2 expression were detected in all 13 NSCLC cell lines analyzed, ΔDNMT3B4 expression in 12 of the 13 cell lines, and ΔDNMT3B6 expression in 7 of the 13 cell lines in contrast, ΔDNMT3B3, ΔDNMT3B5, and ΔDNMT3B7 were expressed infrequently (FIG. 8B). Interestingly, the DNMT3B variants were expressed less frequently and at lower levels in these cell lines (FIG. 8C). In a multiplex PCR analysis, the relative amplification efficiencies of the primer sets were determined for DNMT3B and ΔDNMT3B using DNA templates containing various concentrations of DNMT3B and ΔDNMT3B1 (FIG. 8D). The robust amplification of DNMT3B1 (FIG. 8D) indicated that the lack or very low levels of RT-PCR products in the cell lines reflected the low level of the corresponding transcripts.

Moreover, Table 3 illustrates characteristics and expression of ΔDNMT3B variants in primary NSCLC.

TABLE 3

Characterization and Expression of ΔDNMT3B Variants In Primary NSCLC

| | | Δ3B1 | Δ3B2 | Δ3B3 | Δ3B4 | Δ3B5 | Δ3B6 | Δ3B7 | p16 | RASSF |
|---|---|---|---|---|---|---|---|---|---|---|
| Sex | | | | | | | | | | |
| F | 45 | 25 (56%) | 30 (67%) | 14 (31%) | 17 (38%) | 9 (20%) | 12 (27%) | 4 (9%) | 23 (51%) | 16 (36%) |
| M | 64 | 41 (64%) | 51 (80%) | 18 (28%) | 32 (50%) | 17 (27%) | 28 (44%) | 11 (17%) | 32 (50%) | 26 (41%) |
| Smoke | | | | | | | | | | |
| N | 37 | 24 (65%) | 26 (70%) | 14 (38%) | 18 (49%) | 8 (22%) | 14 (38%) | 6 (16%) | 18 (49%) | 16 (43%) |
| Y | 72 | 42 (58%) | 55 (76%) | 18 (25%) | 31 (43%) | 18 (25%) | 26 (36%) | 9 (13%) | 37 (51%) | 26 (36%) |
| Pathology | | | | | | | | | | |
| Adeno | 56 | 34 (61%) | 41 (73%) | 18 (32%) | 24 (43%) | 10 (18%) | 20 (36%) | 5 (9%) | 26 (46%) | 19 (34%) |
| SCC | 44 | 24 (55%) | 32 (73%) | 11 (25%) | 21 (48%) | 14 (32%) | 18 (41%) | 8 (18%) | 23 (52%) | 20 (46%) |
| Differenti | | 5(50%) | 6 | 4 | 4 | 0(0%) | 1 | 0 | 6 | 2 |
| Well | 10 | 27 | (60%) | (40%) | (40%) | 8 | (10%)* | (0%)* | (60%) | (20%) |
| Mod | 42 | (64%) | 32 | 12 | 15 | (19%) | 13 | 6 | 21 | 16 |
| Poor | | 34 | (76%) | (29%) | (36%) | 18 | (31%) | (14%) | (50%) | (38%) |
| — | | — | — | — | — | — | — | — | — | — |
| Stage | | | | | | | | | | |
| I & II | 70 | 43 (61%) | 55 (79%) | 21 (30%) | 34 (49%) | 17 (24%) | 25 (36%) | 8 (11%) | 33 (47%) | 28 (40%) |
| III & IV | 39 | 23 (59%) | 26 (67%) | 11 (28%) | 15 (39%) | 9 (23%) | 15 (39%) | 7 (18%) | 22 (56%) | 14 (36%) |

Example 10

Expression of ΔDNMT3B4 Strongly Correlated with Promoter Methylation of Rassf1a iIn Primary NSCLC In 109 primary NSCLC, the most frequently expressed variant was ΔDNMT3B2 (81 74%), followed by ΔDNMT3B1 (66 61%) and ΔDNMT3B4 (49 45%) (Table 4).

TABLE 4

Association Between Expression of ΔDNMT3B Variants and Promoter Methylation of P16 Or RASSF1A In Primary NSCLC

| | Δ3B1 | Δ3B2 | Δ3B3 | Δ3B4 | Δ3B5 | Δ3B6 | Δ3B7 | P16 |
|---|---|---|---|---|---|---|---|---|
| Δ3B2 | | | | | | | | |
| 0 | 1 (3.6%) | | | | | | | |
| 1 | 65 (80.3%) | | | | | | | |
| | $p < 0.0001$ | | | | | | | |
| Δ3B3 | | | | | | | | |
| 0 | 42 (54.6%) | 53 (68.8%) | | | | | | |
| 1 | 24 (75.0%) | 28 (87.5%) | | | | | | |
| | $p = 0.047$ | $p = 0.03$ | | | | | | |

TABLE 4-continued

Association Between Expression of ΔDNMT3B Variants and Promoter Methylation of P16 Or RASSF1A In Primary NSCLC

| | Δ3B1 | Δ3B2 | Δ3B3 | Δ3B4 | Δ3B5 | Δ3B6 | Δ3B7 | P16 |
|---|---|---|---|---|---|---|---|---|
| Δ3B4 | | | | | | | | |
| 0 | 26 (43.3%) | 35 (58.3%) | 15 (25.0%) | | | | | |
| 1 | 40 (81.6%) | 46 (93.9) | 17 (34.7%) | | | | | |
| | $p < 0.0001$ | $p < 0.0001$ | $p < 0.27$ | | | | | |
| Δ3B5 | | | | | | | | |
| 0 | 44 (53.0%) | 55 (66.3%) | 25 (30.1%) | 26 (31.3%) | | | | |
| 1 | 22 (84.6%) | 26 (100%) | 7 (26.9%) | 23 (88.5%) | | | | |
| | $p < 0.005$ | $p < 0.0002$ | $p < 0.75$ | $p < 0.0001$ | | | | |
| Δ3B6 | | | | | | | | |
| 0 | 34 (49.3%) | 41 (59.4%) | 19 (27.5%) | 20 (29.0%) | 3 (4.4%) | | | |
| 1 | 32 (80.0%) | 40 (100%) | 13 (32.5%) | 29 (72.5%) | 23 (57.5%) | | | |
| | $p < 0.002$ | $p < 0.0001$ | $p < 0.58$ | $p < 0.0001$ | $p < 0.0001$ | | | |
| Δ3B7 | | | | | | | | |
| 0 | 53 (56.4%) | 67 (71.3%) | 26 (27.7%) | 38 (40.4%) | 16 (17.0%) | 27 (28.7%) | | |
| 1 | 13 (86.7%) | 14 (93.3%) | 6 (40.0%) | 11 (73.3%) | 10 (66.7%) | 13 (86.7%) | | |
| | $p < 0.04$ | $p < 0.06$ | $p < 0.33$ | $p < 0.02$ | $p < 0.0002$ | $p < 0.0001$ | | |
| P16 | | | | | | | | |
| 0 | 24 (44.4%) | 33 (61.1%) | 19 (35.2%) | 19 (35.2%) | 11 (20.4%) | 16 (29.6%) | 9 (16.7%) | |
| 1 | 42 (76.4%) | 48 (87.3%) | 13 (23.6%) | 30 (54.6%) | 15 (27.3%) | 24 (43.6%) | 6 (10.9%) | |
| | $p < 0.0007$ | $p < 0.002$ | $p < 0.19$ | $p < 0.04$ | $p < 0.40$ | $p < 0.13$ | $p < 0.38$ | |
| RASSF1 | | | | | | | | |
| 0 | 32 (47.8%) | 42 (62.7%) | 21 (31.3%) | 11 (16.4%) | 6 (9.0%) | 17 (25.4%) | 4 (6.0%) | 25 (37.3%) |
| 1 | 34 (81.0%) | 39 (92.9%) | 11 (26.2%) | 38 (90.5%) | 20 (47.6%) | 23 (54.8%) | 11 (26.2%) | 30 (71.4%) |
| | $p < 0.0006$ | $p < 0.0005$ | $p < 0.57$ | $p < 0.0001$ | $p < 0.001$ | $p < 0.002$ | $p < 0.004$ | $p < 0.0005$ |

The expression of these variants was then correlated with the promoter methylation status of p16 and RASSF1A because these two genes are important in lung tumorigenesis and are frequently inactivated by promoter methylation in NSCLC (Burbee et al., 2001; Dammann et al., 2000; Merlo et al., 1995; Minna et al., 2002). There was a striking correlation between ΔDNMT3B4 expression and RASSF1A promoter methylation: 38 of the 42 (90%) tumors with RASSF1A promoter methylation expressed ΔDNMT3B4, whereas only 11 of the 67 (16%) tumors without RASSF1A promoter methylation expressed ΔDNMT3B4 ($P<0.0001$). The correlation between ΔDNMT3B4 and p16 promoter methylation, however, was not striking 30 of the 55 (55%) tumors with p16 promoter methylation expressed ΔDNMT3B4, and 19 of the 54 (35%) tumors without p16 promoter methylation expressed ΔDNMT3B4 ($P=0.04$). A multivariate analysis that included all the available variables showed that ΔDNMT3B7 expression, p16 promoter methylation, and ΔDNMT3B4 expression were independent factors associated with RASSF1A promoter methylation. Therefore, a logistic regression analysis was performed to adjust for ΔDNMT3B7 expression and p16 promoter methylation, and ΔDNMT3B4 still strongly correlated with RASSF1A promoter methylation ($P<0.0001$) after the adjustment. These data provided strong in vivo evidence that ΔDNMT3B4 is required for promoter methylation of RASSF1A in NSCLC.

Example 11

ΔDNMT3B4/2 Knockout Resulted in Rapid RASSF1A Promoter Demethylation and Reactivation of Gene Expression A small interference RNA (siRNA) and an antisense RNA were designed to specifically target the junction of exon 5 and exon 7 of ΔDNMT3B. Because both ΔDNMT3B4 and ΔDNMT3B2 lack exon 6 (FIG. 8A), these molecules were expected to trigger degradation of both the ΔDNMT3B4 and the ΔDNMT3B2 transcripts. The NSCLC cell line H1299 was used for this study because it shows promoter methylation of both p16 and RASSF1A, lacks p16 and RASSF1A gene expression, and expresses a high level of ΔDNMT3B4 but not DNMT3B (FIGS. 8B and 8C, Table 5).

TABLE 5

Modification of DNA Methylation in Promoters and Repeat Sequences

| Method | MSP | MSP | MSP | MSP | MSP | MSP | MSP | Pyrosequencing | Pyrosequencing |
|---|---|---|---|---|---|---|---|---|---|
| Sequence name | RIZ | p14 | MLH1 | ECAD | RASSF1A | DAPK | p16 | LINE methylation (%) | Alu methylation (%) |
| H1299 control | | | | | M | M&U | M | 50.9 | 31.9 |
| H1299 lipo | | | | | M | M&U | M | 54.9 | 28.4 |

TABLE 5-continued

Modification of DNA Methylation in Promoters and Repeat Sequences

| | Method | | | | | | | | |
|---|---|---|---|---|---|---|---|---|---|
| | MSP | MSP | MSP | MSP | MSP | MSP | MSP | Pyrosequencing | Pyrosequencing |
| | Sequence name | | | | | | | | |
| | RIZ | p14 | MLH1 | ECAD | RASSF1A | DAPK | p16 | LINE methylation (%) | Alu methylation (%) |
| H1299 siRNA | | | | | U | U | M | 35 | 23.6 |
| H358 control | | | | | M | | M | 41.2 | 25.9 |
| H358 lipo | | | | | M | | M | 40.3 | 26.4 |
| H358 siRNA | | | | | U | | M | 39 | 25.3 |
| RKO control | M | M | M | M | M | | M | 41 | 29.8 |
| RKO lipo | M | M | M | M | M | | M | 46.4 | 30.8 |
| RKO siRNA | M | M | M | M | M | | M | 44.6 | 30.5 |
| SW48 control | M | M | M&U | | M | | M | 56.3 | 30.1 |
| SW48 lipo | M | M | M&U | | M | | M | 61.8 | 32.6 |

M: methylated promoter; U: unmethylated promoter; M&U: mixed with both methylated and unmethylated promoters; control: treated with medium alone; lipo: treated with lipofectamine alone; siRNA: treated with ΔDNMT3B4/2-specific siRNA The siRNA or the antisense RNA successfully eliminated transcripts of ΔDNMT3B2 and ΔDNMT3B4 in H1299 cells in a dose- and time-dependent manner but had no effect on ΔDNMT3B1 (FIG. 9A). The effect was specific because the expression levels of the three transcripts in cells treated with medium, lipofectamine alone, lipofectamine plus scramble siRNA, or lipofectamine plus siRNA-glyceraldehyde-3-phosphate dehydrogenase (GAPDH) did not change (FIG. 9A).

The effect of a ΔDNMT3B4/2 knockout was analyzed in the promoter methylation of p16 and RASSF1A. The RASSF1A promoter became partially unmethylated in the cells treated with 20 nM siRNA-ΔDNMT3B4/2 and completely unmethylated (defined as substantially no detectable methylated PCR product in by methylation-specific PCR studies) in cells treated with 40 nM siRNA at 12 h (FIG. 9B). At 24 h, the promoter was completely unmethylated in the cells treated with 20 nM siRNA or 40 nM antisense RNA, whereas it was completely demethylated at 48 h in the cells treated with 10 nM siRNA (FIG. 9B). These results were consistent with the dose-dependent reduction of ΔDNMT3B4 expression resulting from the siRNA or antisense RNA treatment (FIG. 9A). In contrast, promoter methylation of p16 was not affected by the treatment (FIG. 9B). Interestingly, RASSF1A remained completely unmethylated 72 h after the short-term siRNA or antisense RNA treatment (FIG. 9B).

The expression status of RASSF1A was analyzed using RT-PCR. Expression of RASSF1A was restored in cells treated with 40 nM siRNA-ΔDNMT3B4/2 or 40 nM antisense RNA at 12 h, with 20 nM siRNA at 24 h, and with 10 nM siRNA at 48 h (FIG. 9C). RASSF1A expression was restored for at least 72 h after treatment (FIG. 9C). The result was again consistent with the dose-dependent reduction of ΔDNMT3B4 resulting from the siRNA or antisense treatment (FIG. 9A).

Next, bisulfite sequencing of methylation-specific PCR products from cells treated with or without siRNA-ΔDNMT3B4/2 was performed. The fragment sequenced was part of the RASSF1A promoter and contained 10 CpG sites in addition to those in the primer sequences. The cytosine residuals at these 10 CpG sites were not converted to uracil (recognized as thymidine in PCR products) by the bisulfite (an indication of methylation) in any of the 14 clones derived from the cells 12 h after treatment with 40 nM siRNA-GAPDH, whereas the cytosine residuals at all 10 CpG sites were converted to uracil by the bisulfite (an indication of unmethylated status), in all 14 clones derived from the cells 12 h after treatment with 40 nM siRNA-ΔDNMT3B4/2 (FIG. 9D). This difference indicated that the siRNA treatment had completely reversed the methylated CpG sites in the RASSF1A promoter region.

To exclude the possibility that the treatment might affect DNMT1, the major enzyme responsible for maintaining DNA methylation, DNMT1 protein expression was analyzed in H1299 cells treated with siRNA and found no reduction in protein level (FIG. 9E), suggesting that DNMT1 was not the contributing factor to the observed promoter demethylation.

H358 cells were also analyzed, another NSCLC cell line with p16 and RASSF1A promoter methylation and ΔDNMT3B4/2 expression (FIG. 8B). As with H1299, the treatment knocked out ΔDNMT3B4/2 expression and resulted in the demethylation of the RASSF1A promoter but not of the p16 promoter (Table 5).

Example 12

Figure 10:
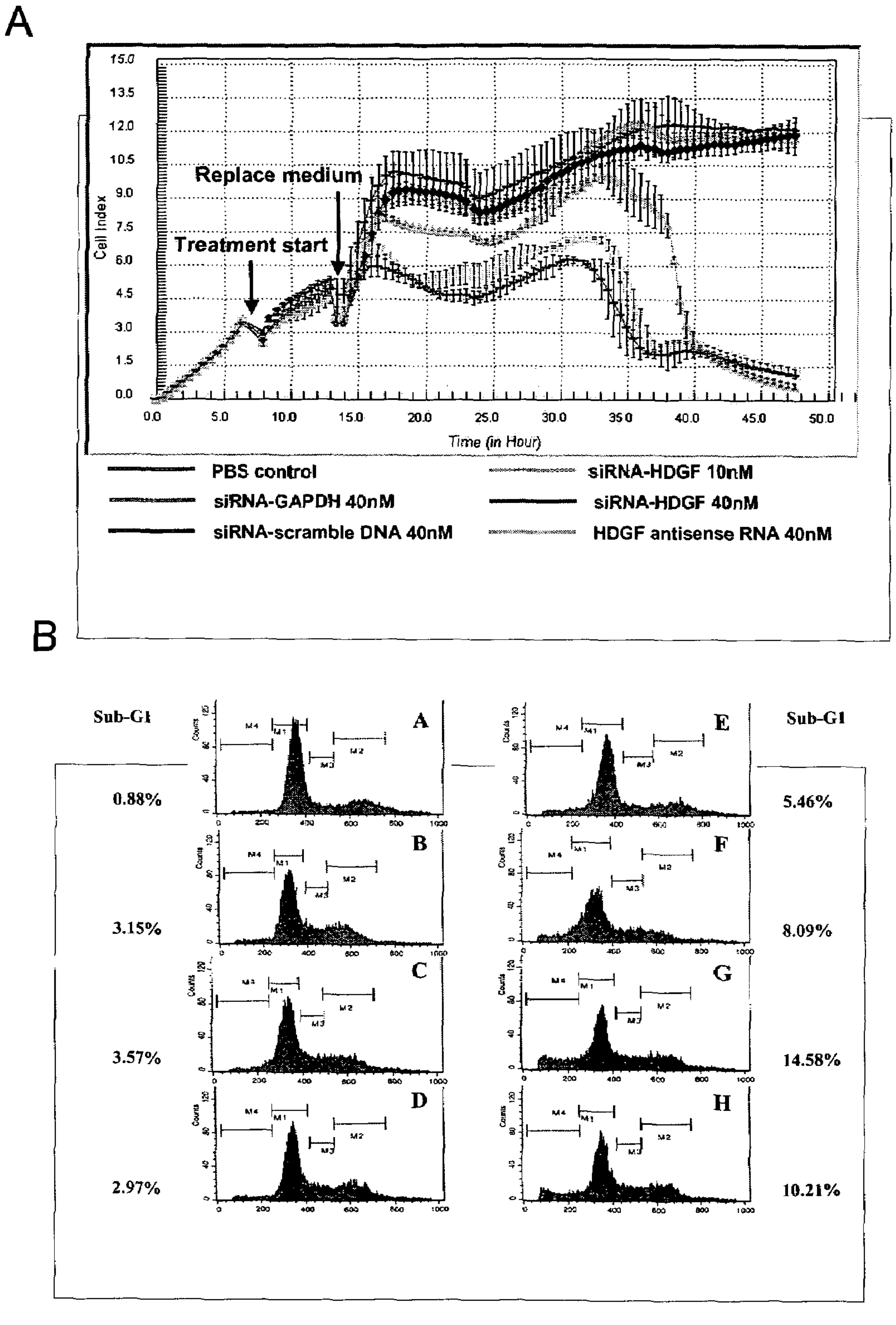
FIG. 10A-10B. Growth inhibition by siRNA to ΔDNMT3B4/2.

ΔDNMT3B4/2 Knockout Suppressed Cell Growth and Increased Cell Death in NSCLC Cells A microelectronic cell sensor system was used (ACEA Biosciences, Inc., San Diego, Calif.) to determine the dynamic change in cell growth affected by the ΔDNMT3B4/2 knockout (measured every 30 min). In the H1299 cells, growth was inhibited at about 10 h after treatment with the siRNA-ΔDNMT3B4/2 in a dose-dependent manner or the antisense RNA (FIG. 10A). To determine the potential mechanism for inhibiting the growth of the ΔDNMT3B4/2 knockout, the cell cycle distribution of the H1299 cells was examined 24 h after treatment using flow cytometry. There was a dose-dependent increase of the sub-G1 fraction in the cells treated with the siRNA-ΔDNMT3B4/2 or the antisense RNA (FIG. 10B). This increase indicated that the treatment had induced cell death.

Example 13

ΔDNMT3B4/2 Knockout had Various Effects on Other CpG Sequences and in Colorectal Cancer Cells By screening other promoters commonly methylated in lung cancers, a 50% methylated death-associated protein (DAP)-kinase promoter in the H1299 cells was identified; such methylation was completely eliminated after the siRNA-ΔDNMT3B4/2 treatment (Table 5). Then, using pyrosequencing, we analyzed the effect of the siRNA-ΔDNMT3B4/2 in repeat DNA sequences (Alu and LINE). This analysis indicated a more global DNA methylation status (Yang et al., 2004). In the H1299 cells, the treatment resulted in reduced DNA methylation in the LINE and Alu sequences but not in the H358 cells (Table 5). Two colorectal cancer cell lines (SW48 and RKO) were analyzed to determine whether the effect of the siRNA-ΔDNMT3B4/2 observed in the NSCLC cell lines also occurred in other tumor types. DNA methylation occurred in these cell lines in more promoters (Table 5), and numerous ΔDNMT3B4/2 transcripts were expressed (data not shown). Interestingly, none of these promoters, including RASSF1A, or the repeat sequences were demethylated after ΔDNMT3B4/2 was knocked out by the siRNA-ΔDNMT3B4/2 (Table 5).

Example 14

Rare ΔDNMT3B Variants and Clinical Outcome

Figure 11:
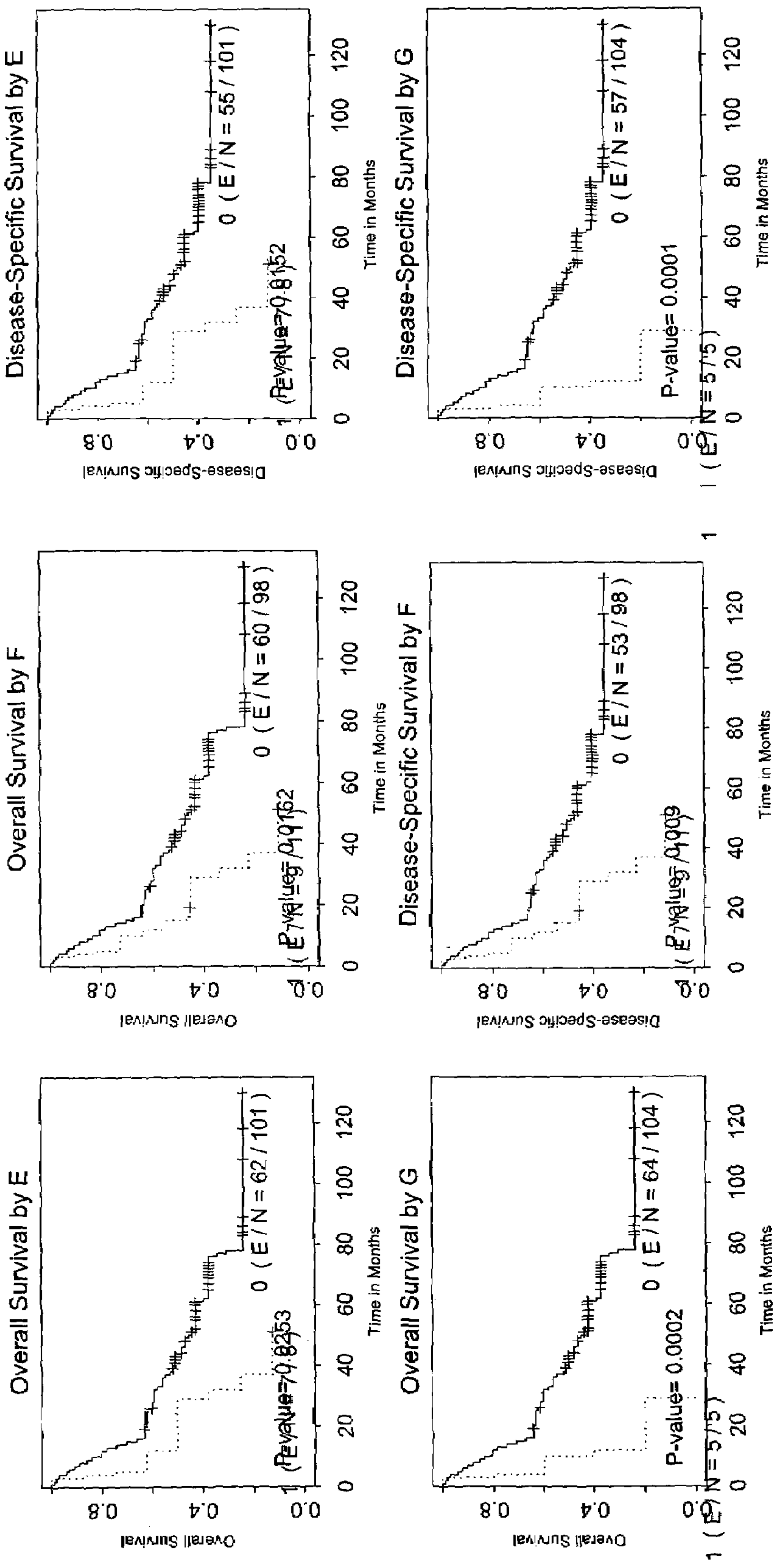
FIG. 11. Expression of Rare ΔDNMT3B5 (E), ΔDNMT3B6 (F), and ΔDNMT3B7 (G) and clinical outcome in NSCLC.

FIG. 11 illustrates expression of rare ΔDNMT3B variants, particularly ΔDNMT3B5, ΔDNMT3B6, and ΔDNMT3B7, and the clinical outcome in patients with NSCLC. For FIG. 11. deltaDNMT3B5-7 (E-G) were less frequently expressed in NSCLC and never detected in normal lung tissues by using PCR primers specific to these isoforms. However, patients whose tumors expressed these rare deltaDNMT3B isoforms showed statistically significant poorer outcome (both overall survival and disease-specific survival) compared to those patients whose tumors had no expression of these rare isoforms. Thus, in specific embodiments, the presence of these isoforms indicates a poor prognosis (decreased survival/lifespan) in patients compared to patients which lack these isoforms.

Figure 12:
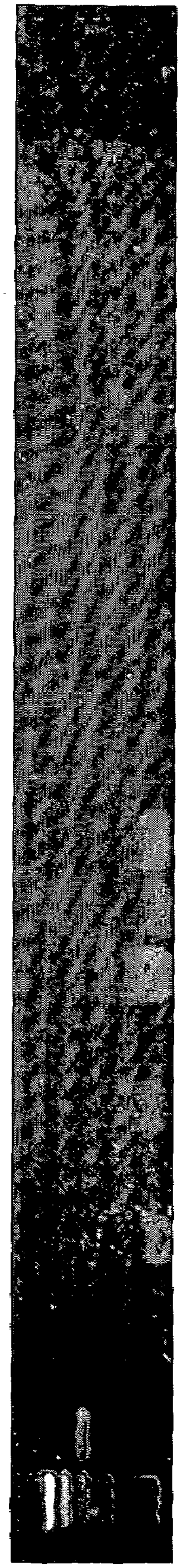
FIG. 12. Expresion of ΔDNMT3B4 in bronchial brush cell.

Furthermore, FIG. 12 demonstrates expression of the ΔDNMT3B4 variant from bronchial brush cells.

Expression of deltaDNMT3B isoforms was analyzed using PCR primers specific to each isoform in 87 bronchial brush specimens obtained from chronic smokers without clinical evidence of lung cancer. We found expression of deltaDNMT3B1 in 30% of the samples, deltaDNMT3B2 in 79% of the samples, and deltaDNMT3B4 in only 1% of the sample, suggesting deltaDNMT3B1/2 are activated in very early stage lung carcinogenesis following long term smoking while activation of deltaDNMT3B4 is a relatively late event. These data are consistent with frequent identification of p16 promoter methylation in such tissues while RASSF1A promoter methylation is rarely identified in these samples. In FIG. 12, however, examples of deltaDNMT3B4 expression in the bronchial brush samples is provided. The only positive sample was shown in the figure. In specific embodiments of the invention, this indicates that the appearance of this variant occurs in later stages of cancer and may be diagnostic thereof.

Example 15

Antibodies for ΔDNMT3B Variants

Antibodies directed to the ΔDNMT3B variants may be generated by standard means in the art. In specific aspects of the invention, the antibodies are monoclonal, although in alternative embodiments the antibodies are polyclonal.

Monoclonal antibodies may be generated, for example, in mice and recognize specific peptides used to generate these antibodies, as well as recombinant isoforms of DNMT3Bs. Antibodies produced in all clones described below are IgG.

Figure 13:
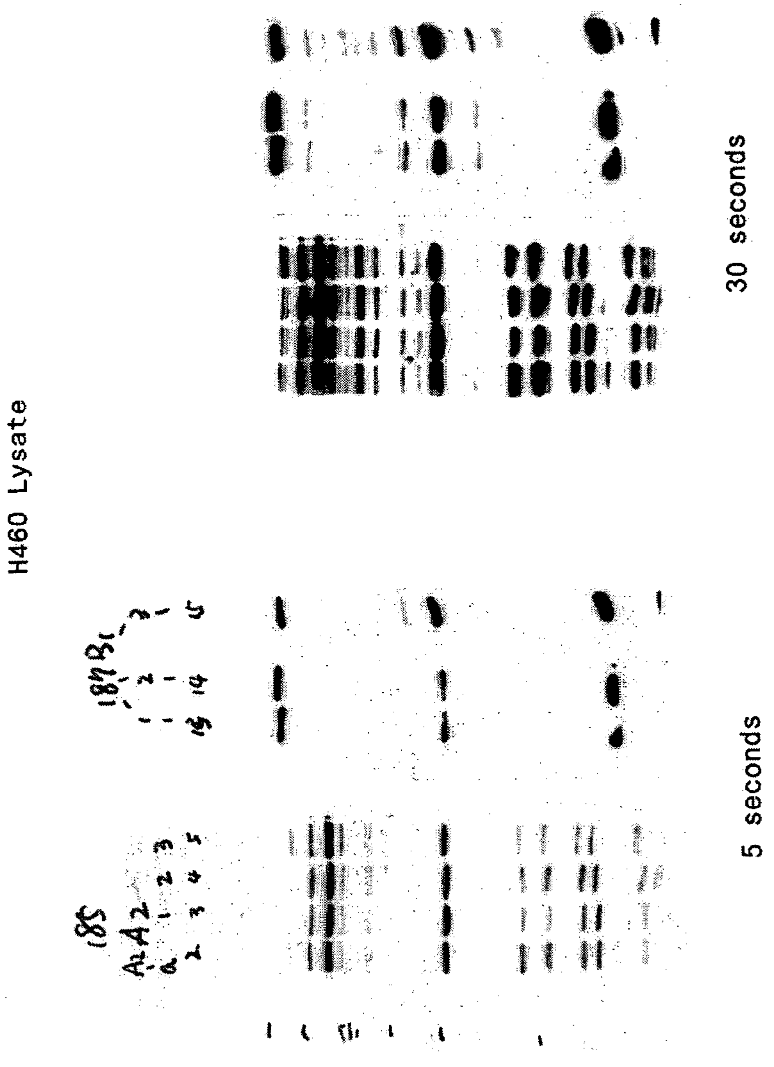
FIG. 13. Antibody recognition of ΔDNMT3B variant proteins in lysate of H460 NSCLC cell line.

Clones 185A1 and 185A2 are generated against peptide sequence: ESPQVEADSGD (SEQ ID NO:66), which is shared by most of the delta isoforms as well as DNMT3Bs. IgG clone 187B1 is generated against peptide sequence: GLKPNNTQP-ENKTRC (SEQ ID NO:67), which contains the junction specific for delta-DNMT3B2/4. All the clones have been confirmed to recognize specific delta-DNMT3B4 recombinant protein generated in *E coli*. FIG. 13 shows proteins recognized by the antibodies in lysate of H460 NSCLC cell line.

In particular aspects of the invention, antibodies are utilized to bind to the corresponding variant(s), thereby providing a therapeutic composition for cancer treatment, such as treatment of NSCLC. That is, antibodies for the variants are generated or provided otherwise, such as through commercial means, and administered to a patient in need thereof, such as a cancer patient. In particular embodiments, the antibodies are administered in addition to another cancer therapy, such as one provided prior to, concomitant with, and/or subsequent to the antibody administration. Additional cancer therapies include chemotherapy, radiation, surgery, gene therapy, immunotherapy hormone therapy, and so forth.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,196,265
U.S. Pat. No. 4,367,110
U.S. Pat. No. 4,418,068
U.S. Pat. No. 4,452,901
U.S. Pat. No. 4,554,101
U.S. Pat. No. 4,664,911
U.S. Pat. No. 4,792,447
U.S. Pat. No. 5,045,451
U.S. Pat. No. 5,221,605
U.S. Pat. No. 5,238,808
U.S. Pat. No. 5,279,721
U.S. Pat. No. 5,310,687
U.S. Pat. No. 5,354,855
U.S. Pat. No. 5,578,706
U.S. Pat. No. 5,686,072
U.S. Pat. No. 5,767,072
Agathanggelou et al., *Oncogene,* 20:1509-1518, 2001.
Arap et al., *Cancer Res.,* 55(6):1351-1354, 1995.
Baglioni et al., *Interferon,* 5:23-42, 1983.
Bajorin et al., *J. Clin. Oncol.,* 6(5):786-792, 1988.

Bakhshi et al., *Cell,* 41(3):899-906, 1985.
Baylin S et al. *Cancer Cell.* 2002 1:299-305.
Belinsky et al., *Proc. Natl. Acad. Sci. USA,* 95:11891-11896, 1998.
Belinsky S A et al. Cancer Res. 2002 62(8):2370-7.
Bosher and Labouesse, *Nat. Cell. Biol.,* 2:E31-E36, 2000.
Brauch et al., *N. Engl. J. Med.,* 317:1109-1113, 1987.
Burbee et al., *J. Natl. Cancer Inst.,* 93:691-699, 2001.
Cairns et al., *Science,* 265:415-417, 1994.
Caldas et al., *Nat. Genet.,* 8(1):27-32, 1994.
Caplen et al., *Proc. Natl. Acad. Sci. USA,* 98:9742-9747, 2001.
Cedar H. Cell. 1988, 53:3-4.
Cheng et al., *Cancer Res.,* 54(21):5547-5551, 1994.
Cleary and Sklar, *Proc. Natl. Acad. Sci. USA,* (21):7439-7443, 1985.
Cleary et al., *J. Exp. Med.,* 164(1):315-320, 1986.
Dammann et al., *Nat. Genet.,* 25:315-319, 2000.
De Jager et al., *Semin. Nucl. Med.,* 23(2):165-179, 1993.
Doolittle and Ben-Zeev, *Methods Mol Biol,* 109:215-237, 1999.
Elbashir et al., *Genes Dev.,* 5(2):188-200, 2001.
Esteller et al., *Cancer Res.,* 61:3225-3229, 2001.
Esteller M. Lancet Oncol. 2003 4:351-8.
Fire et al., *Nature,* 391(6669):806-811, 1998.
Fong et al., *Thorax,* 58:892-900, 2003.
Forgacs et al., *Oncol. Res.,* 7:6-13, 2001.
Forster and Symons, *Cell,* 49(2):211-220, 1987.
Gerlach et al., *Nature* (London), 328:802-805, 1987.
Goding, In: *Monoclonal Antibodies: Principles and Practice,* 2d ed., Academic Press, Orlando, Fla., pp 60-61, 71-74, 1986.
Gonzalez-Quevedo et al., *J. Clin. Oncol.,* 20:254-262, 2002.
Goodman and Gilman's *The Pharmacological Basis Of Therapeutics*, Hardman et al. (Eds.), $10^{th}$ Ed., 32:853-860 35:891-893, 2001.
Greenlee et al., *Cancer J. Clin.,* 50:7-33, 2000.
Greenlee et al., *Cancer J. Clin.,* 51:15-36, 2001.
Grishok et al., *Science,* 287:2494-2497, 2000.
Gulbis and Galand, *Hum Pathol,* 24(12):1271-85, 1993.
Harlow and Lane, In: *Antibodies: A Laboratory Manual,* Cold Spring Harbor Laboratory, Cold Spring Harbor, N.Y., 346-348, 1988.
Hirsch et al., *Clin. Cancer Res.,* 7:5-22, 2001.
Hollstein et al., *Science,* 253(5015):49-53, 1991.
Hussussian et al., *Nat. Genet.,* 8(1):15-21, 1994.
Hutvagner et al., 2001
Hutvagner et al., *Science,* 293:834-838, 2001.
Irie and Morton, *Proc. Natl. Acad. Sci. USA,* 83(22):8694-8698, 1986.
Irie et al., *Lancet.,* 1(8641):786-787, 1989.
Jaenisch, *Trends Genet.,* 13:323-329, 1997.
Jin et al., *Lung Cancer,* 34:207-218, 2001.
Johnson Capaldi et al., 1977
Jones and Gonzalgo, *Proc. Natl. Acad. Sci. USA,* 94:2103-2105, 1997.
Joyce, *Nature,* 338:217-244, 1989.
Kamb et al., *Nat. Genet.,* 8(1):23-26, 1994.
Kamb et al., *Science,* 2674:436-440, 1994.
Kang et al., *Biochem. Biophys. Res. Commun.,* 289:862-868, 2001.
Kaye, *Oncogene,* 21:6908-6914, 2002.
Kerr et al., *Br. J. Cancer,* 26(4):239-257, 1972.
Ketting et al., *Cell,* 99(2):133-141, 1999.
Khokhlatchev et al., *Curr. Biol.,* 12:253-265, 2002.
Kim and Cook, *Proc. Natl. Acad. Sci. USA,* 84(24):8788-8792, 1987.
Kim et al., *Cancer Res.,* 61:3419-3424, 2001.
Kim D H et al. *Cancer Res* 2001 61: 3419-24.
Kim et al., *EMBO J.,* 21:4183-4195, 2002.
Kim et al., *J. Biol. Chem.,* 37538-37543, 1999.
Koh et al., *Nature,* 375:506-510, 1995.
Kononen et al., *Nat. Med.,* 4(7):844-847, 1998.
Kozak, *J. Cell Biol.,* 108:229, 1989.
Kozak, *J. Mol. Biol.* 196:947, 1987a.
Kozak, *Nucl. Acids Res.,* 15:8125, 1987b.
Kyte and Doolittle, *J. Mol. Biol.,* 157(1):105-132, 1982.
Leu et al., *Cancer Res.,* 63:6110-6115, 2003.
Li and Jaenisch, In: *DNA alterations in Cancer* Ehrlich (Ed.), 351-365, Eaton Publishing, Natick, Mass., 2000.
Lin and Avery, *Nature,* 402:128-129, 1999.
Liu et al., *Mol. Cell Biol.,* 23:2709-2719, 2003.
Liu et al., *Oncogene,* 22:8125-8136, 2003.
Merlo et al., *Nat. Med.,* 1:686-692, 1995.
Michel and Westhof, *J. Mol. Biol.,* 216:585-610, 1990.
Mitchell et al., *Ann. NY Acad. Sci.,* 690:153-166, 1993.
Mitchell et al., *J. Clin. Oncol.,* 8(5):856-869, 1990.
Monk et al., *Development,* 99:371-382, 1987.
Montgomery et al., *Proc. Natl. Acad. Sci. USA,* 95:15502-15507, 1998.
Mori et al., *Cancer Res.,* 54(13):3396-3397, 1994.
Morton et al., *Arch. Surg.,* 127:392-399, 1992.
Nakamura et al., In: *Handbook of Experimental Immunology* ($4^{th}$ Ed.), Weir et al (Eds.), 1:27, Blackwell Scientific Publ., Oxford, 1987.
Niklinski et al., *Lung Cancer,* 34(2):S53-58, 2001.
Nobri et al., *Nature* (London), 368:753-756, 1995.
Okamoto et al., *Proc. Natl. Acad. Sci. USA,* 91(23):11045-11049, 1994.
Okano et al., *Cell,* 99:247-257, 1999.
Okano et al., *Nat. Genet.,* 19:219-220, 1998.
Orlow et al., *Cancer Res,* 54(11):2848-2851, 1994.
Ortiz-Vega et al., *Oncogene,* 21:1381-1390, 2002.
Oue et al., *Oncol. Rep.,* 8:1085-1089, 2001.
Pfeifer et al., *Biol. Chem.,* 383:907-914, 2002.
Physicians Desk Reference
Plasterk and Ketting, *Curr. Opin. Genet. Dev.,* 10:562-567, 2000.
Ravindranath and Morton, 1991
Reik W, Dean W, Walter J. Science. 2001, 293:1089-93.
Reinhold-Hurek and Shub, *Nature,* 357:173-176, 1992.
Remington's Pharmaceutical Sciences, 16th Ed. Mack Publishing Company, 1980.
Rhee et al., *Nature,* 404:1003-1007, 2000.
Rhee et al., *Nature,* 416:552-556, 2002.
Robertson and Wolffe, *Nat. Rev. Genet.,* 1: 11-19, 2000.
Robertson K D et al. Nucleic Acids Res. 2000 28:2108-13.
Robertson et al., *Nucl. Aci. Res.,* 27:2291-2298, 1999.
Saito et al., *Proc. Natl. Acad. Sci. USA,* 99:10060-10065, 2002.
Sambrook et al., In: *Molecular cloning*, Cold Spring Harbor Laboratory Press, Cold Spring Harbor, N.Y., 2001.
Sarver et al., *Science,* 247:1222-1225, 1990.
Sato et al., *Oncogene,* 21:4822-4829, 2002.
Scanlon et al., *Proc. Natl. Acad. Sci. USA,* 88:10591-10595, 1991.
Serrano et al., *Nature,* 366:704-707, 1993.
Serrano et al., *Science,* 267(5195):249-252, 1995.
Sharp and Zamore, *Science,* 287:2431-2433, 2000.
Sharp, *Genes Dev.,* 13:139-141, 1999.
Shen et al., *Cancer Res.,* 62:4992-4995, 2002.
Shivakumar et al., *Mol. Cell Biol.,* 22:4309-4318, 2002.
Song et al., *Nat. Cell Biol.,* 6:129-137, 2004.
Soria et al., *Cancer Res.,* 62:351-352, 2002.

Surani, *Cell,* 93:309-312, 1998.
Tabara et al., *Cell,* 99(2):123-132, 1999.
Tang X, et al. *Journal of the National Cancer Institute,* 2000 92(18):1511-6.
Tomizawa et al., *Clin. Cancer Res.,* 8:2362-2368, 2002.
Toyooka et al., *Mol. Cancer Ther.,* 1:61-67, 2001.
Tsujimoto and Croce, *Proc. Natl. Acad. Sci. USA,* 83(14): 5214-5218, 1986.
Tsujimoto et al., *Science,* 228(4706):1440-1443, 1985.
Tuschl, *Chembiochem.,* 2:239-245, 2001.
Waterhouse et al., *Nature,* 411:834-842, 2001.
Weinberg, *Science,* 254(5035):1138-1146, 1991.
Weisenberger et al. (2004) Mol Cancer Res. 2004 2:62-72.
Williams, *Biochem. Soc. Trans.,* 25(2):509-513, 1997.
Yakushiji et al., *Int. J. Oncol.,* 22:1201-1207, 2003.
Zamore, *Nat. Struct. Biol.,* 8:746-750, 2001.
Zhang et al., *Cell,* 97:53-61, 1999.
Zöchbauer-Müller et al., *Annu. Rev. Physiol.,* 64:681-708, 2002.
Zöchbauer-Müller et al., *Cancer Res.,* 249-255, 2001.

---

What is claimed is:

1. An isolated nucleic acid sequence encoding a DNA methyltransferase-3B variant having the amino acid sequence selected from the group consisting of SEQ ID NO:16, SEQ ID NO:17, and SEQ ID NO:18.

2. The nucleic acid sequence of claim 1, comprising a DNA methyltransferase-3B variant nucleic acid sequence selected from the group consisting of SEQ ID NO:2, SEQ ID NO:3, and SEQ ID NO:4.

3. The isolated nucleic acid of claim 2, wherein the nucleic acid sequence is comprised in an expression vector.

4. The isolated nucleic acid of claim 3, wherein the expression vector is further defined as a viral or plasmid vector.

5. The isolated nucleic acid of claim 4, wherein the viral vector is an adenoviral vector, an adeno-associated viral vector, a retroviral vector, a lentiviral vector, a herpes viral vector, polyoma viral vector or hepatitis B viral vector.

6. The isolated nucleic acid sequence of claim 3, wherein the expression vector is comprised in a non-viral delivery system.

7. The isolated nucleic acid sequence of claim 6, wherein the non-viral delivery system comprises one or more lipids.

8. The isolated nucleic acid sequence of claim 2, wherein the nucleic acid sequence is operatively linked to a promoter.

9. A host cell comprising a nucleic acid sequence encoding a DNA methyltransferase-3B variant according to claim 2.

10. The host cell of claim 9, wherein the nucleic acid sequence is comprised in a vector.

11. An isolated DNA methyltransferase-3B variant having the amino acid sequence selected from the group consisting of SEQ ID NO:16, SEQ ID NO:17, and SEQ ID NO:18.

12. The nucleic acid sequence of claim 2, wherein said sequence is SEQ ID NO:2.

13. The nucleic acid sequence of claim 2, wherein said sequence is SEQ ID NO:3.

14. The nucleic acid sequence of claim 2, wherein said sequence is SEQ ID NO:4.

15. The nucleic acid sequence of claim 1, encoding a DNA methyltransferase-3B variant having the amino acid sequence of SEQ ID NO:16.

16. The nucleic acid sequence of claim 1, encoding a DNA methyltransferase-3B variant having the amino acid sequence of SEQ ID NO:17.

17. The nucleic acid sequence of claim 1, encoding a DNA methyltransferase-3B variant having the amino acid sequence of SEQ ID NO:18.

18. The DNA methyltransferase-3B variant of claim 11, having the amino acid sequence of SEQ ID NO:16.

19. The DNA methyltransferase-3B variant of claim 11, having the amino acid sequence of SEQ ID NO:17.

20. The DNA methyltransferase-3B variant of claim 11, having the amino acid sequence of SEQ ID NO:18.

* * * * *

UNITED STATES PATENT AND TRADEMARK OFFICE

CERTIFICATE OF CORRECTION

PATENT NO. : 7,405,287 B2 Page 1 of 1
APPLICATION NO. : 11/189279
DATED : July 29, 2008
INVENTOR(S) : Li Mao et al.

It is certified that error appears in the above-identified patent and that said Letters Patent is hereby corrected as shown below:

Column 1, line 9, should read

-- This invention was made with government support under grant number DAMD17-01-1-01689-1 awarded by the Department of Defense and under grant numbers CA 68437 and CA 91844 awarded by the National Cancer Institute. The government has certain rights in the invention. --

Signed and Sealed this

Thirty-first Day of March, 2009

John Doll

JOHN DOLL
*Acting Director of the United States Patent and Trademark Office*